US008283519B2

(12) United States Patent
Creelman et al.

(10) Patent No.: US 8,283,519 B2
(45) Date of Patent: Oct. 9, 2012

(54) PLANT TRANSCRIPTIONAL REGULATORS OF ABIOTIC STRESS

(75) Inventors: Robert A. Creelman, Castro Valley, CA (US); Oliver Ratcliffe, Oakland, CA (US); Roderick W. Kumimoto, San Bruno, CA (US); Neal I. Gutterson, Oakland, CA (US); T. Lynne Reuber, San Mateo, CA (US); Jeffrey M. Libby, Cupertino, CA (US); Jacqueline E. Heard, Stonington, CT (US); Jose Luis Riechmann, Pasadena, CA (US); Omaira Pineda, Vero Beach, FL (US)

(73) Assignee: Mendel Biotechnology, Inc., Hayward, CA (US)

( * ) Notice: Subject to any disclaimer, the term of this patent is extended or adjusted under 35 U.S.C. 154(b) by 2043 days.

(21) Appl. No.: 10/838,616

(22) Filed: May 4, 2004

(65) Prior Publication Data
US 2006/0008874 A1 Jan. 12, 2006

Related U.S. Application Data

(60) Continuation-in-part of application No. 10/456,882, filed on Jun. 6, 2003, now abandoned, and a continuation-in-part of application No. 10/685,922, filed on Oct. 14, 2003, which is a continuation-in-part of application No. 09/934,455, filed on Aug. 22, 2001, now abandoned, and a continuation-in-part of application No. 09/533,029, filed on Mar. 22, 2000, now Pat. No. 6,664,446, which is a continuation-in-part of application No. 10/412,699, filed on Apr. 10, 2003, and a continuation-in-part of application No. 10/374,780, filed on Feb. 25, 2003, and a continuation-in-part of application No. 10/225,068, filed on Aug. 9, 2002, which is a continuation-in-part of application No. 10/171,468, filed on Jun. 14, 2002, now abandoned, and a continuation-in-part of application No. 09/837,944, filed on Apr. 18, 2001, now abandoned, which is a continuation-in-part of application No. 10/225,066, filed on Aug. 9, 2002, and a continuation-in-part of application No. 10/225,067, filed on Aug. 9, 2002, and a continuation-in-part of application No. 10/278,536, filed on Oct. 22, 2002, which is a division of application No. 09/532,591, filed on Mar. 22, 2000, now abandoned, which is a continuation-in-part of application No. 10/278,173, filed on Oct. 21, 2002, which is a division of application No. 09/533,392, filed on Mar. 22, 2000, now abandoned, which is a continuation-in-part of application No. 10/295,403, filed on Nov. 15, 2002, which is a division of application No. 09/394,519, filed on Sep. 13, 1999, now abandoned.

(60) Provisional application No. 60/565,948, filed on Apr. 26, 2004, provisional application No. 60/336,049, filed on Nov. 19, 2001, provisional application No. 60/310,847, filed on Aug. 9, 2001, provisional application No. 60/125,814, filed on Mar. 23, 1999, provisional application No. 60/101,349, filed on Sep. 22, 1998, provisional application No. 60/108,734, filed on Nov. 17, 1998.

(51) Int. Cl.
*A01H 4/00* (2006.01)
(52) U.S. Cl. ........ 800/262; 800/298; 800/287; 800/278; 536/24.1; 530/350
(58) Field of Classification Search ........................ None
See application file for complete search history.

(56) References Cited

U.S. PATENT DOCUMENTS

| | | | |
|---|---|---|---|
| 6,417,428 | B1 | 7/2002 | Thomashow et al. |
| 6,664,446 | B2 | 12/2003 | Heard |
| 7,135,616 | B2 | 11/2006 | Heard et al. |
| 7,169,972 | B2 | 1/2007 | Stepanova et al. |
| 7,193,129 | B2 | 3/2007 | Reuber et al. |
| 7,238,860 | B2 | 7/2007 | Ratcliffe et al. |
| 2002/0023281 | A1 | 2/2002 | Gorlach et al. |
| 2003/0061637 | A1 | 3/2003 | Jiang et al. |
| 2003/0101481 | A1 | 5/2003 | Zhang et al. |
| 2003/0119165 | A1 | 6/2003 | Cahoon et al. |
| 2003/0121070 | A1 | 6/2003 | Adam et al. |
| 2003/0131386 | A1 | 7/2003 | Samaha |
| 2003/0233670 | A1 | 12/2003 | Edgerton et al. |
| 2004/0019927 | A1 | 1/2004 | Sherman et al. |
| 2004/0034888 | A1 | 2/2004 | Liu et al. |
| 2004/0045049 | A1 | 3/2004 | Zhang et al. |

(Continued)

FOREIGN PATENT DOCUMENTS
EP 1033405 9/2000
(Continued)

OTHER PUBLICATIONS

Riechmann, J.L. et al. (Jun. 1998). "The AP2/EREBP Family of Plant Transcription Factors," Biological Chemistry 379:633-646.

(Continued)

*Primary Examiner* — Jim Ketter
(74) *Attorney, Agent, or Firm* — Jeffrey M. Libby

(57) ABSTRACT

The invention relates to plant transcription factor polypeptides, polynucleotides that encode them, homologs from a variety of plant species, variants of naturally-occurring sequences, and methods of using the polynucleotides and polypeptides to produce transgenic plants having advantageous properties, including improved cold and other osmotic stress tolerance, as compared to wild-type or reference plants. The invention also pertains to expression systems that may be used to regulate these transcription factor polynucleotides, providing constitutive, transient, inducible and tissue-specific regulation.

28 Claims, 13 Drawing Sheets

U.S. PATENT DOCUMENTS

| | | | |
|---|---|---|---|
| 2004/0078852 | A1 | 4/2004 | Thomashow et al. |
| 2004/0098764 | A1 | 5/2004 | Heard et al. |
| 2005/0108791 | A1 | 5/2005 | Edgerton et al. |
| 2005/0193443 | A1 | 9/2005 | Dale Rock et al. |
| 2006/0123505 | A1 | 6/2006 | Kikuchi et al. |
| 2006/0150283 | A1 | 7/2006 | Alexandrov et al. |
| 2006/0195944 | A1 | 8/2006 | Heard et al. |
| 2006/0236419 | A1 | 10/2006 | La Rosa et al. |
| 2006/0242738 | A1 | 10/2006 | Sherman et al. |
| 2006/0272060 | A1 | 11/2006 | Heard et al. |
| 2007/0022495 | A1 | 1/2007 | Reuber et al. |
| 2007/0089180 | A1 | 4/2007 | Glazebrook et al. |
| 2007/0186308 | A1 | 8/2007 | Reuber et al. |

FOREIGN PATENT DOCUMENTS

| | | |
|---|---|---|
| EP | 1229780 | 8/2002 |
| EP | 1406483 | 4/2004 |
| EP | 1566444 | 8/2005 |
| EP | 1601758 | 12/2005 |
| WO | WO-97/35965 | 10/1997 |
| WO | WO9735965 | 10/1997 |
| WO | WO-01/35725 | 5/2001 |
| WO | WO0135725 A2 | 5/2001 |
| WO | WO0136444 | 5/2001 |
| WO | 0216655 A1 | 2/2002 |
| WO | WO0215675 | 2/2002 |
| WO | WO02074917 A2 | 9/2002 |
| WO | WO02089555 A2 | 11/2002 |
| WO | WO03000906 A2 | 1/2003 |
| WO | WO-2004/076638 | 9/2004 |
| WO | WO2005001050 A2 | 1/2005 |
| WO | WO2005038034 | 4/2005 |
| WO | WO2005047516 A2 | 5/2005 |
| WO | WO2006069201 | 6/2006 |
| WO | WO2006132616 | 12/2006 |

OTHER PUBLICATIONS

Qiang, L. et al. (Aug. 1998). "Two Transcription Factors, DREB1 and DREB2, with an EREBP/AP2 DNA Binding Domain Separate Two Cellular Signal Transduction Pathways in Drought- and Low-Temperature-Responsive Gene Expression, respectively, in *Arabidopsis*," Plant Cell, American Society of Plant Physiologists, Rockville, MD, US, 10(8):1391-1406.

Fowler, S. et al. (Aug. 2002). "*Arabidopsis* Transcriptome Profiling Indicates that Multiple Regulatory Pathways are Activated during Cold Acclimation in addition to the CBF Cold Response Pathway," Plant Cell 14(8):1675-1690, XP002333729 ISSN:1040-4651.

Hu, Y.X. et al. (Feb. 2004). "*Arabidopsis* RAV1 is Down-Regulated by Brassinosteroid and May Act as a Negative Regulator during Plant Development," Cell Research 14(1):8-15.

Kagaya, Yasuaki et al., (1999) "RAV1, a novel DNA-binding protein, binds to bipartite recognition sequence through two distinct DNA-binding domains uniquely found in higher plants," Nucleic Acids Research, 27(2): 470-478.

Sasaki, T. et al., (Jun. 1, 2001) "Q9AWS7_ORYSA," Uniprot database accession No. Q9AWS7.

U.S. Appl. No. 11/728,567, Ratcliffe, O.R. et al.

U.S. Appl. No. 11/793,466, Libby, J. M. et al. 74PCT/US.

Theologis, A., et al. NP_172784. 2001.

Anderson, O.D., NCBI. acc. BF146073. 2000.

Bohnert, H.J. NCBI. acc. BE034380. 2000.

Carson C.B., et al. The quiescent/colorless alleles of viviparous1 show that the conserved B3 domain of VP1 is not essential for ABA. 1997. Plant J 12, 1231-1240.

Cordonnier-Pratt, M.-M. et al. NCBI acc. BE596262. 2000.

Ezcurra et al. Transactivation of the *Brassica napus* napin promoter by ABI3 requires interaction of the conserved B2 and B3 domains of ABI3 . . . 2000. Plant J 24, 57-66.

Fedorova, M. NCBI acc. BF520598. 2000.

Finklestein, R.R., et al. The *Arabidopsis* abscisic acid response locus ABI4 encodes an APETALA 2 domain protein. 1998. Plant Cell 10, 1043-1054.

Finklestein and Lynch. The *Arabidopsis* abscisic acid response gene ABI5 encodes a basic leucine zipper transcription factor. 2000. Plant Cell 12, 599-609.

Gampala, S.S.L., et al. Functional Genomics of Abscisic Acid-Insensitive-1-, -3- and -5-Like Gene Families. 2004. Intl Conf *Arabidopsis* Res. Berlin Abstract # T04-085.

Giraudat, J., et al. Isolation of the *Arabidopsis* ABI3 gene by positional cloning. 1992. Plant Cell 4, 1251-1261.

Guiltinan, M.J., et al. A plant leucine zipper protein that recognizes an abscisic acid response element. 1990. Science 250, 267-271.

Hahn, M.G. et al. NCBI acc. BG648173. 2001.

Hao, D., et al. Unique mode of GCC box recognition by the DNA-binding domain of ethylene-responsive element-binding factor (ERF domain) i . . . 1998. J Biol Chem 273, 26857-26861.

Hao, D. et al. Determinants in the sequence specific binding of two plant transcription factors, CBF1 and NtERF2, to the DRE and GCC motifs. 2002. Biochemistry 41, 4202-4208.

Harris, L.J. et al. NCBI. acc. BG836160. 2001.

Hattori, T. et al. The Viviparous-1 gene and abscisic acid activate the C1 regulatory gene for anthocyanin biosynthesis during seed maturation . . . 1992. Genes Dev 6, 609-618.

Hobo T et al. ACGT-containing abscisic acid response element (ABRE) and coupling element 3 (CE3) are functionally equivalent. 1999a. Plant J 19, 679-689.

Hobo T et al. A bZIP factor, TRAB1, interacts with VP1 and mediates abscisic acid-induced transcription. 1999b. Proc Natl Acad Sci USA 96, 15348-15353.

Hoecker, U. et al. Integrated control of seed maturation and germination programs by activator and repressor functions of Viviparous-1 of maize. 1995. Genes Dev 9, 2459-2469.

Hu, Y.X. et al. *Arabidopsis* RAV1 is down-regulated by brassinosteroid and may act as a negative regulator during plant development. 2004. Cell Res 14, 8-15.

Jaglo, K.R.,et al. Components of the *Arabidopsis* C-repeat/dehydration-responsive element binding factor cold-response pathway are conserved . . . 2001. Plant Physiol 127, 910-917.

Jaglo-Ottosen, K.R., *Arabidopsis* CBF1 overexpression induces COR genes and enhances freezing tolerance. 1998. Science 280, 104-106.

Jakoby, M., et al. bZIP transcription factors in *Arabidopsis*. 2002. Trends Plant Sci 7.

Jofuku, K.D. et al. Control of *Arabidopsis* flower and seed development by the homeotic gene APETALA2. 1994. Plant Cell 6, 1211-1225.

Kagaya et al. NCBI acc. AB013886. 1998.

Keith, K., et al. fusca3: A Heterochronic Mutation Affecting Late Embryo Development in *Arabidopsis*. 1994. Plant Cell 6, 589-600.

Lefstin, J.A., and Yamamoto, K.R. Allosteric effects of DNA on transcriptional regulators. 1998. Nature 392, 885-888.

Lin, X. et al. NCBI acc. AAG12735. 2000.

Liscum, E., and Reed, J.W. Genetics of Aux/IAA and ARF action in plant growth and development. 2002. Plant Mol Biol 49, 387-400.

Liu, Q. et al. Two transcription factors, DREB1 and DREB2, with an EREBP/AP2 DNA binding domain separate two cellular signal transduction . . . 1998. Plant Cell 10, 1391-1406.

Liu, L., W. et al. Transcription factors and their genes in higher plants functional domains, evolution and regulation. 1999. Eur J Biochem 262, 247-257.

Luerssen, H. et al. FUSCA3 encodes a protein with a conserved VP1/AB13-like B3 domain which is of functional importance for the regulation of seed . . . 1998. Plant J 15, 755-764.

McCarty, D.R., et al. Molecular Analysis of viviparous-1: An Abscisic Acid-Insensitive Mutant of Maize. 1989. Plant Cell 1, 523-532.

McCarty, D.R., et al. The Viviparous-1 developmental gene of maize encodes a novel transcriptional activator. 1991. Cell 66, 895-905.

McCarty, D.R., et al. . 1991. NCBI. acc. AAA33506.

Meinke, D. A homeotic mutant of *Arabidopsis thaliana* with leafy cotyledons. 1992. Science 258, 1647-1650.

Meinke, D. et al. Leafy Cotyledon Mutants of *Arabidopsis*. 1994. Plant Cell 6, 1049-1064.

Nakamura, Y. 2000. NCBI acc. BAA95760.

Nambara E., et al. A regulatory role for the ABI3 gene in the establishment of embryo maturation in *Arabidopsis thaliana*. 1995. Development 121, 629-636.
Newman, T. et al. NCBI acc. N37218. 1996.
(Source Unknown) NCBI acc. No. NM_101197. 2002.
(Source Unknown) NCBI acc. No. NM_103991. 2002.
Ohme-Takagi, M., and Shinshi, H. Ethylene-inducible DNA binding proteins that interact with an ethylene-responsive element. 1995. Plant Cell 7, 173-182.
Ohta, M. et al. Repression domains of class II ERF transcriptional repressors share an essential motif for active repression. 2001. Plant Cell 13, 1959-1968.
Okamura, J.K., et al. The AP2 domain of APETALA2 defines a large new family of DNA binding proteins in *Arabidopsis*. 1997. Proc Natl Acad Sci USA 94, 7076-7081.
Ooms, J. et al. 1993. Acquisition of Desiccation Tolerance and Longevity in Seeds of *Arabidopsis thaliana* (A Comparative Study Using Abscisic . . . Plant Physiol 102, 1185-1191.
Parcy, F. et al. 1997. The ABSCISIC ACID-INSENSITIVE3, FUSCA3, and LEAFY COTYLEDON1 loci act in concert to control multiple aspects of *Arabidopsis* . . . Plant Cell 9, 1265-1277.
Parcy, F. & Girdat, J. Interactions between the ABI1 and the ectopically expressed ABI3 genes in controlling abscisic acid responses in . . . 1992. Plant J 11, 693-702.
Paz-Arez, J. et al. NCBI. acc. DR750701 2005.
Paz-Ares., J. et al. NCBI acc. DR750702. 2005.
Podkowinski, J. NCBI. acc. BG149141. 2001.
Reidt, W. et al. Gene regulation during late embryogenesis: the RY motif of maturation-specific gene promoters is a direct target of the FUS3 . . . 2000. Plant J. 21, 401-408.
Riechmann. J.L. et al. *Arabidopsis* transcription factors: genome-wide comparative analysis among eukaryotes. 2000. Science 290, 2105-2110.
Sakuma, Y. et al. NA-binding specificity of the ERF/AP2 domain of *Arabidopsis* DREBs, transcription factors involved in . . . 2002. Biochem Biophys Res Commun 290, 998-1009.
Sasaki, T. NCBI. acc. AP002913. 2000.
Sasaki, T. NCBI. acc. AP003450. 2001.
Sasaki, T. NCBI. acc. BAB21211. 2001.
Sasaki, T. NCBI. acc. BAB21218. 2001.
Savitch. NCBI acc. CB686050. 2003.
Shoemaker, R. et al. NCBI acc. AW099253. 2004.
Shoemaker, R. et al. NCBI acc. BF424857. 2004.
Sivamani, E. et al. 2000. Improved biomass productivity and water use efficiency under water deficit conditions in transgenic wheat constitutively . . . Plant Science 155, 1-9.
Sohn. Expression and functional roles of the pepper pathogen-induced transcription factor RAV1 in bacterial disease resistance, and drought . . . 2006. Plant Mol Biol 61, 897-915.

Stockinger, E.J. et al. *Arabidopsis thaliana* CBF1 encodes an AP2 domain-containing transcriptional activator that binds to the . . . 1997. Proc Natl Acad Sci USA 94, 1035-1040.
Stone, S.L. LEAFY COTYLEDON2 encodes a B3 domain transcription factor that induces embryo development. 2001. Proc Natl Acad Sci USA 98, 11806-11811.
Suzuki, M. et al. The conserved B3 domain of VIVIPAROUS1 has a cooperative DNA binding activity. 1997. Plant Cell 9, 799-807.
Suzuki, M. et al. Viviparous1 alters global gene expression patterns through regulation of abscisic acid signaling. 2003. Plant Physiol 132, 1664-1677.
Tamminen, I. et al. Ectopic expression of ABI3 gene enhances freezing tolerance in response to abscisic acid and low temperature in *Arabidopsis thaliana*. 2001. Plant J 25, 1-8.
Tiwari, S.B. et al. AUX/IAA proteins are active repressors, and their stability and activity are modulated by auxin. 2001. Plant Cell 13, 2809-2822.
Tiwari, S.B. et al. The roles of auxin response factor domains in auxin-responsive transcription. 2003. Plant Cell 15, 533-543.
Ulmasov, T. Het al. ARF1, a transcription factor that binds to auxin response elements. 1997. Science 276, 1865-1868.
Van Der Hoeven, R. et al. NCBI acc. No. BG124312. 2001.
Weigel, D. et al. The APETALA2 domain is related to a novel type of DNA binding domain. 1995. Plant Cell 7, 388-389.
Weigel, D. et al. Activation tagging in *Arabidopsis*. 2000. Plant Physiol 122, 1003-1013.
Wing, R. et al. NCBI acc No. BG366969. 2001.
Wobus & Weber. Seed maturation: genetic programmes and control signals. 1999. Curr Opin Plant Biol 2, 33-38.
Xu, D. et al. Expression of a late embryogenesis abundant protein gene, HVA1, from barley confers tolerance to water deficit and . . . 1996. Plant Physiol 110, 249-257.
Yamada, K. et al. NCBI acc. No. AAK26022. 2001.
Yamada, K. et al. NCBI acc. No. AAL07247. 2001.
Yamada, K. et al. NCBI acc. No. AAL36211. 2001.
Yamada, K. et al. NCBI acc. No. AAM13889. 2002.
Yamada, K. et al. NCBI acc. No. AAM14230. 2002.
Yamada, K. et al. NCBI acc. No. AAM67474. 2001.
Yamada, K. et al. NCBI acc. No. AF360312.. 2001.
Yamada, K. et al. NCBI acc. No. AY056169. 2001.
Yamasaki, K. Solution structure of the B3 DNA binding domain of the *Arabidopsis* cold-responsive transcription factor RAV1. 2004. Plant Cell 16, 3448-3459.
Zhang, P. et al. NCBI acc. No. BG590382. 2003.
Zhou, J. et al. The tomato gene Pti1 encodes a serine/threonine kinase that is phosphorylated by Pto and is involved in the hypersensitive response. 1995. Cell 83, 925-935.

FIGURE 4A

Sequence alignment (positions 1–50):

```
                    10         20         30         40         50
G3433                                   MDSA    SSL  LVDD T S        GG ACT TDKL
G3390                                   MDSS    TSS  LLVDD A TS       SG ASTTDKK
G3391                                   MDDS    SSC  CLVDD TT         SG GASTT DKK
G3432                                   MDDS    SSA  SLVDD T S        GG ACSTT DKL
G3389                                   MDSQ    EAA  MVVDD TN         G  SSTAT TDDD
G3388                              MEQ  E       G    VFS          S    SSTTTTDS
G867                                    MES    SSST  SDD           E   ESTSTDH
G1930                                   MDAM    AMS  SDD           E   ESSSDH I
G3451                                   MDES    TT   TES           SSE KAKPSDMI
G3452                                                 L SLSPTS      MDGG C VIT I
G3453                                    L SISLS                    MDG   ETT T
G993                               MEYSC    VDDS  TTSE                  KPTT
G9                                 MDSS    CID   STT                  SEFSA
G2690                                             MDMDEMSN           T SNDA
G2687                                             MNNIDDA            APPA H
AP004178           LALAVVHTEMD     EEEEQDEEEEEAAA  TASS SPAH V
AL662987                          MEQEQDEEEEEAA PT  MT  SAA  AAA    S TSVS
G1957         FSMEFTTSSRFSKEEED E A G R R E I P F M T                 SP
G1010                              MEQEQDEEEEEAA P  E I PFMT          MD LSLA
Consensus                                                                  M M
```

| | | 410 | | 420 | | 430 | | 440 | | 450 |
|---|---|---|---|---|---|---|---|---|---|---|
| G3433 | P P A V | K A | L T A A A P E L Q D A G G A A M T K S K R A M D A M A E S Q | A H | V V F K |
| G3390 | S - P V | K A V | R L F G V D L L I A P A P V E Q M A G C K R A R - - D L A A T T P P Q | A Q | A A F K |
| G3391 | | | | | |
| G3432 | | | | | |
| G3389 | - - V V | V K L F G V D I A G D K T R | | | |
| G3388 | G A E P | R V L R L F G V D D N | S P E S - - R | E - - - R N D G Q E V V H Q R T P A L G A | | |
| G867 | L D A G | R V M R L F G V D D N | H I - - L N A | - - M - - R N D T E M L S S L V C S K K |
| G1930 | L E T G | R I Q M V R L F G V D D N | S - - L K L P | G - - - - I V G N N A S G S L R C K K |
| G3451 | V E P I | Q M V R L F G V D D N | L - - K K L L | P - - - - N N N E T T E V L M S L L E C K K |
| G3452 | V E P V | Q M V R L F G V N L L | K L P - - - - | V P G S D G - V G K R K E M E L F A F E C C K |
| G3453 | | | | | |
| G993 | S P V Q | T V V R L F G V N I F | N V S - - - - | - - N E K P N D V A V E C V G G K R S R E D D L F S L G C S K |
| G9 | N P V Q | T V V R L F G V D D I F | N V T - - - - | - - T V K P N D V V A D V C G G K V E E - E T K S E E N K G F M L F G |
| G2690 | G N G F | V V P E E V N K T S M T | V H D S V P T | - - D E E M K K T E T L F T S K V E E - E T K S E E N K G F M L F G |
| G2687 | D N G S | V V A E E V S M T V E Q | S W Q C T T T | R A P D E E M K K T E N L V S S M L E D K E I K S E E N K G F M V R C I |
| AP004178 | R R R R | R R R R Y H L I T N S T L R C C T T T R A P | | | |
| AL662987 | R R R R | R R R H L L T I N S T L R C T T T R A P | | | |
| G1957 | S T A G | K R L R L F G V N M E C C G N - - D Y N Q Q E E E S - - - I A S S P P P W R R V R R C I |
| G1010 | - T A G | K R L R L F G V D M E C G G E S G M I N S T E E E S S G G S L P R G - G G G A S S S S F |
| Consensus | | R L F G V | | | |

FIGURE 4J

PLANT TRANSCRIPTIONAL REGULATORS OF ABIOTIC STRESS

RELATIONSHIP TO COPENDING APPLICATIONS

This application claims the benefit of commonly assigned U.S. provisional application No. 60/565,948, filed Apr. 26, 2004; and is continuation-in-part of the following and commonly assigned applications: U.S. Non-provisional application Ser. No. 10/456,882, filed Jun. 6, 2003, now abandoned which claims priority from U.S. Non-provisional application Ser. No. 09/713,994, filed Nov. 16, 2000, now abandoned, which in turn claims the benefit of U.S. Provisional Application No. 60/166,228, filed Nov. 17, 1999, and U.S. Provisional Application No. 60/227,439, filed Aug. 22, 2000; U.S. non-provisional patent application Ser. No. 10/685,922, filed Oct. 14, 2003, which is a continuation-in-part of U.S. Non-provisional application Ser. No. 09/934,455, filed Aug. 22, 2001, now abandoned, and a continuation-in-part of U.S. Non-provisional application Ser. No. 09/533,029, filed Mar. 22, 2000, now U.S. Pat. No. 6,664,446; U.S. patent application Ser. No. 10/412,699, filed Apr. 10, 2003; U.S. Non-provisional application Ser. No. 10/374,780, filed Feb. 25, 2003; U.S. Non-provisional application Ser. No. 10/225,068, filed Aug. 9, 2002, which claims the benefit of U.S. Provisional Application No. 60/336,049, filed Nov. 19, 2001, U.S. Provisional Patent Application No. 60/310,847, filed Aug. 9, 2001, and is a continuation-in-part of U.S. Non-provisional application Ser. No. 10/171,468, filed Jun. 14, 2002 (now abandoned), and a continuation-in-part of U.S. Non-provisional application Ser. No. 09/837,944, filed Apr. 18, 2001, now abandoned; U.S. Non-provisional application Ser. No. 10/225,066, filed Aug. 9, 2002; U.S. Non-provisional application Ser. No. 10/225,067, filed Aug. 9, 2002; U.S. Non-provisional application Ser. No. 10/278,536, filed Oct. 22, 2002, which is a divisional application of U.S. Non-provisional application Ser. No. 09/532,591, filed Mar. 22, 2000, now abandoned; U.S. Non-provisional application Ser. No. 10/278,173, filed Oct. 21, 2002, which is a divisional application of U.S. Non-provisional application Ser. No. 09/533,392, filed Mar. 22, 2000, now abandoned, which in turn claims the benefit of U.S. Provisional Application No. 60/125,814, filed Mar. 23, 1999; U.S. Non-provisional application Ser. No. 10/295,403, filed Nov. 15, 2002, which is a divisional application of U.S. Non-provisional application Ser. No. 09/394,519, filed Sep. 13, 1999, now abandoned, which in turn claims the benefit of U.S. Provisional Application No. 60/101,349, filed Sep. 22, 1998, and U.S. Provisional Application No. 60/108,734, filed Nov. 17, 1998; the entire contents of these applications are hereby incorporated by reference.

The claimed invention, in the field of functional genomics and the characterization of plant genes for the improvement of plants, was made by or on behalf of Mendel Biotechnology, Inc. and Monsanto Company as a result of activities undertaken within the scope of a joint research agreement, in effect on or before the date the claimed invention was made.

FIELD OF THE INVENTION

The present invention relates to compositions and methods for modifying a plant phenotypically, said plant having altered sugar sensing and an altered response to abiotic stresses, including abiotic stresses such as cold and osmotic stresses.

BACKGROUND OF THE INVENTION

A plant's traits, such as its biochemical, developmental, or phenotypic characteristics, may be controlled through a number of cellular processes. One important way to manipulate that control is through transcription factors, proteins that influence the expression of a particular gene or sets of genes. Transformed and transgenic plants that comprise cells having altered levels of at least one selected transcription factor, for example, possess advantageous or desirable traits. Strategies for manipulating traits by altering a plant cell's transcription factor content can therefore result in plants and crops with new and/or improved commercially valuable properties.

Transcription factors can modulate gene expression, either increasing or decreasing (inducing or repressing) the rate of transcription. This modulation results in differential levels of gene expression at various developmental stages, in different tissues and cell types, and in response to different exogenous (e.g., environmental) and endogenous stimuli throughout the life cycle of the organism.

Phylogenetic relationships among organisms have been demonstrated many times, and studies from a diversity of prokaryotic and eukaryotic organisms suggest a more or less gradual evolution of biochemical and physiological mechanisms and metabolic pathways. Despite different evolutionary pressures, proteins that regulate the cell cycle in yeast, plant, nematode, fly, rat, and man have common chemical or structural features and modulate the same general cellular activity. Comparisons of *Arabidopsis* gene sequences with those from other organisms where the structure and/or function may be known allow researchers to draw analogies and to develop model systems for testing hypotheses. These model systems are of great importance in developing and testing plant varieties with novel traits that may have an impact upon agronomy.

Because transcription factors are key controlling elements of biological pathways, altering the expression levels of one or more transcription factors can change entire biological pathways in an organism. For example, manipulation of the levels of selected transcription factors may result in increased expression of economically useful proteins or biomolecules in plants or improvement in other agriculturally relevant characteristics. Conversely, blocked or reduced expression of a transcription factor may reduce biosynthesis of unwanted compounds or remove an undesirable trait. Therefore, manipulating transcription factor levels in a plant offers tremendous potential in agricultural biotechnology for modifying a plant's traits, including traits that improve a plant's survival and yield during periods of abiotic stress, including germination in cold and hot conditions, and osmotic stress, including drought, salt stress, and other abiotic stresses, as noted below.

Problems associated with drought. A drought is a period of abnormally dry weather that persists long enough to produce a serious hydrologic imbalance (for example crop damage, water supply shortage, etc.). While much of the weather that we experience is brief and short-lived, drought is a more gradual phenomenon, slowly taking hold of an area and tightening its grip with time. In severe cases, drought can last for many years and can have devastating effects on agriculture and water supplies. With burgeoning population and chronic shortage of available fresh water, drought is not only the number one weather related problem in agriculture, it also ranks as one of the major natural disasters of all time, causing not only economic damage, but also loss of human lives. For example, losses from the US drought of 1988 exceeded $40 billion, exceeding the losses caused by Hurricane Andrew in 1992, the Mississippi River floods of 1993, and the San Francisco earthquake in 1989. In some areas of the world, the effects of drought can be far more severe. In the Horn of Africa the 1984-1985 drought led to a famine that killed 750,000 people.

Problems for plants caused by low water availability include mechanical stresses caused by the withdrawal of cellular water. Drought also causes plants to become more susceptible to various diseases (Simpson (1981). "The Value of Physiological Knowledge of Water Stress in Plants", In *Water Stress on Plants*, (Simpson, G. M., ed.), Praeger, N.Y., pp. 235-265).

In addition to the many land regions of the world that are too arid for most if not all crop plants, overuse and over-utilization of available water is resulting in an increasing loss of agriculturally-usable land, a process which, in the extreme, results in desertification. The problem is further compounded by increasing salt accumulation in soils, as described above, which adds to the loss of available water in soils.

Problems associated with high salt levels. One in five hectares of irrigated land is damaged by salt, an important historical factor in the decline of ancient agrarian societies. This condition is only expected to worsen, further reducing the availability of arable land and crop production, since none of the top five food crops—wheat, corn, rice, potatoes, and soybean—can tolerate excessive salt.

Detrimental effects of salt on plants are a consequence of both water deficit resulting in osmotic stress (similar to drought stress) and the effects of excess sodium ions on critical biochemical processes. As with freezing and drought, high saline causes water deficit; the presence of high salt makes it difficult for plant roots to extract water from their environment (Buchanan et al. (2000) in *Biochemistry and Molecular Biology of Plants*, American Society of Plant Physiologists, Rockville, Md.). Soil salinity is thus one of the more important variables that determines where a plant may thrive. In many parts of the world, sizable land areas are uncultivable due to naturally high soil salinity. To compound the problem, salination of soils that are used for agricultural production is a significant and increasing problem in regions that rely heavily on agriculture. The latter is compounded by over-utilization, over-fertilization and water shortage, typically caused by climatic change and the demands of increasing population. Salt tolerance is of particular importance early in a plant's lifecycle, since evaporation from the soil surface causes upward water movement, and salt accumulates in the upper soil layer where the seeds are placed. Thus, germination normally takes place at a salt concentration much higher than the mean salt level in the whole soil profile.

Problems associated with excessive heat. Germination of many crops is very sensitive to temperature. A transcription factor that would enhance germination in hot conditions would be useful for crops that are planted late in the season or in hot climates. Seedlings and mature plants that are exposed to excess heat may experience heat shock, which may arise in various organs, including leaves and particularly fruit, when transpiration is insufficient to overcome heat stress. Heat also damages cellular structures, including organelles and cytoskeleton, and impairs membrane function (Buchanan et al. (2000) in *Biochemistry and Molecular Biology of Plants*, American Society of Plant Physiologists, Rockville, Md.).

Heat shock may produce a decrease in overall protein synthesis, accompanied by expression of heat shock proteins. Heat shock proteins function as chaperones and are involved in refolding proteins denatured by heat.

Heat stress often accompanies conditions of low water availability. Heat itself is seen as an interacting stress and adds to the detrimental effects caused by water deficit conditions. Evaporative demand exhibits near exponential increases with increases in daytime temperatures and can result in high transpiration rates and low plant water potentials (Hall et al. (2000) *Plant Physiol.* 123: 1449-1458). High-temperature damage to pollen almost always occurs in conjunction with drought stress, and rarely occurs under well-watered conditions. Thus, separating the effects of heat and drought stress on pollination is difficult. Combined stress can alter plant metabolism in novel ways; therefore understanding the interaction between different stresses may be important for the development of strategies to enhance stress tolerance by genetic manipulation.

Problems associated with excessive chilling conditions. The term "chilling sensitivity" has been used to describe many types of physiological damage produced at low, but above freezing, temperatures. Most crops of tropical origins, such as soybean, rice, maize, and cotton are easily damaged by chilling. Typical chilling damage includes wilting, necrosis, chlorosis or leakage of ions from cell membranes. The underlying mechanisms of chilling sensitivity are not completely understood yet, but probably involve the level of membrane saturation and other physiological deficiencies. For example, photoinhibition of photosynthesis (disruption of photosynthesis due to high light intensities) often occurs under clear atmospheric conditions subsequent to cold late summer/autumn nights. For example, chilling may lead to yield losses and lower product quality through the delayed ripening of maize. Another consequence of poor growth is the rather poor ground cover of maize fields in spring, often resulting in soil erosion, increased occurrence of weeds, and reduced uptake of nutrients. A retarded uptake of mineral nitrogen could also lead to increased losses of nitrate into the ground water. By some estimates, chilling accounts for monetary losses in the United States (US) behind only to drought and flooding.

Desirability of altered sugar sensing. Sugars are key regulatory molecules that affect diverse processes in higher plants including germination, growth, flowering, senescence, sugar metabolism and photosynthesis. Sucrose, for example, is the major transport form of photosynthate and its flux through cells has been shown to affect gene expression and alter storage compound accumulation in seeds (source-sink relationships). Glucose-specific hexose-sensing has also been described in plants and is implicated in cell division and repression of "famine" genes (photosynthetic or glyoxylate cycles).

Water deficit is a common component of many plant stresses. Water deficit occurs in plant cells when the whole plant transpiration rate exceeds the water uptake. In addition to drought, other stresses, such as salinity and low temperature, produce cellular dehydration (McCue and Hanson (1990) *Trends Biotechnol.* 8: 358-362

Salt and drought stress signal transduction consist of ionic and osmotic homeostasis signaling pathways. The ionic aspect of salt stress is signaled via the SOS pathway where a calcium-responsive SOS3-SOS2 protein kinase complex controls the expression and activity of ion transporters such as SOS1. The pathway regulating ion homeostasis in response to salt stress has been reviewed recently by Xiong and Zhu (2002) *Plant Cell Environ.* 25: 131-139.

The osmotic component of salt stress involves complex plant reactions that overlap with drought and/or cold stress responses.

Common aspects of drought, cold and salt stress response have been reviewed recently by Xiong and Zhu (2002) supra).

Those include:
(a) transient changes in the cytoplasmic calcium levels very early in the signaling event (Knight, (2000) *Int. Rev. Cytol.* 195: 269-324; Sanders et al. (1999) *Plant Cell* 11: 691-706);
(b) signal transduction via mitogen-activated and/or calcium dependent protein kinases (CDPKs; see Xiong et al., 2002) and protein phosphatases (Merlot et al. (2001) *Plant J.* 25: 295-303; Tähtiharju and Palva (2001) *Plant J.* 26: 461-470);
(c) increases in abscisic acid levels in response to stress triggering a subset of responses (Xiong et al. (2002) supra, and references therein);
(d) inositol phosphates as signal molecules (at least for a subset of the stress responsive transcriptional changes (Xiong et al. (2001) *Genes Dev.* 15: 1971-1984);
(e) activation of phospholipases which in turn generate a diverse array of second messenger molecules, some of which might regulate the activity of stress responsive kinases (phospholipase D functions in an ABA independent pathway, Frank et al. (2000) *Plant Cell* 12: 111-124);
(f) induction of late embryogenesis abundant (LEA) type genes including the CRT/DRE responsive COR/RD genes (Xiong and Zhu (2002) supra);
(g) increased levels of antioxidants and compatible osmolytes such as proline and soluble sugars (Hasegawa et al. (2000) *Annu. Rev. Plant Mol. Plant Physiol.* 51: 463-499); and
(h) accumulation of reactive oxygen species such as superoxide, hydrogen peroxide, and hydroxyl radicals (Hasegawa et al. (2000) supra).

Abscisic acid biosynthesis is regulated by osmotic stress at multiple steps. Both ABA-dependent and -independent osmotic stress signaling first modify constitutively expressed transcription factors, leading to the expression of early response transcriptional activators, which then activate downstream stress tolerance effector genes.

Based on the commonality of many aspects of cold, drought and salt stress responses, it can be concluded that genes that increase tolerance to cold or salt stress can also improve drought stress protection. In fact this has already been demonstrated for transcription factors (in the case of AtCBF/DREB1) and for other genes such as OsCDPK7 (Saijo et al. (2000) *Plant J.* 23: 319-327), or AVP1 (a vacuolar pyrophosphatase-proton-pump, Gaxiola et al. (2001) *Proc. Natl. Acad. Sci.* USA 98: 11444-11449).

The present invention relates to methods and compositions for producing transgenic plants with modified traits, particularly traits that address agricultural and food needs. These traits, including altered sugar sensing and tolerance to abiotic and osmotic stress (e.g., tolerance to cold, high salt concentrations and drought), may provide significant value in that they allow the plant to thrive in hostile environments, where, for example, high or low temperature, low water availability or high salinity may limit or prevent growth of non-transgenic plants.

We have identified polynucleotides encoding transcription factors, including *Arabidopsis* sequences G867, G9, G993, G1930, rice sequences G3389, G3390, and G3391, and soy sequences G3451, G3452, G3455, their equivalogs found in other species and listed in the Sequence Listing, and structurally and functionally similar sequences (including variants), developed numerous transgenic plants using these polynucleotides, and have analyzed the plants for their tolerance to abiotic stresses, including those associated with drought, excessive salt, cold and heat. In so doing, we have identified important polynucleotide and polypeptide sequences for producing commercially valuable plants and crops as well as the methods for making them and using them. Other aspects and embodiments of the invention are described below and can be derived from the teachings of this disclosure as a whole. We have identified polynucleotides encoding transcription factors, promoter-gene combinations that alleviate the growth penalty that is sometimes associated with transcription factor overexpression, developed numerous transgenic plants using these polynucleotides, and have analyzed the plants for their tolerance to abiotic stresses, including those associated with cold or osmotic stresses such as drought and salt tolerance. In so doing, we have identified important promoter gene combinations and polynucleotide and polypeptide sequences for producing commercially valuable plants and crops as well as the methods for making them and using them. Other aspects and embodiments of the invention are described below and can be derived from the teachings of this disclosure as a whole.

SUMMARY OF THE INVENTION

The invention pertains to a method for increasing a plant's tolerance to abiotic stress. This is accomplished by providing a vector, plasmid or other nucleic acid construct that contains a transcription factor polynucleotide and regulatory elements for transcriptional regulation of the polynucleotide. The polynucleotide is a sequence that encodes a member of the G867 clade of transcription factor polypeptides, which are derived from a common polypeptide ancestor (FIG. 3), and which contain three subsequences the presence of which identifies the clade members. The G867 clade member sequences that have been successfully used to confer increased tolerance to abiotic stress derive from a number of diverse species, including dicots such as *Arabidopsis* and soy, and monocots including rice. The subsequences found within the clade member polypeptides are, in order from N-terminal to C-terminal, an AP2 domain, a DML motif, and a B3 domain, each of which are further characterized in the specification below. As noted, the vector, plasmid or nucleic acid construct also contains a regulatory element. This may be an inducible or tissue specific promoter that controls expression of the polynucleotide sequence. The vector, plasmid or nucleic acid construct is then introduced into a target plant, thus transforming the plant into one that has increased tolerance to abiotic stress relative to other members of the same species not transformed in this or by any other means. Inducible promoters may include, for example, the DREB2A and RD29A promoters. The RD29A promoter has been used to regulate expression of the G867 polynucleotide and confer increased abiotic stress tolerance. Examples of tissue specific promoters that may be used in this fashion include the ARSK1 (root specific) promoter, the RBSC3 (leaf specific) promoter, and the SUC2 (vascular specific) promoter. The SUC2 promoter is one such promoter that has been shown to regulate expression of G867 and confer increased abiotic stress tolerance.

The method also pertains to increasing a plant's tolerance to abiotic stress with a multiple vector approach. In this case, a first vector that comprises a promoter cloned in front of a LexA DNA binding domain fused to a GAL4 activation domain is introduced into the plant. A second vector is then introduced into the same plant; this second vector comprises a polynucleotide sequence encoding a G867 polypeptide clade member. The plant is then allowed to overexpress the G867 member polypeptide, which increases the plant's tolerance to abiotic stress. The promoter cloned in front of a LexA DNA binding domain may be, for example, the RD29A promoter, although other promoters that function in a similar capacity and which may be expressed in an inducible or tissue-specific manner are readily envisioned and also encompassed by the present invention.

The methods encompassed by the invention may also be extended to propagation techniques used to generate plants. For example, a target plant that has been transformed with a polynucleotide encoding a G867 polypeptide clade member and which has increased abiotic stress tolerance (relative to a wild-type or non-transformed control) may be "selfed" (i.e., self-pollinated) or crossed with another plant to produce seed. Progeny plants may be grown from this seed, thus generating transformed progeny plants with increased tolerance to abiotic stress, as compared to non-transformed plants of the same species that do not overexpress the member of the G867 polypeptide clade member.

Transgenic plants and seed from these plants produced by the methods of the invention are also encompassed by the invention.

BRIEF DESCRIPTION OF THE SEQUENCE LISTING AND FIGURES

The Sequence Listing provides exemplary polynucleotide and polypeptide sequences of the invention. The traits associated with the use of the sequences are included in the Examples.

CD Copy 1, CD Copy 2 and CD Copy 3 are read-only memory computer-readable compact discs and each disc contains a copy of the Sequence Listing in ASCII text format. The Sequence Listing is named "MBI0069CIP.ST25.txt", the Sequence Listing was created on May 4, 2004, and the Sequence Listing is 145 kilobytes in size. The copies of the Sequence Listing on the CD-ROM discs CD Copy 1, CD Copy 2 and CD Copy 3 are hereby incorporated by reference in their entirety.

FIG. 1 shows a conservative estimate of phylogenetic relationships among the orders of flowering plants (modified from Angiosperm Phylogeny Group (1998) *Ann. Missouri Bot. Gard.* 84: 1-49). Those plants with a single cotyledon (monocots) are a monophyletic clade nested within at least two major lineages of dicots; the eudicots are further divided into rosids and asterids. *Arabidopsis* is a rosid eudicot classified within the order Brassicales; rice is a member of the monocot order Poales. FIG. 1 was adapted from Daly et al. (2001) *Plant Physiol.* 127: 1328-1333.

FIG. 2 shows a phylogenic dendogram depicting phylogenetic relationships of higher plant taxa, including clades containing tomato and *Arabidopsis*; adapted from Ku et al. (2000) *Proc. Natl. Acad. Sci.* 97: 9121-9126; and Chase et al. (1993) *Ann. Missouri Bot. Gard.* 80: 528-580.

Figure 4C:
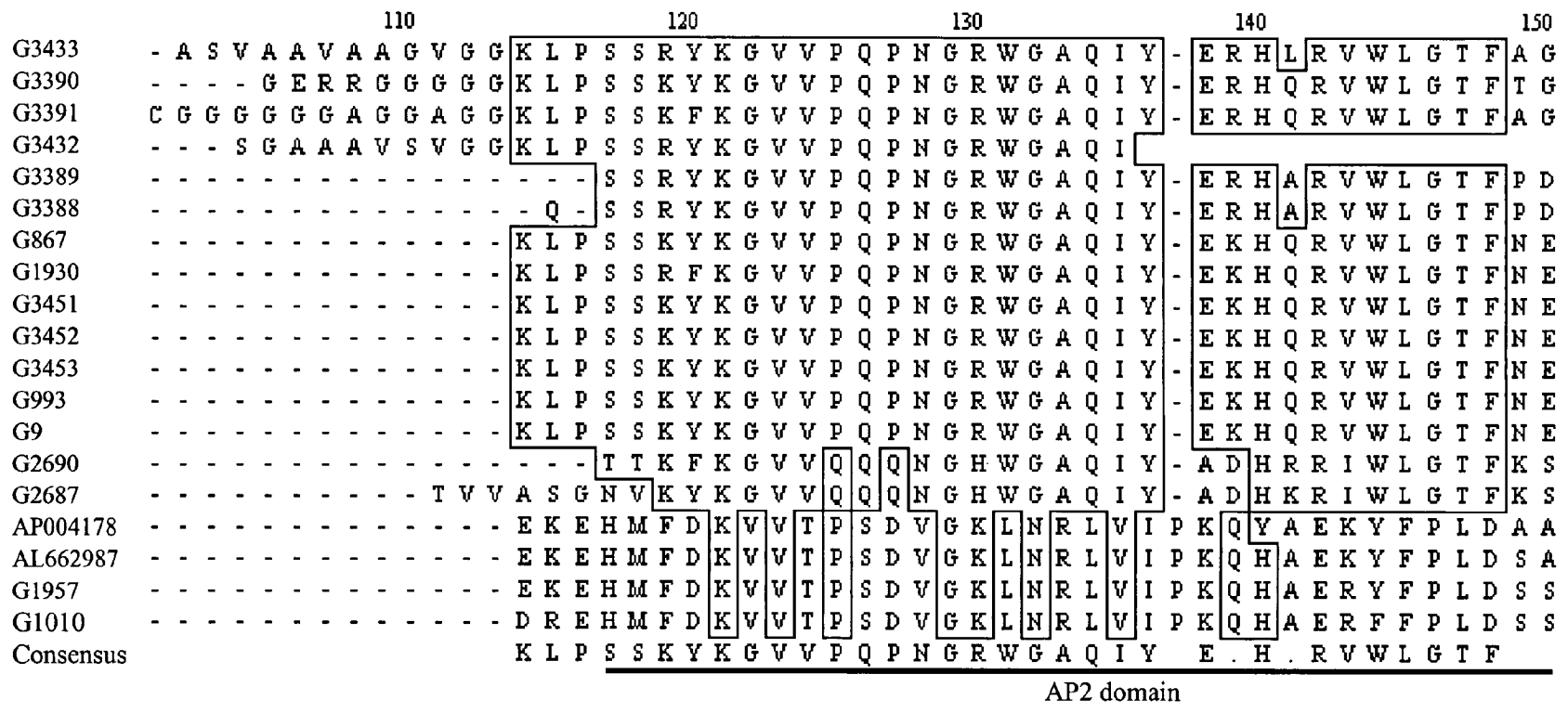
Figure 4E:
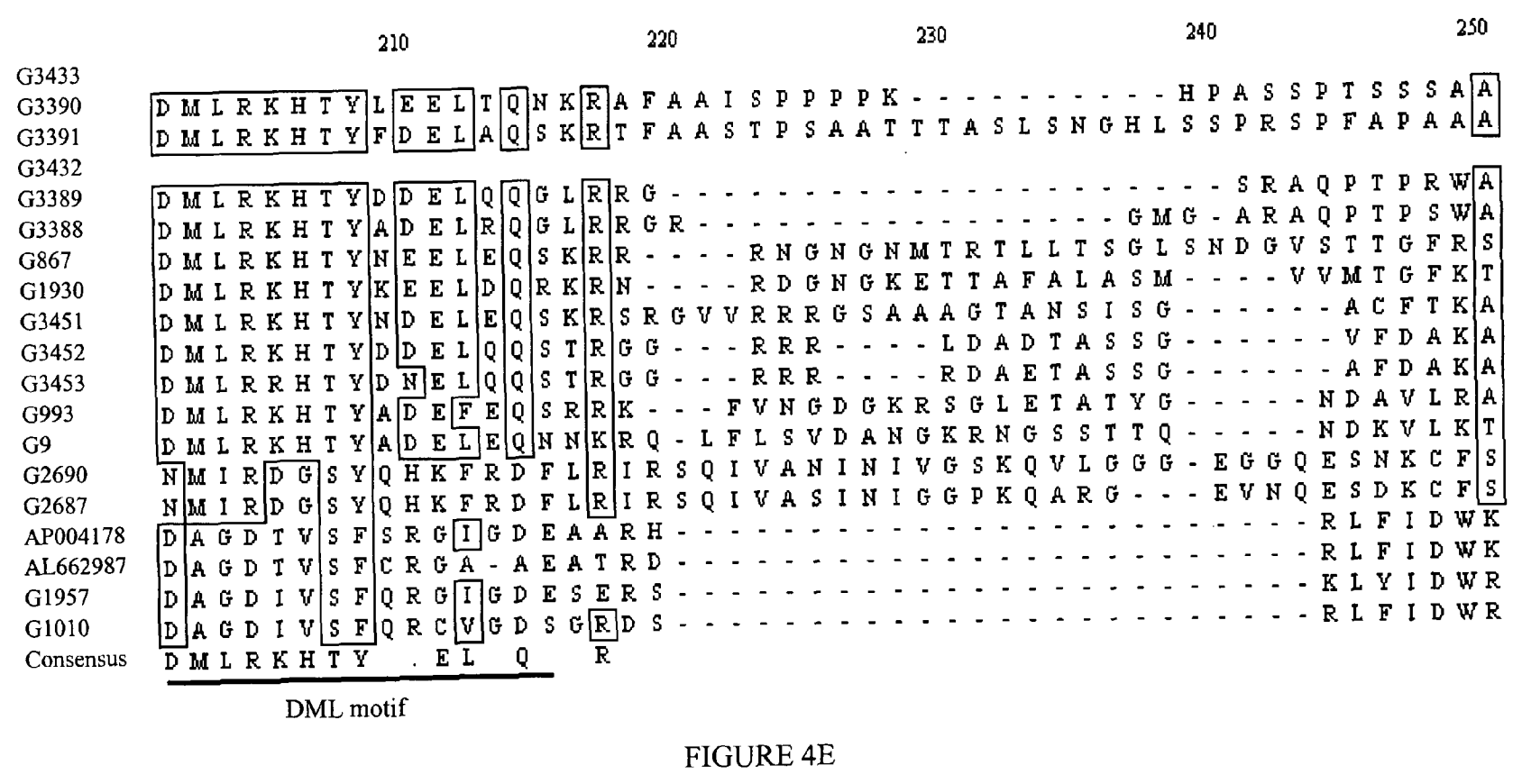
Figure 4F:
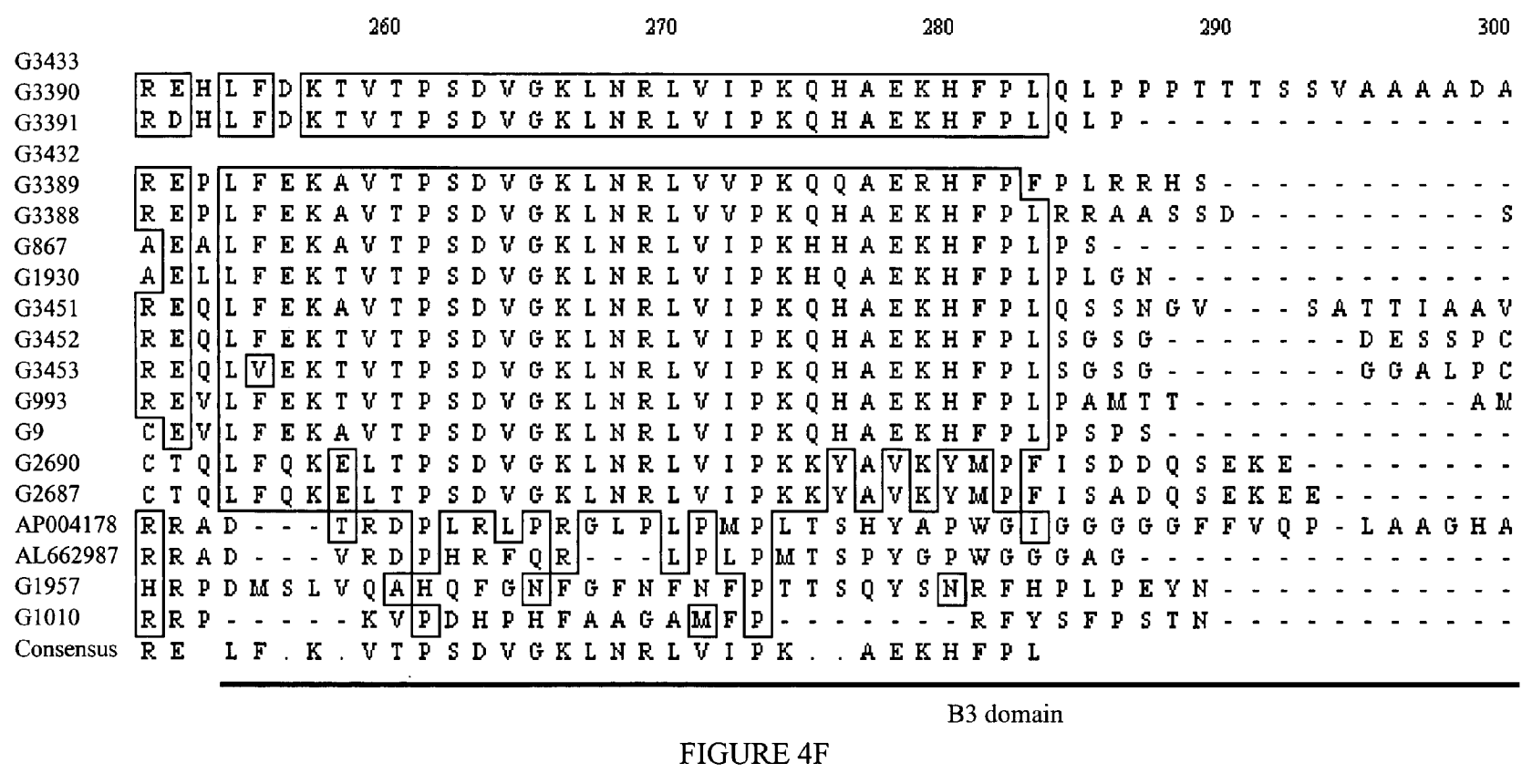
Figure 4G:
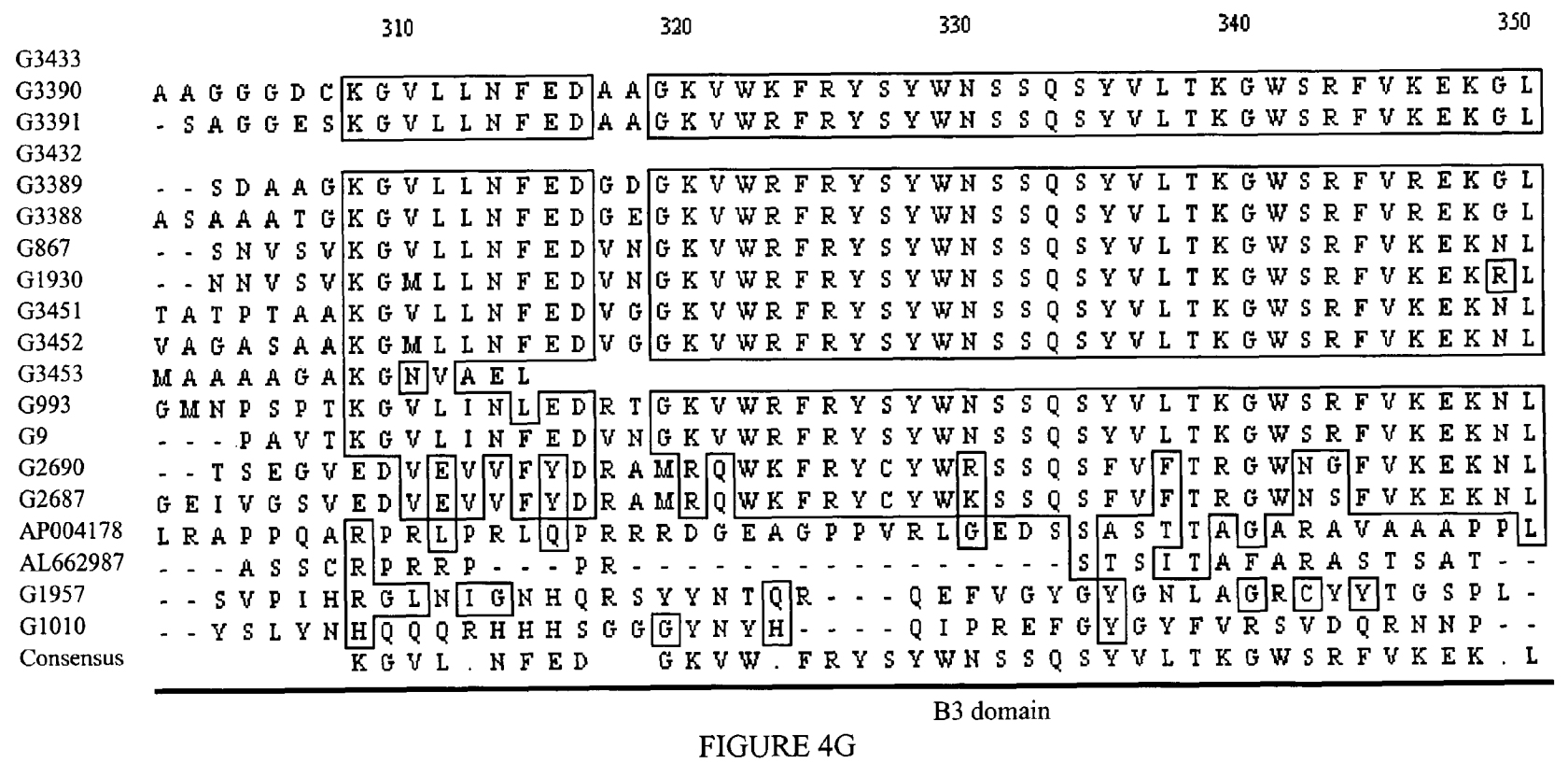
Figure 4H:
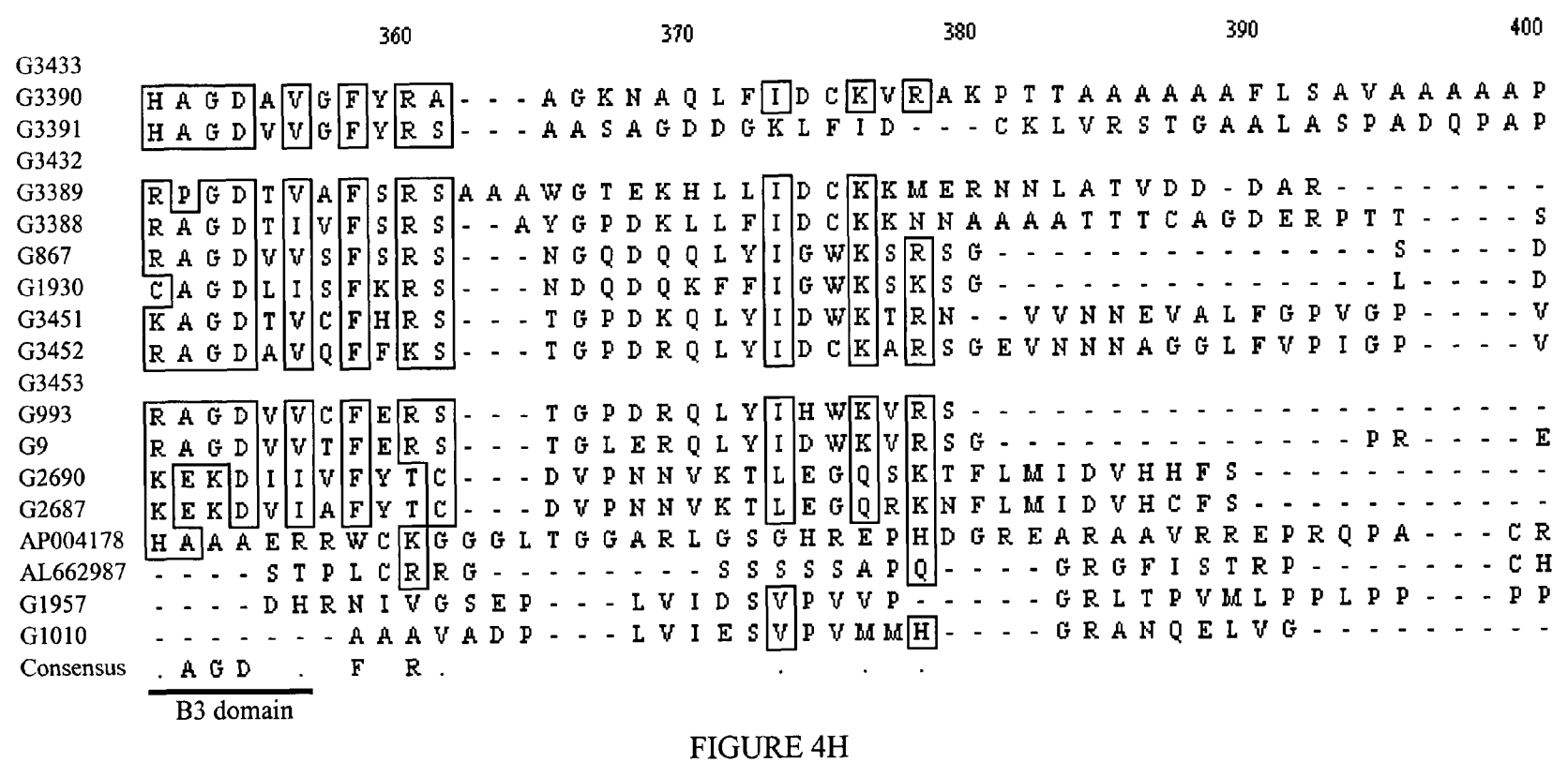
Figure 4J:
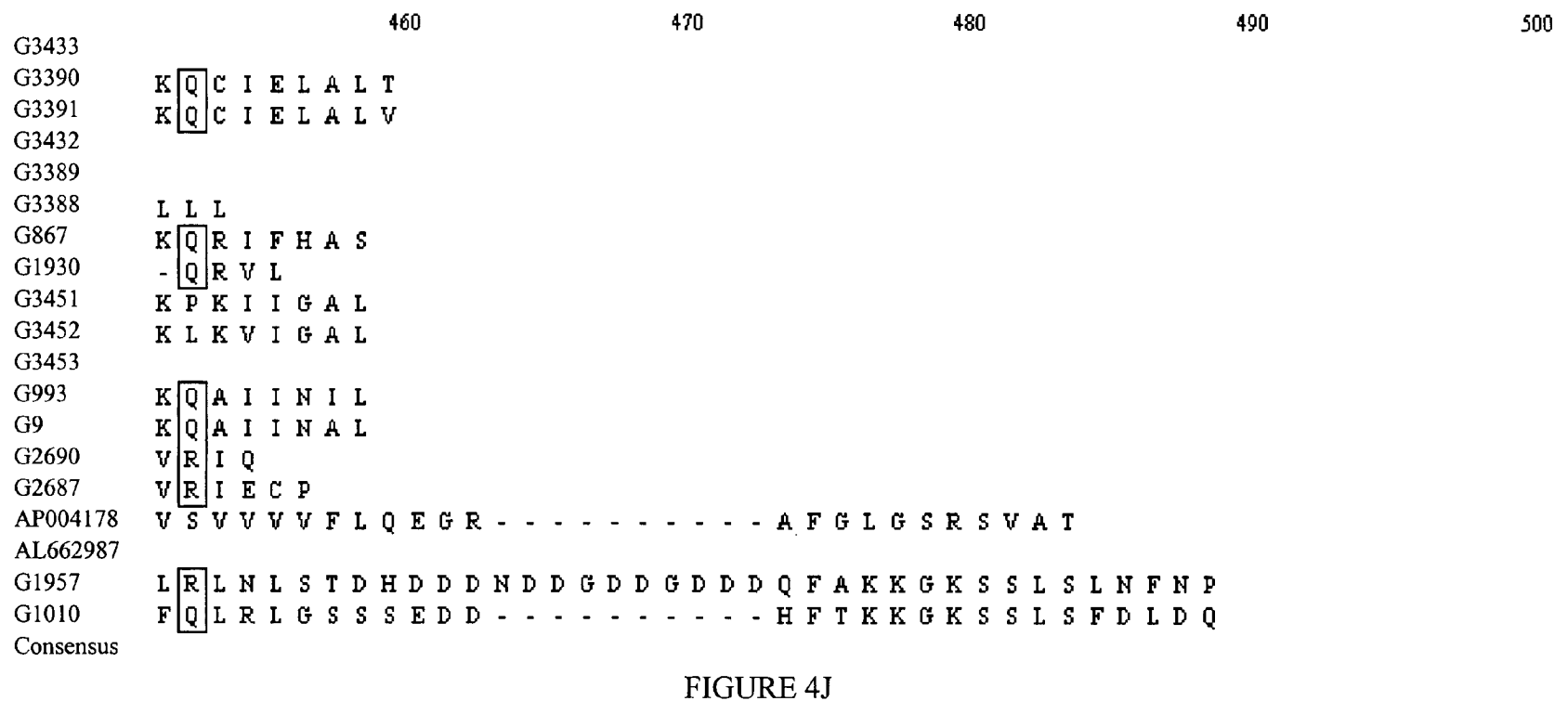

FIGS. 4A-4J show an alignment of AP2 transcription factors from *Arabidopsis*, soybean, rice and corn, showing conserved (identical or similar residues) and the AP2 domains, DML motifs, and B3 domains (SEQ ID NOS:40, 34, 36, 38, 32, 30, 2, 8, 18, 22, 24, 3 and 4).

DESCRIPTION OF THE INVENTION

Figure 1:
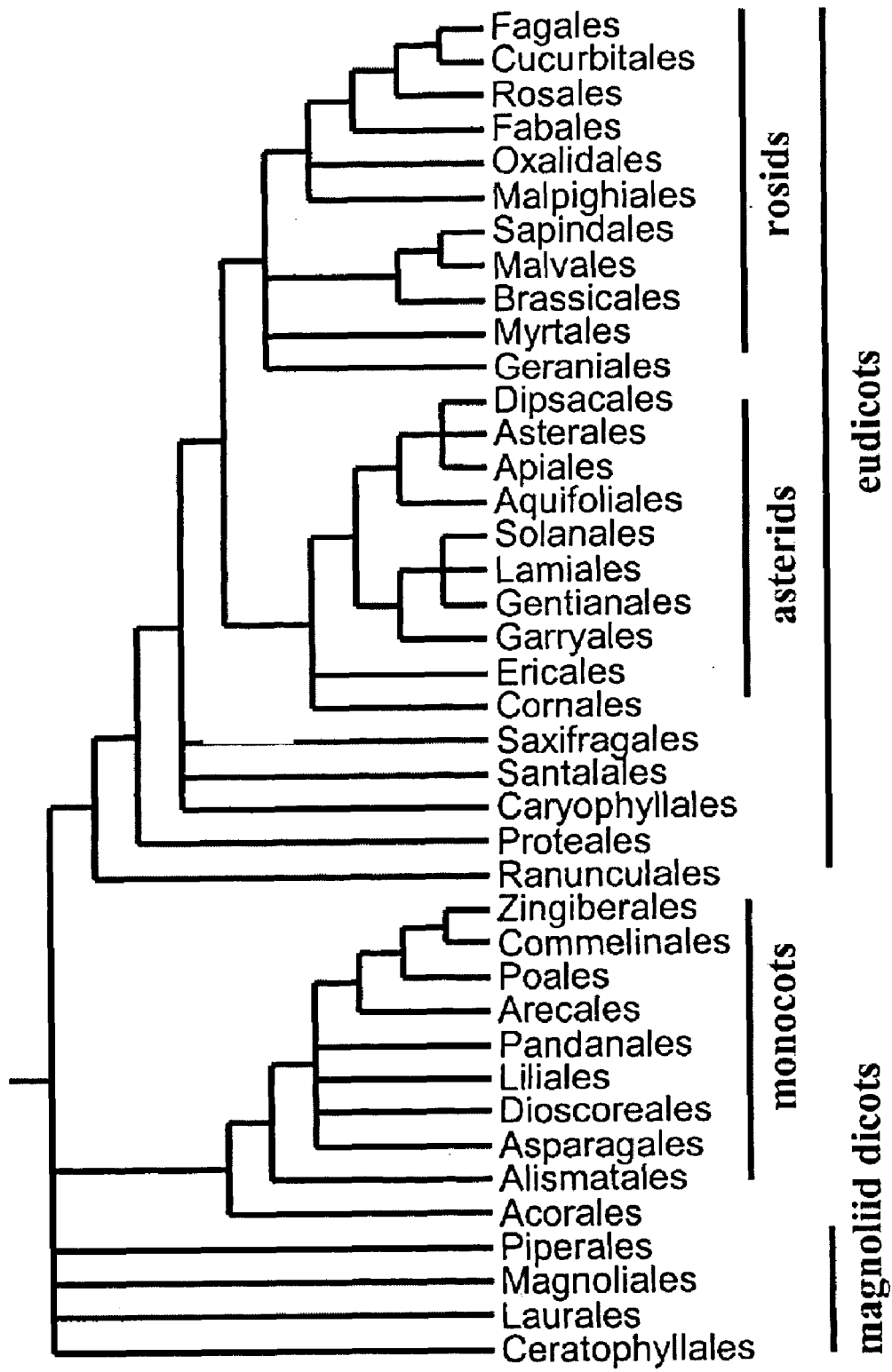

In an important aspect, the present invention relates to polynucleotides and polypeptides, for example, for modifying phenotypes of plants, particularly those associated with osmotic stress tolerance. Throughout this disclosure, various information sources are referred to and/or are specifically incorporated. The information sources include scientific journal articles, patent documents, textbooks, and World Wide Web browser-inactive page addresses, for example. While the reference to these information sources clearly indicates that they can be used by one of skill in the art, each and every one of the information sources cited herein are specifically incorporated in their entirety, whether or not a specific mention of "incorporation by reference" is noted. The contents and teachings of each and every one of the information sources can be relied on and used to make and use embodiments of the invention.

As used herein and in the appended claims, the singular forms "a," "an," and "the" include plural reference unless the context clearly dictates otherwise. Thus, for example, a reference to "a plant" includes a plurality of such plants, and a reference to "a stress" is a reference to one or more stresses and equivalents thereof known to those skilled in the art, and so forth.

DEFINITIONS

"Nucleic acid molecule" refers to a oligonucleotide, polynucleotide or any fragment thereof. It may be DNA or RNA of genomic or synthetic origin, double-stranded or single-stranded, and combined with carbohydrate, lipids, protein, or other materials to perform a particular activity such as transformation or form a useful composition such as a peptide nucleic acid (PNA).

"Polynucleotide" is a nucleic acid molecule comprising a plurality of polymerized nucleotides, e.g., at least about 15 consecutive polymerized nucleotides, optionally at least about 30 consecutive nucleotides, at least about 50 consecutive nucleotides. A polynucleotide may be a nucleic acid, oligonucleotide, nucleotide, or any fragment thereof. In many instances, a polynucleotide comprises a nucleotide sequence encoding a polypeptide (or protein) or a domain or fragment thereof. Additionally, the polynucleotide may comprise a promoter, an intron, an enhancer region, a polyadenylation site, a translation initiation site, 5' or 3' untranslated regions, a reporter gene, a selectable marker, or the like. The polynucleotide can be single stranded or double stranded DNA or RNA. The polynucleotide optionally comprises modified bases or a modified backbone. The polynucleotide can be, e.g., genomic DNA or RNA, a transcript (such as an mRNA), a cDNA, a PCR product, a cloned DNA, a synthetic DNA or RNA, or the like. The polynucleotide can be combined with carbohydrate, lipids, protein, or other materials to perform a particular activity such as transformation or form a useful composition such as a peptide nucleic acid (PNA). The polynucleotide can comprise a sequence in either sense or antisense orientations. "Oligonucleotide" is substantially equivalent to the terms amplimer, primer, oligomer, element, target, and probe and is preferably single stranded.

"Gene" or "gene sequence" refers to the partial or complete coding sequence of a gene, its complement, and its 5' or 3' untranslated regions. A gene is also a functional unit of inheritance, and in physical terms is a particular segment or sequence of nucleotides along a molecule of DNA (or RNA, in the case of RNA viruses) involved in producing a polypeptide chain. The latter may be subjected to subsequent processing such as splicing and folding to obtain a functional protein or polypeptide. A gene may be isolated, partially isolated, or be found with an organism's genome. By way of example, a transcription factor gene encodes a transcription factor polypeptide, which may be functional or require processing to function as an initiator of transcription.

Operationally, genes may be defined by the cis-trans test, a genetic test that determines whether two mutations occur in the same gene and which may be used to determine the limits of the genetically active unit (Rieger et al. (1976) *Glossary of Genetics and Cytogenetics: Classical and Molecular*, 4th ed., Springer Verlag. Berlin). A gene generally includes regions preceding ("leaders"; upstream) and following ("trailers"; downstream) the coding region. A gene may also include intervening, non-coding sequences, referred to as "introns", located between individual coding segments, referred to as "exons". Most genes have an associated promoter region, a regulatory sequence 5' of the transcription initiation codon (there are some genes that do not have an identifiable promoter). The function of a gene may also be regulated by enhancers, operators, and other regulatory elements.

A "recombinant polynucleotide" is a polynucleotide that is not in its native state, e.g., the polynucleotide comprises a nucleotide sequence not found in nature, or the polynucleotide is in a context other than that in which it is naturally found, e.g., separated from nucleotide sequences with which it typically is in proximity in nature, or adjacent (or contiguous with) nucleotide sequences with which it typically is not in proximity. For example, the sequence at issue can be cloned into a vector, or otherwise recombined with one or more additional nucleic acid.

An "isolated polynucleotide" is a polynucleotide whether naturally occurring or recombinant, that is present outside the cell in which it is typically found in nature, whether purified or not. Optionally, an isolated polynucleotide is subject to one or more enrichment or purification procedures, e.g., cell lysis, extraction, centrifugation, precipitation, or the like.

"Fragment", with respect to a polynucleotide, refers to a clone or any part of a polynucleotide molecule that retains a usable, functional characteristic. Useful fragments include oligonucleotides and polynucleotides that may be used in hybridization or amplification technologies or in the regulation of replication, transcription or translation. A "polynucleotide fragment" refers to any subsequence of a polynucleotide, typically, of at least about 9 consecutive nucleotides, preferably at least about 30 nucleotides, more preferably at least about 50 nucleotides, of any of the sequences provided herein. Exemplary polynucleotide fragments are the first sixty consecutive nucleotides of the transcription factor polynucleotides listed in the Sequence Listing. Exemplary fragments also include fragments that comprise a region that encodes an AP2 domain of a transcription factor.

Fragments may also include subsequences of polypeptides and protein molecules, or a subsequence of the polypeptide. Fragments may have uses in that they may have antigenic potential. In some cases, the fragment or domain is a subsequence of the polypeptide which performs at least one biological function of the intact polypeptide in substantially the same manner, or to a similar extent, as does the intact polypeptide. For example, a polypeptide fragment can comprise a recognizable structural motif or functional domain such as a DNA-binding site or domain that binds to a DNA promoter region, an activation domain, or a domain for protein-protein interactions, and may initiate transcription. Fragments can vary in size from as few as 3 amino acid residues to the full length of the intact polypeptide, but are preferably at least about 30 amino acid residues in length and more preferably at least about 60 amino acid residues in length. Exemplary polypeptide fragments are the first twenty consecutive amino acids of a mammalian protein encoded by are the first twenty consecutive amino acids of the transcription factor polypeptides listed in the Sequence Listing. Exemplary fragments also include fragments that comprise an AP2 binding or a B3 domain of a transcription factor, for example, amino acid residues 59-124 or amino acid residues 187-272 of G867 (SEQ ID NO: 2), as noted in Table 1.

The invention also encompasses production of DNA sequences that encode transcription factors and transcription factor derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding transcription factors or any fragment thereof.

A "polypeptide" is an amino acid sequence comprising a plurality of consecutive polymerized amino acid residues e.g., at least about 15 consecutive polymerized amino acid residues, optionally at least about 30 consecutive polymerized amino acid residues, at least about 50 consecutive polymerized amino acid residues. In many instances, a polypeptide comprises a polymerized amino acid residue sequence that is a transcription factor or a domain or portion or fragment thereof. Additionally, the polypeptide may comprise 1) a localization domain, 2) an activation domain, 3) a repression domain, 4) an oligomerization domain, or 5) a DNA-binding domain, or the like. The polypeptide optionally comprises modified amino acid residues, naturally occurring amino acid residues not encoded by a codon, non-naturally occurring amino acid residues.

"Protein" refers to an amino acid sequence, oligopeptide, peptide, polypeptide or portions thereof whether naturally occurring or synthetic.

With respect to a polypeptide, "portion", as used herein refers to any part of a polypeptide used for any purpose, including the screening of a library of molecules which specifically bind to that portion or for the production of antibodies.

A "recombinant polypeptide" is a polypeptide produced by translation of a recombinant polynucleotide. A "synthetic polypeptide" is a polypeptide created by consecutive polymerization of isolated amino acid residues using methods well known in the art. An "isolated polypeptide," whether a naturally occurring or a recombinant polypeptide, is more enriched in (or out of) a cell than the polypeptide in its natural state in a wild-type cell, e.g., more than about 5% enriched, more than about 10% enriched, or more than about 20%, or more than about 50%, or more, enriched, i.e., alternatively denoted: 105%, 110%, 120%, 150% or more, enriched relative to wild type standardized at 100%. Such an enrichment is not the result of a natural response of a wild-type plant. Alternatively, or additionally, the isolated polypeptide is separated from other cellular components with which it is typically associated, e.g., by any of the various protein purification methods herein.

"Homology" refers to sequence similarity between a reference sequence and at least a fragment of a newly sequenced clone insert or its encoded amino acid sequence.

"Identity" or "similarity" refers to sequence similarity between two polynucleotide sequences or between two polypeptide sequences, with identity being a more strict comparison. The phrases "percent identity" and "% identity" refer to the percentage of sequence similarity found in a comparison of two or more polynucleotide sequences or two or more polypeptide sequences. "Sequence similarity" refers to the percent similarity in base pair sequence (as determined by any suitable method) between two or more polynucleotide sequences. Two or more sequences can be anywhere from 0-100% similar, or any integer value therebetween. Identity or similarity can be determined by comparing a position in each sequence that may be aligned for purposes of comparison. When a position in the compared sequence is occupied by the same nucleotide base or amino acid, then the molecules are identical at that position. A degree of similarity or identity between polynucleotide sequences is a function of the number of identical or matching nucleotides at positions shared by the polynucleotide sequences. A degree of identity of polypeptide sequences is a function of the number of identical amino acids at positions shared by the polypeptide sequences. A degree of homology or similarity of polypeptide sequences is a function of the number of amino acids at positions shared by the polypeptide sequences.

With regard to polypeptides, the terms "substantial identity" or "substantially identical" may refer to sequences of sufficient similarity and structure to the transcription factors in the Sequence Listing to produce similar function when expressed or overexpressed in a plant; in the present invention, this function is increased tolerance to abiotic stress. Sequences that are at least about 80% identical, to the instant polypeptide sequences, including AP2 and B3 domain sequences, are considered to have "substantial identity" with the latter. Sequences having lesser degrees of identity but comparable biological activity are considered to be equivalents. The structure required to maintain proper functionality is related to the tertiary structure of the polypeptide. There are discreet domains and motifs within a transcription factor that must be present within the polypeptide to confer function and specificity. These specific structures are required so that interactive sequences will be properly oriented to retain the desired activity. "Substantial identity" may thus also be used with regard to subsequences, for example, motifs, that are of sufficient structure and similarity, being at least about 80% identical to similar motifs in other related sequences so that each confers or is required for increased tolerance to abiotic stress.

"Alignment" refers to a number of nucleotide or amino acid residue sequences aligned by lengthwise comparison so that components in common (i.e., nucleotide bases or amino acid residues) may be visually and readily identified. The fraction or percentage of components in common is related to the homology or identity between the sequences. Alignments such as those found in FIGS. 4A-4J may be used to identify AP2, DML and B3 domains and relatedness within these domains. An alignment may suitably be determined by means of computer programs known in the art, such as MacVector (1999) (Accelrys, Inc., San Diego, Calif.).

A "conserved domain" or "conserved region" as used herein refers to a region in heterologous polynucleotide or polypeptide sequences where there is a relatively high degree of sequence identity between the distinct sequences. AP2 binding domains and B3 domains are examples of conserved domain.

With respect to polynucleotides encoding presently disclosed transcription factors, a conserved domain is preferably at least 10 base pairs (bp) in length.

A "conserved domain", with respect to presently disclosed polypeptides refers to a domain within a transcription factor family that exhibits a higher degree of sequence homology, such as at least 70% sequence similarity, including conservative substitutions, and more preferably at least 79% sequence identity, and even more preferably at least 81%, or at least about 86%, or at least about 87%, or at least about 89%, or at least about 91%, or at least about 95%, or at least about 98% amino acid residue sequence identity of a polypeptide of consecutive amino acid residues. A fragment or domain can be referred to as outside a conserved domain, outside a consensus sequence, or outside a consensus DNA-binding site that is known to exist or that exists for a particular transcription factor class, family, or sub-family. In this case, the fragment or domain will not include the exact amino acids of a consensus sequence or consensus DNA-binding site of a transcription factor class, family or sub-family, or the exact amino acids of a particular transcription factor consensus sequence or consensus DNA-binding site. Furthermore, a particular fragment, region, or domain of a polypeptide, or a polynucleotide encoding a polypeptide, can be "outside a conserved domain" if all the amino acids of the fragment, region, or domain fall outside of a defined conserved domain(s) for a polypeptide or protein. Sequences having lesser degrees of identity but comparable biological activity are considered to be equivalents.

As one of ordinary skill in the art recognizes, conserved domains may be identified as regions or domains of identity to a specific consensus sequence (see, for example, Riechmann et al. (2000) supra). Thus, by using alignment methods well known in the art, the conserved domains (i.e., the AP2 domains) of the AP2 plant transcription factors (Riechmann and Meyerowitz (1998) *Biol. Chem.* 379:633-646) may be determined.

The AP2-binding and B3 (or conserved) domains for SEQ ID NO: 2, 4, 6, and 8 and numerous orthologs are listed in Table 1. Also, the polypeptides of Table 1 have AP2-binding and B3 domains specifically indicated by start and stop sites. A comparison of the regions of the polypeptides in Table 1 allows one of skill in the art to identify AP2-binding and B3 domains for any of the polypeptides listed or referred to in this disclosure.

"Complementary" refers to the natural hydrogen bonding by base pairing between purines and pyrimidines. For example, the sequence A-C-G-T (5'->3') forms hydrogen bonds with its complements A-C-G-T (5'->3') or A-C-G-U (5'->3'). Two single-stranded molecules may be considered partially complementary, if only some of the nucleotides bond, or "completely complementary" if all of the nucleotides bond. The degree of complementarity between nucleic acid strands affects the efficiency and strength of the hybridization and amplification reactions. "Fully complementary" refers to the case where bonding occurs between every base pair and its complement in a pair of sequences, and the two sequences have the same number of nucleotides.

The terms "highly stringent" or "highly stringent condition" refer to conditions that permit hybridization of DNA strands whose sequences are highly complementary, wherein these same conditions exclude hybridization of significantly mismatched DNAs. Polynucleotide sequences capable of hybridizing under stringent conditions with the polynucleotides of the present invention may be, for example, variants of the disclosed polynucleotide sequences, including allelic or splice variants, or sequences that encode orthologs or paralogs of presently disclosed polypeptides. Nucleic acid hybridization methods are disclosed in detail by Kashima et al. (1985) *Nature* 313:402-404, and Sambrook et al. (1989) *Molecular Cloning: A Laboratory Manual*, 2nd Ed., Cold Spring Harbor Laboratory, Cold Spring Harbor, N.Y. ("Sambrook"); and by Haymes et al., "Nucleic Acid Hybridization: A Practical Approach", IRL Press, Washington, D.C. (1985), which references are incorporated herein by reference.

In general, stringency is determined by the temperature, ionic strength, and concentration of denaturing agents (e.g., formamide) used in a hybridization and washing procedure (for a more detailed description of establishing and determining stringency, see below). The degree to which two nucleic acids hybridize under various conditions of stringency is correlated with the extent of their similarity. Thus, similar nucleic acid sequences from a variety of sources, such as within a plant's genome (as in the case of paralogs) or from another plant (as in the case of orthologs) that may perform similar functions can be isolated on the basis of their ability to hybridize with known transcription factor sequences. Numerous variations are possible in the conditions and means by which nucleic acid hybridization can be performed to isolate transcription factor sequences having similarity to transcription factor sequences known in the art and are not limited to those explicitly disclosed herein. Such an approach may be used to isolate polynucleotide sequences having various degrees of similarity with disclosed transcription factor sequences, such as, for example, transcription factors having 60% identity, or more preferably greater than about 70% identity, most preferably 72% or greater identity with disclosed transcription factors.

Regarding the terms "paralog" and "ortholog", homologous polynucleotide sequences and homologous polypeptide sequences may be paralogs or orthologs of the claimed polynucleotide or polypeptide sequence. Orthologs and paralogs are evolutionarily related genes that have similar sequence and similar functions. Orthologs are structurally related genes in different species that are derived by a speciation event. Paralogs are structurally related genes within a single species that are derived by a duplication event. Sequences that are sufficiently similar to one another will be appreciated by those of skill in the art and may be based upon percentage identity of the complete sequences, percentage identity of a conserved domain or sequence within the complete sequence, percentage similarity to the complete sequence, percentage similarity to a conserved domain or sequence within the complete sequence, and/or an arrangement of contiguous nucleotides or peptides particular to a conserved domain or complete sequence. Sequences that are sufficiently similar to one another will also bind in a similar manner to the same DNA binding sites of transcriptional regulatory elements using methods well known to those of skill in the art.

The term "equivalog" describes members of a set of homologous proteins that are conserved with respect to function since their last common ancestor. Related proteins are grouped into equivalog families, and otherwise into protein families with other hierarchically defined homology types. This definition is provided at the Institute for Genomic Research (TIGR) world wide web (www) website, "tigr.org" under the heading "Terms associated with TIGRFAMs".

The term "variant", as used herein, may refer to polynucleotides or polypeptides, that differ from the presently disclosed polynucleotides or polypeptides, respectively, in sequence from each other, and as set forth below.

With regard to polynucleotide variants, differences between presently disclosed polynucleotides and polynucleotide variants are limited so that the nucleotide sequences of the former and the latter are closely similar overall and, in many regions, identical. Due to the degeneracy of the genetic code, differences between the former and latter nucleotide sequences may be silent (i.e., the amino acids encoded by the polynucleotide are the same, and the variant polynucleotide sequence encodes the same amino acid sequence as the presently disclosed polynucleotide. Variant nucleotide sequences may encode different amino acid sequences, in which case such nucleotide differences will result in amino acid substitutions, additions, deletions, insertions, truncations or fusions with respect to the similar disclosed polynucleotide sequences. These variations result in polynucleotide variants encoding polypeptides that share at least one functional characteristic. The degeneracy of the genetic code also dictates that many different variant polynucleotides can encode identical and/or substantially similar, polypeptides in addition to those sequences illustrated in the Sequence Listing.

Also within the scope of the invention is a variant of a transcription factor nucleic acid listed in the Sequence Listing, that is, one having a sequence that differs from the one of the polynucleotide sequences in the Sequence Listing, or a complementary sequence, that encodes a functionally equivalent polypeptide (i.e., a polypeptide having some degree of equivalent or similar biological activity) but differs in sequence from the sequence in the Sequence Listing, due to degeneracy in the genetic code. Included within this definition are polymorphisms that may or may not be readily detectable using a particular oligonucleotide probe of the polynucleotide encoding polypeptide, and improper or unexpected hybridization to allelic variants, with a locus other than the normal chromosomal locus for the polynucleotide sequence encoding polypeptide.

"Allelic variant" or "polynucleotide allelic variant" refers to any of two or more alternative forms of a gene occupying the same chromosomal locus. Allelic variation arises naturally through mutation, and may result in phenotypic polymorphism within populations. Gene mutations may be "silent" or may encode polypeptides having altered amino acid sequence. "Allelic variant" and "polypeptide allelic variant" may also be used with respect to polypeptides, and in this case the term refer to a polypeptide encoded by an allelic variant of a gene.

"Splice variant" or "polynucleotide splice variant" as used herein refers to alternative forms of RNA transcribed from a gene. Splice variation naturally occurs as a result of alternative sites being spliced within a single transcribed RNA molecule or between separately transcribed RNA molecules, and may result in several different forms of mRNA transcribed from the same gene. Thus, splice variants may encode polypeptides having different amino acid sequences, which may or may not have similar functions in the organism. "Splice variant" or "polypeptide splice variant" may also refer to a polypeptide encoded by a splice variant of a transcribed mRNA.

As used herein, "polynucleotide variants" may also refer to polynucleotide sequences that encode paralogs and orthologs of the presently disclosed polypeptide sequences. "Polypeptide variants" may refer to polypeptide sequences that are paralogs and orthologs of the presently disclosed polypeptide sequences.

Differences between presently disclosed polypeptides and polypeptide variants are limited so that the sequences of the former and the latter are closely similar overall and, in many regions, identical. Presently disclosed polypeptide sequences and similar polypeptide variants may differ in amino acid sequence by one or more substitutions, additions, deletions, fusions and truncations, which may be present in any combination. These differences may produce silent changes and result in a functionally equivalent transcription factor. Thus, it will be readily appreciated by those of skill in the art, that any of a variety of polynucleotide sequences is capable of encoding the transcription factors and transcription factor homolog polypeptides of the invention. A polypeptide sequence variant may have "conservative" changes, wherein a substituted amino acid has similar structural or chemical properties. Deliberate amino acid substitutions may thus be made on the basis of similarity in polarity, charge, solubility, hydrophobicity, hydrophilicity, and/or the amphipathic nature of the residues, as long as the functional or biological activity of the transcription factor is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine (for more detail on conservative substitutions, see Table 3). More rarely, a variant may have "non-conservative" changes, for example, replacement of a glycine with a tryptophan. Similar minor variations may also include amino acid deletions or insertions, or both. Related polypeptides may comprise, for example, additions and/or deletions of one or more N-linked or O-linked glycosylation sites, or an addition and/or a deletion of one or more cysteine residues. Guidance in determining which and how many amino acid residues may be substituted, inserted or deleted without abolishing functional or biological activity may be found using computer programs well known in the art, for example, DNASTAR software (see U.S. Pat. No. 5,840,544).

"Modulates" refers to a change in activity (biological, chemical, or immunological) or lifespan resulting from specific binding between a molecule and either a nucleic acid molecule or a protein.

Figure 2:
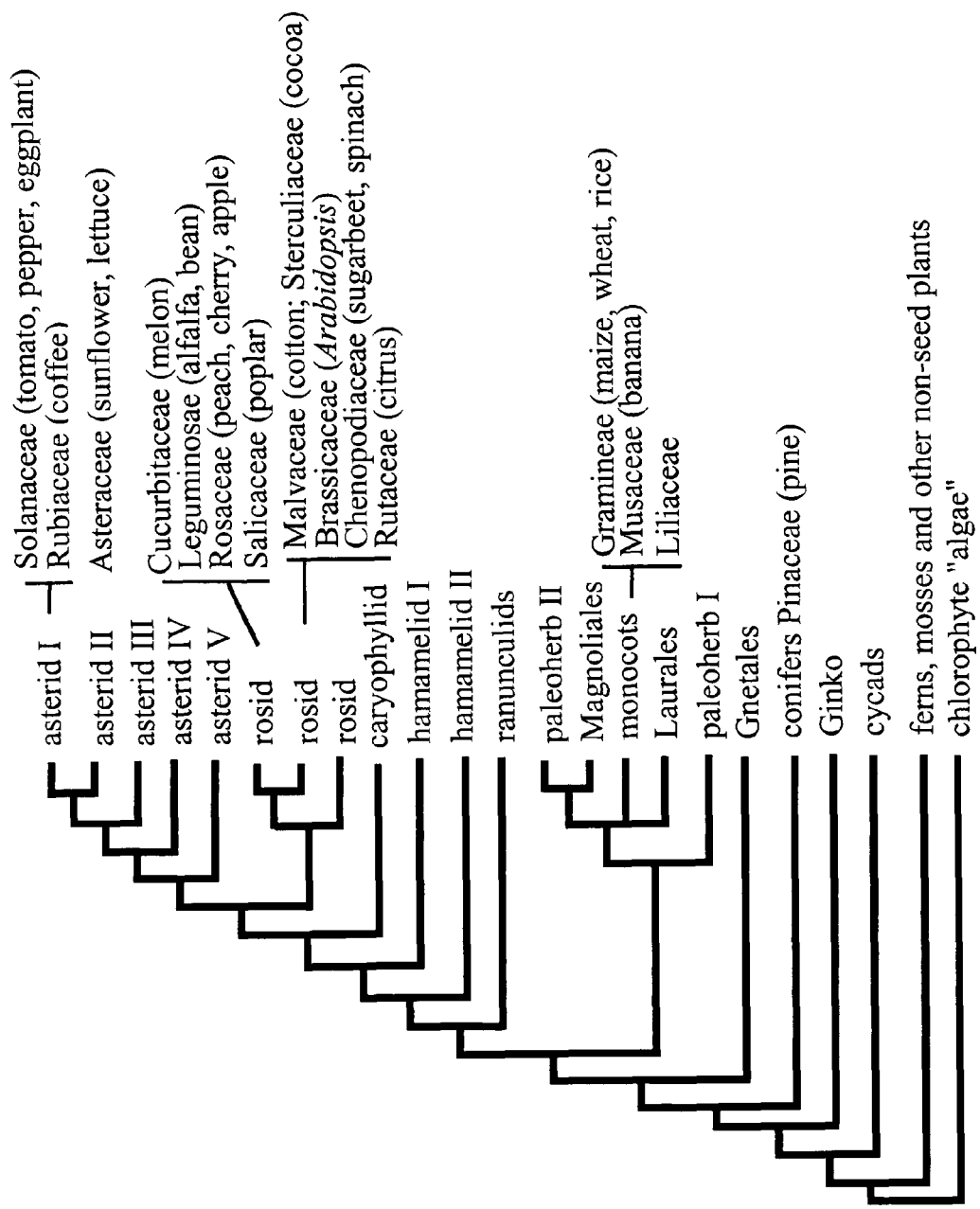

The term "plant" includes whole plants, shoot vegetative organs/structures (for example, leaves, stems and tubers), roots, flowers and floral organs/structures (for example, bracts, sepals, petals, stamens, carpels, anthers and ovules), seed (including embryo, endosperm, and seed coat) and fruit (the mature ovary), plant tissue (for example, vascular tissue, ground tissue, and the like) and cells (for example, guard cells, egg cells, and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, horsetails, psilophytes, lycophytes, bryophytes, and multicellular algae. (See for example, FIG. 1, adapted from Daly et al. (2001) *Plant Physiol.* 127: 1328-1333; FIG. 2, adapted from Ku et al. (2000) *Proc. Natl. Acad. Sci.* 97: 9121-9126; and see also Tudge in *The Variety of Life*, Oxford University Press, New York, N.Y. (2000) pp. 547-606).

A "transgenic plant" refers to a plant that contains genetic material not found in a wild-type plant of the same species, variety or cultivar. The genetic material may include a transgene, an insertional mutagenesis event (such as by transposon or T-DNA insertional mutagenesis), an activation tagging sequence, a mutated sequence, a homologous recombination event or a sequence modified by chimeraplasty. Typically, the foreign genetic material has been introduced into the plant by human manipulation, but any method can be used as one of skill in the art recognizes.

A transgenic plant may contain an expression vector or cassette. The expression vector or cassette typically comprises a polypeptide-encoding sequence operably linked (i.e., under regulatory control of) to appropriate inducible or constitutive regulatory sequences that allow for the expression of polypeptide. The expression vector or cassette can be introduced into a plant by transformation or by breeding after transformation of a parent plant. A plant refers to a whole plant as well as to a plant part, such as seed, fruit, leaf, or root, plant tissue, plant cells or any other plant material, for example, a plant explant, as well as to progeny thereof, and to in vitro systems that mimic biochemical or cellular components or processes in a cell.

"Wild type" or "wild-type", as used herein, refers to a plant cell, seed, plant component, plant tissue, plant organ or whole plant that has not been genetically modified or treated in an experimental sense. Wild-type cells, seed, components, tissue, organs or whole plants may be used as controls to compare levels of expression and the extent and nature of trait modification with cells, tissue or plants of the same species in which a transcription factor expression is altered, e.g., in that it has been knocked out, overexpressed, or ectopically expressed.

A "control plant" as used in the present invention refers to a plant cell, seed, plant component, plant tissue, plant organ or whole plant used to compare against transgenic or genetically modified plant for the purpose of identifying an enhanced phenotype in the transgenic or genetically modified plant. A control plant may in some cases be a transgenic plant line that comprises an empty vector or marker gene, but does not contain the recombinant polynucleotide of the present invention that is expressed in the transgenic or genetically modified plant being evaluated. In general, a control plant is a plant of the same line or variety as the transgenic or genetically modified plant being tested. A suitable control plant would include a genetically unaltered or non-transgenic plant of the parental line used to generate a transgenic plant herein.

"Derivative" refers to the chemical modification of a nucleic acid molecule or amino acid sequence. Chemical modifications can include replacement of hydrogen by an alkyl, acyl, or amino group or glycosylation, pegylation, or any similar process that retains or enhances biological activity or lifespan of the molecule or sequence.

A "trait" refers to a physiological, morphological, biochemical, or physical characteristic of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g. by measuring tolerance to water deprivation or particular salt or sugar concentrations, or by the observation of the expression level of a gene or genes, for example, by employing Northern analysis, RT-PCR, microarray gene expression assays, or reporter gene expression systems, or by agricultural observations such as osmotic stress tolerance or yield. Any technique can be used to measure the amount of, comparative level of, or difference in any selected chemical compound or macromolecule in the transgenic plants, however.

"Trait modification" refers to a detectable difference in a characteristic in a plant ectopically expressing a polynucleotide or polypeptide of the present invention relative to a plant not doing so, such as a wild-type plant. In some cases, the trait modification can be evaluated quantitatively. For example, the trait modification can entail at least about a 2% increase or decrease in an observed trait (difference), at least a 5% difference, at least about a 10% difference, at least about a 20% difference, at least about a 30%, at least about a 50%, at least about a 70%, or at least about a 100%, or an even greater difference compared with a wild-type plant. It is known that there can be a natural variation in the modified trait. Therefore, the trait modification observed entails a change of the normal distribution of the trait in the plants compared with the distribution observed in wild-type plants.

When two or more plants have "similar morphologies", "substantially similar morphologies" or "a morphology that is substantially similar", the plants have comparable forms or appearances, including analogous features such as overall dimensions, height, width, mass, root mass, shape, glossiness, color, stem diameter, leaf size, leaf dimension, leaf density, internode distance, branching, root branching, number and form of inflorescences, and other macroscopic characteristics, and the individual plants are not readily distinguishable based on morphological characteristics alone.

The term "transcript profile" refers to the expression levels of a set of genes in a cell in a particular state, particularly by comparison with the expression levels of that same set of genes in a cell of the same type in a reference state. For example, the transcript profile of a particular transcription factor in a suspension cell is the expression levels of a set of genes in a cell repressing or overexpressing that transcription factor compared with the expression levels of that same set of genes in a suspension cell that has normal levels of that transcription factor. The transcript profile can be presented as a list of those genes whose expression level is significantly different between the two treatments, and the difference ratios. Differences and similarities between expression levels may also be evaluated and calculated using statistical and clustering methods.

"Ectopic expression or altered expression" in reference to a polynucleotide indicates that the pattern of expression in, for example, a transgenic plant or plant tissue, is different from the expression pattern in a wild-type plant or a reference plant of the same species. The pattern of expression may also be compared with a reference expression pattern in a wild-type plant of the same species. For example, the polynucleotide or polypeptide is expressed in a cell or tissue type other than a cell or tissue type in which the sequence is expressed in the wild-type plant, or by expression at a time other than at the time the sequence is expressed in the wild-type plant, or by a response to different inducible agents, such as hormones or environmental signals, or at different expression levels (either higher or lower) compared with those found in a wild-type plant. The term also refers to altered expression patterns that are produced by lowering the levels of expression to below the detection level or completely abolishing expression. The resulting expression pattern can be transient or stable, constitutive or inducible. In reference to a polypeptide, the term "ectopic expression or altered expression" further may relate to altered activity levels resulting from the interactions of the polypeptides with exogenous or endogenous modulators or from interactions with factors or as a result of the chemical modification of the polypeptides.

The term "overexpression" as used herein refers to a greater expression level of a gene in a plant, plant cell or plant tissue, compared to expression in a wild-type plant, cell or tissue, at any developmental or temporal stage for the gene. Overexpression can occur when, for example, the genes encoding one or more transcription factors are under the control of a strong expression signal, such as one of the promoters described herein (for example, the cauliflower mosaic virus 35S atranscription initiation region). Overexpression may occur throughout a plant or in specific tissues of the plant, depending on the promoter used, as described below.

Overexpression may take place in plant cells normally lacking expression of polypeptides functionally equivalent or identical to the present transcription factors. Overexpression may also occur in plant cells where endogenous expression of the present transcription factors or functionally equivalent molecules normally occurs, but such normal expression is at a lower level. Overexpression thus results in a greater than normal production, or "overproduction" of the transcription factor in the plant, cell or tissue.

The term "transcription regulating region" refers to a DNA regulatory sequence that regulates expression of one or more genes in a plant when a transcription factor having one or more specific binding domains binds to the DNA regulatory sequence. Transcription factors of the present invention possess an AP2 domain, a B3 domain, or both of these binding domains. The AP2 domain of the transcription factor binds to a transcription regulating region comprising the motif CAACA, and the B3 domain of the same transcription factor binds to a transcription regulating region comprising the motif CACCTG. The transcription factors of the invention also comprise an amino acid subsequence that forms a transcription activation domain that regulates expression of one or more abiotic stress tolerance genes in a plant when the transcription factor binds to the regulating region.

A "sample" with respect to a material containing nucleic acid molecules may comprise a bodily fluid; an extract from a cell, chromosome, organelle, or membrane isolated from a cell; genomic DNA, RNA, or cDNA in solution or bound to a substrate; a cell; a tissue; a tissue print; a forensic sample; and the like. In this context "substrate" refers to any rigid or semi-rigid support to which nucleic acid molecules or proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores. A substrate may also refer to a reactant in a chemical or biological reaction, or a substance acted upon (for example, by an enzyme).

DETAILED DESCRIPTION

Transcription Factors Modify Expression of Endogenous Genes

A transcription factor may include, but is not limited to, any polypeptide that can activate or repress transcription of a single gene or a number of genes. As one of ordinary skill in the art recognizes, transcription factors can be identified by the presence of a region or domain of structural similarity or identity to a specific consensus sequence or the presence of a specific consensus DNA-binding site or DNA-binding site motif (see, for example, Riechmann et al. (2000) Science 290: 2105-2110). The plant transcription factors may belong to the AP2 protein transcription factor family (Riechmann and Meyerowitz (1998) supra).

Generally, the transcription factors encoded by the present sequences are involved in cell differentiation and proliferation and the regulation of growth. Accordingly, one skilled in the art would recognize that by expressing the present sequences in a plant, one may change the expression of autologous genes or induce the expression of introduced genes. By affecting the expression of similar autologous sequences in a plant that have the biological activity of the present sequences, or by introducing the present sequences into a plant, one may alter a plant's phenotype to one with improved traits related to osmotic stresses. The sequences of the invention may also be used to transform a plant and introduce desirable traits not found in the wild-type cultivar or strain. Plants may then be selected for those that produce the most desirable degree of over- or under-expression of target genes of interest and coincident trait improvement.

The sequences of the present invention may be from any species, particularly plant species, in a naturally occurring form or from any source whether natural, synthetic, semi-synthetic or recombinant. The sequences of the invention may also include fragments of the present amino acid sequences. Where "amino acid sequence" is recited to refer to an amino acid sequence of a naturally occurring protein molecule, "amino acid sequence" and like terms are not meant to limit the amino acid sequence to the complete native amino acid sequence associated with the recited protein molecule.

In addition to methods for modifying a plant phenotype by employing one or more polynucleotides and polypeptides of the invention described herein, the polynucleotides and polypeptides of the invention have a variety of additional uses. These uses include their use in the recombinant production (i.e., expression) of proteins; as regulators of plant gene expression, as diagnostic probes for the presence of complementary or partially complementary nucleic acids (including for detection of natural coding nucleic acids); as substrates for further reactions, for example, mutation reactions, PCR reactions, or the like; as substrates for cloning for example, including digestion or ligation reactions; and for identifying exogenous or endogenous modulators of the transcription factors. In many instances, a polynucleotide comprises a nucleotide sequence encoding a polypeptide (or protein) or a domain or fragment thereof. Additionally, the polynucleotide may comprise a promoter, an intron, an enhancer region, a polyadenylation site, a translation initiation site, 5' or 3' untranslated regions, a reporter gene, a selectable marker, or the like. The polynucleotide can be single stranded or double stranded DNA or RNA. The polynucleotide optionally comprises modified bases or a modified backbone. The polynucleotide can be, for example, genomic DNA or RNA, a transcript (such as an mRNA), a cDNA, a PCR product, a cloned DNA, a synthetic DNA or RNA, or the like. The polynucleotide can comprise a sequence in either sense or antisense orientations.

Expression of genes that encode transcription factors that modify expression of endogenous genes, polynucleotides, and proteins are well known in the art. In addition, transgenic plants comprising isolated polynucleotides encoding transcription factors may also modify expression of endogenous genes, polynucleotides, and proteins. Examples include Peng et al. (1997) *Genes Development* 11: 3194-3205, and Peng et al. (1999) *Nature,* 400: 256-261). In addition, many others have demonstrated that an *Arabidopsis* transcription factor expressed in an exogenous plant species elicits the same or very similar phenotypic response (see, for example, Fu et al. (2001) *Plant Cell* 13: 1791-1802; Nandi et al. (2000) *Curr. Biol.* 10: 215-218; Coupland (1995) *Nature* 377: 482-483; and Weigel and Nilsson (1995) *Nature* 377: 482-500).

In another example, Mandel et al. (1992) *Cell* 71-133-143; and Suzuki et al. (2001) *Plant J.* 28: 409-418 teach that a transcription factor expressed in another plant species elicits the same or very similar phenotypic response of the endogenous sequence, as often predicted in earlier studies of *Arabidopsis* transcription factors in *Arabidopsis* (see Mandel et al. (1992) supra; Suzuki et al. (2001) supra).

Other examples include Müller et al. (2001) *Plant J.* 28: 169-179; Kim et al. (2001) *Plant J.* 25: 247-259; Kyozuka and Shimamoto (2002) *Plant Cell Physiol.* 43: 130-135; Boss and Thomas (2002) *Nature,* 416: 847-850; He et al. (2000) *Transgenic Res.* 9: 223-227; and Robson et al. (2001) *Plant J.* 28: 619-631.

In yet another example, Gilmour et al. (1998) *Plant J.* 16: 433-442, teach an *Arabidopsis* AP2 transcription factor, CBF1 (SEQ ID NO: 55), which, when overexpressed in transgenic plants, increases plant freezing tolerance. Jaglo et al. (2001) *Plant Physiol.* 127: 910-917, further identified sequences in *Brassica napus* which encode CBF-like genes and that transcripts for these genes accumulated rapidly in response to low temperature. Transcripts encoding CBF-like proteins were also found to accumulate rapidly in response to low temperature in wheat, as well as in tomato. An alignment of the CBF proteins from *Arabidopsis, B. napus,* wheat, rye, and tomato revealed the presence of conserved consecutive amino acid residues, PKK/RPAGRxKFxETRHP (SEQ ID NO: 69) and DSAWR (SEQ ID NO: 70), that bracket the AP2/EREBP DNA binding domains of the proteins and distinguish them from other members of the AP2/EREBP protein family (Jaglo et al. (2001) supra).

Transcription factors mediate cellular responses and control traits through altered expression of genes containing cis-acting nucleotide sequences that are targets of the introduced transcription factor. It is well appreciated in the art that the effect of a transcription factor on cellular responses or a cellular trait is determined by the particular genes whose expression is either directly or indirectly (for example, by a cascade of transcription factor binding events and transcriptional changes) altered by transcription factor binding. In a global analysis of transcription comparing a standard condition with one in which a transcription factor is overexpressed, the resulting transcript profile associated with transcription factor overexpression is related to the trait or cellular process controlled by that transcription factor. For example, the PAP2 gene (and other genes in the MYB family) have been shown to control anthocyanin biosynthesis through regulation of the expression of genes known to be involved in the anthocyanin biosynthetic pathway (Bruce et al. (2000) *Plant Cell,* 12: 65-79; Borevitz et al. (2000) *Plant Cell* 12: 2383-93). Further, global transcript profiles have been used successfully as diagnostic tools for specific cellular states (for example, cancerous vs. non-cancerous; Bhattacharjee et al. (2001) *Proc Natl. Acad. Sci., USA,* 98: 13790-13795; Xu et al. (2001) *Proc. Natl. Acad. Sci., USA,* 98: 15089-15094). Consequently, it is evident to one skilled in the art that similarity of transcript profile upon overexpression of different transcription factors would indicate similarity of transcription factor function.

Polypeptides and Polynucleotides of the Invention

The present invention provides, among other things, transcription factors (TFs), and transcription factor homolog polypeptides, and isolated or recombinant polynucleotides encoding the polypeptides, or novel sequence variant polypeptides or polynucleotides encoding novel variants of transcription factors derived from the specific sequences provided here. These polypeptides and polynucleotides may be employed to modify a plant's characteristics.

The sequences of G867 and G9 were previously identified in U.S. provisional patent application 60/101,349, filed Sep. 22, 1998, at which time these sequences were identified as encoding or being transcription factors, which were defined as polypeptides having the ability to effect transcription of a target gene. Sequences that have gene-regulating activity have been determined to have specific and substantial utility (Federal Register (2001) 66(4): 1095). The functions of G867 and G9 were previously disclosed in U.S. provisional patent application 60/227,439, filed Aug. 22, 2000, and 60/166,228, filed Nov. 17, 1999, respectively. The sequence of G993 was previously identified in U.S. provisional application 60/108, 734, filed Nov. 17, 1998, and 60/125,814, filed Mar. 23, 1999. The function of G993 was implied from its homologous relationship with G867, as disclosed in U.S. non-provisional application Ser. No. 09/934,455, filed Aug. 22, 2001. The sequence of G1930 was previously identified in U.S. non-provisional application Ser. No. 09/934,455, filed Aug. 22, 2001. The functions of G1930 were previously disclosed in U.S. non-provisional patent application Ser. No. 09/934,455, filed Aug. 22, 2001.

In some cases, exemplary polynucleotides encoding the polypeptides of the invention were identified in the *Arabidopsis thaliana* GenBank database using publicly available sequence analysis programs and parameters. Sequences initially identified were then further characterized to identify sequences comprising specified sequence strings corresponding to sequence motifs present in families of known transcription factors. In addition, further exemplary polynucleotides encoding the polypeptides of the invention were identified in the plant GenBank database using publicly available sequence analysis programs and parameters. Sequences initially identified were then further characterized to identify sequences comprising specified sequence strings corresponding to sequence motifs present in families of known transcription factors. Polynucleotide sequences meeting such criteria were confirmed as transcription factors.

Additional polynucleotides of the invention were identified by screening *Arabidopsis thaliana* and/or other plant cDNA libraries with probes corresponding to known transcription factors under low stringency hybridization conditions. Additional sequences, including full length coding sequences were subsequently recovered by the rapid amplification of cDNA ends (RACE) procedure, using a commercially available kit according to the manufacturer's instructions. Where necessary, multiple rounds of RACE are performed to isolate 5' and 3' ends. The full-length cDNA was then recovered by a routine end-to-end polymerase chain reaction (PCR) using primers specific to the isolated 5' and 3' ends. Exemplary sequences are provided in the Sequence Listing.

The polynucleotides of the invention can be or were ectopically expressed in overexpressor or knockout plants and the changes in the characteristic(s) or trait(s) of the plants observed. Therefore, the polynucleotides and polypeptides can be employed to improve the characteristics of plants.

The polynucleotides of the invention can be or were ectopically expressed in overexpressor plant cells and the changes in the expression levels of a number of genes, polynucleotides, and/or proteins of the plant cells observed. Therefore, the polynucleotides and polypeptides can be employed to change expression levels of a genes, polynucleotides, and/or proteins of plants.

G867, which we have determined to confer osmotic stress tolerance in plants when overexpressed, has been described in the literature as related to ABI3/VP1 (RAV1; Kagaya et al. (1999) *Nucleic Acids Res.* 27: 470478) based on the presence of a B3 domain (which is also found in the ABI3/VP1 family of transcription factors). The protein also contains an AP2 domain, and is therefore presently included in the AP2/ERF family of transcription factors. Both the AP2 domain transcription factors and the B3 domain transcription factors are described below.

AP2 domain transcription factors. Ohme-Takagi and Shinshi (1995). Plant Cell 7, 173-182) determined that the function of the AP2 domain is DNA binding. The AP2 region of the putative tobacco transcription factor EREBP2 is responsible for its binding to the cis-acting ethylene response DNA element referred to as the GCC-repeat. As discussed by Ohme-Takagi and Shinshi (1995) supra), the DNA-binding or AP2 domain of EREBP2 contains no significant amino acid sequence similarities or obvious structural similarities with other known transcription factors or DNA binding motifs beyond AP2 transcription factors. Thus, the domain appears to be a novel DNA-binding motif that, to date, has only been found in plant proteins.

The RAV-like proteins, including G867 and other members of the G867 clade of transcription factor polypeptides, form a small subgroup in the AP2/ERF family of AP2 transcription factors. This large gene family includes at least 145 transcription factors, and can be further divided in three larger subfamilies:

(a) The APETALA2 class is characterized by the presence of two AP2 DNA binding domains, and contains fourteen genes.

(b) The RAV subgroup, which includes six genes, is characterized by the presence of a B3 DNA binding domain in addition to the AP2 DNA binding domain.

(c) The AP2/ERF subfamily, which is the largest subfamily and includes 125 genes, is characterized by the presence of only one AP2 DNA binding domain, and includes genes that are involved in abiotic and biotic stress responses. This subfamily is composed of two relatively equal size subgroups, the DREB and ERF subgroups (Sakuma et al. (2002) *Biochem and Biophys Res Comm* 290: 998-1009), which are distinguished on the basis of specific residues in the AP2 DNA binding domain.

The binding characteristics of G867 (RAV1) have been characterized by Kagaya et al. ((1999) *Nucleic Acids Res.* 27: 470-478; see below). There is no published information on the biological function of the RAV-like transcription factors.

B3 domain transcription factors. Transcription factors of the ABI3/VP1 family have been implicated in seed maturation processes. ABI3 (G621) plays an important role in the acquisition of desiccation tolerance in late embryogenesis. This process is related to dehydration tolerance as evidenced by the protective function of late embryogenesis abundant (LEA) genes such as HVA 1 (Xu et al. (1996) *Plant Physiol.* 110: 249-257; Sivamani et al. (2000) *Plant Science* 155: 1-9). Mutants for *Arabidopsis* ABI3 (Ooms et al. (1993) *Plant Physiol.* 102: 1185-1191) and the maize ortholog VP1 (Carson et al. (1997) *Plant J.* 12: 1231-1240) and references therein) show severe defects in the attainment of desiccation tolerance. Also, 35S::ABI3 overexpression in combination with increased levels of abscisic acid results in an induction of several ABA/cold/drought-responsive genes such as RAB18 and RD29A and increased freezing tolerance in *Arabidopsis* (Tamminen et al. (2001) *Plant J.* 25: 1-8). This illustrates the relatedness of desiccation and dehydration tolerance and demonstrates that the seed-specific ABI3 transcription factor does not require additional seed-specific proteins to function in vegetative tissues.

Both in *Arabidopsis* and maize, the B3 domain of ABI3/VP 1 binds the RY/SPH motif (Ezcurra et al. (2000) *Plant J.* 24: 57-66); Carson et al. (1997) supra) while the B2 domain interacts with the ABRE elements in a complex involving bZIP transcription factors (TRAB 1 in maize, Hobo et al. (1999) *Proc. Natl. Acad. Sci. USA* 96: 15348-15353). While in *Arabidopsis* the B3 domain of ABI3 is essential for abscisic acid dependent activation of late embryogenesis genes (Ezcurra et al. (2000) supra), the B3 domain of VP1 is not essential for ABA regulated gene expression in maize seed (Carson et al. (1997) supra; McCarty et al. (1989) *Plant Cell* 1: 523-532). This difference in the regulatory network between *Arabidopsis* and maize can be explained by differential usage of the RY/SPH versus the ABRE element in the control of seed maturation gene expression (motif (Ezcurra et al. (2000) supra). The RY/SPH element is a key element in gene regulation during late embryogenesis in *Arabidopsis* (Reidt et al. (2000) *Plant J.* 21: 401-408) while it seems to be less important for seed maturation in maize (McCarty et al. (1989) supra).

Mutations in two other B3 domain transcription factors, FUS3 (G1014) and LEC2 (G3035) result in pleiotropic effects. In the case of fus3, these effects are mainly restricted to seed development during late embryogenesis (Keith et al. (1994) *Plant Cell* 6: 589-600). Overexpression of LEC2 results in somatic embryo formation on the cotyledons (Stone et al. (2001) *Proc. Natl. Acad. Sci. USA* 98: 11806-11811). The FUS3 protein can be considered as a natural truncation of the ABI3 protein (Luerssen et al. (1998) *Plant J.* 15: 755-764); like the latter, it binds to the RY/SPH element, and can activate the expression from target promoters even in non-seed tissues (Reidt et al. (2000) supra).

Singh et al. (2003) have recently submitted a polynucleotide sequence (Accession No. CB686050) from a transgenic *Brassica napus* (CBF 17) that has been shown to be constitutively frost resistant. The predicted polypeptide sequence has a DML motif that is 90% identical, and a B3 domain that is 95% identical, to the DML motif and B3 domain of G867, respectively. The protein predicted from this sequence does not comprise an AP2 domain.

The G867 clade of Transcription Factor Polypeptides

Kagaya et al. ((1999) supra) cloned and characterized G867 (RAV1) and G9 (RAV2) from *Arabidopsis thaliana*. The two transcription factors were found to contain two distinct amino acid sequence domains found only in higher plant species, the AP2 and B3 domains. The N-terminal regions of G867 and G9 were shown to be homologous to the AP2 DNA-binding domain present in the *Arabidopsis* APETALA2 and tobacco EREBP proteins families, while the C-terminal region exhibited homology to the B3 domain of VP1/ABI3 transcription factors. Binding site selection assays using a recombinant glutathione S-transferase fusion protein revealed that G867 bound specifically to bipartite recognition sequences composed of two unrelated motifs, 5'-CAACA-3' and 5'-CACCTG-3', separated by various spacings in two different relative orientations. Analyses using various deletion derivatives of the RAV1 fusion protein showed that the AP2 and B3-like domains of RAV1 bind autonomously to the CAACA and CACCTG motifs, respectively, and together achieve a high affinity and specificity of binding. Kagaya et al. concluded that the AP2 and B3-like domains of RAV1 are connected by a highly flexible structure enabling the two domains to bind to the CAACA and CACCTG motifs in various spacings and orientations.

The RAV-like proteins, including G867 and other members of the G867 clade of transcription factor polypeptides (e.g., G9, G993, G1930, *G*3389, G3390, G3391, G3451, G3452, and G3455), generally have both AP2 and B3 domains. Within the G867 clade of transcription factor polypeptides, there is a high degree of conservation of the AP2 and B3 domains in all members of the clade. The proteins in the G867 clade were also found to possess a subsequence with a high degree of conservation between the AP2 and B3 domains. This subsequence was designated DML motif. The DML motif does not appear to be present in transcription factors outside of the G867 clade (more detailed description of the DML motif appears below, and a list of DML motif sequences may be found in Table 2).

Table 1 shows the polypeptides identified by polypeptide SEQ ID NO and Mendel Gene ID (GID) No., presented in order of similarity to G867 by AP2 domain, and includes the AP2 and B3 binding domains of the polypeptide in amino acid coordinates, the respective AP2 domain sequences, the extent of identity in percentage terms to the AP2 domain of G867, the respective B3 domains, and the extent of identity in percentage terms to the B3 domain of G867. A number of these sequences have been shown to confer abiotic stress tolerant phenotypes when overexpressed in plants, as indicated in the last column of Table 1. These functional polypeptide sequences include AP2 and B3 domains with 81% and 78% or greater identity to the AP2 domains of G867, respectively.

TABLE 1

Binding domains of the G867 clade of transcription factor polypeptides

| SEQ ID NO: | GID No. | AP2 and B3 Domains in AA Coordinates | AP2 Domain | % ID to Domain of G867 | B3 Domain | % ID to B3 Domain of G867 | Abiotic Stress Tolerance Phenotype |
|---|---|---|---|---|---|---|---|
| 2 | G867 | AP2: 59-124<br>B3: 187-272 | SSKYKGVVPQPNG<br>RWGAQIYEKHQRV<br>WLGTFNEEDEAAR<br>AYDVAVHRFRRRD<br>AVTNFKDVKMDEDE | 100% | LFEKAVTPSDVGKLN<br>RLVIPKHHAEKHFPL<br>PSSNVSVKGVLLNFE<br>DVNGKVWRFRYSY<br>WNSSQSYVLTKGWS<br>RFVKEKNLRAGDVV | 100% | Yes |
| 6 | G993 | AP2: 69-134<br>B3: 194-286 | SSKYKGVVPQPNG<br>RWGAQIYEKHQRV<br>WLGTFNEEEEAASS<br>YDIAVRRFRGRDA<br>VTNFKSQVDGNDA | 89% | LFEKTVTPSDVGKLN<br>RLVIPKQHAEKHFPL<br>PAMTTAMGMNPSPT<br>KGVLINLEDRTGKV<br>WRFRYSYWNSSQSY<br>VLTKGWSRFVKEKN<br>LRAGDVV | 79% | Yes |
| 42 | BZ458719 | AP2: 42-107<br>B3: 172-258 | SSKFKGVVPQPNG<br>RWGAQIYEKHKRV<br>WLGTFNEEEEAAR<br>VYDVAAHRFRGSD<br>AVTNFKPDTTFRNG | 87% | LFEKTVTPSDVGKLN<br>RLVIPKHQAEKHFPL<br>PLTGDVSVRGTLLNF<br>EDVNGKVWRFRYSY<br>WNSSQSYVLTKGWS<br>RFVKEKRLCAGDLI | 86% | No data |
| 8 | G1930 | AP2: 59-124<br>B3: 182-269 | SSRFKGVVPQPNGR<br>WGAQIYEKHQRV<br>WLGTFNEEDEAAR<br>AYDVAAHRFRGRD<br>AVTNFKDTTFEEEV | 86% | LFEKTVTPSDVGKLN<br>RLVIPKHQAEKHFPL<br>PLGNNNVSVKGMLL<br>NFEDVNGKVWRFRY<br>SYWNSSQSYVLTKG<br>WSRFVKEKRLCAGDLI | 87% | Yes |

TABLE 1-continued

Binding domains of the G867 clade of transcription factor polypeptides

| SEQ ID NO: | GID No. | AP2 and B3 Domains in AA Coordinates | AP2 Domain | % ID to Domain of G867 | B3 Domain | % ID to B3 Domain of G867 | Abiotic Stress Tolerance Phenotype |
|---|---|---|---|---|---|---|---|
| 36 | G3391 | AP2: 79-145<br>B3: 215-302 | SSKFKGVVPQPNG<br>RWGAQIYERHQRV<br>WLGTFAGEDDAAR<br>AYDVAAQRFRGRD<br>AVTNFRPLAEADPDA | 84% | LFDKTVTPSDVGKLN<br>RLVIPKQHAEKHFPL<br>QLPSAGGESKGVLLN<br>FEDAAGKVWRFRYS<br>YWNSSQSYVLTKGW<br>SRFVKEKGLHADGKL | 83% | Yes |
| 46 | BU025988 | AP2: 25-90<br>B3: 152-236 | SSRYKGVVPQPNG<br>RWGAQIYEKHQRV<br>WLGTFNDEDEAAK<br>AYDVAVQRFRGRD<br>AVTINKQVDADDKE | 83% | LFQKTVTPSDVGKLN<br>RLVIPKQHAEKHFPV<br>QKGSNSKGLLHFED<br>KGSKVWRFRYSYWN<br>SSQSYVLTKGWSRFV<br>KEKNLKAGDSV | 81% | No data |
| 28 | G3455 | AP2: 74-139<br>B3: 204-296 | SSKYKGVVPQPNG<br>RWGSQIYEKHQRV<br>WLGTFNEEDEAAR<br>AYDVAVQRFRGKD<br>AVTNFKPLSGTDDD | 83% | LFQKAVTPSDVGKLN<br>RLVIPKQHAEKHFPL<br>QSAANGVSATATAA<br>KGVLLNFEDVGGKV<br>WRFRYSYWNSSQSY<br>VLTKGWSRFVKEKN<br>LKAGDTV | 81% | Yes |
| 22 | G3452 | AP2: 51-116<br>B3: 171-266 | SSKYKGVVPQPNG<br>RWGAQIYEKHQRV<br>WLGTFNEEDEAAR<br>AYDIAALRFRGPDA<br>VTNFKPPAASDDA | 83% | LFEKTVTPSDVGKLN<br>RLVIPKQHAEKHFPL<br>SGSGDESSPCVAGAS<br>AAKGMLLNFEDVGG<br>KVWRFRYSYWNSSQ<br>SYVLTKGWSRFVKE<br>KNLRAGDAV | 78% | Yes |
| 24 | G3453 | AP2: 57-122<br>B3: 177-272 | SSKYKGVVPQPNG<br>RWGAQIYEKHQRV<br>WLGTFNEEDEAVR<br>AYDIVAHRFRGRD<br>AVTNFKPLAGADDA | 83% | LVEKTVTPSDVGKLN<br>RLVIPKQHAEKHFPL<br>SGSGGGALPCMAAA<br>AGAKGMLLNFEDVG<br>GKVWRFRYSYWNSS<br>QSYVLTKGWSRFVK<br>EKNLRAGDAV | 77% | No data |
| 38 | G3432 | AP2: 75-141<br>B3: 212-299 | SSRYKGVVPQPNG<br>RWGAQIYERHQRV<br>WLGTFAGEADAAR<br>AYDVAAQRFRGRD<br>AVTNFRLPLADADPDA | 82% | LFDKTVTPSDVGKLN<br>RLVIPKQHAEKHFPL<br>QLPSAGGESKGVLLN<br>LEDAAGKVWRFRYS<br>YWNSSQSYVLTKGW<br>SRFVKEKGLQAGDVV | 82% | Yes* |
| 32 | G3389 | AP2: 64-129<br>B3: 177-266 | SSRYKGVVPQPNG<br>RWGAQIYERHARV<br>WLGTFPDEEAAAR<br>AYDVAALRFRGRD<br>AVTNRAPAAEAGASA | 82% | LFEKAVTPSDVGKLN<br>RLVVPKQQAERHFPE<br>PLRRHSSDAAGKGVL<br>LNFEDGDGKVWRFR<br>YSYWNSSQSYVLTK<br>GWSRFVREKGLRPG<br>DTV | 78% | Yes |
| 40 | G3433 | AP2: 80-146<br>B3: 210-291 | SSRYKGVVPQPNG<br>RWGAQIYERHLRV<br>WLGTFTGEAEAAR<br>AYDVAAQRFRGRD<br>AVTNFRPLAESDLDP | 82% | MFDKVLTPSDVGKL<br>NRLVVPKQHAERFFP<br>AAGAGSTQLCFQDR<br>GGALWQFRYSYWGS<br>SQSYVMTKGWSRFV<br>RAARLAAGDTV | 59% | No data |
| 4 | G9 | AP2: 62-127<br>B3: 187-273 | SSKYKGVVPQPNG<br>RWGAQIYEKHQRV<br>WLGTFNEQEEAAR<br>SYDIAACRFRGRDA<br>VVNFKNVLEDGDL | 81% | LFEKAVTPSDVGKLN<br>RLVIPKQHAEKHFPL<br>PSPSPAVTKGVLINFE<br>DVNGKVWRFRYSY<br>WNSSQSYVLTKGWS<br>RFVKEKNLRAGDVV | 91% | Yes |
| 44 | BQ971511 | AP2: 21-86<br>B3: 147-231 | SSRYKGVVPQANG<br>RWGAQIYEKHQRV<br>WLGTFNDEDEAAK<br>AYDVAVQRFRGRD<br>AVTNFKQLVTDDNA | 81% | LFQKTVTPSDVGKLN<br>RLVIPKQHAEKHFPV<br>QKGISSKGVLLHFED<br>TESKVWRFRYSYWN<br>SSQSYVLTKGWSRFV<br>KEKNLKAGDSV | 81% | No data |

TABLE 1-continued

Binding domains of the G867 clade of transcription factor polypeptides

| SEQ ID NO: | GID No. | AP2 and B3 Domains in AA Coordinates | AP2 Domain | % ID to Domain of G867 | B3 Domain | % ID to B3 Domain of G867 | Abiotic Stress Tolerance Phenotype |
|---|---|---|---|---|---|---|---|
| 18 | G3451 | AP2: 80-146<br>B3: 209-308 | SSKYKGVVPQPNG<br>RWGAQIYEKHQRV<br>WLGTFNEEDEAAR<br>AYDIAAQRFRGKD<br>AVTNFKPLAGADDDD | 81% | LFEKAVTPSDVGKLN<br>RLVIPKQHAEKHFPL<br>QSSNGVSATTIAAVT<br>ATPTAAKGVLLNFED<br>VGGKVWRFRYSYW<br>NSSQSYVLTKGWSRF<br>VKEKNLKAGDTV | 78% | Yes |
| 26 | G3454 | AP2: 74-139<br>B3: 203-302 | SSKYKGVVPQPNG<br>RWGSQIYEKHQRV<br>WLGTFNEEDEAAR<br>AYDVAVQRFRGKD<br>SVTNFKPLAGADDD | 81% | LFEKAVTPSDVWKL<br>NRLVIPKQHAEKHFP<br>LQSSNGVSATTIAAV<br>TATPTAAKGVLLNFE<br>DVGGKVWRFRYSY<br>WNSSQSYVLTKGWS<br>RFVKEKNLKAGDTV | 77% | No data |
| 30 | G3388 | AP2: 66-131<br>B3: 181-274 | SSRYKGVVPQPNG<br>RWGAQIYERHARV<br>WLGTFPDEEAAAR<br>AYDVAALRYRGRD<br>AATNFPGAAASAAE | 78% | LFEKAVTPSDVGKLN<br>RLVVPKQHAEKHFPL<br>RRAASSDSASAAATG<br>KGVLLNFEDGEGKV<br>WRFRYSYWNSSQSY<br>VLTKGWSRFVREKG<br>LRAGDTI | 76% | No data |
| 50 | CC616336 | AP2: 63-128<br>B3: 197-291 | SSKYKGVVPQPNG<br>RWGAQIYERHQRV<br>WLGTFTGEAEAAR<br>AYDVAAQRFRGRD<br>AVTNFRPLAESEPE | 78% | LFDKTVTPSDVGKLN<br>RLVIPKQHAEKHFPL<br>QLPAAAAAGVGSGG<br>ECKGVLLNFEDAAG<br>KAWRFRYSYWNSSQ<br>SYVLTKGWSRFVKE<br>KGLHAGDAV | 74% | No data |
| 34 | G3390 | AP2: 66-131<br>B3: 192-294 | SSKYKGVVPQPNG<br>RWGAQIYERHQRV<br>WLGTFTGEAEAAR<br>AYDVAAQRFRGRD<br>AVTNFRPLAESDPE | 77% | LFDKTVTPSDVGKLN<br>RLVIPKQHAEKHFPL<br>QLPPPTTTSSVAAAA<br>DAAAGGGDCKGVLL<br>NFEDAAGKVWKFRY<br>SYWNSSQSYVLTKG<br>WSRFVKEKGLHAGDAV | 70% | Yes |
| 52 | AAAA01000997 | AP2: 66-131<br>B3: 192-294 | SSKYKGVVPQPNG<br>RWGAQIYERHQRV<br>WLGTFTGEAEAAR<br>AYDVAAQRFRGRD<br>AVTNFRPLAESDPE | 77% | LFDKTVTPSDVGKLN<br>RLVIPKQHAEKHFPL<br>QLPPPTTTSSVAAAA<br>DAAAGGGECKGVLL<br>NFEDAAGKVWKFRY<br>SYWNSSQSYVLTKG<br>WSRFVKDKGLHAGDAV | 69% | No data |
| 48 | BT009310 | AP2: 64-129<br>B3: 200-291 | SSKYKGVVPQPNG<br>RWGAQIYERHQRV<br>WLGTFTGEAEAAR<br>AYDAAAQRFRGRD<br>AVTNFRPLTESDPE | 75% | LFDKTVTPSDVGKLN<br>RLVIPKQHAEKHFPL<br>QLPSAGAAVSGECKG<br>MLLNFDDSAGKVWR<br>FRYSYWNSSQSYVLT<br>KGWSRFVKEKGLHA<br>DGAV | 78% | No data |

*preliminary data indicates a "borderline hit" having an ABA insensitive phenotype in one overexpressing line; one line is also more tolerant to sucrose and cold in germination assays Generally, the transcription factors of the present invention possess an AP2 domain and a B3 domain (examples of useful artificial constructs that lack one or the other domain are noted in Example X). The present invention also includes fragments of such transcription factors, which may be comprised of both, or only one, of these binding domains. The latter is true for the full-length orthologs of G867 found by BLAST analysis, as described below. Generally, the AP2 domain of the transcription factors will bind to a transcription regulating region comprising the motif CAACA, and the B3 domain of the same transcription factor binds to a second transcription regulating region comprising the motif CAC- CTG. Each of these transcription factors also comprise an amino acid subsequence that forms a transcription activation domain that regulates expression of one or more abiotic stress tolerance genes in a plant when the transcription factor binds to the regulating region. As shown in Table 1, the AP2 and B3 domains of the transcription factors within the G867 clade are at least 75% (for the AP2 domain) and 69% (for the B3 domain) identical to the corresponding domains of G867, and all four of these transcription factors, which rely on the binding specificity of their conserved AP2 and B3 domains, have very similar or identical functions in plants, conferring increased abiotic, including osmotic, stress tolerance when overexpressed.

Therefore, the invention provides polynucleotides comprising: *Arabidopsis* SEQ ID NOs: 1, 3, 5, 7, and fragments thereof; and non-*Arabidopsis* sequences SEQ ID NOs: 11, 13, 15, 17, 19, 21, 23, 25, 27, 29, 31, 33, 35, 37, 39, 41, 43, 45, 47, 49, 51, paralogs, orthologs, equivalogs, and fragments thereof. The invention also provides polypeptides and the polynucleotides that encode them, said polypeptides comprising: *Arabidopsis* SEQ ID NOs: 2, 4, 6, 8, and fragments thereof, and non-*Arabidopsis* SEQ ID NOs: 10, 12, 14, 16, 18, 20, 22, 24, 26, 28, 30, 32, 34, 36, 38, 40, 42, 44, 46, 48, 50, 52, 53, paralogs, orthologs, equivalogs, and fragments thereof. A number of these polynucleotides have been shown to have a strong association with osmotic stress tolerance, in that plants that overexpress these sequences are more tolerant to these stresses. The invention also encompasses a complement of the polynucleotides. The polynucleotides are useful for screening libraries of molecules or compounds for specific binding and for creating transgenic plants having increased osmotic stress tolerance.

A number of the polynucleotides of the invention have been, and the remainder of the polynucleotides of the invention may be, ectopically expressed in overexpressor or knockout plants and the changes in the characteristic(s) or trait(s) of the plants observed. Therefore, the polynucleotides and polypeptides can be employed to improve the characteristics of plants.

The polynucleotides are particularly useful when they are hybridizable array elements in a microarray. Such a microarray can be employed to monitor the expression of genes that are differentially expressed in response to osmotic stresses. The microarray can be used in large scale genetic or gene expression analysis of a large number of polynucleotides; or in the diagnosis of osmotic stress before phenotypic symptoms are evident. Furthermore, the microarray can be employed to investigate cellular responses, such as cell proliferation, transformation, and the like.

When the polynucleotides of the invention may also be used as hybridizable array elements in a microarray, the array elements are organized in an ordered fashion so that each element is present at a specified location on the substrate. Because the array elements are at specified locations on the substrate, the hybridization patterns and intensities (which together create a unique expression profile) can be interpreted in terms of expression levels of particular genes and can be correlated with a particular stress, pathology, or treatment.

The invention also entails an agronomic composition comprising a polynucleotide of the invention in conjunction with a suitable carrier and a method for altering a plant's trait using the composition.

The invention also encompasses transcription factor polypeptides that comprise the DML motif, which, in the case of G867, is HSKSEIVDMLRKHTYNEELEQS (SEQ ID NO: 64), or a motif that has 71% or greater identity to the DML motif of G867, and having substantially similar activity with that of SEQ ID NO: 2.

*Arabidopsis* sequences thought to be paralogous or otherwise highly related evolutionarily to G867 were aligned using Clustal X (version 1.81, Jun. 2000). Additionally, by BLASTP analysis of proprietary and public databases with protein sequences of this set, additional sequences were identified with a high degree of sequence relatedness to G867. A number of these genes and encoded sequences that are members of the G867 clade of transcription factor polypeptides are now known to enhance abiotic stress tolerance when overexpressed, and include *Arabidopsis* sequences G867 (SEQ ID NO: 1 and 2), G9 (SEQ ID NO: 3 and 4), G993 (SEQ ID NO: 5 and 6), G1930 (SEQ ID NO: 7 and 8), rice sequences G3389 (SEQ ID NO: 31 and 32), G3390 (SEQ ID NO: 33 and 34) and G3391 (SEQ ID NO: 35 an 36), and soy sequences G3451 (SEQ ID NO: 17 and 18), G3452 (SEQ ID NO: 21 and 22), and G3455 (SEQ ID NO: 27 and 28). These sequences were then aligned again, and a neighbor-joining algorithm used to generate a phylogenetic tree, using Clustal X v1.81's phylogenetic capabilities. In this alignment, G867 and it paralogs G9, G993 and G1930 appeared in a clade along with two soybean sequences and several rice sequences. Based on the utility of the *Arabidopsis* sequences, as noted below, and the evolutionary history revealed by analysis of the phylogenetic tree (that the last common ancestor of the monocots and the eudicots had only one gene corresponding to transcription factors of the present invention, which functioned in abiotic stress tolerance), transcription factors of the G867 clade comprise a number of genes involved in the control of abiotic stress tolerance.

Examination of the alignment of only those sequences in the G867 clade (having monocot and dicot subnodes), indicates 1) a high degree of conservation of the AP2 domains in all members of the clade, 2) a high degree of conservation of the B3 domains in all members of the clade; and 3) a high degree of conservation of an additional motif, the DML motif found between the AP2 and B3 domains in all members of the clade: (H/R S K Xa E/G I/V V D M L R K/R H T Y Xa E/D/N E L/F Xa Q/H S/N/R/G (where Xa is any amino acid), constituting positions 135-152 in G867, SEQ ID NO: 64. As a conserved motif found in G867 and its paralogs, the DML motif was used to identify additional orthologs of SEQ ID NO: 2. A significant number of sequences were found that had a minimum of 71% identity to the 22 residue DML motif of G867, a number of these motifs are shown in Table 2.

Upon translation of these nucleotide sequences in a frame that provided the identified conserved motif, all the resulting protein sequences were found to have either a conserved AP2 domain before the DMF motif, or a B3 domain after DML motif (i.e., in BU024575, BQ405698, BF424857, BZ458719, AP002913, and AX654438). The protein sequences having conserved AP2 and/or B3 domains in the expected location were aligned with the previously aligned set of AP2 and B3 sequences, and a neighbor-joining algorithm was used to generate a phylogenetic tree, as described above. In this tree, the additional sequences identified through the DML motif all were found within the G867 clade identified previously, indicating that the DML motif was successfully used to identify new orthologs of G867, listed in Table 2. Many of these sequences confer abiotic stress tolerant phenotypes when overexpressed in plants, as indicated in the last column of Table 2 (an empty cell in this column indicates a sequence that has not yet been tested in this study). These functional polypeptide sequences include DML motifs with 76% or greater identity to the DML motif of G867.

TABLE 2

Similarity of the DML motifs in G867 clade sequences

| SEQ ID NO: | Identifier or Accession No. | Species | DML motif | SEQ ID NO: of DML motif | Identity (%) with the DML motif of G867 | Abiotic Stress Tolerance Phenotype |
|---|---|---|---|---|---|---|
| 2 | G867 | *Arabidopsis thaliana* | HSKSEIVDMLRKHTYNEELEQS | 64 | 100% | Yes |
| 28 | G3455 | *Glycine max* | HSKSEIVDMLRKHTYNDELEQS | 96 | 95% | Yes |
| 71 | BU024575 | *Helianthus annuus* | HSKSEIVDMLRKHTYNDELEQS | 96 | 95% | |
| 72 | BQ137035 | *Medicago truncatula* | HSKSEIVDMLRKHTYNDELEQS | 96 | 95% | |
| 73 | AV412541 | *Lotus japonicus* | HSKSEIVDMLRKHTYNDELEQS | 96 | 95% | |
| 8 | G1930 | *Arabidopsis thaliana* | HSKSEIVDMLRKHTYKEELDQR | 97 | 90% | Yes |
| 18 | G3451 | *Glycine max* | HSKPEIVDMLRKHTYNDELEQS | 98 | 90% | Yes |
| 42 | BZ458719 | *Brassica oleracea* | HSKYEIVDMLRKHTYKEELEQR | 99 | 90% | |
| 74 | BU871082 | *Populus balsamifera* subsp. *Trichocarpa* | HSKAEIVDMLRKHTYNDELEQS | 100 | 90% | |
| 75 | BG524914 | *Stevia rebaudiana* | HSKAEIVDMLRKHTYNDELEQS | 100 | 90% | |
| 76 | BQ405698 | *Gossypium arboreum* | HSKAEIVDMLRKHTYNDELEQS | 100 | 90% | |
| 77 | BF424857 | *Glycine max* | HSKPEIVDMLRKHTYDNELEQS | 98 | 90% | |
| 78 | CB686050 | *Brassica napus* | HSKSGIVDMLRKHTYSEELEQS | 101 | 90% | |
| 46 | BU025988 | *Helianthus annuus* | HSESEIVDMLRKHTYNDELEQS | 102 | 90% | |
| 79 | BQ855250 | *Lactuca sativa* | HSKAEIVDMLRKHTYNDELQQS | 103 | 86% | |
| 80 | BM878902 | *Ipomoea batatas* | HSKAEIVDMLRKHTYADELEQS | 104 | 86% | |
| 81 | BG590382 | *Solanum tuberosum* | HSKAEIVDMLRKHTYLDELEQS | 105 | 86% | |
| 82 | BG124312 | *Lycopersicon esculentum* | HSKAEIVDMLRKHTYIDELEQS | 106 | 86% | |
| 26 | G3454 | *Glycine max* | HSKPEIVDMLRKHTYNDELEHS | 107 | 86% | |
| 44 | BQ971511 | *Helianthus annuus* | HSKSEIVDMLRKHTYNDELEQS | 96 | 86% | |
| 50 | CC616336 | *Zea mays* | RSKAEVVDMLRKHTYGEELAHN | 108 | 83% | |
| 4 | G9 | *Arabidopsis thaliana* | HSKAEIVDMLRKHTYADELEQN | 109 | 81% | Yes |
| 6 | G993 | *Arabidopsis thaliana* | HSKAEIVDMLRKHTYADEFEQS | 110 | 81% | Yes |
| 22 | G3452 | *Glycine max* | HSKFEIVDMLRKHTYDDELQQS | 111 | 81% | Yes |
| 24 | G3453 | *Glycine max* | HSKSEIVDMLRRHTYDNELQQS | 112 | 81% | |
| 30 | G3388 AP002913 | *Oryza sativa* (japonica cultivar-group) | HSKAEIVDMLRKHTYADELRQG | 113 | 80% | |
| 83 | CA004137 | *Hordeum vulgare* subsp. *vulgare* | HSKAEIVMLRKHTYDDELRQG | 114 | 80% | |
| 32 | G3389 | *Oryza sativa* (japonica cultivar-group) | HSKAEVVDMLRKHTYDDELQQG | 115 | 76% | Yes |
| 34 | G3390 | *Oryza sativa* (japonica cultivar-group) | RSKAEVVDMLRKHTYLEELTQN | 116 | 76% | Yes |
| 36 | G3391 | *Oryza sativa* (japonica cultivar-group) | RSKAEVVDMLRKHTYFDELAQS | 117 | 76% | Yes |
| 40 | G3433 | *Zea mays* | RSKAEVVDMLRKHTYGEELAQN | 118 | 76% | |
| 84 | AX654438 | *Oryza sativa* | HSKAEVVDMLRKHTYDDELQQG | 115 | 76% | |

TABLE 2-continued

Similarity of the DML motifs in G867 clade sequences

| SEQ ID NO: | Identifier or Accession No. | Species | DML motif | SEQ ID NO: of DML motif | Identity (%) with the DML motif of G867 | Abiotic Stress Tolerance Phenotype |
|---|---|---|---|---|---|---|
| 52 | AAAA01000997 | Oryza sativa | RSKAEVVDMLRKHTYLEELTQN | 116 | 76% | |
| 48 | BT009310 | Triticum aestivum | RSKAEVVDMLRKHTYPDELAQY | 119 | 75% | |
| 38 | G3432 | Zea mays | RSKAEVVDMLRKHTYFDELAQN | 120 | 71% | Yes* |

Figure 3:
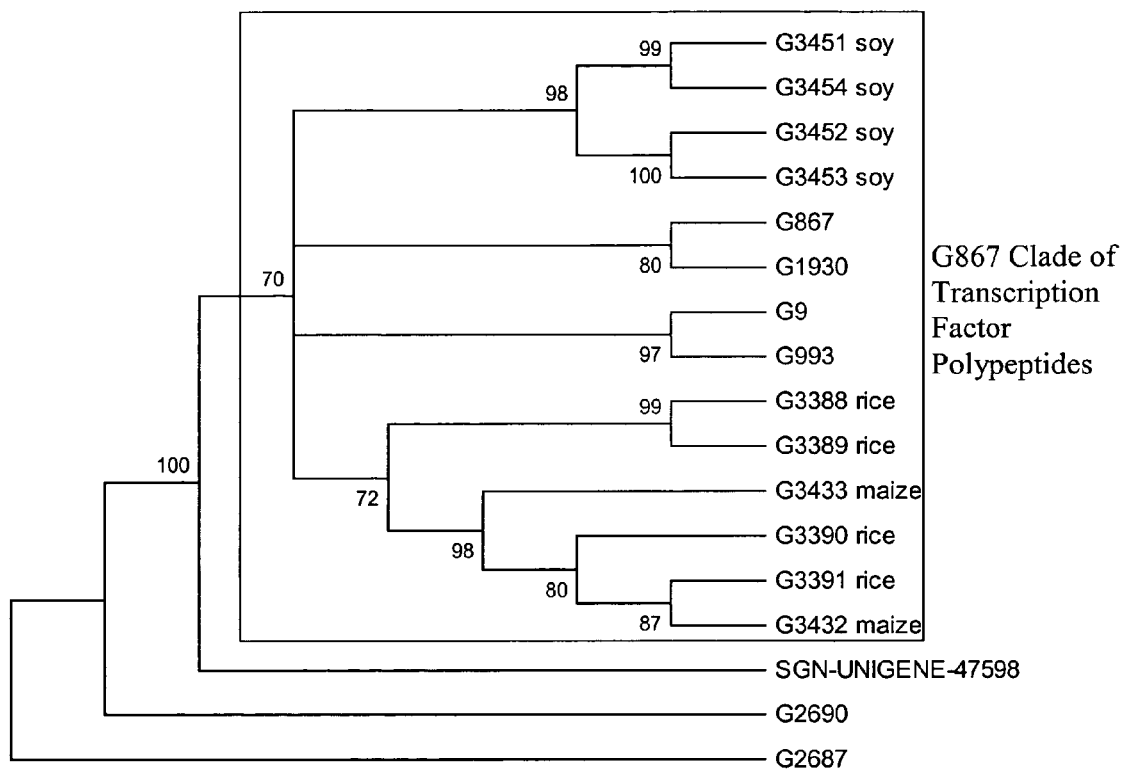
FIG. 3 depicts a phylogenetic tree of several members of the RAV family, identified through BLAST analysis of proprietary (using corn, soy and rice genes) and public data sources (all plant species). This tree was generated as a Clustal X 1.81 alignment: MEGA2 tree, Maximum Parsimony, bootstrap consensus.
Figure 4D:
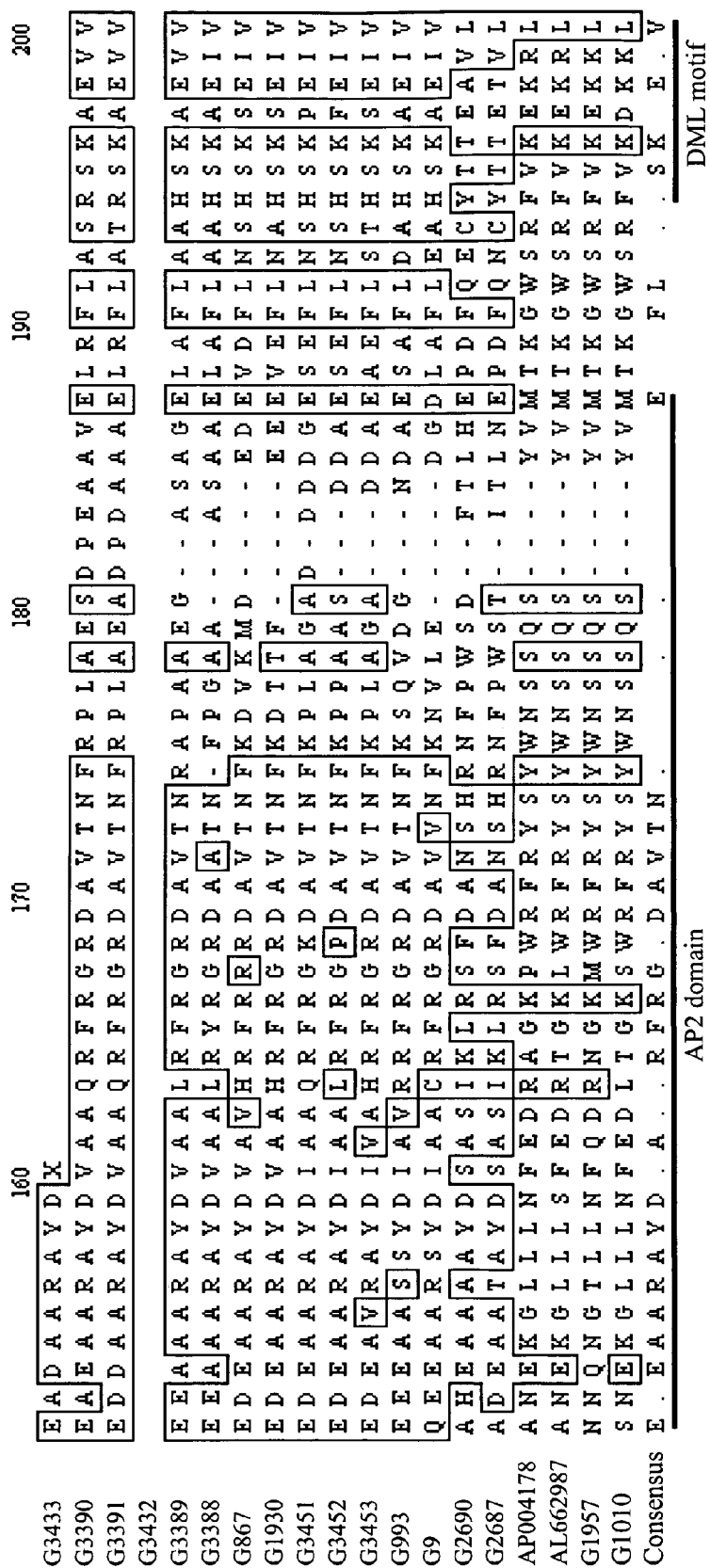

*preliminary data indicates a "borderline hit" having an ABA insensitive phenotype in one overexpressing line; one line is also more tolerant to sucrose and cold in germination assays Characteristics of the G867 Clade of Transcription Factor Polypeptides The polypeptide members of the invention belong to the G867 clade of transcription factor polypeptides, and, being a set of equivalogs, have conserved functional characteristics and derive from a last common ancestor as shown in FIG. 3. The G867 clade of transcription factor polypeptides each have, in order from N– to C termini, an AP2 domain, a DML motif, and a B3 domain. The AP2 and B3 domains bind to bipartite recognition sequences of DNA.

The DML motif, for which a function has not yet been determined, will generally comprise the consensus sequence:
Ser-Lys-Xaa-Glu-Xaa-Val-Asp-Met-Leu-Arg-Lys-His-Thr-Tyr-Xaa-Xaa-Glu (SEQ ID NO: 85) where Xaa can be any amino acid residue.

Producing Polypeptides

The polynucleotides of the invention include sequences that encode transcription factors and transcription factor homolog polypeptides and sequences complementary thereto, as well as unique fragments of coding sequence, or sequence complementary thereto. Such polynucleotides can be, for example, DNA or RNA, the latter including mRNA, cRNA, synthetic RNA, genomic DNA, cDNA synthetic DNA, oligonucleotides, etc. The polynucleotides are either double-stranded or single-stranded, and include either, or both sense (i.e., coding) sequences and antisense (i.e., non-coding, complementary) sequences. The polynucleotides include the coding sequence of a transcription factor, or transcription factor homolog polypeptide, in isolation, in combination with additional coding sequences (e.g., a purification tag, a localization signal, as a fusion-protein, as a pre-protein, or the like), in combination with non-coding sequences (for example, introns or inteins, regulatory elements such as promoters, enhancers, terminators, and the like), and/or in a vector or host environment in which the polynucleotide encoding a transcription factor or transcription factor homolog polypeptide is an endogenous or exogenous gene.

A variety of methods exist for producing the polynucleotides of the invention. Procedures for identifying and isolating DNA clones are well known to those of skill in the art, and are described in, for example, Berger and Kimmel, *Guide to Molecular Cloning Techniques, Methods in Enzymology*, vol. 152 Academic Press, Inc., San Diego, Calif. ("Berger"); Sambrook et al. *Molecular Cloning—A Laboratory Manual* (2nd Ed.), Vol. 1-3, Cold Spring Harbor Laboratory, Cold Spring Harbor, N.Y., 1989 ("Sambrook") and *Current Protocols in Molecular Biology*, Ausubel et al. eds., Current Protocols, a joint venture between Greene Publishing Associates, Inc. and John Wiley & Sons, Inc., (supplemented through 2000) ("Ausubel").

Alternatively, polynucleotides of the invention, can be produced by a variety of in vitro amplification methods adapted to the present invention by appropriate selection of specific or degenerate primers. Examples of protocols sufficient to direct persons of skill through in vitro amplification methods, including the polymerase chain reaction (PCR) the ligase chain reaction (LCR), Qbeta-replicase amplification and other RNA polymerase mediated techniques (for example, NASBA), e.g., for the production of the homologous nucleic acids of the invention are found in Berger (supra), Sambrook (supra), and Ausubel (supra), as well as Mullis et al. (1987) *PCR Protocols A Guide to Methods and Applications* (Innis et al. eds) Academic Press Inc. San Diego, Calif. (1990) (Innis). Improved methods for cloning in vitro amplified nucleic acids are described in Wallace et al. U.S. Pat. No. 5,426,039. Improved methods for amplifying large nucleic acids by PCR are summarized in Cheng et al. (1994) *Nature* 369: 684-685 and the references cited therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, e.g., Ausubel, Sambrook and Berger, all supra.

Alternatively, polynucleotides and oligonucleotides of the invention can be assembled from fragments produced by solid-phase synthesis methods. Typically, fragments of up to approximately 100 bases are individually synthesized and then enzymatically or chemically ligated to produce a desired sequence, e.g., a polynucleotide encoding all or part of a transcription factor. For example, chemical synthesis using the phosphoramidite method is described, e.g., by Beaucage et al. (1981) *Tetrahedron Letters* 22: 1859-1869; and Matthes et al. (1984) *EMBO J.* 3: 801-805. According to such methods, oligonucleotides are synthesized, purified, annealed to their complementary strand, ligated and then optionally cloned into suitable vectors. And if so desired, the polynucleotides and polypeptides of the invention can be custom ordered from any of a number of commercial suppliers.

Homologous Sequences

Sequences homologous, i.e., that share significant sequence identity or similarity, to those provided in the Sequence Listing, derived from *Arabidopsis thaliana* or from other plants of choice, are also an aspect of the invention. Homologous sequences can be derived from any plant including monocots and dicots and in particular agriculturally important plant species, including but not limited to, crops such as soybean, wheat, corn (maize), potato, cotton, rice, rape, oilseed rape (including canola), sunflower, alfalfa, clover, sugarcane, and turf; or fruits or fruit trees, vegetables such as banana, blackberry, blueberry, strawberry, and raspberry, cantaloupe, carrot, cauliflower, coffee, cucumber, eggplant, grapes, honeydew, lettuce, mango, melon, onion, papaya, peas, peppers, pineapple, pumpkin, spinach, squash, sweet corn, tobacco, tomato, tomatillo, watermelon, rosaceous fruits (such as apple, peach, pear, cherry and plum) and brassicas (such as broccoli, cabbage, cauliflower, Brussels sprouts, and kohlrabi). Other crops, including fruits and vegetables, whose phenotype can be changed and which comprise homologous sequences include barley; rye; millet; sorghum; currant; avocado; citrus fruits such as oranges, lemons, grapefruit and tangerines, artichoke, cherries; nuts such as the walnut and peanut; endive; leek; roots such as arrowroot, beet, cassaya, turnip, radish, yam, and sweet potato; and beans. The homologous sequences may also be derived from woody species, such pine, poplar and eucalyptus, or mint or other labiates. In addition, homologous sequences may be derived from plants that are evolutionarily related to crop plants, but which may not have yet been used as crop plants. Examples include deadly nightshade (*Atropa belladona*), related to tomato; jimson weed (*Datura strommium*), related to peyote; and teosinte (*Zea* species), related to corn (maize).

Orthologs and Paralogs

Homologous sequences as described above can comprise orthologous or paralogous sequences. Several different methods are known by those of skill in the art for identifying and defining these functionally homologous sequences. Three general methods for defining orthologs and paralogs are described; an ortholog, paralog or homolog may be identified by one or more of the methods described below.

Orthologs and paralogs are evolutionarily related genes that have similar sequence and similar functions. Orthologs are structurally related genes in different species that are derived by a speciation event. Paralogs are structurally related genes within a single species that are derived by a duplication event.

Within a single plant species, gene duplication may cause two copies of a particular gene, giving rise to two or more genes with similar sequence and often similar function known as paralogs. A paralog is therefore a similar gene formed by duplication within the same species. Paralogs typically cluster together or in the same dade (a group of similar genes) when a gene family phylogeny is analyzed using programs such as CLUSTAL (Thompson et al. (1994) *Nucleic Acids Res.* 22: 4673-4680; Higgins et al. (1996) *Methods Enzymol.* 266: 383-402). Groups of similar genes can also be identified with pair-wise BLAST analysis (Feng and Doolittle (1987) *J. Mol. Evol.* 25: 351-360). For example, a clade of very similar MADS domain transcription factors from *Arabidopsis* all share a common function in flowering time (Ratcliffe et al. (2001) *Plant Physiol.* 126: 122-132), and a group of very similar AP2 domain transcription factors from *Arabidopsis* are involved in tolerance of plants to freezing (Gilmour et al. (1998) *Plant J* 16: 433-442). Analysis of groups of similar genes with similar function that fall within one clade can yield sub-sequences that are particular to the lade. These sub-sequences, known as consensus sequences, can not only be used to define the sequences within each clade, but define the functions of these genes; genes within a dade may contain paralogous sequences, or orthologous sequences that share the same function (see also, for example, Mount (2001), in *Bioinformatics: Sequence and Genome Analysis* Cold Spring Harbor Laboratory Press, Cold Spring Harbor, N.Y., page 543.)

Speciation, the production of new species from a parental species, can also give rise to two or more genes with similar sequence and similar function. These genes, termed orthologs, often have an identical function within their host plants and are often interchangeable between species without losing function. Because plants have common ancestors, many genes in any plant species will have a corresponding orthologous gene in another plant species. Once a phylogenic tree for a gene family of one species has been constructed using a program such as CLUSTAL (Thompson et al. (1994) *Nucleic Acids Res.* 22: 4673-4680; Higgins et al. (1996) supra) potential orthologous sequences can be placed into the phylogenetic tree and their relationship to genes from the species of interest can be determined. Orthologous sequences can also be identified by a reciprocal BLAST strategy. Once an orthologous sequence has been identified, the function of the ortholog can be deduced from the identified function of the reference sequence.

Transcription factor gene sequences are conserved across diverse eukaryotic species lines (Goodrich et al. (1993) *Cell* 75: 519-530; Lin et al. (1991) *Nature* 353: 569-571; Sadowski et al. (1988) *Nature* 335: 563-564). Plants are no exception to this observation; diverse plant species possess transcription factors that have similar sequences and functions.

Orthologous genes from different organisms have highly conserved functions, and very often essentially identical functions (Lee et al. (2002) *Genome Res.* 12: 493-502; Remm et al. (2001) *J. Mol. Biol.* 314: 1041-1052). Paralogous genes, which have diverged through gene duplication, may retain similar functions of the encoded proteins. In such cases, paralogs can be used interchangeably with respect to certain embodiments of the instant invention (for example, transgenic expression of a coding sequence). An example of such highly related paralogs is the CBF family, with four well-defined members in *Arabidopsis* (SEQ ID NOs: 54, 56, 58, and GenBank accession number AB015478) and at least one ortholog in *Brassica napus*, (SEQ ID NO: 60), all of which control pathways involved in both freezing and drought stress (Gilmour et al. (1998) *Plant J.* 16: 433-442; Jaglo et al. (1998) *Plant Physiol.* 127: 910-917).

The following references represent a small sampling of the many studies that demonstrate that conserved transcription factor genes from diverse species are likely to function similarly (i.e., regulate similar target sequences and control the same traits), and that transcription factors may be transformed into diverse species to confer or improve traits.

(1) The *Arabidopsis* NPR1 gene regulates systemic acquired resistance (SAR) (Cao et al. (1997) *Cell* 88: 57-63); over-expression of NPR1 leads to enhanced resistance in *Arabidopsis*. When either *Arabidopsis* NPR1 or the rice NPR1 ortholog was overexpressed in rice (which, as a monocot, is diverse from *Arabidopsis*), challenge with the rice bacterial blight pathogen *Xanthomonas oryzae* pv. *Oryzae*, the transgenic plants displayed enhanced resistance (Chern et al. (2001) *Plant J* 27: 101-113). NPR1 acts through activation of expression of transcription factor genes, such as TGA2 (Fan and Dong (2002) *Plant Cell* 14: 1377-1389).

(2) E2F genes are involved in transcription of plant genes for proliferating cell nuclear antigen (PCNA). Plant E2Fs share a high degree of similarity in amino acid sequence between monocots and dicots, and are even similar to the conserved domains of the animal E2Fs. Such conservation indicates a functional similarity between plant and animal E2Fs. E2F transcription factors that regulate meristem development act through common cis-elements, and regulate related (PCNA) genes (Kosugi and Ohashi, (2002) *Plant J.* 29: 45-59).

(3) The ABI5 gene (ABA insensitive 5) encodes a basic leucine zipper factor required for ABA response in the seed and vegetative tissues. Co-transformation experiments with ABI5 cDNA constructs in rice protoplasts resulted in specific transactivation of the ABA-inducible wheat, *Arabidopsis*, bean, and barley promoters. These results demonstrate that sequentially similar ABI5 transcription factors are key targets of a conserved ABA signaling pathway in diverse plants. (Gampala et al. (2001) *J. Biol. Chem.* 277: 1689-1694).

(4) Sequences of three *Arabidopsis* GAMYB-like genes were obtained on the basis of sequence similarity to GAMYB genes from barley, rice, and *L. temulentum*. These three *Arabadopsis* genes were determined to encode transcription factors (AtMYB33, AtMYB65, and AtMYB101) and could substitute for a barley GAMYB and control alpha-amylase expression (Gocal et al. (2001) *Plant Physiol.* 127: 1682-1693).

(5) The floral control gene LEAFY from *Arabidopsis* can dramatically accelerate flowering in numerous dictoyledonous plants. Constitutive expression of *Arabidopsis* LEAFY also caused early flowering in transgenic rice (a monocot), with a heading date that was 26-34 days earlier than that of wild-type plants. These observations indicate that floral regulatory genes from *Arabidopsis* are useful tools for heading date improvement in cereal crops (He et al. (2000) *Transgenic Res.* 9: 223-227).

(6) Bioactive gibberellins (GAs) are essential endogenous regulators of plant growth. GA signaling tends to be conserved across the plant kingdom. GA signaling is mediated via GAI, a nuclear member of the GRAS family of plant transcription factors. *Arabidopsis* GAI has been shown to function in rice to inhibit gibberellin response pathways (Fu et al. (2001) *Plant Cell* 13: 1791-1802).

(7) The *Arabidopsis* gene SUPERMAN (SUP), encodes a putative transcription factor that maintains the boundary between stamens and carpels. By over-expressing *Arabidopsis* SUP in rice, the effect of the gene's presence on whorl boundaries was shown to be conserved. This demonstrated that SUP is a conserved regulator of floral whorl boundaries and affects cell proliferation (Nandi et al. (2000) *Curr. Biol.* 10: 215-218).

(8) Maize, petunia and *Arabidopsis* myb transcription factors that regulate flavonoid biosynthesis are very genetically similar and affect the same trait in their native species, therefore sequence and function of these myb transcription factors correlate with each other in these diverse species (Borevitz et al. (2000) *Plant Cell* 12: 2383-2394).

(9) Wheat reduced height-1 (Rht-B1/Rht-D1) and maize dwarf-8 (d8) genes are orthologs of the *Arabidopsis* gibberellin insensitive (GAI) gene. Both of these genes have been used to produce dwarf grain varieties that have improved grain yield. These genes encode proteins that resemble nuclear transcription factors and contain an SH2-like domain, indicating that phosphotyrosine may participate in gibberellin signaling. Transgenic rice plants containing a mutant GAI allele from *Arabidopsis* have been shown to produce reduced responses to gibberellin and are dwarfed, indicating that mutant GAI orthologs could be used to increase yield in a wide range of crop species (Peng et al. (1999) *Nature* 400: 256-261).

Transcription factors that are homologous to the listed sequences will typically share at least about 75% and 69% amino acid sequence identity in the AP2 and B3 domains, respectively. More closely related transcription factors can share at least about 81% and about 78% amino acid sequence identity in the AP2 and B3 domains, respectively, or more sequence identity with the listed sequences, or with the listed sequences but excluding or outside a known consensus sequence or consensus DNA-binding site, or with the listed sequences excluding one or all conserved domains. At the nucleotide level, the sequences will typically share at least about 40% nucleotide sequence identity, preferably at least about 50%, about 60%, about 70% or about 80% sequence identity, and more preferably about 85%, about 90%, about 95% or about 97% or more sequence identity to one or more of the listed sequences, or to a listed sequence but excluding or outside a known consensus sequence or consensus DNA-binding site, or outside one or all conserved domain. The degeneracy of the genetic code enables major variations in the nucleotide sequence of a polynucleotide while maintaining the amino acid sequence of the encoded protein. AP2 domains within the AP2 transcription factor family may exhibit a higher degree of sequence homology, such as at least 77% amino acid sequence identity including conservative substitutions, and preferably at least 80% sequence identity, and more preferably at least 85%, or at least about 86%, or at least about 87%, or at least about 88%, or at least about 90%, or at least about 95%, or at least about 98% sequence identity. Transcription factors that are homologous to the listed sequences should share at least 30%, or at least about 60%, or at least about 75%, or at least about 80%, or at least about 90%, or at least about 95% amino acid sequence identity over the entire length of the polypeptide or the homolog.

Percent identity can be determined electronically, e.g., by using the MEGALIGN program (DNASTAR, Inc. Madison, Wis.). The MEGALIGN program can create alignments between two or more sequences according to different methods, for example, the clustal method. (See, for example, Higgins and Sharp (1988) *Gene* 73: 237-244.) The clustal algorithm groups sequences into clusters by examining the distances between all pairs. The clusters are aligned pairwise and then in groups. Other alignment algorithms or programs may be used, including FASTA, BLAST, or ENTREZ, FASTA and BLAST, and which may be used to calculate percent similarity. These are available as a part of the GCG sequence analysis package (University of Wisconsin, Madison, Wis.), and can be used with or without default settings. ENTREZ is available through the National Center for Biotechnology Information. In one embodiment, the percent identity of two sequences can be determined by the GCG program with a gap weight of 1, e.g., each amino acid gap is weighted as if it were a single amino acid or nucleotide mismatch between the two sequences (see U.S. Pat. No. 6,262,333).

Other techniques for alignment are described in *Methods in Enzymology*, vol. 266, *Computer Methods for Macromolecular Sequence Analysis* (1996), ed. Doolittle, Academic Press, Inc., San Diego, Calif., USA. Preferably, an alignment program that permits gaps in the sequence is utilized to align the sequences. The Smith-Waterman is one type of algorithm that permits gaps in sequence alignments (see Shpaer (1997) *Methods Mol. Biol.* 70: 173-187). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

The percentage similarity between two polypeptide sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between polynucleotide sequences can also be counted or calculated by other methods known in the art, e.g., the Jotun Hein method. (See, e.g., Hein (1990) *Methods Enzymol.* 183: 626-645.) Identity between sequences can also be determined by other methods known in the art, e.g., by varying hybridization conditions (see U.S. Patent Application No. 20010010913).

Thus, the invention provides methods for identifying a sequence similar or paralogous or orthologous or homologous to one or more polynucleotides as noted herein, or one or more target polypeptides encoded by the polynucleotides, or otherwise noted herein and may include linking or associating a given plant phenotype or gene function with a sequence. In the methods, a sequence database is provided (locally or across an internet or intranet) and a query is made against the sequence database using the relevant sequences herein and associated plant phenotypes or gene functions.

In addition, one or more polynucleotide sequences or one or more polypeptides encoded by the polynucleotide sequences may be used to search against a BLOCKS (Bairoch et al. (1997) *Nucleic Acids Res.* 25: 217-221), PFAM, and other databases which contain previously identified and annotated motifs, sequences and gene functions. Methods that search for primary sequence patterns with secondary structure gap penalties (Smith et al. (1992) *Protein Engineering* 5: 35-51) as well as algorithms such as Basic Local Alignment Search Tool (BLAST; Altschul (1993) *J. Mol. Evol.* 36: 290-300; Altschul et al. (1990) supra), BLOCKS (Henikoff and Henikoff (1991) *Nucleic Acids Res.* 19: 6565-6572), Hidden Markov Models (HMM; Eddy (1996) *Curr. Opin. Str. Biol.* 6: 361-365; Sonnhammer et al. (1997) *Proteins* 28: 405-420), and the like, can be used to manipulate and analyze polynucleotide and polypeptide sequences encoded by polynucleotides. These databases, algorithms and other methods are well known in the art and are described in Ausubel et al. (1997; *Short Protocols in Molecular Biology*, John Wiley & Sons, New York, N.Y., unit 7.7) and in Meyers (1995; *Molecular Biology and Biotechnology*, Wiley VCH, New York, N.Y., p 856-853).

A further method for identifying or confirming that specific homologous sequences control the same function is by comparison of the transcript profile(s) obtained upon overexpression or knockout of two or more related transcription factors. Since transcript profiles are diagnostic for specific cellular states, one skilled in the art will appreciate that genes that have a highly similar transcript profile (e.g., with greater than 50% regulated transcripts in common, more preferably with greater than 70% regulated transcripts in common, most preferably with greater than 90% regulated transcripts in common) will have highly similar functions. Fowler et al. (2002, *Plant Cell*, 14: 1675-79) have shown that three paralogous AP2 family genes (CBF1, CBF2 and CBF3), each of which is induced upon cold treatment, and each of which can condition improved freezing tolerance, have highly similar transcript profiles. Once a transcription factor has been shown to provide a specific function, its transcript profile becomes a diagnostic tool to determine whether putative paralogs or orthologs have the same function.

Furthermore, methods using manual alignment of sequences similar or homologous to one or more polynucleotide sequences or one or more polypeptides encoded by the polynucleotide sequences may be used to identify regions of similarity and AP2 binding domains. Such manual methods are well-known of those of skill in the art and can include, for example, comparisons of tertiary structure between a polypeptide sequence encoded by a polynucleotide which comprises a known function with a polypeptide sequence encoded by a polynucleotide sequence which has a function not yet determined. Such examples of tertiary structure may comprise predicted alpha helices, beta-sheets, amphipathic helices, leucine zipper motifs, zinc finger motifs, proline-rich regions, cysteine repeat motifs, and the like.

Orthologs and paralogs of presently disclosed transcription factors may be cloned using compositions provided by the present invention according to methods well known in the art. cDNAs can be cloned using mRNA from a plant cell or tissue that expresses one of the present transcription factors. Appropriate mRNA sources may be identified by interrogating Northern blots with probes designed from the present transcription factor sequences, after which a library is prepared from the mRNA obtained from a positive cell or tissue. Transcription factor-encoding cDNA is then isolated using, for example, PCR, using primers designed from a presently disclosed transcription factor gene sequence, or by probing with a partial or complete cDNA or with one or more sets of degenerate probes based on the disclosed sequences. The cDNA library may be used to transform plant cells. Expression of the cDNAs of interest is detected using, for example, methods disclosed herein such as microarrays, Northern blots, quantitative PCR, or any other technique for monitoring changes in expression. Genomic clones may be isolated using similar techniques to those.

Identifying Polynucleotides or Nucleic Acids by Hybridization

Polynucleotides homologous to the sequences illustrated in the Sequence Listing and tables can be identified, e.g., by hybridization to each other under stringent or under highly stringent conditions. Single stranded polynucleotides hybridize when they associate based on a variety of well characterized physical-chemical forces, such as hydrogen bonding, solvent exclusion, base stacking and the like. The stringency of a hybridization reflects the degree of sequence identity of the nucleic acids involved, such that the higher the stringency, the more similar are the two polynucleotide strands. Stringency is influenced by a variety of factors, including temperature, salt concentration and composition, organic and non-organic additives, solvents, etc. present in both the hybridization and wash solutions and incubations (and number thereof), as described in more detail in the references cited above.

Encompassed by the invention are polynucleotide sequences that are capable of hybridizing to the claimed polynucleotide sequences, including any of the transcription factor polynucleotides within the Sequence Listing, and fragments thereof under various conditions of stringency (See, for example, Wahl and Berger (1987) *Methods Enzymol.* 152: 399-407; and Kimmel (1987) *Methods Enzymol.* 152: 507-511). In addition to the nucleotide sequences in the Sequence Listing, full length cDNA, orthologs, and paralogs of the present nucleotide sequences may be identified and isolated using well-known methods. The cDNA libraries, orthologs, and paralogs of the present nucleotide sequences may be screened using hybridization methods to determine their utility as hybridization target or amplification probes.

With regard to hybridization, conditions that are highly stringent, and means for achieving them, are well known in the art. See, for example, Sambrook et al. (1989) "*Molecular Cloning: A Laboratory Manual*" (2nd ed., Cold Spring Harbor Laboratory); Berger and Kimmel, eds., (1987) "Guide to Molecular Cloning Techniques", In *Methods in Enzymology:* 152: 467-469; and Anderson and Young (1985) "Quantitative Filter Hybridisation." In: Harnes and Higgins, ed., *Nucleic Acid Hybridisation, A Practical Approach*. Oxford, IRL Press, 73-111.

Stability of DNA duplexes is affected by such factors as base composition, length, and degree of base pair mismatch.

Hybridization conditions may be adjusted to allow DNAs of different sequence relatedness to hybridize. The melting temperature ($T_m$) is defined as the temperature when 50% of the duplex molecules have dissociated into their constituent single strands. The melting temperature of a perfectly matched duplex, where the hybridization buffer contains formamide as a denaturing agent, may be estimated by the following equations:

$$T_m(°C.)=81.5+16.6(\log [Na+])+0.41(\% G+C)-0.62(\% \text{formamide})-500/L \quad \text{(I) DNA-DNA}$$

$$T_m(°C.)=79.8+18.5(\log [Na+])+0.58(\% G+C)+0.12(\% G+C)^2-0.5(\% \text{formamide})-820/L \quad \text{(II) DNA-RNA}$$

$$T_m(°C.)=79.8+18.5(\log [Na+])+0.58(\% G+C)+0.12(\% G+C)^2-0.35(\% \text{formamide})-820/L \quad \text{(III) RNA-RNA}$$

where L is the length of the duplex formed, [Na+] is the molar concentration of the sodium ion in the hybridization or washing solution, and % G+C is the percentage of (guanine+cytosine) bases in the hybrid. For imperfectly matched hybrids, approximately 1° C. is required to reduce the melting temperature for each 1% mismatch.

Hybridization experiments are generally conducted in a buffer of pH between 6.8 to 7.4, although the rate of hybridization is nearly independent of pH at ionic strengths likely to be used in the hybridization buffer (Anderson et al. (1985) supra). In addition, one or more of the following may be used to reduce non-specific hybridization: sonicated salmon sperm DNA or another non-complementary DNA, bovine serum albumin, sodium pyrophosphate, sodium dodecylsulfate (SDS), polyvinyl-pyrrolidone, ficoll and Denhardt's solution. Dextran sulfate and polyethylene glycol 6000 act to exclude DNA from solution, thus raising the effective probe DNA concentration and the hybridization signal within a given unit of time. In some instances, conditions of even greater stringency may be desirable or required to reduce non-specific and/or background hybridization. These conditions may be created with the use of higher temperature, lower ionic strength and higher concentration of a denaturing agent such as formamide.

Stringency conditions can be adjusted to screen for moderately similar fragments such as homologous sequences from distantly related organisms, or to highly similar fragments such as genes that duplicate functional enzymes from closely related organisms. The stringency can be adjusted either during the hybridization step or in the post-hybridization washes. Salt concentration, formamide concentration, hybridization temperature and probe lengths are variables that can be used to alter stringency (as described by the formula above). As a general guidelines high stringency is typically performed at $T_m$-5° C. to $T_m$-20° C., moderate stringency at $T_m$-20° C. to $T_m$-35° C. and low stringency at $T_m$-35° C. to $T_m$-50° C. for duplex>150 base pairs. Hybridization may be performed at low to moderate stringency (25-50° C. below $T_m$), followed by post-hybridization washes at increasing stringencies. Maximum rates of hybridization in solution are determined empirically to occur at $T_m$-25° C. for DNA-DNA duplex and $T_m$-15° C. for RNA-DNA duplex. Optionally, the degree of dissociation may be assessed after each wash step to determine the need for subsequent, higher stringency wash steps.

High stringency conditions may be used to select for nucleic acid sequences with high degrees of identity to the disclosed sequences. An example of stringent hybridization conditions obtained in a filter-based method such as a Southern or northern blot for hybridization of complementary nucleic acids that have more than 100 complementary residues is about 5° C. to 20° C. lower than the thermal melting point ($T_m$) for the specific sequence at a defined ionic strength and pH. Conditions used for hybridization may include about 0.02 M to about 0.15 M sodium chloride, about 0.5% to about 5% casein, about 0.02% SDS or about 0.1% N-laurylsarcosine, about 0.001 M to about 0.03 M sodium citrate, at hybridization temperatures between about 50° C. and about 70° C. More preferably, high stringency conditions are about 0.02 M sodium chloride, about 0.5% casein, about 0.02% SDS, about 0.001 M sodium citrate, at a temperature of about 50° C. Nucleic acid molecules that hybridize under stringent conditions will typically hybridize to a probe based on either the entire DNA molecule or selected portions, e.g., to a unique subsequence, of the DNA.

Stringent salt concentration will ordinarily be less than about 750 mM NaCl and 75 mM trisodium citrate. Increasingly stringent conditions may be obtained with less than about 500 mM NaCl and 50 mM trisodium citrate, to even greater stringency with less than about 250 mM NaCl and 25 mM trisodium citrate. Low stringency hybridization can be obtained in the absence of organic solvent, e.g., formamide, whereas high stringency hybridization may be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. with formamide present. Varying additional parameters, such as hybridization time, the concentration of detergent, e.g., sodium dodecyl sulfate (SDS) and ionic strength, are well known to those skilled in the art. Various levels of stringency are accomplished by combining these various conditions as needed.

The washing steps that follow hybridization may also vary in stringency; the post-hybridization wash steps primarily determine hybridization specificity, with the most critical factors being temperature and the ionic strength of the final wash solution. Wash stringency can be increased by decreasing salt concentration or by increasing temperature. Stringent salt concentration for the wash steps will preferably be less than about 30 mM NaCl and 3 mM trisodium citrate, and most preferably less than about 15 mM NaCl and 1.5 mM trisodium citrate.

Thus, hybridization and wash conditions that may be used to bind and remove polynucleotides with less than the desired homology to the nucleic acid sequences or their complements that encode the present transcription factors include, for example:

6×SSC at 65° C.;
50% formamide, 4×SSC at 42° C.; or
0.5×SSC, 0.1% SDS at 65° C.;

with, for example, two wash steps of 10-30 minutes each. Useful variations on these conditions will be readily apparent to those skilled in the art.

A person of skill in the art would not expect substantial variation among polynucleotide species encompassed within the scope of the present invention because the highly stringent conditions set forth in the above formulae yield structurally similar polynucleotides.

If desired, one may employ wash steps of even greater stringency, including about 0.2×SSC, 0.1% SDS at 65° C. and washing twice, each wash step being about 30 min, or about 0.1×SSC, 0.1% SDS at 65° C. and washing twice for 30 min. The temperature for the wash solutions will ordinarily be at least about 25° C., and for greater stringency at least about 42° C. Hybridization stringency may be increased further by using the same conditions as in the hybridization steps, with the wash temperature raised about 3° C. to about 5° C., and stringency may be increased even further by using the same conditions except the wash temperature is raised about 6° C. to about 9° C. For identification of less closely related homologs, wash steps may be performed at a lower temperature, e.g., 50° C.

An example of a low stringency wash step employs a solution and conditions of at least 25° C. in 30 mM NaCl, 3 mM trisodium citrate, and 0.1% SDS over 30 min. Greater stringency may be obtained at 42° C. in 15 mM NaCl, with 1.5 mM trisodium citrate, and 0.1% SDS over 30 min. Even higher stringency wash conditions are obtained at 65° C.-68° C. in a solution of 15 mM NaCl, 1.5 mM trisodium citrate, and 0.1% SDS. Wash procedures will generally employ at least two final wash steps. Additional variations on these conditions will be readily apparent to those skilled in the art (see, for example, U.S. Patent Application No. 20010010913).

Stringency conditions can be selected such that an oligonucleotide that is perfectly complementary to the coding oligonucleotide hybridizes to the coding oligonucleotide with at least about a 5-10× higher signal to noise ratio than the ratio for hybridization of the perfectly complementary oligonucleotide to a nucleic acid encoding a transcription factor known as of the filing date of the application. It may be desirable to select conditions for a particular assay such that a higher signal to noise ratio, that is, about 15× or more, is obtained. Accordingly, a subject nucleic acid will hybridize to a unique coding oligonucleotide with at least a 2× or greater signal to noise ratio as compared to hybridization of the coding oligonucleotide to a nucleic acid encoding known polypeptide. The particular signal will depend on the label used in the relevant assay, e.g., a fluorescent label, a calorimetric label, a radioactive label, or the like. Labeled hybridization or PCR probes for detecting related polynucleotide sequences may be produced by oligolabeling, nick translation, end-labeling, or PCR amplification using a labeled nucleotide.

Encompassed by the invention are polynucleotide sequences that are capable of hybridizing to the claimed polynucleotide sequences, and, in particular, to those shown in SEQ ID NO: 1, 3, 5, 7, 9, 11, 13, 15, 17, 19, 21, 23, 25, 27, 29, 31, 33, 35, 37, 39, 41, 43, 45, 47, 49, 51, and fragments thereofunder various conditions of stringency. (See, e.g., Wahl and Berger (1987) *Methods Enzymol.* 152: 399407; Kimmel (1987) *Methods Enzymol.* 152: 507-511). Estimates of homology are provided by either DNA-DNA or DNA-RNA hybridization under conditions of stringency as is well understood by those skilled in the art (Hames and Higgins, Eds. (1985) *Nucleic Acid Hybridisation*, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

Identifying Polynucleotides or Nucleic Acids with Expression Libraries

In addition to hybridization methods, transcription factor homolog polypeptides can be obtained by screening an expression library using antibodies specific for one or more transcription factors. With the provision herein of the disclosed transcription factor, and transcription factor homolog nucleic acid sequences, the encoded polypeptide(s) can be expressed and purified in a heterologous expression system (e.g., *E. coli*) and used to raise antibodies (monoclonal or polyclonal) specific for the polypeptide(s) in question. Antibodies can also be raised against synthetic peptides derived from transcription factor, or transcription factor homolog, amino acid sequences. Methods of raising antibodies are well known in the art and are described in Harlow and Lane (1988), *Antibodies: A Laboratory Manual*, Cold Spring Harbor Laboratory, New York. Such antibodies can then be used to screen an expression library produced from the plant from which it is desired to clone additional transcription factor homologs, using the methods described above. The selected cDNAs can be confirmed by sequencing and enzymatic activity.

Sequence Variations

It will readily be appreciated by those of skill in the art, that any of a variety of polynucleotide sequences are capable of encoding the transcription factors and transcription factor homolog polypeptides of the invention. Due to the degeneracy of the genetic code, many different polynucleotides can encode identical and/or substantially similar polypeptides in addition to those sequences illustrated in the Sequence Listing. Nucleic acids having a sequence that differs from the sequences shown in the Sequence Listing, or complementary sequences, that encode functionally equivalent peptides (i.e., peptides having some degree of equivalent or similar biological activity) but differ in sequence from the sequence shown in the Sequence Listing due to degeneracy in the genetic code, are also within the scope of the invention.

Altered polynucleotide sequences encoding polypeptides include those sequences with deletions, insertions, or substitutions of different nucleotides, resulting in a polynucleotide encoding a polypeptide with at least one functional characteristic of the instant polypeptides. Included within this definition are polymorphisms which may or may not be readily detectable using a particular oligonucleotide probe of the polynucleotide encoding the instant polypeptides, and improper or unexpected hybridization to allelic variants, with a locus other than the normal chromosomal locus for the polynucleotide sequence encoding the instant polypeptides.

Allelic variant refers to any of two or more alternative forms of a gene occupying the same chromosomal locus. Allelic variation arises naturally through mutation, and may result in phenotypic polymorphism within populations. Gene mutations can be silent (i.e., no change in the encoded polypeptide) or may encode polypeptides having altered amino acid sequence. The term allelic variant is also used herein to denote a protein encoded by an allelic variant of a gene. Splice variant refers to alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Those skilled in the art would recognize that, for example, G867, SEQ ID NO: 2, represents a single transcription factor; allelic variation and alternative splicing may be expected to occur. Allelic variants of SEQ ID NO: 1 can be cloned by probing cDNA or genomic libraries from different individual organisms according to standard procedures. Allelic variants of the DNA sequence shown in SEQ ID NO: 1, including those containing silent mutations and those in which mutations result in amino acid sequence changes, are within the scope of the present invention, as are proteins which are allelic variants of SEQ ID NO: 2. cDNAs generated from alternatively spliced mRNAs, which retain the properties of the transcription factor are included within the scope of the present invention, as are polypeptides encoded by such cDNAs and mRNAs. Allelic variants and splice variants of these sequences can be cloned by probing cDNA or genomic libraries from different individual organisms or tissues according to standard procedures known in the art (see U.S. Pat. No. 6,388,064).

Thus, in addition to the sequences set forth in the Sequence Listing, the invention also encompasses related nucleic acid molecules that include allelic or splice variants of SEQ ID NO: 1, 3, 5, 7, 9, 11, 13, 15, 17, 19, 21, 23, 25, 27, 29, 31, 33, 35, 37, 39, 41, 43, 45, 47, 49, 51, and include sequences which are complementary to any of the above nucleotide sequences. Related nucleic acid molecules also include nucleotide sequences encoding a polypeptide comprising or consisting essentially of a substitution, modification, addition and/or deletion of one or more amino acid residues compared to the polypeptide as set forth in any of SEQ ID NO: 2, 4, 6, 8, 10, 12, 14, 16, 18, 20, 22, 24, 26, 28, 30, 32, 34, 36, 38, 40, 42, 44, 46, 48, 50, 52, or 53. Such related polypeptides may comprise, for example, additions and/or deletions of one or more N-linked or O-linked glycosylation sites, or an addition and/or a deletion of one or more cysteine residues.

For example, Table 3 illustrates, e.g., that the codons AGC, AGT, TCA, TCC, TCG, and TCT all encode the same amino acid: serine. Accordingly, at each position in the sequence where there is a codon encoding serine, any of the above trinucleotide sequences can be used without altering the encoded polypeptide.

TABLE 3

| Amino Acid | | | Possible Codons |
|---|---|---|---|
| Alanine | Ala | A | GCA GCC GCG GCT |
| Cysteine | Cys | C | TGC TGT |
| Aspartic acid | Asp | D | GAC GAT |
| Glutamic acid | Glu | E | GAA GAG |
| Phenylalanine | Phe | F | TTC TTT |
| Glycine | Gly | G | GGA GGC GGG GGT |
| Histidine | His | H | CAC CAT |
| Isoleucine | Ile | I | ATA ATC ATT |
| Lysine | Lys | K | AAA AAG |
| Leucine | Leu | L | TTA TTG CTA CTC CTG CTT |
| Methionine | Met | M | ATG |
| Asparagine | Asn | N | AAC AAT |
| Proline | Pro | P | CCA CCC CCG CCT |
| Glutamine | Gln | Q | CAA CAG |
| Arginine | Arg | R | AGA AGG CGA CGC CGG CGT |
| Serine | Ser | S | AGC AGT TCA TCC TCG TCT |
| Threonine | Thr | T | ACA ACC ACG ACT |
| Valine | Val | V | GTA GTC GTG GTT |
| Tryptophan | Trp | W | TGG |
| Tyrosine | Tyr | Y | TAC TAT |

Sequence alterations that do not change the amino acid sequence encoded by the polynucleotide are termed "silent" variations. With the exception of the codons ATG and TGG, encoding methionine and tryptophan, respectively, any of the possible codons for the same amino acid can be substituted by a variety of techniques, e.g., site-directed mutagenesis, available in the art. Accordingly, any and all such variations of a sequence selected from the above table are a feature of the invention.

In addition to silent variations, other conservative variations that alter one, or a few amino acid residues in the encoded polypeptide, can be made without altering the function of the polypeptide, these conservative variants are, likewise, a feature of the invention.

For example, substitutions, deletions and insertions introduced into the sequences provided in the Sequence Listing, are also envisioned by the invention. Such sequence modifications can be engineered into a sequence by site-directed mutagenesis (Wu (ed.) *Methods Enzymol.* (1993) vol. 217, Academic Press) or the other methods noted below. Amino acid substitutions are typically of single residues; insertions usually will be on the order of about from 1 to 10 amino acid residues; and deletions will range about from 1 to 30 residues. In preferred embodiments, deletions or insertions are made in adjacent pairs, e.g., a deletion of two residues or insertion of two residues. Substitutions, deletions, insertions or any combination thereof can be combined to arrive at a sequence. The mutations that are made in the polynucleotide encoding the transcription factor should not place the sequence out of reading frame and should not create complementary regions that could produce secondary mRNA structure. Preferably, the polypeptide encoded by the DNA performs the desired function.

Conservative substitutions are those in which at least one residue in the amino acid sequence has been removed and a different residue inserted in its place. Such substitutions generally are made in accordance with the Table 4 when it is desired to maintain the activity of the protein. Table 4 shows amino acids which can be substituted for an amino acid in a protein and which are typically regarded as conservative substitutions.

TABLE 4

| Residue | Conservative Substitutions |
|---|---|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

Similar substitutions are those in which at least one residue in the amino acid sequence has been removed and a different residue inserted in its place. Such substitutions generally are made in accordance with the Table 5 when it is desired to maintain the activity of the protein. Table 5 shows amino acids which can be substituted for an amino acid in a protein and which are typically regarded as structural and functional substitutions. For example, a residue in column 1 of Table 5 may be substituted with a residue in column 2; in addition, a residue in column 2 of Table 5 may be substituted with the residue of column 1.

TABLE 5

| Residue | Similar Substitutions |
|---------|----------------------|
| Ala | Ser; Thr; Gly; Val; Leu; Ile |
| Arg | Lys; His; Gly |
| Asn | Gln; His; Gly; Ser; Thr |
| Asp | Glu, Ser; Thr |
| Gln | Asn; Ala |
| Cys | Ser; Gly |
| Glu | Asp |
| Gly | Pro; Arg |
| His | Asn; Gln; Tyr; Phe; Lys; Arg |
| Ile | Ala; Leu; Val; Gly; Met |
| Leu | Ala; Ile; Val; Gly; Met |
| Lys | Arg; His; Gln; Gly; Pro |
| Met | Leu; Ile; Phe |
| Phe | Met; Leu; Tyr; Trp; His; Val; Ala |
| Ser | Thr; Gly; Asp; Ala; Val; Ile; His |
| Thr | Ser; Val; Ala; Gly |
| Trp | Tyr; Phe; His |
| Tyr | Trp; Phe; His |
| Val | Ala; Ile; Leu; Gly; Thr; Ser; Glu |

Substitutions that are less conservative than those in Table 5 can be selected by picking residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

Further Modifying Sequences of the Invention—Mutation/Forced Evolution

In addition to generating silent or conservative substitutions as noted, above, the present invention optionally includes methods of modifying the sequences of the Sequence Listing. In the methods, nucleic acid or protein modification methods are used to alter the given sequences to produce new sequences and/or to chemically or enzymatically modify given sequences to change the properties of the nucleic acids or proteins.

Thus, in one embodiment, given nucleic acid sequences are modified, e.g., according to standard mutagenesis or artificial evolution methods to produce modified sequences. The modified sequences may be created using purified natural polynucleotides isolated from any organism or may be synthesized from purified compositions and chemicals using chemical means well known to those of skill in the art. For example, Ausubel, supra, provides additional details on mutagenesis methods. Artificial forced evolution methods are described, for example, by Stemmer (1994) *Nature* 370: 389-391, Stemmer (1994) *Proc. Nat. Acad. Sci.* 91: 10747-10751, and U.S. Pat. Nos. 5,811,238, 5,837,500, and 6,242,568. Methods for engineering synthetic transcription factors and other polypeptides are described, for example, by Zhang et al. (2000) *J. Biol. Chem.* 275: 33850-33860, Liu et al. (2001) *J. Biol. Chem.* 276: 11323-11334, and Isalan et al. (2001) *Nature Biotechnol.* 19: 656-660. Many other mutation and evolution methods are also available and expected to be within the skill of the practitioner.

Similarly, chemical or enzymatic alteration of expressed nucleic acids and polypeptides can be performed by standard methods. For example, sequence can be modified by addition of lipids, sugars, peptides, organic or inorganic compounds, by the inclusion of modified nucleotides or amino acids, or the like. For example, protein modification techniques are illustrated in Ausubel, supra. Further details on chemical and enzymatic modifications can be found herein. These modification methods can be used to modify any given sequence, or to modify any sequence produced by the various mutation and artificial evolution modification methods noted herein.

Accordingly, the invention provides for modification of any given nucleic acid by mutation, evolution, chemical or enzymatic modification, or other available methods, as well as for the products produced by practicing such methods, e.g., using the sequences herein as a starting substrate for the various modification approaches.

For example, optimized coding sequence containing codons preferred by a particular prokaryotic or eukaryotic host can be used e.g., to increase the rate of translation or to produce recombinant RNA transcripts having desirable properties, such as a longer half-life, as compared with transcripts produced using a non-optimized sequence. Translation stop codons can also be modified to reflect host preference. For example, preferred stop codons for *Saccharomyces cerevisiae* and mammals are TAA and TGA, respectively. The preferred stop codon for monocotyledonous plants is TGA, whereas insects and *E. coli* prefer to use TAA as the stop codon.

The polynucleotide sequences of the present invention can also be engineered in order to alter a coding sequence for a variety of reasons, including but not limited to, alterations which modify the sequence to facilitate cloning, processing and/or expression of the gene product. For example, alterations are optionally introduced using techniques which are well known in the art, e.g., site-directed mutagenesis, to insert new restriction sites, to alter glycosylation patterns, to change codon preference, to introduce splice sites, etc.

Furthermore, a fragment or domain derived from any of the polypeptides of the invention can be combined with domains derived from other transcription factors or synthetic domains to modify the biological activity of a transcription factor. For instance, a DNA-binding domain derived from a transcription factor of the invention can be combined with the activation domain of another transcription factor or with a synthetic activation domain. A transcription activation domain assists in initiating transcription from a DNA-binding site. Examples include the transcription activation region of VP 16 or GAL4 (Moore et al. (1998) *Proc. Natl. Acad. Sci.* 95: 376-381; Aoyama et al. (1995) *Plant Cell* 7: 1773-1785), peptides derived from bacterial sequences (Ma and Ptashne (1987) *Cell* 51: 113-119) and synthetic peptides (Giniger and Ptashne (1987) *Nature* 330: 670-672).

Expression and Modification of Polypeptides

Typically, polynucleotide sequences of the invention are incorporated into recombinant DNA (or RNA) molecules that direct expression of polypeptides of the invention in appropriate host cells, transgenic plants, in vitro translation systems, or the like. Due to the inherent degeneracy of the genetic code, nucleic acid sequences which encode substantially the same or a functionally equivalent amino acid sequence can be substituted for any listed sequence to provide for cloning and expressing the relevant homolog.

The transgenic plants of the present invention comprising recombinant polynucleotide sequences are generally derived from parental plants, which may themselves be non-transformed (or non-transgenic) plants. These transgenic plants may either have a transcription factor gene "knocked out" (for example, with a genomic insertion by homologous recombination, an antisense or ribozyme construct) or expressed to a normal or wild-type extent. However, overexpressing transgenic "progeny" plants will exhibit greater mRNA levels, wherein the mRNA encodes a transcription factor, that is, a DNA-binding protein that is capable of binding to a DNA regulatory sequence and inducing transcription, and preferably, expression of a plant trait gene. Preferably, the mRNA expression level will be at least three-fold greater than that of the parental plant, or more preferably at least ten-fold greater mRNA levels compared to said parental plant, and most preferably at least fifty-fold greater compared to said parental plant.

Vectors Promoters, and Expression Systems

The present invention includes recombinant constructs comprising one or more of the nucleic acid sequences herein. The constructs typically comprise a vector, such as a plasmid, a cosmid, a phage, a virus (e.g., a plant virus), a bacterial artificial chromosome (BAC), a yeast artificial chromosome (YAC), or the like, into which a nucleic acid sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available.

General texts that describe molecular biological techniques useful herein, including the use and production of vectors, promoters and many other relevant topics, include Berger, Sambrook, supra and Ausubel, supra. Any of the identified sequences can be incorporated into a cassette or vector, e.g., for expression in plants. A number of expression vectors suitable for stable transformation of plant cells or for the establishment of transgenic plants have been described including those described in Weissbach and Weissbach (1989) *Methods for Plant Molecular Biology*, Academic Press, and Gelvin et al. (1990) *Plant Molecular Biology Manual*, Kluwer Academic Publishers. Specific examples include those derived from a Ti plasmid of *Agrobacterium tumefaciens*, as well as those disclosed by Herrera-Estrella et al. (1983) *Nature* 303: 209, Bevan (1984) *Nucleic Acids Res.* 12: 8711-8721, Klee (1985) *Bio/Technology* 3: 637-642, for dicotyledonous plants.

Alternatively, non-Ti vectors can be used to transfer the DNA into monocotyledonous plants and cells by using free DNA delivery techniques. Such methods can involve, for example, the use of liposomes, electroporation, microprojectile bombardment, silicon carbide whiskers, and viruses. By using these methods transgenic plants such as wheat, rice (Christou (1991) *Bio/Technology* 9: 957-962) and corn (Gordon-Kamm (1990) *Plant Cell* 2: 603-618) can be produced. An immature embryo can also be a good target tissue for monocots for direct DNA delivery techniques by using the particle gun (Weeks et al. (1993) *Plant Physiol.* 102: 1077-1084; Vasil (1993) *Bio/Technology* 10: 667-674; Wan and Lemeaux (1994) *Plant Physiol.* 104: 37-48, and for *Agrobacterium*-mediated DNA transfer (Ishida et al. (1996) *Nature Biotechnol.* 14: 745-750).

Typically, plant transformation vectors include one or more cloned plant coding sequence (genomic or cDNA) under the transcriptional control of 5' and 3' regulatory sequences and a dominant selectable marker. Such plant transformation vectors typically also contain a promoter (e.g., a regulatory region controlling inducible or constitutive, environmentally—or developmentally-regulated, or cell- or tissue-specific expression), a transcription initiation start site, an RNA processing signal (such as intron splice sites), a transcription termination site, and/or a polyadenylation signal.

A potential utility for the transcription factor polynucleotides disclosed herein is the isolation of promoter elements from these genes that can be used to program expression in plants of any genes. Each transcription factor gene disclosed herein is expressed in a unique fashion, as determined by promoter elements located upstream of the start of translation, and additionally within an intron of the transcription factor gene or downstream of the termination codon of the gene. As is well known in the art, for a significant portion of genes, the promoter sequences are located entirely in the region directly upstream of the start of translation. In such cases, typically the promoter sequences are located within 2.0 kb of the start of translation, or within 1.5 kb of the start of translation, frequently within 1.0 kb of the start of translation, and sometimes within 0.5 kb of the start of translation.

The promoter sequences can be isolated according to methods known to one skilled in the art.

Examples of constitutive plant promoters which can be useful for expressing the TF sequence include: the cauliflower mosaic virus (CaMV) $^{35}$S apromoter, which confers constitutive, high-level expression in most plant tissues (see, e.g., Odell et al. (1985) *Nature* 313: 810-812); the nopaline synthase promoter (An et al. (1988) *Plant Physiol.* 88: 547-552); and the octopine synthase promoter (Fromm et al. (1989) *Plant Cell* 1: 977-984).

The transcription factors of the invention may be operably linked with a specific promoter that causes the transcription factor to be expressed in response to environmental, tissue-specific or temporal signals. A variety of plant gene promoters that regulate gene expression in response to environmental, hormonal, chemical, developmental signals, and in a tissue-active manner can be used for expression of a TF sequence in plants. Choice of a promoter is based largely on the phenotype of interest and is determined by such factors as tissue (e.g., seed, fruit, root, pollen, vascular tissue, flower, carpel, etc.), inducibility (e.g., in response to drought, wounding, heat, cold, light, pathogens, etc.), timing, developmental stage, and the like. Numerous known promoters have been characterized and can favorably be employed to promote expression of a polynucleotide of the invention in a transgenic plant or cell of interest. For example, tissue specific promoters include: seed-specific promoters (such as the napin, phaseolin or DC3 promoter described in U.S. Pat. No. 5,773,697), fruit-specific promoters that are active during fruit ripening (such as the dru 1 promoter (U.S. Pat. No. 5,783,393), or the 2A11 promoter (U.S. Pat. No. 4,943,674) and the tomato polygalacturonase promoter (Bird et al. (1988) *Plant Mol. Biol.* 11: 651-662), root-specific promoters, such as those disclosed in U.S. Pat. Nos. 5,618,988, 5,837,848 and 5,905,186, pollen-active promoters such as PTA29, PTA26 and PTA13 (U.S. Pat. No. 5,792,929), promoters active in vascular tissue (Ringli and Keller (1998) *Plant Mol. Biol.* 37: 977-988), flower-specific (Kaiser et al. (1995) *Plant Mol. Biol.* 28: 231-243), pollen (Baerson et al. (1994) *Plant Mol. Biol.* 26: 1947-1959), carpels (Ohl et al. (1990) *Plant Cell* 2: 837-848), pollen and ovules (Baerson et al. (1993) *Plant Mol. Biol.* 22: 255-267), auxin-inducible promoters (such as that described in van der Kop et al. (1999) *Plant Mol. Biol.* 39: 979-990 or Baumann et al., (1999) *Plant Cell* 11: 323-334), cytokinin-inducible promoter (Guevara-Garcia (1998) *Plant*

*Mol. Biol.* 38: 743-753), promoters responsive to gibberellin (Shi et al. (1998) *Plant Mol. Biol.* 38: 1053-1060, Willmott et al. (1998) *Plant Molec. Biol.* 38: 817-825) and the like. Additional promoters are those that elicit expression in response to heat (Ainley et al. (1993) *Plant Mol. Biol.* 22: 13-23), light (e.g., the pea rbcS-3A promoter, Kuhlemeier et al. (1989) *Plant Cell* 1: 471-478, and the maize rbcS promoter, Schafffier and Sheen (1991) *Plant Cell* 3: 997-1012); wounding (e.g., wunI, Siebertz et al. (1989) *Plant Cell* 1: 961-968); pathogens (such as the PR-1 promoter described in Buchel et al. (1999) *Plant Mol. Biol.* 40: 387-396, and the PDF1.2 promoter described in Manners et al. (1998) *Plant Mol. Biol.* 38: 1071-1080), and chemicals such as methyl jasmonate or salicylic acid (Gatz (1997) *Annu. Rev. Plant Physiol. Plant Mol. Biol.* 48: 89-108). In addition, the timing of the expression can be controlled by using promoters such as those acting at senescence (Gan and Amasino (1995) *Science* 270: 1986-1988); or late seed development (Odell et al. (1994) *Plant Physiol.* 106: 447-458).

Plant expression vectors can also include RNA processing signals that can be positioned within, upstream or downstream of the coding sequence. In addition, the expression vectors can include additional regulatory sequences from the 3'-untranslated region of plant genes, e.g., a 3' terminator region to increase mRNA stability of the mRNA, such as the PI-II terminator region of potato or the octopine or nopaline synthase 3' terminator regions.

Additional Expression Elements

Specific initiation signals can aid in efficient translation of coding sequences. These signals can include, e.g., the ATG initiation codon and adjacent sequences. In cases where a coding sequence, its initiation codon and upstream sequences are inserted into the appropriate expression vector, no additional translational control signals may be needed. However, in cases where only coding sequence (e.g., a mature protein coding sequence), or a portion thereof, is inserted, exogenous transcriptional control signals including the ATG initiation codon can be separately provided. The initiation codon is provided in the correct reading frame to facilitate transcription. Exogenous transcriptional elements and initiation codons can be of various origins, both natural and synthetic. The efficiency of expression can be enhanced by the inclusion of enhancers appropriate to the cell system in use.

Expression Hosts

The present invention also relates to host cells which are transduced with vectors of the invention, and the production of polypeptides of the invention (including fragments thereof) by recombinant techniques. Host cells are genetically engineered (i.e., nucleic acids are introduced, e.g., transduced, transformed or transfected) with the vectors of this invention, which may be, for example, a cloning vector or an expression vector comprising the relevant nucleic acids herein. The vector is optionally a plasmid, a viral particle, a phage, a naked nucleic acid, etc. The engineered host cells can be cultured in conventional nutrient media modified as appropriate for activating promoters, selecting transformants, or amplifying the relevant gene. The culture conditions, such as temperature, pH and the like, are those previously used with the host cell selected for expression, and will be apparent to those skilled in the art and in the references cited herein, including, Sambrook, supra and Ausubel, supra.

The host cell can be a eukaryotic cell, such as a yeast cell, or a plant cell, or the host cell can be a prokaryotic cell, such as a bacterial cell. Plant protoplasts are also suitable for some applications. For example, the DNA fragments are introduced into plant tissues, cultured plant cells or plant protoplasts by standard methods including electroporation (Fromm et al. (1985) *Proc. Natl. Acad. Sci.* 82: 5824-5828, infection by viral vectors such as cauliflower mosaic virus (CaMV) (Hohn et al. (1982) *Molecular Biology of Plant Tumors* Academic Press, New York, N.Y., pp. 549-560; U.S. Pat. No. 4,407,956), high velocity ballistic penetration by small particles with the nucleic acid either within the matrix of small beads or particles, or on the surface (Klein et al. (1987) *Nature* 327: 70-73), use of pollen as vector (WO 85/01856), or use of *Agrobacterium tumefaciens* or *A. rhizogenes* carrying a T-DNA plasmid in which DNA fragments are cloned. The T-DNA plasmid is transmitted to plant cells upon infection by *Agrobacterium tumefaciens*, and a portion is stably integrated into the plant genome (Horsch et al. (1984) *Science* 233: 496-498; Fraley et al. (1983) *Proc. Natl. Acad. Sci.* 80: 4803-4807).

The cell can include a nucleic acid of the invention that encodes a polypeptide, wherein the cell expresses a polypeptide of the invention. The cell can also include vector sequences, or the like. Furthermore, cells and transgenic plants that include any polypeptide or nucleic acid above or throughout this specification, e.g., produced by transduction of a vector of the invention, are an additional feature of the invention.

For long-term, high-yield production of recombinant proteins, stable expression can be used. Host cells transformed with a nucleotide sequence encoding a polypeptide of the invention are optionally cultured under conditions suitable for the expression and recovery of the encoded protein from cell culture. The protein or fragment thereof produced by a recombinant cell may be secreted, membrane-bound, or contained intracellularly, depending on the sequence and/or the vector used. As will be understood by those of skill in the art, expression vectors containing polynucleotides encoding mature proteins of the invention can be designed with signal sequences which direct secretion of the mature polypeptides through a prokaryotic or eukaryotic cell membrane.

Modified Amino Acid Residues

Polypeptides of the invention may contain one or more modified amino acid residues. The presence of modified amino acids may be advantageous in, for example, increasing polypeptide half-life, reducing polypeptide antigenicity or toxicity, increasing polypeptide storage stability, or the like. Amino acid residue(s) are modified, for example, co-translationally or post-translationally during recombinant production or modified by synthetic or chemical means.

Non-limiting examples of a modified amino acid residue include incorporation or other use of acetylated amino acids, glycosylated amino acids, sulfated amino acids, prenylated (e.g., farnesylated, geranylgeranylated) amino acids, PEG modified (e.g., "PEGylated") amino acids, biotinylated amino acids, carboxylated amino acids, phosphorylated amino acids, etc. References adequate to guide one of skill in the modification of amino acid residues are replete throughout the literature.

The modified amino acid residues may prevent or increase affinity of the polypeptide for another molecule, including, but not limited to, polynucleotide, proteins, carbohydrates, lipids and lipid derivatives, and other organic or synthetic compounds.

Identification of Additional Protein Factors

A transcription factor provided by the present invention can also be used to identify additional endogenous or exogenous molecules that can affect a phentoype or trait of interest. Such molecules include endogenous molecules that are acted upon either at a transcriptional level by a transcription factor of the invention to modify a phenotype as desired. For example, the transcription factors can be employed to identify one or more downstream genes that are subject to a regulatory effect of the transcription factor. In one approach, a transcription factor or transcription factor homolog of the invention is expressed in a host cell, e.g., a transgenic plant cell, tissue or explant, and expression products, either RNA or protein, of likely or random targets are monitored, e.g., by hybridization to a microarray of nucleic acid probes corresponding to genes expressed in a tissue or cell type of interest, by two-dimensional gel electrophoresis of protein products, or by any other method known in the art for assessing expression of gene products at the level of RNA or protein. Alternatively, a transcription factor of the invention can be used to identify promoter sequences (such as binding sites on DNA sequences) involved in the regulation of a downstream target. After identifying a promoter sequence, interactions between the transcription factor and the promoter sequence can be modified by changing specific nucleotides in the promoter sequence or specific amino acids in the transcription factor that interact with the promoter sequence to alter a plant trait. Typically, transcription factor DNA-binding sites are identified by gel shift assays. After identifying the promoter regions, the promoter region sequences can be employed in double-stranded DNA arrays to identify molecules that affect the interactions of the transcription factors with their promoters (Bulyk et al. (1999) *Nature Biotechnol.* 17: 573-577).

The identified transcription factors are also useful to identify proteins that modify the activity of the transcription factor. Such modification can occur by covalent modification, such as by phosphorylation, or by protein-protein (homo or -heteropolymer) interactions. Any method suitable for detecting protein-protein interactions can be employed. Among the methods that can be employed are co-immunoprecipitation, cross-linking and co-purification through gradients or chromatographic columns, and the two-hybrid yeast system.

The two-hybrid system detects protein interactions in vivo and is described in Chien et al. ((1991) *Proc. Natl. Acad. Sci.* 88: 9578-9582) and is commercially available from Clontech (Palo Alto, Calif.). In such a system, plasmids are constructed that encode two hybrid proteins: one consists of the DNA-binding domain of a transcription activator protein fused to the TF polypeptide and the other consists of the transcription activator protein's activation domain fused to an unknown protein that is encoded by a cDNA that has been recombined into the plasmid as part of a cDNA library. The DNA-binding domain fusion plasmid and the cDNA library are transformed into a strain of the yeast *Saccharomyces cerevisiae* that contains a reporter gene (e.g., lacZ) whose regulatory region contains the transcription activator's binding site. Either hybrid protein alone cannot activate transcription of the reporter gene. Interaction of the two hybrid proteins reconstitutes the functional activator protein and results in expression of the reporter gene, which is detected by an assay for the reporter gene product. Then, the library plasmids responsible for reporter gene expression are isolated and sequenced to identify the proteins encoded by the library plasmids. After identifying proteins that interact with the transcription factors, assays for compounds that interfere with the TF protein-protein interactions can be preformed.

Subsequences

Also contemplated are uses of polynucleotides, also referred to herein as oligonucleotides, typically having at least 12 bases, preferably at least 15, more preferably at least 20, 30, or 50 bases, which hybridize under at least highly stringent (or ultra-high stringent or ultra-ultra-high stringent conditions) conditions to a polynucleotide sequence described above. The polynucleotides may be used as probes, primers, sense and antisense agents, and the like, according to methods as noted supra.

Subsequences of the polynucleotides of the invention, including polynucleotide fragments and oligonucleotides are useful as nucleic acid probes and primers. An oligonucleotide suitable for use as a probe or primer is at least about 15 nucleotides in length, more often at least about 18 nucleotides, often at least about 21 nucleotides, frequently at least about 30 nucleotides, or about 40 nucleotides, or more in length. A nucleic acid probe is useful in hybridization protocols, e.g., to identify additional polypeptide homologs of the invention, including protocols for microarray experiments. Primers can be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods. See Sambrook, supra, and Ausubel, supra.

In addition, the invention includes an isolated or recombinant polypeptide including a subsequence of at least about 15 contiguous amino acids encoded by the recombinant or isolated polynucleotides of the invention. For example, such polypeptides, or domains or fragments thereof, can be used as immunogens, e.g., to produce antibodies specific for the polypeptide sequence, or as probes for detecting a sequence of interest. A subsequence can range in size from about 15 amino acids in length up to and including the full length of the polypeptide.

To be encompassed by the present invention, an expressed polypeptide which comprises such a polypeptide subsequence performs at least one biological function of the intact polypeptide in substantially the same manner, or to a similar extent, as does the intact polypeptide. For example, a polypeptide fragment can comprise a recognizable structural motif or functional domain such as a DNA binding domain that activates transcription, e.g., by binding to a specific DNA promoter region an activation domain, or a domain for protein-protein interactions.

Production of Transgenic Plants

Modification of Traits

The polynucleotides of the invention are favorably employed to produce transgenic plants with various traits, or characteristics, that have been modified in a desirable manner, e.g., to improve the seed characteristics of a plant. For example, alteration of expression levels or patterns (e.g., spatial or temporal expression patterns) of one or more of the transcription factors (or transcription factor homologs) of the invention, as compared with the levels of the same protein found in a wild-type plant, can be used to modify a plant's traits. An illustrative example of trait modification, improved characteristics, by altering expression levels of a particular transcription factor is described further in the Examples and the Sequence Listing.

*Arabidopsis* as a Model System

*Arabidopsis thaliana* is the object of rapidly growing attention as a model for genetics and metabolism in plants. *Arabidopsis* has a small genome, and well-documented studies are available. It is easy to grow in large numbers and mutants defining important genetically controlled mechanisms are either available, or can readily be obtained. Various methods to introduce and express isolated homologous genes are available (see Koncz et al., eds., *Methods in Arabidopsis Research* (1992) World Scientific, New Jersey, N.J., in "Preface"). Because of its small size, short life cycle, obligate autogamy and high fertility, *Arabidopsis* is also a choice organism for the isolation of mutants and studies in morphogenetic and development pathways, and control of these pathways by transcription factors (Koncz supra, p. 72). A number of studies introducing transcription factors into *A. thaliana* have demonstrated the utility of this plant for understanding the mechanisms of gene regulation and trait alteration in plants. (See, for example, Koncz supra, and U.S. Pat. No. 6,417,428).

*Arabidopsis* Genes in Transgenic Plants.

Expression of genes which encode transcription factors modify expression of endogenous genes, polynucleotides, and proteins are well known in the art. In addition, transgenic plants comprising isolated polynucleotides encoding transcription factors may also modify expression of endogenous genes, polynucleotides, and proteins. Examples include Peng et al. (1997 *Genes and Development* 11: 3194-3205) and Peng et al. (1999 *Nature* 400: 256-261). In addition, many others have demonstrated that an *Arabidopsis* transcription factor expressed in an exogenous plant species elicits the same or very similar phenotypic response. See, for example, Fu et al. (2001 *Plant Cell* 13: 1791-1802); Nandi et al. (2000 *Curr. Biol.* 10: 215-218); Coupland (1995 *Nature* 377: 482-483); and Weigel and Nilsson (1995, *Nature* 377: 482-500).

Homologous Genes Introduced into Transgenic Plants.

Homologous genes that may be derived from any plant, or from any source whether natural, synthetic, semi-synthetic or recombinant, and that share significant sequence identity or similarity to those provided by the present invention, may be introduced into plants, for example, crop plants, to confer desirable or improved traits. Consequently, transgenic plants may be produced that comprise a recombinant expression vector or cassette with a promoter operably linked to one or more sequences homologous to presently disclosed sequences. The promoter may be, for example, a plant or viral promoter.

The invention thus provides for methods for preparing transgenic plants, and for modifying plant traits. These methods include introducing into a plant a recombinant expression vector or cassette comprising a functional promoter operably linked to one or more sequences homologous to presently disclosed sequences. Plants and kits for producing these plants that result from the application of these methods are also encompassed by the present invention.

Transcription Factors of Interest for the Modification of Plant Traits

Currently, the existence of a series of maturity groups for different latitudes represents a major barrier to the introduction of new valuable traits. Any trait (e.g. drought tolerance) has to be bred into each of the different maturity groups separately, a laborious and costly exercise. The availability of single strain, which could be grown at any latitude, would therefore greatly increase the potential for introducing new traits to crop species such as soybean and cotton.

For the specific effects, traits and utilities conferred to plants, one or more transcription factor genes of the present invention may be used to increase or decrease, or improve or prove deleterious to a given trait. For example, knocking out a transcription factor gene that naturally occurs in a plant, or suppressing the gene (with, for example, antisense suppression), may cause decreased tolerance to an osmotic stress relative to non-transformed or wild-type plants. By overexpressing this gene, the plant may experience increased tolerance to the same stress. More than one transcription factor gene may be introduced into a plant, either by transforming the plant with one or more vectors comprising two or more transcription factors, or by selective breeding of plants to yield hybrid crosses that comprise more than one introduced transcription factor.

Genes, Traits and Utilities that Affect Plant Characteristics

Plant transcription factors can modulate gene expression, and, in turn, be modulated by the environmental experience of a plant. Significant alterations in a plant's environment invariably result in a change in the plant's transcription factor gene expression pattern. Altered transcription factor expression patterns generally result in phenotypic changes in the plant. Transcription factor gene product(s) in transgenic plants then differ(s) in amounts or proportions from that found in wild-type or non-transformed plants, and those transcription factors likely represent polypeptides that are used to alter the response to the environmental change. By way of example, it is well accepted in the art that analytical methods based on altered expression patterns may be used to screen for phenotypic changes in a plant far more effectively than can be achieved using traditional methods.

Sugar Sensing and Effects on Yield.

In addition to their important role as an energy source and structural component of the plant cell, sugars are central regulatory molecules that control several aspects of plant physiology, metabolism and development (Hsieh et al. (1998) *Proc. Natl. Acad. Sci.* 95: 13965-13970). It is thought that this control is achieved by regulating gene expression and, in higher plants, sugars have been shown to repress or activate plant genes involved in many essential processes such as photosynthesis, glyoxylate metabolism, respiration, starch and sucrose synthesis and degradation, pathogen response, wounding response, cell cycle regulation, pigmentation, flowering and senescence. The mechanisms by which sugars control gene expression are not understood.

Several sugar sensing mutants have turned out to be allelic to abscisic acid (ABA) and ethylene mutants. ABA is found in all photosynthetic organisms and acts as a key regulator of transpiration, stress responses, embryogenesis, and seed germination. Most ABA effects are related to the compound acting as a signal of decreased water availability, whereby it triggers a reduction in water loss, slows growth, and mediates adaptive responses. However, ABA also influences plant growth and development via interactions with other phytohormones. Physiological and molecular studies indicate that maize and *Arabidopsis* have almost identical pathways with regard to ABA biosynthesis and signal transduction. For further review, see Finkelstein and Rock (2002) "Abscisic acid biosynthesis and response", (in The *Arabidopsis Book*, Editors: Somerville and Meyerowitz (American Society of Plant Biologists, Rockville, Md.).

This potentially implicates G867, G9, G993, G1930, G3389, G3391, G3451, G3452, and G3455 in hormone signaling based on the sucrose sugar sensing phenotype of transgenic lines overexpressing these sequences (see Example VIII, below). On the other hand, the sucrose treatment used in these experiments (9.4% w/v) could also be an osmotic stress. Therefore, one could interpret these data as an indication that these transgenic lines are more tolerant to osmotic stress. However, it is well known that plant responses to ABA, osmotic and other stress may be linked, and these different treatments may even act in a synergistic manner to increase the degree of a response. For example, Xiong, Ishitani, and Zhu ((1999) *Plant Physiol.* 119: 205-212) have shown that genetic and molecular studies may be used to show extensive interaction between osmotic stress, temperature stress, and ABA responses in plants. These investigators analyzed the expression of RD29A-LUC in response to various treatment regimes in *Arabidopsis*. The RD29A promoter contains both the ABA-responsive and the dehydration-responsive element—also termed the C-repeat—and can be activated by osmotic stress, low temperature, or ABA treatment. Transcription of the RD29A gene in response to osmotic and cold stresses is mediated by both ABA-dependent and ABA-independent pathways (Xiong, Ishitani, and Zhu (1999) supra). LUC refers to the firefly luciferase coding sequence, which, in this case, was driven by the stress responsive RD29A promoter. The results revealed both positive and negative interactions, depending on the nature and duration of the treatments. Low temperature stress was found to impair osmotic signaling but moderate heat stress strongly enhanced osmotic stress induction, thus acting synergistically with osmotic signaling pathways. In this study, the authors reported that osmotic stress and ABA can act synergistically by showing that the treatments simultaneously induced transgene and endogenous gene expression. Similar results were reported by Bostock and Quatrano ((1992) *Plant Physiol.* 98: 1356-1363), who found that osmotic stress and ABA act synergistically and induce maize Em gene expression. Ishitani et al (1997) *Plant Cell* 9: 1935-1949) isolated a group of *Arabidopsis* single-gene mutations that confer enhanced responses to both osmotic stress and ABA. The nature of the recovery of these mutants from osmotic stress and ABA treatment suggested that although separate signaling pathways exist for osmotic stress and ABA, the pathways share a number of components; these common components may mediate synergistic interactions between osmotic stress and ABA. Thus, contrary to the previously-held belief that ABA-dependent and ABA-independent stress signaling pathways act in a parallel manner, our data reveal that these pathways crosstalk and converge to activate stress gene expression.

Because sugars are important signaling molecules, the ability to control either the concentration of a signaling sugar or how the plant perceives or responds to a signaling sugar could be used to control plant development, physiology or metabolism. For example, the flux of sucrose (a disaccharide sugar used for systemically transporting carbon and energy in most plants) has been shown to affect gene expression and alter storage compound accumulation in seeds. Manipulation of the sucrose signaling pathway in seeds may therefore cause seeds to have more protein, oil or carbohydrate, depending on the type of manipulation. Similarly, in tubers, sucrose is converted to starch which is used as an energy store. It is thought that sugar signaling pathways may partially determine the levels of starch synthesized in the tubers. The manipulation of sugar signaling in tubers could lead to tubers with a higher starch content.

Thus, the presently disclosed transcription factor genes that manipulate the sugar signal transduction pathway, including G867, G9, G993, G1930, *G*3389, G3391, G3451, G3452, and G3455, along with their equivalogs, may lead to altered gene expression to produce plants with desirable traits. In particular, manipulation of sugar signal transduction pathways could be used to alter source-sink relationships in seeds, tubers, roots and other storage organs leading to increase in yield.

Abiotic stress: drought and low humidity tolerance and effects on yield. Exposure to dehydration invokes similar survival strategies in plants as does freezing stress (see, for example, Yelenosky (1989) *Plant Physiol* 89: 444-451) and drought stress induces freezing tolerance (see, for example, Siminovitch et al. (1982) *Plant Physiol* 69: 250-255; and Guy et al. (1992) *Planta* 188: 265-270). In addition to the induction of cold-acclimation proteins, strategies that allow plants to survive in low water conditions may include, for example, reduced surface area, or surface oil or wax production. Modifying the expression of a number of presently disclosed transcription factor genes, such as G867, may be used to increase a plant's tolerance to low water conditions and provide the benefits of improved increased yield, survival and an extended geographic and temporal planting range.

Osmotic stress and effects on yield. Modification of the expression of a number of presently disclosed transcription factor genes, e.g., G867, G9, G993, G1930, *G*3389, G3390, G3391, G3451, G3452, and G3455, and their equivalogs, may be used to increase germination rate or growth under adverse osmotic conditions, which could impact survival and yield of seeds and plants. Osmotic stresses may be regulated by specific molecular control mechanisms that include genes controlling water and ion movements, functional and structural stress-induced proteins, signal perception and transduction, and free radical scavenging, and many others (Wang et al. (2001) *Acta Hort.* (ISHS) 560: 285-292). Instigators of osmotic stress include freezing, drought and high salinity, each of which are discussed in more detail below.

In many ways, freezing, high salt and drought have similar effects on plants, not the least of which is the induction of common polypeptides that respond to these different stresses. For example, freezing is similar to water deficit in that freezing reduces the amount of water available to a plant. Exposure to freezing temperatures may lead to cellular dehydration as water leaves cells and forms ice crystals in intercellular spaces (Buchanan, supra). As with high salt concentration and freezing, the problems for plants caused by low water availability include mechanical stresses caused by the withdrawal of cellular water. Thus, the incorporation of transcription factors that modify a plant's response to osmotic stress into, for example, a crop or ornamental plant, may be useful in increasing yield by reducing damage or loss. Specific effects caused by freezing, high salt and drought are addressed below.

Salt and Drought Tolerance

Plants are subject to a range of environmental challenges. Several of these, including salt stress, general osmotic stress, drought stress and freezing stress, have the ability to impact whole plant and cellular water availability. Not surprisingly, then, plant responses to this collection of stresses are related. In a recent review, Zhu notes that "most studies on water stress signaling have focused on salt stress primarily because plant responses to salt and drought are closely related and the mechanisms overlap" (Zhu (2002) *Ann. Rev. Plant Biol.* 53: 247-273). Many examples of similar responses and pathways to this set of stresses have been documented. For example, the CBF transcription factors have been shown to condition resistance to salt, freezing and drought (Kasuga et al. (1999) *Nature Biotech.* 17: 287-291). The *Arabidopsis* rd29B gene is induced in response to both salt and dehydration stress, a process that is mediated largely through an ABA signal transduction process (Uno et al. (2000) *Proc. Natl. Acad. Sci. USA* 97: 11632-11637), resulting in altered activity of transcription factors that bind to an upstream element within the rd29B promoter. In *Mesembryanthemum crystallinum* (ice plant), Patharker and Cushman have shown that a calcium-dependent protein kinase (McCDPK1) is induced by exposure to both drought and salt stresses (Patharker and Cushman (2000) *Plant J.* 24: 679-691). The stress-induced kinase was also shown to phosphorylate a transcription factor, presumably altering its activity, although transcript levels of the target transcription factor are not altered in response to salt or drought stress. Similarly, Saijo et al. demonstrated that a rice salt/drought-induced calmodulin-dependent protein kinase (OsCDPK7) conferred increased salt and drought tolerance to rice when overexpressed (Saijo et al. (2000) *Plant J.* 23: 319-327).

Exposure to dehydration invokes similar survival strategies in plants as does freezing stress (see, for example, Yelenosky (1989) *Plant Physiol* 89: 444-451) and drought stress induces freezing tolerance (see, for example, Siminovitch et al. (1982) *Plant Physiol* 69: 250-255; and Guy et al. (1992) *Planta* 188: 265-270). In addition to the induction of cold-acclimation proteins, strategies that allow plants to survive in low water conditions may include, for example, reduced surface area, or surface oil or wax production.

Consequently, one skilled in the art would expect that some pathways involved in resistance to one of these stresses, and hence regulated by an individual transcription factor, will also be involved in resistance to another of these stresses, regulated by the same or homologous transcription factors. Of course, the overall resistance pathways are related, not identical, and therefore not all transcription factors controlling resistance to one stress will control resistance to the other stresses. Nonetheless, if a transcription factor conditions resistance to one of these stresses, it would be apparent to one skilled in the art to test for resistance to these related stresses.

The genes of the sequence listing, including, for example, G867, G9, G993, G1930, *G3389*, G3391, G3451, G3452 and their equivalogs, that provide tolerance to salt may be used to engineer salt tolerant crops and trees that can flourish in soils with high saline content or under drought conditions. In particular, increased salt tolerance during the germination stage of a plant enhances yield and survival. Presently disclosed transcription factor genes that provide increased salt tolerance during germination, the seedling stage, and throughout a plant's life cycle, would find particular value for imparting survival and yield in areas where a particular crop would not normally prosper.

Root growth and vigor. Some of the genes in the Sequence Listing, including G867, G9, G993, G3390, G3451, G3452 and G3455 have been shown to increase root growth and to produce hairy roots on media containing methyl jasmonate. Thus, these genes could potentially be used to increase root growth and vigor, which might in turn allow better plant growth and yield during periods of osmotic stress, or limited nutrient availability.

Summary of altered plant characteristics. A dade of structurally and functionally related sequences that derive from a wide range of plants, including polynucleotide SEQ ID NOs 1, 3, 5, 7, 9, 11, 13, 15, 17, 19, 21, 23, 25, 27, 29, 31, 33, 35, 37, 39, 41, 43, 45, 47, 49, or 51, polynucleotides that encode polypeptide SEQ ID NOs: 2, 4, 6, 8, 10, 12, 14, 16, 18, 20, 22, 24, 26, 28, 30, 32, 34, 36, 38, 40, 42, 44, 46, 48, 50, 52, or 53, fragments thereof, paralogs, orthologs, equivalogs, and fragments thereof, is provided. These sequences have been shown in laboratory and field experiments to confer increased size in transformed plants as compared to wild-type plants in conditions of abiotic stress. The invention also provides polypeptides comprising SEQ ID NOs: 2, 4, 6, 8, 10, 12, 14, 16, 18, 20, 22, 24, 26, 28, 30, 32, 34, 36, 38, 40, 42, 44, 46, 48, 50, 52, or 53, and fragments thereof, conserved domains thereof, paralogs, orthologs, equivalogs, and fragments thereof. Plants that overexpress these sequences have been observed to be more tolerant to a wide variety of abiotic stresses, including, germination in heat and cold, and osmotic stresses such as drought and high salt levels. Many of the orthologs of these sequences are listed in the Sequence Listing, and due to the high degree of structural similarity to the sequences of the invention, it is expected that these sequences may also function to increase abiotic stress tolerance and yield. The invention also encompasses the complements of the polynucleotides. The polynucleotides are useful for screening libraries of molecules or compounds for specific binding and for creating transgenic plants having increased abiotic stress tolerance.

Antisense and Co-Suppression

In addition to expression of the nucleic acids of the invention as gene replacement or plant phenotype modification nucleic acids, the nucleic acids are also useful for sense and anti-sense suppression of expression, e.g. to down-regulate expression of a nucleic acid of the invention, e.g. as a further mechanism for modulating plant phenotype. That is, the nucleic acids of the invention, or subsequences or anti-sense sequences thereof, can be used to block expression of naturally occurring homologous nucleic acids. A variety of sense and anti-sense technologies are known in the art, e.g. as set forth in Lichtenstein and Nellen (1997) *Antisense Technology: A Practical Approach* IRL Press at Oxford University Press, Oxford, U.K. Antisense regulation is also described in Crowley et al. (1985) *Cell* 43: 633-641; Rosenberg et al. (1985) *Nature* 313: 703-706; Preiss et al. (1985) *Nature* 313: 27-32; Melton (1985) *Proc. Natl. Acad. Sci.* 82: 144-148; Izant and Weintraub (1985) *Science* 229: 345-352; and Kim and Wold (1985) *Cell* 42: 129-138. Additional methods for antisense regulation are known in the art. Antisense regulation has been used to reduce or inhibit expression of plant genes in, for example in European Patent Publication No. 271988. Antisense RNA may be used to reduce gene expression to produce a visible or biochemical phenotypic change in a plant (Smith et al. (1988) *Nature,* 334: 724-726; Smith et al. (1990) *Plant Mol. Biol.* 14: 369-379). In general, sense or anti-sense sequences are introduced into a cell, where they are optionally amplified, e.g. by transcription. Such sequences include both simple oligonucleotide sequences and catalytic sequences such as ribozymes.

For example, a reduction or elimination of expression (i.e., a "knock-out") of a transcription factor or transcription factor homolog polypeptide in a transgenic plant, e.g., to modify a plant trait, can be obtained by introducing an antisense construct corresponding to the polypeptide of interest as a cDNA. For antisense suppression, the transcription factor or homolog cDNA is arranged in reverse orientation (with respect to the coding sequence) relative to the promoter sequence in the expression vector. The introduced sequence need not be the full length cDNA or gene, and need not be identical to the cDNA or gene found in the plant type to be transformed. Typically, the antisense sequence need only be capable of hybridizing to the target gene or RNA of interest. Thus, where the introduced sequence is of shorter length, a higher degree of homology to the endogenous transcription factor sequence will be needed for effective antisense suppression. While antisense sequences of various lengths can be utilized, preferably, the introduced antisense sequence in the vector will be at least 30 nucleotides in length, and improved antisense suppression will typically be observed as the length of the antisense sequence increases. Preferably, the length of the antisense sequence in the vector will be greater than 100 nucleotides. Transcription of an antisense construct as described results in the production of RNA molecules that are the reverse complement of mRNA molecules transcribed from the endogenous transcription factor gene in the plant cell.

Suppression of endogenous transcription factor gene expression can also be achieved using RNA interference-, or RNAi. RNAi is a post-transcriptional, targeted gene-silencing technique that uses double-stranded RNA (dsRNA) to incite degradation of messenger RNA (mRNA) containing the same sequence as the dsRNA (Constans, (2002) *The Scientist* 16:36). Small interfering RNAs, or siRNAs are produced in at least two steps: an endogenous ribonuclease cleaves longer dsRNA into shorter, 21-23 nucleotide-long RNAs. The siRNA segments then mediate the degradation of the target mRNA (Zamore, (2001) *Nature Struct. Biol.,* 8:746-50). RNAi has been used for gene function determination in a manner similar to antisense oligonucleotides (Constans, (2002) *The Scientist* 16:36). Expression vectors that continually express siRNAs in transiently and stably transfected cells have been engineered to express small hairpin RNAs (shRNAs), which get processed in vivo into siRNAs-like molecules capable of carrying out gene-specific silencing (Brummelkamp et al., (2002) *Science* 296:550-553, and Paddison, et al. (2002) *Genes & Dev.* 16:948-958). Post-transcriptional gene silencing by double-stranded RNA is discussed in further detail by Hammond et al. (2001) *Nature Rev Gen* 2: 110-119, Fire et al. (1998) *Nature* 391: 806-811 and Timmons and Fire (1998) *Nature* 395: 854. Vectors in which RNA encoded by a transcription factor or transcription factor homolog cDNA is over-expressed can also be used to obtain co-suppression of a corresponding endogenous gene, e.g., in the manner described in U.S. Pat. No. 5,231,020 to Jorgensen. Such co-suppression (also termed sense suppression) does not require that the entire transcription factor cDNA be introduced into the plant cells, nor does it require that the introduced sequence be exactly identical to the endogenous transcription factor gene of interest. However, as with antisense suppression, the suppressive efficiency will be enhanced as specificity of hybridization is increased, e.g., as the introduced sequence is lengthened, and/or as the sequence similarity between the introduced sequence and the endogenous transcription factor gene is increased.

Vectors expressing an untranslatable form of the transcription factor mRNA, e.g., sequences comprising one or more stop codon, or nonsense mutation) can also be used to suppress expression of an endogenous transcription factor, thereby reducing or eliminating its activity and modifying one or more traits. Methods for producing such constructs are described in U.S. Pat. No. 5,583,021. Preferably, such constructs are made by introducing a premature stop codon into the transcription factor gene. Alternatively, a plant trait can be modified by gene silencing using double-stranded RNA (Sharp (1999) *Genes and Development* 13: 139-141). Another method for abolishing the expression of a gene is by insertion mutagenesis using the T-DNA of *Agrobacterium tumefaciens*. After generating the insertion mutants, the mutants can be screened to identify those containing the insertion in a transcription factor or transcription factor homolog gene. Plants containing a single transgene insertion event at the desired gene can be crossed to generate homozygous plants for the mutation. Such methods are well known to those of skill in the art (See for example Koncz et al. (1992) *Methods in Arabidopsis Research*, World Scientific Publishing Co. Pte. Ltd., River Edge, N.J.).

Alternatively, a plant phenotype can be altered by eliminating an endogenous gene, such as a transcription factor or transcription factor homolog, e.g., by homologous recombination (Kempin et al. (1997) *Nature* 389: 802-803).

A plant trait can also be modified by using the Cre-lox system (for example, as described in U.S. Pat. No. 5,658,772). A plant genome can be modified to include first and second lox sites that are then contacted with a Cre recombinase. If the lox sites are in the same orientation, the intervening DNA sequence between the two sites is excised. If the lox sites are in the opposite orientation, the intervening sequence is inverted.

The polynucleotides and polypeptides of this invention can also be expressed in a plant in the absence of an expression cassette by manipulating the activity or expression level of the endogenous gene by other means, such as, for example, by ectopically expressing a gene by T-DNA activation tagging (Ichikawa et al. (1997) *Nature* 390 698-701; Kakimoto et al. (1996) *Science* 274: 982-985). This method entails transforming a plant with a gene tag containing multiple transcriptional enhancers and once the tag has inserted into the genome, expression of a flanking gene coding sequence becomes deregulated. In another example, the transcriptional machinery in a plant can be modified so as to increase transcription levels of a polynucleotide of the invention (See, e.g., PCT Publications WO 96/06166 and WO 98/53057 which describe the modification of the DNA-binding specificity of zinc finger proteins by changing particular amino acids in the DNA-binding motif).

The transgenic plant can also include the machinery necessary for expressing or altering the activity of a polypeptide encoded by an endogenous gene, for example, by altering the phosphorylation state of the polypeptide to maintain it in an activated state.

Transgenic plants (or plant cells, or plant explants, or plant tissues) incorporating the polynucleotides of the invention and/or expressing the polypeptides of the invention can be produced by a variety of well established techniques as described above. Following construction of a vector, most typically an expression cassette, including a polynucleotide, e.g., encoding a transcription factor or transcription factor homolog, of the invention, standard techniques can be used to introduce the polynucleotide into a plant, a plant cell, a plant explant or a plant tissue of interest. Optionally, the plant cell, explant or tissue can be regenerated to produce a transgenic plant.

The plant can be any higher plant, including gymnosperms, monocotyledonous and dicotyledenous plants. Suitable protocols are available for *Leguminosae* (alfalfa, soybean, clover, etc.), *Umbelliferae* (carrot, celery, parsnip), *Cruciferae* (cabbage, radish, rapeseed, broccoli, etc.), *Curcurbitaceae* (melons and cucumber), *Gramineae* (wheat, corn, rice, barley, millet, etc.), *Solanaceae* (potato, tomato, tobacco, peppers, etc.), and various other crops. See protocols described in Ammirato et al., eds., (1984) *Handbook of Plant Cell Culture—Crop Species*, Macmillan Publ. Co., New York, N.Y.; Shimamoto et al. (1989) *Nature* 338: 274-276; Fromm et al. (1990) *Bio/Technol.* 8: 833-839; and Vasil et al. (1990) *Bio/Technol.* 8: 429-434.

Transformation and regeneration of both monocotyledonous and dicotyledonous plant cells is now routine, and the selection of the most appropriate transformation technique will be determined by the practitioner. The choice of method will vary with the type of plant to be transformed; those skilled in the art will recognize the suitability of particular methods for given plant types. Suitable methods can include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium tumefaciens* mediated transformation. Transformation means introducing a nucleotide sequence into a plant in a manner to cause stable or transient expression of the sequence.

Successful examples of the modification of plant characteristics by transformation with cloned sequences which serve to illustrate the current knowledge in this field of technology, and which are herein incorporated by reference, include: U.S. Pat. Nos. 5,571,706; 5,677,175; 5,510,471; 5,750,386; 5,597,945; 5,589,615; 5,750,871; 5,268,526; 5,780,708; 5,538,880; 5,773,269; 5,736,369 and 5,610,042.

Following transformation, plants are preferably selected using a dominant selectable marker incorporated into the transformation vector. Typically, such a marker will confer antibiotic or herbicide resistance on the transformed plants, and selection of transformants can be accomplished by exposing the plants to appropriate concentrations of the antibiotic or herbicide.

After transformed plants are selected and grown to maturity, those plants showing a modified trait are identified. The modified trait can be any of those traits described above. Additionally, to confirm that the modified trait is due to changes in expression levels or activity of the polypeptide or polynucleotide of the invention can be determined by analyzing mRNA expression using Northern blots, RT-PCR or microarrays, or protein expression using immunoblots or Western blots or gel shift assays.

Integrated Systems—Sequence Identity

Additionally, the present invention may be an integrated system, computer or computer readable medium that comprises an instruction set for determining the identity of one or more sequences in a database. In addition, the instruction set can be used to generate or identify sequences that meet any specified criteria. Furthermore, the instruction set may be used to associate or link certain functional benefits, such improved characteristics, with one or more identified sequence.

For example, the instruction set can include, e.g., a sequence comparison or other alignment program, e.g., an available program such as, for example, the Wisconsin Package Version 10.0, such as BLAST, FASTA, PILEUP, FINDPATTERNS or the like (GCG, Madison, Wis.). Public sequence databases such as GenBank, EMBL, Swiss-Prot and PIR or private sequence databases such as PHYTOSEQ sequence database (Incyte Genomics, Palo Alto, Calif.) can be searched.

Alignment of sequences for comparison can be conducted by the local homology algorithm of Smith and Waterman (1981) *Adv. Appl. Math.* 2: 482489, by the homology alignment algorithm of Needleman and Wunsch (1970) *J. Mol. Biol.* 48: 443453, by the search for similarity method of Pearson and Lipman (1988) *Proc. Natl. Acad. Sci.* 85: 2444-2448, by computerized implementations of these algorithms. After alignment, sequence comparisons between two (or more) polynucleotides or polypeptides are typically performed by comparing sequences of the two sequences over a comparison window to identify and compare local regions of sequence similarity. The comparison window can be a segment of at least about 20 contiguous positions, usually about 50 to about 200, more usually about 100 to about 150 contiguous positions. A description of the method is provided in Ausubel et al. supra.

A variety of methods for determining sequence relationships can be used, including manual alignment and computer assisted sequence alignment and analysis. This later approach is a preferred approach in the present invention, due to the increased throughput afforded by computer assisted methods. As noted above, a variety of computer programs for performing sequence alignment are available, or can be produced by one of skill.

One example algorithm that is suitable for determining percent sequence identity and sequence similarity is the BLAST algorithm, which is described in Altschul et al. (1990) *J. Mol. Biol.* 215: 403410. Software for performing BLAST analyses is publicly available, e.g., through the National Library of Medicine's National Center for Biotechnology Information (ncbi.nlm.nih; see at world wide web (www) National Institutes of Health US government (gov) website). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff (1992) *Proc. Natl. Acad. Sci.* 89: 10915-10919). Unless otherwise indicated, "sequence identity" here refers to the % sequence identity generated from a tblastx using the NCBI version of the algorithm at the default settings using gapped alignments with the filter "off" (see, for example, NIH NLM NCBI website at ncbi.nlm.nih, supra).

In addition to calculating percent sequence identity, the BLAST algorithm also performs a statistical analysis of the similarity between two sequences (see, e.g. Karlin and Altschul (1993) *Proc. Natl. Acad. Sci.* 90: 5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence (and, therefore, in this context, homologous) if the smallest sum probability in a comparison of the test nucleic acid to the reference nucleic acid is less than about 0.1, or less than about 0.01, and or even less than about 0.001. An additional example of a useful sequence alignment algorithm is PILEUP. PILEUP creates a multiple sequence alignment from a group of related sequences using progressive, pairwise alignments. The program can align, e.g., up to 300 sequences of a maximum length of 5,000 letters.

The integrated system, or computer typically includes a user input interface allowing a user to selectively view one or more sequence records corresponding to the one or more character strings, as well as an instruction set which aligns the one or more character strings with each other or with an additional character string to identify one or more region of sequence similarity. The system may include a link of one or more character strings with a particular phenotype or gene function. Typically, the system includes a user readable output element that displays an alignment produced by the alignment instruction set.

The methods of this invention can be implemented in a localized or distributed computing environment. In a distributed environment, the methods may be implemented on a single computer comprising multiple processors or on a multiplicity of computers. The computers can be linked, e.g. through a common bus, but more preferably the computer(s) are nodes on a network. The network can be a generalized or a dedicated local or wide-area network and, in certain preferred embodiments, the computers may be components of an intra-net or an internet.

Thus, the invention provides methods for identifying a sequence similar or homologous to one or more polynucleotides as noted herein, or one or more target polypeptides encoded by the polynucleotides, or otherwise noted herein and may include linking or associating a given plant phenotype or gene function with a sequence. In the methods, a sequence database is provided (locally or across an inter or intra net) and a query is made against the sequence database using the relevant sequences herein and associated plant phenotypes or gene functions.

Any sequence herein can be entered into the database, before or after querying the database. This provides for both expansion of the database and, if done before the querying step, for insertion of control sequences into the database. The control sequences can be detected by the query to ensure the general integrity of both the database and the query. As noted, the query can be performed using a web browser based interface. For example, the database can be a centralized public database such as those noted herein, and the querying can be done from a remote terminal or computer across an internet or intranet.

Any sequence herein can be used to identify a similar, homologous, paralogous, or orthologous sequence in another plant. This provides means for identifying endogenous sequences in other plants that may be useful to alter a trait of progeny plants, which results from crossing two plants of different strain. For example, sequences that encode an ortholog of any of the sequences herein that naturally occur in a plant with a desired trait can be identified using the sequences disclosed herein. The plant is then crossed with a second plant of the same species but which does not have the desired trait to produce progeny which can then be used in further crossing experiments to produce the desired trait in the second plant. Therefore the resulting progeny plant contains no transgenes; expression of the endogenous sequence may also be regulated by treatment with a particular chemical or other means, such as EMR. Some examples of such compounds well known in the art include: ethylene; cytokinins; phenolic compounds, which stimulate the transcription of the genes needed for infection; specific monosaccharides and acidic environments which potentiate vir gene induction; acidic polysaccharides which induce one or more chromosomal genes; and opines; other mechanisms include light or dark treatment (for a review of examples of such treatments, see, Winans (1992) *Microbiol. Rev.* 56: 12-31; Eyal et al. (1992) *Plant Mol. Biol.* 19: 589-599; Chrispeels et al. (2000) *Plant Mol. Biol.* 42: 279-290; Piazza et al. (2002) *Plant Physiol.* 128: 1077-1086).

Table 6 lists sequences discovered to be orthologous to a number of representative transcription factors of the present invention, in decreasing order of similarity to G867. The column headings include the transcription factors listed by (a) the SEQ ID NO: of the homolog (paralog or ortholog) or the nucleotide encoding the homolog; (b) the GID sequence identifier; (c) the Sequence Identifier or GenBank Accession Number; (d) the species from which the homologs (orthologs or paralogs) to the transcription factors are derived; and (e) the smallest sum probability relationship to G867 determined by BLAST analysis.

TABLE 6

Homologs of Representative *Arabidopsis* Transcription Factor Genes Identified using BLAST

| SEQ ID NO: of Homolog or Nucleotide Encoding Homolog | GID No. | Sequence Identifier or Accession Number | Species from Which Homolog is Derived | Smallest Sum Probability to G867 |
| --- | --- | --- | --- | --- |
| 1 | G867 | | *Arabidopsis thaliana* | 0.0 |
| 7 | G1930 | | *Arabidopsis thaliana* | 1.00E−132 |
| 3 | G9 | | *Arabidopsis thaliana* | 1.00E−115 |
| 5 | G993 | | *Arabidopsis thaliana* | 1.00E−115 |
| 41 | | BZ458719 | *Brassica oleracea* | 1.00E−113 |
| 17 | G3451 | GLYMA-28NOV01-CLUSTER19062_3 | *Glycine max* | 1.00E−110 |
| 25 | G3454 | | *Glycine max* | 1.00E−109 |
| 21 | G3452 | GLYMA-28NOV01-CLUSTER19062_7 | *Glycine max* | 2.00E−99 |
| 23 | G3453 | | *Glycine max* | 3.0E−98 |
| 78 | | CB686050 | *Brassica napus* | 1.00E−97 |
| 43 | | BQ971511 | *Helianthus annuus* | 2.00E−94 |
| 45 | | BU025988 | *Helianthus annuus* | 3.00E−92 |
| 86 | | BQ971525 | *Helianthus annuus* | 2.00E−92 |
| 37 | G3432 | | *Zea mays* | 1.00E−87 |
| 35 | | AP003450 | *Oryza sativa* | 9.00E−85 |
| 87 | | gi1856433 | *Oryza sativa* (*japonica* cultivar-group) | 3.00E−85 |
| 33 | G3390 | AC130725 | *Oryza sativa* | 8.00E−84 |
| 47 | | BT009310 | *Triticum aestivum* | 4.00E−82 |
| 35 | G3391 | AP003450 | *Oryza sativa* | 1.00E−82 |
| 29 | G3388 | OSC21673.C1.p5.fg AP002913 | *Oryza sativa* | 2.00E−80 |
| 49 | | CC616336 | *Zea mays* | 2.00E−80 |
| 33 | | AC130725 | *Oryza sativa* (*japonica* cultivar-group) | 1.00E−80 |

TABLE 6-continued

Homologs of Representative *Arabidopsis* Transcription Factor Genes Identified using BLAST

| SEQ ID NO: of Homolog or Nucleotide Encoding Homolog | GID No. | Sequence Identifier or Accession Number | Species from Which Homolog is Derived | Smallest Sum Probability to G867 |
|---|---|---|---|---|
| 88 | | AC136492 | *Oryza sativa* (*japonica* cultivar-group) | 1.00E−80 |
| 51 | | AAAA01000997 | *Oryza sativa* (*indica* cultivar-group) | 1.00E−79 |
| 31 | G3389 | OSC21674.C1.p12.fg AP002913 | *Oryza sativa* | 1.00E−79 |
| 76 | | BQ405698 | *Gossypium arboreum* | 2.00E−77 |
| 39 | G3433 | | *Zea mays* | 2.00E−73 |
| 27 | G3455 | GLYMA-27NOV01-CLUSTER19062_5 | *Glycine max* | 3.00E−70 |
| 89 | | BZ015521 | *Brassica oleracea* | 5.00E−69 |
| 90 | | BF520598 | *Medicago truncatula* | 2.00E−66 |
| 91 | | BU994579 | *Hordeum vulgare* subsp. *vulgare* | 5.00E−64 |
| 92 | | CD814840 | *Brassica napus* | 4.00E−64 |
| 93 | | CB894555 | *Medicago truncatula* | 3.00E−64 |
| 77 | | BF424857 | *Glycine max* | 2.00E−62 |
| 74 | | BU871082 | *Populus balsamifera* subsp. *trichocarpa* | 2.00E−61 |
| 79 | | BQ855250 | *Lactuca sativa* | 7.00E−61 |

Molecular Modeling

Another means that may be used to confirm the utility and function of transcription factor sequences that are orthologous or paralogous to presently disclosed transcription factors is through the use of molecular modeling software. Molecular modeling is routinely used to predict polypeptide structure, and a variety of protein structure modeling programs, such as "Insight II" (Accelrys, Inc.) are commercially available for this purpose. Modeling can thus be used to predict which residues of a polypeptide can be changed without altering function (Crameri et al. (2003) U.S. Pat. No. 6,521,453). Thus, polypeptides that are sequentially similar can be shown to have a high likelihood of similar function by their structural similarity, which may, for example, be established by comparison of regions of superstructure. The relative tendencies of amino acids to form regions of superstructure (for example, helixes and _-sheets) are well established. For example, O'Neil et al. ((1990) *Science* 250: 646-651) have discussed in detail the helix forming tendencies of amino acids. Tables of relative structure forming activity for amino acids can be used as substitution tables to predict which residues can be functionally substituted in a given region, for example, in DNA-binding domains of known transcription factors and equivalogs. Homologs that are likely to be functionally similar can then be identified.

Of particular interest is the structure of a transcription factor in the region of its conserved domains, such as those identified in Table 1. Structural analyses may be performed by comparing the structure of the known transcription factor around its conserved domain with those of orthologs and paralogs. Analysis of a number of polypeptides within a transcription factor group or clade, including the functionally or sequentially similar polypeptides provided in the Sequence Listing, may also provide an understanding of structural elements required to regulate transcription within a given family.

EXAMPLES

The invention, now being generally described, will be more readily understood by reference to the following examples, which are included merely for purposes of illustration of certain aspects and embodiments of the present invention and are not intended to limit the invention. It will be recognized by one of skill in the art that a transcription factor that is associated with a particular first trait may also be associated with at least one other, unrelated and inherent second trait which was not predicted by the first trait.

The complete descriptions of the traits associated with each polynucleotide of the invention are fully disclosed in Example VIII. The complete description of the transcription factor gene family and identified AP2 binding domains and B3 domains of the polypeptide encoded by the polynucleotide is fully disclosed in Table 1.

Example I

Full Length Gene Identification and Cloning

Putative transcription factor sequences (genomic or ESTs) related to known transcription factors were identified in the *Arabidopsis thaliana* GenBank database using the tblastn sequence analysis program using default parameters and a P-value cutoff threshold of −4 or −5 or lower, depending on the length of the query sequence. Putative transcription factor sequence hits were then screened to identify those containing particular sequence strings. If the sequence hits contained such sequence strings, the sequences were confirmed as transcription factors.

Alternatively, *Arabidopsis thaliana* cDNA libraries derived from different tissues or treatments, or genomic libraries were screened to identify novel members of a transcription family using a low stringency hybridization approach. Probes were synthesized using gene specific primers in a standard PCR reaction (annealing temperature 60° C.) and labeled with $^{32}$P dCTP using the High Prime DNA Labeling Kit (Boehringer Mannheim Corp. (now Roche Diagnostics Corpa, Indianapolis, Ind.), Purified radiolabelled probes were added to filters immersed in Church hybridization medium (0.5 M $NaPO_4$ pH 7.0, 7% SDS, 1% w/v bovine serum albumin) and hybridized overnight at 60° C. with shaking. Filters were washed two times for 45 to 60 minutes with 1×SCC, 1% SDS at 60° C.

To identify additional sequence 5' or 3' of a partial cDNA sequence in a cDNA library, 5' and 3' rapid amplification of cDNA ends (RACE) was performed using the MARATHON cDNA amplification kit (Clontech, Palo Alto, Calif.). Generally, the method entailed first isolating poly(A) mRNA, performing first and second strand cDNA synthesis to generate double stranded cDNA, blunting cDNA ends, followed by ligation of the MARATHON Adaptor to the cDNA to form a library of adaptor-ligated ds cDNA.

Gene-specific primers were designed to be used along with adaptor specific primers for both 5' and 3' RACE reactions. Nested primers, rather than single primers, were used to increase PCR specificity. Using 5' and 3' RACE reactions, 5' and 3' RACE fragments were obtained, sequenced and cloned. The process can be repeated until 5' and 3' ends of the full-length gene were identified. Then the full-length cDNA was generated by PCR using primers specific to 5' and 3' ends of the gene by end-to-end PCR.

Example II

Construction of Expression Vectors

The sequence was amplified from a genomic or cDNA library using primers specific to sequences upstream and downstream of the coding region. For direct promoter: transcription factor gene fusions, the expression vector was pMEN20 or pMEN65, which are both derived from pMON316 (Sanders et al. (1987) Nucleic Acids Res. 15:1543-1558) and contain the CaMV $^{35}$S apromoter to express transgenes. To clone the sequence into the vector, both pMEN20 and the amplified DNA fragment were digested separately with SalI and NotI restriction enzymes at 37° C. for 2 hours. The digestion products were subject to electrophoresis in a 0.8% agarose gel and visualized by ethidium bromide staining. The DNA fragments containing the sequence and the linearized plasmid were excised and purified by using a QIAQUICK gel extraction kit (Qiagen, Valencia Calif.). The fragments of interest were ligated at a ratio of 3:1 (vector to insert). Ligation reactions using T4 DNA ligase (New England Biolabs, Beverly Mass.) were carried out at 16° C. for 16 hours. The ligated DNAs were transformed into competent cells of the E. coli strain DH5alpha by using the heat shock method. The transformations were plated on LB plates containing 50 mg/l kanamycin (Sigma Chemical Co. St. Louis Mo.). Individual colonies were grown overnight in five milliliters of LB broth containing 50 mg/l kanamycin at 37° C. Plasmid DNA was purified by using Qiaquick Mini Prep kits (Qiagen).

For the two-component system, two separate constructs were used: Promoter::LexA-GAL4TA and opLexA::TF. The first of these (Promoter::LexA-GAL4TA) comprised a desired promoter cloned in front of (that is, at a position that is upstream or closer to the 5' end of the promoter region) a LexA DNA binding domain fused to a GAL4 activation domain. The construct vector backbone (pMEN48; P5375) also carried a kanamycin resistance marker, along with an opLexA::GFP reporter. Transgenic lines were obtained containing this first component, and a line was selected that showed reproducible expression of the reporter gene in the desired pattern through a number of generations. A homozygous population was established for that line, and the population was supertransformed with the second construct (opLexA::TF) carrying the transcription factor of interest cloned behind or after (that is, at a position that is downstream or closer to the 3' end of the operator) a LexA operator site. This second construct vector backbone (pMEN53; P5381) also contained a sulfonamide resistance marker. One example of a desired promoter includes, but is not limited to, the RD29A promoter.

Each of the above methods offered a number of pros and cons. A direct fusion approach allowed for much simpler genetic analysis if a given promoter-transcription factor line was to be crossed into different genetic backgrounds at a later date. The two-component method, on the other hand, potentially allowed for stronger expression to be obtained via an amplification of transcription. A range of two-component constructs were available at the start of this research program.

Example III

Transformation of Agrobacterium with the Expression Vector

After the expression constructs were generated, the constructs were used to transform Agrobacterium tumefaciens cells expressing the gene products. The stock of Agrobacterium tumefaciens cells for transformation were made as described by Nagel et al. (1990) FEMS Microbiol Letts. 67: 325-328. Agrobacterium strain ABI was grown in 250 ml LB medium (Sigma) overnight at 28° C. with shaking until an absorbance over 1 cm at 600 nm ($A_{600}$) of 0.5-1.0 was reached. Cells were harvested by centrifugation at 4,000×g for 15 min at 4° C. Cells were then resuspended in 250 µl chilled buffer (1 mM HEPES, pH adjusted to 7.0 with KOH). Cells were centrifuged again as described above and resuspended in 125 µl chilled buffer. Cells were then centrifuged and resuspended two more times in the same HEPES buffer as described above at a volume of 100 µl and 750 µl, respectively. Resuspended cells were then distributed into 40 µl aliquots, quickly frozen in liquid nitrogen, and stored at −80° C.

Agrobacterium cells were transformed with constructs prepared as described above following the protocol described by Nagel et al. (supra). For each DNA construct to be transformed, 50-100 ng DNA (generally resuspended in 10 mM Tris-HCl, 1 mM EDTA, pH 8.0) was mixed with 40 µl of Agrobacterium cells. The DNA/cell mixture was then transferred to a chilled cuvette with a 2 mm electrode gap and subject to a 2.5 kV charge dissipated at 25 µF and 200 µF using a Gene Pulser II apparatus (Bio-Rad, Hercules, Calif.). After electroporation, cells were immediately resuspended in 1.0 ml LB and allowed to recover without antibiotic selection for 2-4 hours at 28° C. in a shaking incubator. After recovery, cells were plated onto selective medium of LB broth containing 100 µg/ml spectinomycin (Sigma) and incubated for 24-48 hours at 28° C. Single colonies were then picked and inoculated in fresh medium. The presence of the plasmid construct was verified by PCR amplification and sequence analysis.

Example IV

Transformation of Arabidopsis Plants with Agrobacterium tumefaciens

After transformation of Agrobacterium tumefaciens with the constructs or plasmid vectors containing the gene of interest, single Agrobacterium colonies were identified, propagated, and used to transform Arabidopsis plants. Briefly, 500 ml cultures of LB medium containing 50 mg/l kanamycin were inoculated with the colonies and grown at 28° C. with shaking for 2 days until an optical absorbance at 600 nm wavelength over 1 cm ($A_{600}$) of >2.0 is reached. Cells were then harvested by centrifugation at 4,000×g for 10 min, and resuspended in infiltration medium (½× Murashige and Skoog salts (Sigma), 1× Ganaborg's B-5 vitamins (Sigma), 5.0% (w/v) sucrose (Sigma), 0.044 benzylamino purine (Sigma), 200 µl/l Silwet L-77 (Lehle Seeds)) until an $A_{600}$ of 0.8 was reached.

Prior to transformation, Arabidopsis thaliana seeds (ecotype Columbia) were sown at a density of ~10 plants per 4" pot onto Pro-Mix BX potting medium (Hummert International) covered with fiberglass mesh (18 mm×16 mm). Plants were grown under continuous illumination (50-75 µE/m²/sec) at 22-23° C. with 65-70% relative humidity. After about 4 weeks, primary inflorescence stems (bolts) are cut off to encourage growth of multiple secondary bolts. After flowering of the mature secondary bolts, plants were prepared for transformation by removal of all siliques and opened flowers.

The pots were then immersed upside down in the mixture of Agrobacterium infiltration medium as described above for 30 sec, and placed on their sides to allow draining into a 1'×2' flat surface covered with plastic wrap. After 24 h, the plastic wrap was removed and pots are turned upright. The immersion procedure was repeated one week later, for a total of two immersions per pot. Seeds were then collected from each transformation pot and analyzed following the protocol described below.

Example V

Identification of Arabidopsis Primary Transformants

Seeds collected from the transformation pots were sterilized essentially as follows. Seeds were dispersed into in a solution containing 0.1% (v/v) Triton X-100 (Sigma) and sterile water and washed by shaking the suspension for 20 min. The wash solution was then drained and replaced with fresh wash solution to wash the seeds for 20 min with shaking. After removal of the ethanol/detergent solution, a solution containing 0.1% (v/v) Triton X-100 and 30% (v/v) bleach (CLOROX; Clorox Corp. Oakland Calif.) was added to the seeds, and the suspension was shaken for 10 min. After removal of the bleach/detergent solution, seeds were then washed five times in sterile distilled water. The seeds were stored in the last wash water at 4° C. for 2 days in the dark before being plated onto antibiotic selection medium (1× Murashige and Skoog salts (pH adjusted to 5.7 with 1M KOH), 1× Gamborg's B-5 vitamins, 0.9% phytagar (Life Technologies), and 50 mg/l kanamycin). Seeds were germinated under continuous illumination (50-75 µE/m²/sec) at 22-23° C. After 7-10 days of growth under these conditions, kanamycin resistant primary transformants (T1 generation) were visible and obtained. These seedlings were transferred first to fresh selection plates where the seedlings continued to grow for 3-5 more days, and then to soil (Pro-Mix BX potting medium).

Primary transformants were crossed and progeny seeds ($T_2$) collected; kanamycin resistant seedlings were selected and analyzed. The expression levels of the recombinant polynucleotides in the transformants varies from about a 5% expression level increase to a least a 100% expression level increase. Similar observations are made with respect to polypeptide level expression.

Example VI

Identification of Arabidopsis Plants with Transcription Factor Gene Knockouts

The screening of insertion mutagenized Arabidopsis collections for null mutants in a known target gene was essentially as described in Krysan et al. (1999) Plant Cell 11: 2283-2290. Briefly, gene-specific primers, nested by 5-250 base pairs to each other, were designed from the 5' and 3' regions of a known target gene. Similarly, nested sets of primers were also created specific to each of the T-DNA or transposon ends (the "right" and "left" borders). All possible combinations of gene specific and T-DNA/transposon primers were used to detect by PCR an insertion event within or close to the target gene. The amplified DNA fragments were then sequenced which allows the precise determination of the T-DNA/transposon insertion point relative to the target gene. Insertion events within the coding or intervening sequence of the genes were deconvoluted from a pool comprising a plurality of insertion events to a single unique mutant plant for functional characterization. The method is described in more detail in Yu and Adam, U.S. application Ser. No. 09/177,733 filed Oct. 23, 1998.

Example VII

Identification of Modified Phenotypes in Overexpression or Gene Knockout Plants

Experiments were performed to identify those transformants or knockouts that exhibited modified biochemical characteristics.

Calibration of NIRS response was performed using data obtained by wet chemical analysis of a population of Arabidopsis ecotypes that were expected to represent diversity of oil and protein levels.

Experiments were performed to identify those transformants or knockouts that exhibited modified sugar-sensing. For such studies, seeds from transformants were germinated on media containing 5% glucose or 9.4% sucrose which normally partially restrict hypocotyl elongation. Plants with altered sugar sensing may have either longer or shorter hypocotyls than normal plants when grown on this media. Additionally, other plant traits may be varied such as root mass.

In some instances, expression patterns of the stress-induced genes may be monitored by microarray experiments. In these experiments, cDNAs are generated by PCR and resuspended at a final concentration of ~100 ng/ul in 3×SSC or 150 mM Na-phosphate (Eisen and Brown (1999) Methods Enzymol. 303: 179-205). The cDNAs are spotted on microscope glass slides coated with polylysine. The prepared cDNAs are aliquoted into 384 well plates and spotted on the slides using, for example, an x-y-z gantry (OmniGrid) which may be purchased from GeneMachines (Menlo Park, Calif.) outfitted with quill type pins which may be purchased from Telechem International (Sunnyvale, Calif.). After spotting, the arrays are cured for a minimum of one week at room temperature, rehydrated and blocked following the protocol recommended by Eisen and Brown (1999; supra).

Sample total RNA (10 µg) samples are labeled using fluorescent Cy3 and Cy5 dyes. Labeled samples are resuspended in 4×SSC/0.03% SDS/4 µg salmon sperm DNA/2 µg tRNA/50 mM Na-pyrophosphate, heated for 95° C. for 2.5 minutes, spun down and placed on the array. The array is then covered with a glass coverslip and placed in a sealed chamber. The chamber is then kept in a water bath at 62° C. overnight. The arrays are washed as described in Eisen and Brown (1999, supra) and scanned on a General Scanning 3000 laser scanner. The resulting files are subsequently quantified using IMA-GENE, software (BioDiscovery, Los Angeles Calif.).

RT-PCR experiments may be performed to identify those genes induced after exposure to osmotic stress. Generally, the gene expression patterns from ground plant leaf tissue is examined. Reverse transcriptase PCR was conducted using gene specific primers within the coding region for each sequence identified. The primers were designed near the 3' region of each DNA binding sequence initially identified.

Total RNA from these ground leaf tissues was isolated using the CTAB extraction protocol. Once extracted total RNA was normalized in concentration across all the tissue types to ensure that the PCR reaction for each tissue received the same amount of cDNA template using the 28S aband as reference. Poly(A+) RNA was purified using a modified protocol from the Qiagen OLIGOTEX purification kit batch protocol. cDNA was synthesized using standard protocols. After the first strand cDNA synthesis, primers for Actin 2 were used to normalize the concentration of cDNA across the tissue types. Actin 2 is found to be constitutively expressed in fairly equal levels across the tissue types we are investigating.

For RT PCR, cDNA template was mixed with corresponding primers and Taq DNA polymerase. Each reaction consisted of 0.2 µl cDNA template, 2 µl 10× Tricine buffer, 2 µl 10× Tricine buffer and 16.8 µl water, 0.05 µl Primer 1, 0.05 µl, Primer 2, 0.3 µl Taq DNA polymerase and 8.6 µl water.

The 96 well plate is covered with microfilm and set in the thermocycler to start the reaction cycle. By way of illustration, the reaction cycle may comprise the following steps:
Step 1: 93° C. for 3 min;
Step 2: 93° C. for 30 sec;
Step 3: 65° C. for 1 min;
Step 4: 72° C. for 2 min;
Steps 2, 3 and 4 are repeated for 28 cycles;
Step 5: 72° C. for 5 min; and
Step 6 4° C.

To amplify more products, for example, to identify genes that have very low expression, additional steps may be performed: The following method illustrates a method that may be used in this regard. The PCR plate is placed back in the thermocycler for 8 more cycles of steps 2-4.
Step 2 93° C. for 30 sec;
Step 3 65° C. for 1 min;
Step 4 72° C. for 2 min, repeated for 8 cycles; and
Step 5 4° C.

Eight microliters of PCR product and 1.5 µl of loading dye are loaded on a 1.2% agarose gel for analysis after 28 cycles and 36 cycles. Expression levels of specific transcripts are considered low if they were only detectable after 36 cycles of PCR. Expression levels are considered medium or high depending on the levels of transcript compared with observed transcript levels for an internal control such as actin2. Transcript levels are determined in repeat experiments and compared to transcript levels in control (e.g., non-transformed) plants.

Modified phenotypes observed for particular overexpressor or knockout plants are provided. For a particular overexpressor that shows a less beneficial characteristic, it may be more useful to select a plant with a decreased expression of the particular transcription factor. For a particular knockout that shows a less beneficial characteristic, it may be more useful to select a plant with an increased expression of the particular transcription factor.

The sequences of the Sequence Listing, can be used to prepare transgenic plants and plants with altered osmotic stress tolerance. The specific transgenic plants listed below are produced from the sequences of the Sequence Listing, as noted.

Example VIII

Genes that Confer Significant Improvements to Plants

This example provides experimental evidence for increased tolerance to abiotic stress of plants that are transformed and have increased expression of transcription factor polynucleotides of the invention, when the plants are subjected to abiotic stress. Increased tolerance to these stresses will generally result in increased yields as compared to wild type under conditions of stress. Examples of specific genes and homologs that confer improvements to plants overexpressing a number of members of the G867 clade of transcription factor polypeptides are noted below.

Salt stress assays are intended to find genes that confer better germination, seedling vigor or growth in high salt. Evaporation from the soil surface causes upward water movement and salt accumulation in the upper soil layer where the seeds are placed. Thus, germination normally takes place at a salt concentration much higher than the mean salt concentration in the whole soil profile. Plants differ in their tolerance to NaCl depending on their stage of development, therefore seed germination, seedling vigor, and plant growth responses are evaluated.

Osmotic stress assays (including NaCl and mannitol assays) are intended to determine if an osmotic stress phenotype is NaCl-specific or if it is a general osmotic stress related phenotype. Plants tolerant to osmotic stress could also have more tolerance to drought and/or freezing.

Desiccation assays are intended to find genes that mediate better plant survival after short-term, severe water deprivation. Ion leakage may be measured. Desiccation tolerance indicates a drought-tolerant phenotype.

Temperature stress assays are intended to find genes that confer better germination, seedling vigor or plant growth under temperature stress (cold, freezing and heat).

Sugar sensing assays are intended to find genes involved in sugar sensing by germinating seeds on high concentrations of sucrose and glucose and looking for degrees of hypocotyl elongation. The germination assay on mannitol controls for responses related to osmotic stress. Sugars are key regulatory molecules that affect diverse processes in higher plants including germination, growth, flowering, senescence, sugar metabolism and photosynthesis. Sucrose is the major transport form of photosynthate and its flux through cells has been shown to affect gene expression and alter storage compound accumulation in seeds (source-sink relationships). Glucose-specific hexose-sensing has also been described in plants and is implicated in cell division and repression of "famine" genes (photosynthetic or glyoxylate cycles).

Germination assays followed modifications of the same basic protocol. Sterile seeds were sown on the conditional media listed below. Plates were incubated at 22° C. under 24-hour light (120-130 µEin/m$^2$/s) in a growth chamber. Evaluation of germination and seedling vigor was conducted 3 to 15 days after planting. The basal media was 80% Murashige-Skoog medium (MS)+vitamins.

For salt and osmotic stress germination experiments, the medium was supplemented with 150 mM NaCl or 300 mM mannitol. Growth regulator sensitivity assays were performed in MS media, vitamins, and either 0.3 µM ABA, 9.4% sucrose, or 5% glucose.

Temperature stress cold germination experiments were carried out at 8° C. Heat stress germination experiments were conducted at 32° C. to 37° C. for 6 hours of exposure.

For stress experiments conducted with more mature plants, seeds were germinated and grown for seven days on MS+vitamins+1% sucrose at 22° C. and then transferred to chilling and heat stress conditions. The plants were either exposed to chilling stress (6 hour exposure to 4-8° C.), or heat stress (32° C. was applied for five days, after which the plants were transferred back 22° C. for recovery and evaluated after 5 days relative to controls not exposed to the depressed or elevated temperature).

Results:

As noted below, overexpression of G867 and many related sequences, including *Arabidopsis* sequences G9, G993, G1930, soy sequences G3451, G3452, G3455, and rice sequences G3389, G3390, and G3391, has been shown to increase osmotic stress tolerance.

G867 (SEQ ID NO: 1 and 2)

Published Information

There are six RAV-like proteins in *Arabidopsis*. One of them, G867, has been described in the literature as related to ABI3/VP1 (RAV1; Kagaya et al. (1999) *Nucleic Acids Res.* 27: 470478) based on the presence of a B3 domain (which is also found in the ABI3/VP1 family of transcription factors). G867/RAV1 belongs to a small subgroup within the AP2/EREBP family of transcription factors, whose distinguishing characteristic is that its members contain a second DNA-binding domain, in addition to the conserved AP2 domain, that is related to the B3 domain of VP1/ABI3 (Kagaya et al., 1999) supra). Analyses using various deletion derivatives of the RAV 1 fusion protein showed that the two DNA-binding domains of G867, the AP2 and B3 domains, separately recognize each of two motifs that constitute a bipartite binding sequence, CAACA and CACCTG, respectively, and together cooperatively enhance the DNA-binding affinity and specificity of the transcription factor (Kagaya et al., 1999) supra). No functional data are available for G867/RAV1.

Experimental Observations

*Arabidopsis* lines were generated in which G867 was overexpressed with a $^{35}$S adirect promoter fusion construct (P383). These 35S::G867 plants displayed a number of pleiotropic and variable alterations in overall morphology relative to wild-type controls, including a reduction in overall size and alterations in leaf orientation. In some lines, changes in leaf shape, flowering time and non-specific floral abnormalities that reduced fertility were observed. Several lines had small and chlorotic seedlings and had a low germination efficiency.

T1 lines 301-320: all lines appeared slightly reduced in size and #304, 310, 316, 318 showed abnormalities in rosette leaf orientation.

T2-305: all were rather small, marginally early flowering, had rather narrow leaves, and show floral abnormalities (flowers fail to properly open).

T2-306: all were rather small, marginally early flowering, had rather narrow leaves, and show floral abnormalities (flowers fail to properly open).

T2-309: all were small, had narrow, upward oriented leaves, and showed abnormal flowers.

T3-5: all plants were distinctly smaller than wild-type controls, slightly pale and have narrow leaves.

T3-6: all plants were distinctly smaller than wild-type controls, and 4/7 were tiny, dark in color, and perished early in development.

T3-8: 2/7 plants examined were tiny and died at early stages of development, 5/7 were distinctly small.

Lines 309, 312, 313, 314, 316, and 318 showed a segregation on selection plates in the T2 generation that was compatible with the transgene being present at a single locus. Lines 302, 310, 311, 317 showed segregation that was compatible with insertions at multiple loci.

In our earlier genomics program, G867 overexpressing lines were shown to have increased seedling vigor in germination assays on both high salt and high sucrose containing media compared to wild-type controls. In later studies, indicated in the following graph, these results were confirmed. Ten of the 35S::G867 direct-fusion lines were subjected to plate based treatments. All of these lines out-performed wild-type controls in at least one or more of the assays, and particularly strong tolerance was observed to sodium chloride, sucrose, and ABA in germination tests, and to low temperatures in a growth assay.

In the present study, we also sought to test whether use of a two-component overexpression system would produce any strengthening of the phenotype relative to the use of a 35 S adirect promoter-fusion. At various stages of growth, a number of lines were small in size and late developing. Other lines showed no consistent morphological differences with wild-type controls.

TABLE 7

35S::G867 (*Arabidopsis*) Constitutive Promoter Abiotic Stress Assay Results

| Project Type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| Direct promoter-fusion | 302 | wt | wt | wt | wt | wt | wt | wt | wt | + |
| Direct promoter-fusion | 309 | wt | wt | wt | wt | wt | wt | wt | wt | + |
| Direct promoter-fusion | 310 | ++ | wt | + | + | wt | wt | wt | wt | wt |
| Direct promoter-fusion | 311 | ++ | wt | + | + | wt | wt | wt | wt | + |
| Direct promoter-fusion | 312 | wt | wt | + | ++ | wt | wt | wt | wt | + |

TABLE 7-continued

35S::G867 (*Arabidopsis*) Constitutive Promoter Abiotic Stress Assay Results

| Project Type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| Direct promoter-fusion | 313 | wt | wt | wt | wt | wt | wt | wt | wt | + |
| Direct promoter-fusion | 314 | + | wt | + | + | wt | wt | wt | wt | wt |
| Direct promoter-fusion | 316 | wt | wt | + | wt | wt | wt | wt | wt | + |
| Direct promoter-fusion | 317 | + | wt | wt | + | wt | wt | wt | wt | wt |
| Direct promoter-fusion | 318 | + | wt | wt | wt | wt | wt | wt | wt | wt |
| Direct promoter-fusion | 305-1 | wt | wt | wt | + | wt | + | wt | wt | wt |
| Direct promoter-fusion | 305-2 | wt | wt | wt | + | wt | + | wt | wt | wt |
| Direct promoter-fusion | 5-5 | wt | wt | wt | wt | wt | wt | wt | wt | wt |
| Direct promoter-fusion | 5-5 | wt | wt | wt | wt | wt | wt | wt | wt | wt |
| Direct promoter-fusion | 6-10 | wt | wt | wt | + | wt | wt | wt | + | wt |
| Direct promoter-fusion | 6-10 | wt | wt | wt | + | wt | wt | wt | wt | wt |
| 2-components-supTfn | 1622 | + | wt | + | ++ | wt | wt | wt | wt | wt |
| 2-components-supTfn | 1623 | + | wt | + | + | wt | wt | wt | wt | wt |
| 2-components-supTfn | 1625 | wt | wt | wt | + | wt | wt | wt | wt | wt |
| 2-components-supTfn | 1626 | ++ | wt | + | + | wt | wt | wt | wt | wt |
| 2-components-supTfn | 1630 | wt | wt | + | + | wt | wt | wt | wt | wt |
| 2-components-supTfn | 1631 | wt | wt | wt | wt | wt | wt | wt | wt | wt |
| 2-components-supTfn | 1633 | wt | wt | + | ++ | wt | wt | wt | wt | wt |
| 2-components-supTfn | 1634 | + | wt | + | wt | wt | wt | wt | wt | wt |
| 2-components-supTfn | 1635 | wt | wt | wt | wt | wt | wt | wt | wt | wt |
| 2-components-supTfn | 1636 | + | + | + | ++ | wt | wt | wt | wt | wt |

Utilities

Most ABA effects are related to the compound acting as a signal of decreased water availability, whereby it triggers a reduction in water loss, slows growth, and mediates adaptive responses, and thus increased ABA sensitivity is a likely indicator of an enhanced stress response. These observation, and those in salt, and sucrose tolerance assays, indicate that G867 or its equivalogs can be used to increase or facilitate seed germination and seedling or plant growth under adverse conditions such osmotic stresses, including drought and salt stress, which may extend a crops planting season or range, or improve yield or performance.

The enhanced performance of 35S:: G867 seedlings in a cold environment indicates that the gene or its equivalogs might be applied to engineer crops that show better growth under cold stress conditions, which may extend a crops planting season or range, or improve yield or performance.

We have obtained comparable developmental effects as well as a strong enhancement of drought related stress tolerance in overexpression lines for the all three of the putative paralogs; G9, G1930 and G993. The almost identical phenotypic effects observed for the four genes strongly suggest that they are functionally equivalent.

G9 (SEQ ID NO: 3 and 4)
Published Information

G9 was first identified in a partial cDNA clone, and the corresponding gene named RAP2.8 (Okamuro et al., 1997). It has also been named RAV2 (Kagaya et al. (1999) *Nucleic Acids Res.* 27: 470-478). G9/RAV2/RAP2.8 belongs to a small subgroup within the AP2/EREBP family of transcription factors, whose distinguishing characteristic is that its members contain a second DNA-binding domain, in addition to the conserved AP2 domain, that is related to the B3 domain of VP1/ABI3 (Kagaya et al., 1999) supra). It has been shown that the two DNA-binding domains of RAV1 (another member of this subgroup of proteins) can separately recognize each of two motifs that constitute a bipartite binding sequence and together cooperatively enhance its DNA-binding affinity and specificity (Kagaya et al., 1999) supra). No functional data are available for G9/RAV2/RAP2.8 or RAV1.

Experimental Observations

The complete sequence of G9 was determined. G9 appeared to be constitutively expressed. However, overexpression of G9 caused phenotypic changes in the roots: more root growth on MS plates, and hairy roots on media containing 10 μM methyl jasmonate (MeJ).

Increased seedling vigor, manifested by increased expansion of the cotyledons of G9 overexpressing plants, was observed in germination assays on both high salt (150 mM NaCl) and high sucrose-containing media (9.4% sucrose), as compared to wild-type controls. A number of these lines were also insensitive to ABA. 35S::G9 transgenic plants were more tolerant to chilling (4°-8° C. for 6 h) compared to the wild-type controls in seedling growth assays (Table 8).

Several G9 overexpressing lines were found to be more sensitive to 0.3 μM ABA.

TABLE 8

35S::G9 (*Arabidopsis*) Constitutive Promoter Abiotic Stress Assay Results

| Project type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| Direct promoter-fusion | 302 | + | wt | + | wt | wt | wt | wt | wt | + |
| Direct promoter-fusion | 304 | + | wt | wt | wt | wt | wt | wt | wt | wt |
| Direct promoter-fusion | 305 | ++ | wt | + | wt | wt | wt | wt | wt | + |
| Direct promoter-fusion | 306 | + | wt | wt | wt | wt | wt | wt | wt | wt |
| Direct promoter-fusion | 307 | + | wt | wt | wt | wt | wt | wt | wt | wt |
| Direct promoter-fusion | 310 | + | wt | + | ++ | wt | wt | wt | wt | + |
| Direct promoter-fusion | 311 | ++ | wt | + | wt | wt | wt | wt | wt | + |
| Direct promoter-fusion | 312 | ++ | wt | wt | + | wt | wt | wt | wt | + |
| Direct promoter-fusion | 313 | + | wt | + | + | wt | wt | wt | wt | + |
| Direct promoter-fusion | 318 | ++ | wt | + | wt | wt | wt | wt | wt | wt |
| 2-components-supTfn | 483 | wt | wt | + | + | wt | wt | wt | wt | wt |
| 2-components-supTfn | 485 | + | wt | wt | wt | wt | wt | wt | wt | wt |
| 2-components-supTfn | 486 | wt | wt | wt | wt | wt | wt | wt | wt | wt |
| 2-components-supTfn | 488 | + | wt | + | ++ | wt | wt | wt | wt | wt |
| 2-components-supTfn | 489 | + | wt | wt | ++ | wt | wt | wt | wt | wt |

TABLE 8-continued

35S::G9 (*Arabidopsis*) Constitutive Promoter Abiotic Stress Assay Results

| Project type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| 2-components-supTfn | 490 | wt | wt | + | ++ | wt | wt | wt | wt | wt |
| 2-components-supTfn | 491 | wt | wt | + | ++ | wt | + | wt | wt | wt |
| 2-components-supTfn | 493 | wt | wt | + | ++ | wt | wt | wt | wt | wt |
| 2-components-supTfn | 494 | + | wt | wt | ++ | wt | wt | wt | wt | wt |
| 2-components-supTfn | 498 | + | wt | + | ++ | wt | wt | wt | wt | wt |

Utilities

G9 or its equivalogs could potentially be used to increase root growth/vigor, which might in turn allow better plant growth under adverse conditions (for example, limited water or nutrient availability).

Most ABA effects are related to the compound acting as a signal of decreased water availability, whereby it triggers a reduction in water loss, slows growth, and mediates adaptive responses, and thus increased ABA sensitivity is a likely indicator of an enhanced stress response. These observations, coupled with the root growth results and the salt and sucrose tolerance assays, indicate that G9 or its equivalogs could potentially be used to increase or facilitate seed germination and seedling or plant growth, and yield, under adverse conditions such osmotic stresses, including drought and salt stress.

The enhanced performance of 35S:: G9 seedlings under chilling conditions indicates that the gene or its equivalogs might be applied to engineer crops that show better growth under cold conditions, which may extend a crops planting season or range, or improve yield or performance.

G993 (SEQ ID NO: 5 and 6)

Published Information

G993 corresponds to gene F2J7.3 (AAG12735). No information is available about the function(s) of G993.

Closely Related Genes from Other Species

G993 shows some sequence similarity, outside of the conserved AP2/EREBP and B3 domains, to other RAV proteins from different species, such as a putative DNA binding protein RAV2 from *Oryza sativa* (GenBank accession number gi12328560).

Experimental Observations

The function of G993 was studied using transgenic plants in which the gene was expressed under the control of the $^{35}$S apromoter.

Overexpression of G993 produced highly pleiotropic effects on plant development and influenced growth rate, overall plant size, branching pattern and fertility. 35S::G993 seedlings were small, developed slowly, and produced inflorescences markedly later than wild-type controls. They also showed a reduction in apical dominance and disorganized rosettes, as multiple axillary shoots developed simultaneously. Inflorescence stems were generally shorter than wild type, and produced an increased number of cauline leaf nodes leading to a leafy, bushy, appearance. In addition, the seed yield of 35S::G993 plants was generally very poor, and senescence occurred later than in wild-type controls. The transformation rate attained with the G993 construct was relatively low, suggesting that high levels of G993 activity might produce lethal effects. No alterations were detected in 35S::G993 plants in the biochemical analyses that were performed.

G993 is ubiquitously expressed and does not appear to be significantly induced by any of the conditions tested.

Increased seedling vigor, manifested by increased expansion of the cotyledons of G993 overexpressing plants, was observed in germination assays on both high salt (150 mM) and high sucrose (9.4%) containing-media, as compared to wild-type controls.

In addition, several 35S::G993 transgenic lines were more tolerant to cold germination (8° C.) and numerous lines were more tolerant to chilling (4°-8° C. for 6 h) compared to the wild-type controls, in both germination as well as seedling growth assays, respectively.

TABLE 9

35S::G993 (*Arabidopsis*) Constitutive Promoter Abiotic Stress Assay Results

| Project Type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| Direct promoter-fusion | 302 | + | wt | + | wt | wt | wt | wt | wt | + |
| Direct promoter-fusion | 304 | + | wt | wt | wt | wt | wt | wt | wt | wt |

TABLE 9-continued

35S::G993 (*Arabidopsis*) Constitutive Promoter Abiotic Stress Assay Results

| Project Type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| Direct promoter-fusion | 305 | ++ | wt | + | wt | wt | wt | wt | wt | + |
| Direct promoter-fusion | 306 | + | wt | wt | wt | wt | wt | wt | wt | wt |
| Direct promoter-fusion | 307 | + | wt | wt | wt | wt | wt | wt | wt | wt |
| Direct promoter-fusion | 310 | + | wt | + | ++ | wt | wt | wt | wt | + |
| Direct promoter-fusion | 311 | ++ | wt | + | wt | wt | wt | wt | wt | + |
| Direct promoter-fusion | 312 | ++ | wt | wt | + | wt | wt | wt | wt | + |
| Direct promoter-fusion | 313 | + | wt | + | + | wt | wt | wt | wt | + |
| Direct promoter-fusion | 318 | ++ | wt | + | wt | wt | wt | wt | wt | wt |
| 2-components-supTfn | 483 | wt | wt | + | + | wt | wt | wt | wt | wt |
| 2-components-supTfn | 485 | + | wt | wt | wt | wt | wt | wt | wt | wt |
| 2-components-supTfn | 486 | wt | wt | wt | wt | wt | wt | wt | wt | wt |
| 2-components-supTfn | 488 | + | wt | + | ++ | wt | wt | wt | wt | wt |
| 2-components-supTfn | 489 | + | wt | wt | ++ | wt | wt | wt | wt | wt |
| 2-components-supTfn | 490 | wt | wt | + | ++ | wt | wt | wt | wt | wt |
| 2-components-supTfn | 491 | wt | wt | + | ++ | wt | + | wt | wt | wt |
| 2-components-supTfn | 493 | wt | wt | + | ++ | wt | wt | wt | wt | wt |
| 2-components-supTfn | 494 | + | wt | wt | ++ | wt | wt | wt | wt | wt |
| 2-components-supTfn | 498 | + | wt | + | ++ | wt | wt | wt | wt | wt |

Utilities

The salt and sucrose tolerance assays indicate that G993 or its equivalogs could potentially be used to increase or facilitate seed germination and seedling or plant growth and yield under adverse conditions such osmotic stresses, including drought and salt stress.

The enhanced performance of 35S:: G993 seedlings under cold germination and chilling conditions indicates that the gene or its equivalogs might be applied to engineer crops that show better germination and growth under cold conditions, which may extend a crops planting season or range, or improve yield or performance.

G1930 (SEQ ID NO: 7 and 8)
Published Information

G1930 was identified in the sequence of P1 clone K13N2 (gene K13N2.7, GenBank protein accession number BAA95760). No information is available about the function(s) of G1930.

Experimental Observations

G1930 is ubiquitously expressed and does not appear to be induced by any of the conditions tested.

The function of G1930 was studied using transgenic plants in which this gene was expressed under the control of the $^{35}$S apromoter.

35S::G1930 T1 plants were generally small and developed spindly inflorescences. The fertility of these plants was low and flowers often failed to open or pollinate.

G1930 overexpressors were more tolerant to osmotic stress conditions. The plants responded to high NaCl (150 mM) and high sucrose (9.4%) on plates with more seedling vigor compared to wild-type control plants. In addition, an increase in the amount of chlorophylls a and b in seeds of two T2 lines was detected.

In addition, 35S::several G1930 transgenic lines were more tolerant to cold germination conditions (8° C. for 6 h) and numerous G1930 transgenic lines were more tolerant to chilling (4°-8° C. for 6 h) compared to the wild-type controls, in both germination as well as seedling growth assays, respectively.

Several G1930 overexpressing lines were found to be more sensitive to 0.3 μM ABA.

TABLE 10

35S::G1930 (*Arabidopsis*) Constitutive Promoter Abiotic Stress Assay Results

| Project type | Line | Germ in High NaCl | Germ in High Mannitol | Germ in High Sucrose | ABA | Germ in Heat | Germ in Cold | Growth in Heat | Desiccation | Growth in cold |
|---|---|---|---|---|---|---|---|---|---|---|
| Direct promoter-fusion | 304 | + | wt | wt | wt | wt | wt | wt | wt | wt |
| Direct promoter-fusion | 305 | wt | wt | ++ | wt | wt | + | wt | wt | wt |
| Direct promoter-fusion | 306 | + | wt | wt | wt | wt | wt | wt | wt | + |
| Direct promoter-fusion | 308 | wt | wt | ++ | wt | wt | wt | wt | wt | + |
| Direct promoter-fusion | 309 | wt | wt | wt | wt | wt | wt | wt | wt | + |
| Direct promoter-fusion | 311 | wt | wt | + | wt | wt | + | wt | wt | + |
| 2-components-supTfn | 321 | + | wt | ++ | wt | wt | wt | wt | wt | + |
| 2-components-supTfn | 322 | + | wt | + | + | wt | wt | wt | wt | + |
| 2-components-supTfn | 324 | + | wt | + | + | wt | wt | wt | wt | + |
| 2-components-supTfn | 327 | + | wt | + | wt | wt | wt | wt | wt | wt |
| 2-components-supTfn | 329 | + | wt | + | wt | wt | wt | wt | wt | + |
| 2-components-supTfn | 331 | + | wt | ++ | + | wt | + | wt | wt | + |
| 2-components-supTfn | 332 | + | wt | + | + | wt | wt | wt | wt | wt |
| 2-components-supTfn | 334 | + | wt | wt | wt | wt | wt | wt | wt | wt |
| 2-components-supTfn | 336 | + | wt | ++ | + | wt | wt | wt | wt | + |
| 2-components-supTfn | 339 | + | wt | wt | wt | wt | wt | wt | wt | wt |
| Direct promoter-fusion | 365 | + | wt | ++ | wt | wt | wt | wt | wt | wt |
| Direct promoter-fusion | 367 | + | wt | ++ | wt | wt | wt | wt | wt | + |
| Direct promoter-fusion | 369 | + | wt | wt | wt | wt | wt | wt | wt | + |
| Direct promoter-fusion | 370 | + | wt | wt | wt | wt | wt | wt | wt | + |

Utilities

Most ABA effects are related to the compound acting as a signal of decreased water availability, whereby it triggers a reduction in water loss, slows growth, and mediates adaptive responses, and thus increased ABA sensitivity is a likely indicator of an enhanced stress response. These observations, coupled with the root growth results and the salt and sucrose tolerance assays, indicate that G1930 or its equivalogs could potentially be used to increase or facilitate seed germination and seedling or plant growth under adverse conditions such osmotic stresses, including drought and salt stress.

The enhanced performance of 35S::G1930 seedlings under cold germination and chilling conditions indicates that the gene or its equivalogs might be applied to engineer crops that show better germination and/or growth under cold conditions, which may extend a crop's planting season or range, or improve yield or performance.

G3389 (SEQ ID NO: 31 and 32)

G3389 is a rice gene that was identified by us as a putative ortholog of G867. The aim of this project was to determine whether G3389 has an equivalent function to G867 via the analysis of 35S::G3389 *Arabidopsis* lines.

Experimental Observations

Lines 342-344 appeared to be morphologically similar to wild-type controls. Line 341 may have been slightly smaller than the wild-type controls. Lines 341 and 344 flowered slightly early.

The results of the abiotic stress assays showed that these overexpressors were more tolerant of high NaCl concentrations, and one line (#341) was also more tolerant to high sucrose and insensitive to ABA.

Utilities

The enhanced performance of 35S:: G3389 seedlings under osmotic stress conditions confirms that G867 and members of the same clade of sequences may be used to engineer crops that show better growth under osmotic stress conditions, which may include drought, high salt concentration, freezing, and/or heat stress. These trait improvements may improve yield or performance, or extend a crops planting season or range.

G3451 (SEQ ID NO: 17 and 18)

G3451 is a soy gene that was identified as a putative ortholog of G867. The aim of this project was to determine whether G3451 had an equivalent function to G867 by analysis of 35S::G3451 *Arabidopsis* lines. A number of lines overexpressing a soybean ortholog of G867, G3451 lines have recently been isolated. These seedlings showed a reduction in overall size, similar to what was obtained for 35S::G867 lines.

Experimental Observations

Table 12 displays the increased tolerance to osmotic stress exhibited by G3451 overexpressing plants. A number of 35S::G3451 lines were more tolerant to high salt, high mannitol concentration, and particularly high sucrose concentration, than wild-type control plants that did not overexpress this gene when the overexpressors and wild-type control *Arabidopsis* plants were exposed to the same conditions.

TABLE 11

35S::G3389 (rice) Direct Fusion Constitutive Promoter Abiotic Stress Assay Results

| Project Type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| Direct promoter-fusion | 341 | + | wt | + | + | wt | + | + | wt | wt |
| Direct promoter-fusion | 342 | + | wt | wt | wt | wt | + | + | wt | wt |
| Direct promoter-fusion | 343 | + | wt | wt | wt | wt | + | wt | wt | wt |
| Direct promoter-fusion | 344 | + | wt | wt | wt | wt | + | wt | wt | wt |

TABLE 12

35S::G3451 (soy) Direct Fusion Constitutive Promoter Abiotic Stress Assay Results

| Project Type | Line | Germ in High NaCl | Germ in High Mannitol | Sucrose | ABA | Germ in Heat | Germ in Cold | Growth in Heat | Desiccation | Growth in Cold |
|---|---|---|---|---|---|---|---|---|---|---|
| Direct promoter-fusion | 301 | wt | wt | wt | wt | wt | wt | wt | wt | wt |
| Direct promoter-fusion | 302 | wt | wt | + | wt | wt | wt | wt | wt | wt |
| Direct promoter-fusion | 303 | + | + | wt | wt | wt | wt | wt | wt | wt |
| Direct promoter-fusion | 307 | wt | wt | wt | wt | wt | wt | wt | wt | wt |
| Direct promoter-fusion | 310 | wt | wt | + | wt | wt | wt | wt | wt | wt |
| Direct promoter-fusion | 311 | wt | wt | wt | wt | wt | wt | wt | wt | wt |
| Direct promoter-fusion | 312 | wt | wt | + | wt | wt | wt | wt | wt | wt |
| Direct promoter-fusion | 313 | + | wt | + | wt | wt | wt | wt | wt | wt |
| Direct promoter-fusion | 314 | wt | wt | + | wt | wt | wt | wt | wt | wt |
| Direct promoter-fusion | 315 | wt | wt | + | wt | wt | wt | wt | wt | wt |

Utilities

The enhanced performance of 35S:: G3451 seedlings under osmotic stress conditions confirms that G867 and members of the same clade of sequences may be used to engineer crops that show better growth under osmotic stress conditions, which may include drought, high salt concentration, freezing, and/or heat stress. These trait improvements may improve yield or performance, or extend a crops planting season or range.

G3452 (SEQ ID NO: 21 and 22)

G3452 is a soy gene that was identified as being a putative ortholog of G867. The aim of this project was to determine whether G3452 has an equivalent function to G867 by analysis of 35S::G3452 *Arabidopsis* lines.

Overexpression of G3452 in *Arabidopsis* produced a reduction in overall size compared to wild-type. These 35S:: G3452 lines also appeared pale in coloration. Such effects were highly penetrant and were observed in all eighteen of the T1 lines obtained. A small number of the lines (#301, 306, 314, 316) also exhibited a slight acceleration in the onset of flowering.

TABLE 13

35S::G3452 (soy) Direct Fusion Constitutive Promoter Abiotic Stress Assay Results

| Project Type | Line | Germ in High NaCl | Germ in High Mannitol | Sucrose | ABA | Germ in Heat | Germ in Cold | Growth in Heat | Desiccation | Growth in Cold |
|---|---|---|---|---|---|---|---|---|---|---|
| Direct promoter-fusion | 304 | + | + | + | wt | wt | + | + | + | wt |
| Direct promoter-fusion | 305 | + | wt | + | wt | wt | + | wt | wt | wt |
| Direct promoter-fusion | 310 | wt | wt | wt | wt | wt | wt | wt | wt | wt |
| Direct promoter-fusion | 314 | + | wt | + | wt | wt | wt | wt | wt | wt |
| Direct promoter-fusion | 316 | + | wt | + | wt | wt | wt | wt | wt | wt |
| Direct promoter-fusion | 318 | wt | wt | + | wt | wt | wt | wt | wt | wt |

Utilities

The enhanced performance of 35S:: G3452 seedlings under osmotic stress conditions confirms that G867 and members of the same clade of sequences may be used to engineer crops that show better growth under osmotic stress conditions, which may include drought, high salt concentration, freezing, and/or heat stress. These trait improvements may improve yield or performance, or extend a crops planting season or range.

The accelerated flowering seen in 35S::G3452 plants indicate that the gene could be used to manipulate flowering time. In particular, shortening generation times would also help speed-up breeding programs, particularly in species such as trees, which typically grow for many years before flowering.

Conversely, it might be possible to modify the activity of G3452 (or its equivalogs) to delay flowering in order to achieve an increase in biomass and yield G3390 (SEQ ID NO: 33 and 34)

G3390 is a rice gene identified as a putative ortholog of G867.

35S::G3390 *Arabidopsis* lines were generally smaller and flowered later than wild-type controls, including line 304, which may have performed better than the other lines in these abiotic stress assays. However, a number of lines did not show any significant morphological differences relative to wild-type controls.

Utilities

The enhanced performance of 35S:: G3390 seedlings under osmotic stress conditions confirms that G867 and members of the same clade of sequences may be used to engineer crops that show better growth under osmotic stress conditions, which may include drought, high salt concentration, freezing, and/or heat stress. These trait improvements may improve yield or performance, or extend a crops planting season or range.

G3391 (SEQ ID NO: 35 and 36)

G3391 is a rice gene identified as a putative ortholog of G867. The aim of this project was to determine whether G3391 has an equivalent function to G867 by analyzing 35S:: G3391 *Arabidopsis* lines.

35S::G3391 *Arabidopsis* lines were distinctly small and showed alterations in leaf shape, leaf orientation, flowering time, and floral defects that resulted in poor fertility. Lines 321-335: all lines were markedly small, with narrow pointed leaves. Lines #322, 323, 327, 329, 332, 334 were early flowering. All lines had poor seed yield. Lines 361-374: were tiny and dark in coloration at the seedling stages. As they continued to develop, these plants remained small relative to wild-type controls, and had pointed upright leaves. #362, 365, 368 were very small. #363, 366, 369, 371, 372 were early flowering. All lines showed poor fertility and yielded relatively few seeds.

TABLE 14

35S::G3390 (rice) Direct Fusion Constitutive Promoter Abiotic Stress Assay Results

| Project Type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| Direct promoter-fusion | 302 | wt | wt | wt | + | wt | | | | |
| Direct promoter-fusion | 303 | wt | wt | wt | wt | wt | | | | |
| Direct promoter-fusion | 304 | wt | + | wt | + | + | | | | |
| Direct promoter-fusion | 361 | wt | wt | wt | + | wt | | | | |
| Direct promoter-fusion | 362 | wt | wt | wt | wt | wt | | | | |
| Direct promoter-fusion | 363 | wt | wt | wt | wt | wt | | | | |
| Direct promoter-fusion | 364 | wt | wt | wt | wt | wt | | | | |
| Direct promoter-fusion | 365 | wt | wt | wt | wt | wt | | | | |

TABLE 15

35S::G3391 (rice) Direct Fusion Constitutive Promoter Abiotic Stress Assay Results

| Project Type | Line | Germ in High NaCl | Germ in High Mannitol | Sucrose | ABA | Germ in Heat | Germ in Cold | Growth in Heat | Desiccation | Growth in Cold |
|---|---|---|---|---|---|---|---|---|---|---|
| Direct promoter-fusion | 322 | wt | wt | wt | wt | wt | wt | wt | wt | wt |
| Direct promoter-fusion | 323 | wt | wt | wt | wt | wt | wt | wt | wt | wt |
| Direct promoter-fusion | 324 | + | wt | + | wt | wt | wt | wt | wt | wt |
| Direct promoter-fusion | 326 | + | wt | wt | wt | wt | wt | wt | wt | wt |
| Direct promoter-fusion | 327 | wt | wt | wt | wt | wt | wt | wt | wt | wt |
| Direct promoter-fusion | 329 | wt | wt | wt | wt | wt | wt | wt | wt | wt |
| Direct promoter-fusion | 330 | + | wt | + | wt | wt | wt | wt | wt | wt |
| Direct promoter-fusion | 332 | wt | wt | wt | wt | wt | wt | wt | wt | wt |
| Direct promoter-fusion | 334 | wt | wt | wt | wt | wt | wt | wt | wt | wt |

Utilities

The enhanced performance of 35S:: G3391 seedlings under osmotic stress conditions confirms that G867 and members of the same clade of sequences may be used to engineer crops that show better growth under osmotic stress conditions, which may include drought, high salt concentration, freezing, and/or heat stress. These trait improvements may improve yield or performance, or extend a crops planting season or range.

The G3391 overexpressing lines that showed accelerated flowering suggested that G3391 acts to promote the floral transition, and indicate that the gene could be used to manipulate flowering time. In particular, shortening generation times would also help speed-up breeding programs, particularly in species such as trees, which typically grow for many years before flowering. Conversely, it might be possible to modify the activity of G3391 (or its orthologs) to delay flowering in order to achieve an increase in biomass and yield.

G3455 (SEQ ID NO: 35 and 36)

G3455 is a soy gene that was identified as being a putative ortholog of G867. The aim of this project was to determine whether G3455 has an equivalent function to G867 by analyzing 35S::G3391 *Arabidopsis* lines.

A number of 35S::G3455 *Arabidopsis* lines were somewhat smaller than wild-type control plants at various stages of growth. The former tended to be marginally late developing with partially glabrous leaves. Other plants show considerable size variation but no consistent morphological differences to wild-type controls.

TABLE 16

35S::G3455 (soy) Direct Fusion Constitutive Promoter Abiotic Stress Assay Results

| Project Type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| Direct promoter-fusion | 361 | wt | wt | + | wt | wt | | | |
| Direct promoter-fusion | 366 | wt | wt | + | wt | wt | | | |
| Direct promoter-fusion | 368 | wt | wt | + | wt | wt | | | |
| Direct promoter-fusion | 369 | wt | wt | + | wt | wt | | | |
| Direct promoter-fusion | 372 | wt | wt | + | wt | wt | | | |

TABLE 16-continued

35S::G3455 (soy) Direct Fusion Constitutive Promoter Abiotic Stress Assay Results

| Project Type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| Direct promoter-fusion | 373 | + | wt | + | wt | wt | | | | |
| Direct promoter-fusion | 374 | wt | wt | + | wt | wt | | | | |
| Direct promoter-fusion | 375 | wt | wt | + | wt | wt | | | | |
| Direct promoter-fusion | 376 | wt | wt | wt | wt | wt | | | | |
| Direct promoter-fusion | 377 | wt | wt | + | wt | wt | | | | |

Utilities

While the data for 35S::G3455 seedlings are not yet complete, the enhanced performance of 35S:: G3455 seedlings under osmotic stress conditions confirms that yet another member of the G867 clade of transcription factor sequences may be used to engineer crops that show better growth under osmotic stress conditions, which may include drought, high salt concentration, freezing, and/or heat stress. These trait improvements may improve yield or performance, or extend a crops planting season or range.

G3432 (SEQ ID NO: 35 and 36)

G3432 is a corn gene that was identified as being a putative ortholog of G867. The aim of this project was to determine whether G3432 has an equivalent function to G867 by analyzing 35S:: G3432 *Arabidopsis* lines.

A significant number of 35S:: G3432 *Arabidopsis* lines were late developing, spindly and poorly fertile. Some plants, including line 362, showed no consistent differences to wild-type controls. The abiotic stress data indicate that G3432 confers tolerance in only a few assays when the polypeptide is overexpressed. These borderline results may reflect the relatively low similarity of the DML motif (71% identity) to the analogous motif in G867.

TABLE 17

35S::G3432 (*Arabidopsis*) Direct Fusion Constitutive Promoter Abiotic Stress Assay Results

| Project Type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| Direct promoter-fusion | 302 | wt | wt | wt | wt | wt | wt | wt | wt | wt |
| Direct promoter-fusion | 304 | wt | wt | wt | wt | wt | wt | wt | wt | wt |
| Direct promoter-fusion | 309 | wt | wt | wt | wt | wt | wt | wt | wt | wt |
| Direct promoter-fusion | 312 | wt | wt | wt | wt | wt | wt | wt | wt | wt |
| Direct promoter-fusion | 348 | wt | wt | wt | + | wt | wt | wt | wt | wt |
| Direct promoter-fusion | 362 | wt | wt | + | wt | wt | + | wt | wt | wt |

Utilities

The enhanced performance of 35S:: G3432 seedlings under osmotic stress-related conditions confirms that yet another member of the G867 clade of transcription factor sequences may be used to engineer crops that show better growth under osmotic stress conditions, which may include drought, high salt concentration, freezing, and/or heat stress. These trait improvements may improve yield or performance, or extend a crops planting season or range.

Example IX

Mitigation of Undesirable Morphological Effects Caused by Overexpression of G867 and other Clade Members The abiotic stress results shown in Example VIII provide evidence that members of the G867 clade of transcription factor polypeptides may be used to create plants with the characteristics of improved yield, performance and/or range. However, overexpression of these clade members may also bring about undesirable morphological effects, including low fertility and smaller plant size. This was observed with many, but not all, of the lines generated in the present study. Since it is often desirable to generate plants with wild-type or near-wild-type stature, overexpression of G867 or other clade members under the regulatory control of a constitutive promoter may not always be the optimal approach for improving the abiotic stress tolerance of plants.

This present study also included an investigation in the use of alternative promoter or two-component overexpression systems for the purpose of conferring enhanced stress tolerance and eliminating developmental abnormalities such as reduced size that were associated with G867 constitutive overexpression. In this regard, the present invention also relates to methods and compositions for producing transgenic plants with improved stress performance achieved by altering the expression of G867 and homologous sequences with specific promoter-gene combinations or other regulatory means. These combinations may regulate transcription factor expression patterns in a transient, inducible, or organ- or tissue-specific manner. This approach may be used to generate plants that are morphologically similar to wild-type control plants that have not been transformed with a polynucleotide encoding G867 or another member of the G867 clade of transcription factor polypeptides. Thus, specific regulatory elements may be used to control regulation of a G867 clade member transcription factor gene to alleviate undesirable developmental abnormalities or morphology that would result from overexpressing of the same transcription factor genes with a constitutive promoter (e.g., the $^{35}S$ apromoter). Experimental Observations: SUC2 Vascular Specific Promoter We have isolated SUC2::G867 lines via both a direct-promoter fusion approach and a 2-component approach. Results with the latter are shown in Table 17.

Two-component lines (#381400) were generated in which an opLexA::G867 construct was supertransformed into a SUC2::LexA-GAL4TA promoter driver line (#6). These lines appeared normal at all developmental stages. However, it should be noted that the promoter driver line (#6) used in this set of lines, produced relatively low expression levels.

A direct promoter-fusion construct (P21521) for SUC2::G867 was also available. Fourteen lines (#1581-1594) harboring this construct also showed no consistent differences to wild-type controls.

All lines examined thus far displayed segregation on selection plates in the T2 generation that was compatible with transgene insertions at a single locus.

We have so far tested the 2-component lines in drought related assays: of ten lines tested, seven showed a moderately enhanced resistance to sodium chloride in germination assays. Some of these lines also displayed a better performance, to varying extents, on sucrose germination, cold germination, and under a plate based severe drought assay. These effects were comparable, but slightly weaker that those shown by 35S::G867 plants in plate based assays. The particular SUC2 promoter driver line that was used in the lines isolated so far showed a relatively weak levels of expression, and that resistance might be enhanced by use of stronger promoter line.

TABLE 18

G867 (*Arabidopsis*) - Vascular SUC2 Promoter Abiotic Stress Assay Results

| Project Type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| 2-components-supTfn | 383 | wt | wt | wt | wt | wt | wt | wt | wt | wt |
| 2-components-supTfn | 384 | wt | wt | wt | wt | wt | wt | wt | wt | wt |
| 2-components-supTfn | 385 | + | wt | + | wt | wt | + | wt | wt | wt |
| 2-components-supTfn | 387 | + | wt | wt | wt | wt | wt | wt | wt | wt |
| 2-components-supTfn | 388 | + | wt | wt | wt | wt | wt | wt | + | wt |
| 2-components-supTfn | 389 | + | wt | + | wt | wt | wt | wt | + | wt |
| 2-components-supTfn | 391 | wt | wt | wt | wt | wt | wt | wt | wt | wt |

TABLE 18-continued

G867 (*Arabidopsis*) - Vascular SUC2 Promoter Abiotic Stress Assay Results

| Project Type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| 2-components-supTfn | 393 | + | wt | + | wt | wt | wt | wt | wt | wt |
| 2-components-supTfn | 396 | + | wt | + | wt | wt | + | wt | wt | wt |
| 2-components-supTfn | 398 | + | wt | wt | wt | wt | wt | wt | wt | wt |

Utilities

In contrast to the phenotype seen in 35S::G867 transformants, which showed a variety of undesirable morphological effects, SUC2::G867 lines displayed no obvious developmental abnormalities. Use of a tissue-specific promoter such as the SUC2 promoter, instead of $^{35}$S, thus offers a means to alleviate such problems that may occur with the constitutive overexpression of G867 and other members of the G867 clade of transcription factor polypeptides.

Experimental Observations: RBCS3 Leaf specific Promoter

We have isolated RBCS3::G867 lines via a 2-component approach. With a few exceptions, the RBCS3::G867 lines tested were morphologically similar to wild-type. Results with abiotic stress tolerance tests are shown in Table 19.

TABLE 19

G867 (*Arabidopsis*) - Leaf specific RBCS3 Promoter Abiotic Stress Assay Results

| Project Type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| 2-components-supTfn | 1085 | wt | wt | wt | wt | wt | wt | wt | wt | wt |
| 2-components-supTfn | 1087 | + | + | wt | wt | wt | + | wt | wt | wt |
| 2-components-supTfn | 1089 | wt | wt | wt | wt | wt | wt | wt | wt | wt |
| 2-components-supTfn | 1090 | wt | wt | wt | wt | wt | wt | wt | wt | wt |
| 2-components-supTfn | 1162 | + | wt | wt | wt | wt | wt | wt | wt | wt |
| 2-components-supTfn | 1165 | + | wt | + | wt | wt | + | wt | wt | wt |
| 2-components-supTfn | 1167 | + | wt | wt | wt | wt | wt | wt | wt | wt |
| 2-components-supTfn | 1171 | wt | wt | wt | wt | wt | wt | wt | wt | wt |
| 2-components-supTfn | 1174 | wt | wt | wt | wt | wt | wt | wt | wt | wt |
| 2-components-supTfn | 1176 | wt | wt | wt | wt | wt | wt | wt | wt | wt |

Utilities

In contrast to the phenotype seen in 35S::G867 transformants, which showed a variety of undesirable morphological effects, most RBCS3::G867 lines displayed no obvious developmental abnormalities. Use of a tissue-specific promoter such as the RBCS3 promoter, instead of $^{35}$S, offers a means to alleviate such problems that may occur with the constitutive overexpression G867 and other members of the G867 clade of transcription factor polypeptides.

Experimental Observations: ARSK1 Root-Specific Promoter

We have isolated ARSK1::G867 lines via a 2-component approach. Several lines were small in size, but most lines were morphologically similar to wild-type plants at most stages of growth. Results with abiotic stress tolerance tests are shown in Table 20.

Experimental Observations: RD29A Stress-Inducible Promoter

We have isolated RD29A::G867 lines via a two-component approach with two different RD29A::LexA promoter driver lines: line 2 and line 5. Line 2 had a higher level of background expression than line 5, and thereby is expected to provide somewhat different regulation. Line 2 was observed to have constitutive basal expression of GFP, and to have a marked increase in GFP expression following the onset of stress. In contrast, line 5 exhibited very low background expression, although it still exhibited an up-regulation of expression following the onset of stress. However, the stress-induced levels of GFP expression observed in line 5 were lower than those observed for line 2.

TABLE 20

G867 (*Arabidopsis*) - Root-specific ARSK1 Promoter Abiotic Stress Assay Results

| Project Type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| 2-components-supTfn | 1681 | wt | wt | wt | + | wt | wt | wt | wt | wt |
| 2-components-supTfn | 1683 | wt | wt | wt | wt | wt | wt | wt | wt | wt |
| 2-components-supTfn | 1685 | wt | wt | wt | wt | wt | wt | wt | wt | wt |
| 2-components-supTfn | 1686 | wt | wt | wt | wt | wt | wt | − | wt | wt |
| 2-components-supTfn | 1687 | wt | wt | wt | + | wt | wt | wt | + | wt |
| 2-components-supTfn | 1688 | wt | wt | wt | wt | wt | wt | wt | wt | wt |
| 2-components-supTfn | 1741 | wt | wt | wt | wt | wt | wt | wt | wt | + |
| 2-components-supTfn | 1744 | wt | wt | wt | + | wt | wt | wt | wt | + |
| 2-components-supTfn | 1747 | wt | wt | wt | wt | wt | wt | wt | wt | wt |
| 2-components-supTfn | 1748 | wt | wt | wt | wt | wt | wt | wt | wt | + |

Utilities

In contrast to the phenotype seen in 35S::G867 transformants, which showed a variety of undesirable morphological effects, many of the ARSK1::G867 lines displayed no obvious developmental abnormalities. Use of a tissue-specific promoter such as the ARSK1 promoter, instead of $^{35}$S, offers a means to alleviate such problems that may occur with the The majority of the lines generated with line 2 and line 5 were slightly smaller than wild-type controls, but in other respects exhibited normal morphology. However, the reduction in size seen in these lines was generally significantly less severe than that seen in the 35S::G867 lines. Results with these abiotic stress tolerance tests are shown in Tables 21 (RD29A Line 5) and 22 (RD29A Line 2).

TABLE 21

G867 (*Arabidopsis*) - Root specific RD29A Line 5 Promoter Abiotic Stress Assay Results

| Project Type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| 2-components-supTfn | 1401 | wt | wt | wt | wt | wt | wt | wt | + | wt |
| 2-components-supTfn | 1404 | + | wt | wt | wt | wt | wt | wt | wt | wt |
| 2-components-supTfn | 1405 | wt | wt | wt | wt | wt | wt | wt | wt | wt |
| 2-components-supTfn | 1409 | ++ | ++ | wt | + | wt | wt | wt | wt | wt |
| 2-components-supTfn | 1415 | + | wt | wt | wt | wt | wt | wt | wt | wt |
| 2-components-supTfn | 1462 | wt | wt | wt | wt | wt | wt | wt | wt | wt |
| 2-components-supTfn | 1466 | wt | wt | wt | wt | wt | wt | wt | + | wt |
| 2-components-supTfn | 1468 | wt | wt | wt | wt | wt | wt | wt | wt | wt |
| 2-components-supTfn | 1469 | wt | wt | wt | wt | wt | wt | wt | wt | wt |
| 2-components-supTfn | 1473 | wt | wt | wt | wt | wt | wt | wt | wt | wt |

TABLE 22

G867 (*Arabidopsis*) - Root specific RD29A Line 2 Promoter Abiotic Stress Assay Results

| Project Type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| 2-components-supTfn | 1381 | + | wt | wt | ++ | wt | wt | wt | wt | wt |
| 2-components-supTfn | 1384 | wt | wt | wt | wt | wt | wt | wt | wt | wt |
| 2-components-supTfn | 1385 | wt | wt | wt | wt | wt | wt | wt | wt | wt |
| 2-components-supTfn | 1386 | + | wt | wt | wt | wt | wt | wt | wt | wt |
| 2-components-supTfn | 1387 | wt | wt | wt | wt | wt | wt | wt | wt | wt |
| 2-components-supTfn | 1388 | + | wt | wt | wt | wt | wt | wt | wt | wt |
| 2-components-supTfn | 1391 | + | wt | wt | wt | wt | wt | wt | wt | wt |
| 2-components-supTfn | 1392 | wt | wt | wt | wt | wt | wt | wt | wt | wt |
| 2-components-supTfn | 1393 | wt | wt | wt | + | wt | wt | wt | wt | wt |
| 2-components-supTfn | 1395 | wt | wt | wt | wt | wt | wt | wt | wt | wt |

Utilities

In contrast to the phenotype seen in 35S::G867 transformants, which showed a variety of undesirable morphological effects, lines overexpressing G867 under the regulatory control of the stress inducible promoter RD29A did not display the significant developmental abnormalities seen in G867-overexpressing lines. Use of an inducible promoter such as the RD29A promoter, instead of $^{35}$S, thus offers a means to alleviate such problems that may occur with the constitutive overexpression G867 and other members of the G867 clade of transcription factor polypeptides.

Experimental Observations with G867 (*Arabidopsis*)—Super Activation (C-GAL4-TA)

Overexpression of a super-active form of G867, comprising a GAL4 transactivation domain fused to the C terminus of the protein, produced no consistent effects on *Arabidopsis* morphology. Two batches of lines containing construct P21193 have so far been obtained: 521-531 and 641-645. The majority of these plants appeared wild type, however, a number of lines (522, 523, 525) from the first batch were noted to be small at early stages of development.

Of the ten lines submitted for physiological assays, lines 521, 523, 525, 528, 530, 531, 642, and 643 showed segregation on kanamycin plates in the T2 generation that was compatible with the transgene being present at a single locus. Lines 641 and 644 showed a segregation that was compatible with insertions at multiple loci.

GAL4 super-activation of G867 produced three lines that performed markedly better than wild-type plants on plates containing sucrose in a germination assay. Two of these lines were also less sensitive to ABA in another germination assay, and two lines showed enhanced performance in a chilling growth assay. Two lines that showed enhance abiotic stress tolerance (#523, 525) were small at early stages of development.

differences in morphology compared to wild-type controls. This result contrasts the effects of overexpression of the wild-type form of the G867 protein, which produces a marked reduction in overall size and other developmental abnormalities (see Example VIII). These data indicate that the additional domain added at the C-terminus is able to mitigate the deleterious phenotypes observed when G867 and other clade members are overexpressed under the control of a constitutive promoter.

Experimental Observations with G867 (*Arabidopsis*)—Super Activation (N-GAL4-TA)

Overexpression of a super-active form of G867, comprising a GAL4 transactivation domain fused to the N terminus of the protein, produced no consistent effects on *Arabidopsis* morphology.

Two batches of lines containing construct P21201 have so far been obtained: lines 981-991 and 1141-1160. The majority of these lines appeared wild-type at all developmental stages.

We have now isolated lines that overexpress a version of the G867 protein that has a GAL4 activation domain fused to the N terminus. These transformants showed no consistent differences in morphology compared to wild-type controls. This result contrasts the effects of overexpression of the wild-type form of the G867 protein, which produces a marked reduction in overall size and other developmental abnormalities. Thus, it appears that the additional domain added at the N-terminus blocked the deleterious phenotypes.

These 35S::G867-GAL4 lines have now been tested in plate based assays. Four of the ten lines appeared substantially more resistant to salt in germination assays than wild-type controls, one of these lines was more tolerant to drought in a plate-based assay, and a separate line was more tolerant to osmotic stress and chilling conditions. Therefore, compared

TABLE 23

G867 (*Arabidopsis*) - Super Activation (C-GAL4-TA) Abiotic Stress Assay Results

| Project Type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| GAL4 C-term | 521 | wt | wt | wt | wt | wt | wt | ND | wt | wt |
| GAL4 C-term | 523 | wt | wt | ++ | + | wt | wt | ND | wt | wt |
| GAL4 C-term | 525 | wt | wt | ++ | wt | wt | wt | ND | wt | + |
| GAL4 C-term | 528 | wt | wt | ++ | + | wt | wt | wt | wt | + |
| GAL4 C-term | 530 | wt | wt | wt | wt | wt | wt | wt | wt | wt |
| GAL4 C-term | 531 | wt | wt | wt | wt | wt | wt | wt | wt | wt |
| GAL4 C-term | 641 | wt | wt | wt | wt | wt | wt | wt | wt | wt |
| GAL4 C-term | 642 | wt | wt | wt | wt | wt | wt | wt | wt | + |
| GAL4 C-term | 643 | wt | wt | wt | wt | wt | wt | wt | wt | wt |
| GAL4 C-term | 644 | wt | wt | wt | wt | wt | wt | wt | wt | wt |

Utilities

We have now isolated lines that overexpress a version of the G867 protein that has a GAL4 activation domain fused to the C terminus. A number of these transformants showed a slight reduction in size, but the majority showed no consistent to the regular 35S::G867 lines (where all of the lines tested showed abiotic stress resistance), stress resistance phenotypes were seen at lower frequency in these 35S::G867-GAL4 lines. In this case, however, the lines had wild-type morphologies.

TABLE 24

G867 (*Arabidopsis*) - Super Activation (N-GAL4-TA) Abiotic Stress Assay Results

| Project Type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| GAL4 N-term | 1146 | wt | wt | wt | wt | wt | wt | wt | wt | wt |
| GAL4 N-term | 1147 | + | wt | wt | wt | wt | wt | wt | wt | wt |
| GAL4 N-term | 1148 | wt | wt | + | wt | wt | + | wt | wt | + |
| GAL4 N-term | 1149 | wt | wt | wt | wt | wt | wt | wt | wt | wt |
| GAL4 N-term | 1150 | + | wt | wt | wt | wt | wt | wt | wt | wt |
| GAL4 N-term | 981 | wt | wt | wt | wt | wt | wt | + | wt | wt |
| GAL4 N-term | 982 | wt | wt | wt | wt | wt | wt | wt | wt | − |
| GAL4 N-term | 984 | wt | wt | wt | wt | wt | wt | wt | wt | wt |
| GAL4 N-term | 987 | + | wt | wt | wt | wt | wt | wt | + | wt |
| GAL4 N-term | 988 | + | wt | wt | wt | wt | wt | wt | wt | wt |

Utilities

Based on the data from overexpression studies, G867 and other members of the G867 clade of transcription factor polypeptides are good candidates for improving stress tolerance in commercial species. However, given some of the undesirable morphologies that arise from constitutive overexpression of these sequences, the use of G867 and equivalogs to improve the tolerance of plants to abiotic stresses might be optimized with the use of sequence modifications or tissue-specific or conditional promoters. These stress and morphology results indicate that the addition of an artificial activation domain at the N-terminus might be one such modification that alleviates size reduction while conferring stress tolerance.

Example X

Analysis of G867 (*Arabidopsis*) Protein Variants

Since the G867 polypeptide does not contain any obvious repression or activation domain, we expect that overexpression of "superactive" forms of the G867 protein (comprising N or C-terminal fusions of a GAL4 transactivation domain) might be particularly informative. Also, given that the RAV1 paralogs comprise very similar proteins, and that a homozygous putative null mutant for G867 shows a wild-type phenotype, the four proteins (G867, G9, G11930 and G993) could be functionally redundant. Thus, it seems likely that a RNAi approach targeting the entire clade might reveal whether the G867-group plays an essential role in the protection against abiotic stress. Additionally, because the four proteins could have common target promoters, it was thought that overexpression of a truncated form of G867 containing the DNA binding domain, might be used to generate a mutant phenotype by a dominant negative type mechanism. In this regard, two such "dominant negative" constructs were designed, one encoding a form of the protein that contained the AP2 domain, but not the B3 domain (construct P21275) and one containing the B3 domain, but not the AP2 domain (construct P21276).

Given that the G867 protein lacks any clearly identifiable activation or repression domains, we originally posited that it might be possible to enhance the efficacy of the protein by addition of an artificial GAL4 activation domain. Lines have been made that overexpress a version of G867 with a GAL4 fusion at either the N or the C terminus. Lines for the N-terminal fusion did not show any of the developmental phenotypes observed in the regular 35S::G867 lines. Lines for the C-terminal fusion, were also morphologically wild type in the majority of cases, but a small number of lines showed a slight reduction in size at the seedling stage. The majority of 35S::G867-GAL4 lines gave a wild-type performance in physiology assays, but three of ten lines displayed a markedly enhanced performance in those stress assays.

Lines have been obtained for each of two different G867 dominant negative constructs: P21275 (SEQ ID NO: 65) and P21276 (SEQ ID NO: 66). P21275 is an overexpression construct encoding a truncated version of the G867 protein containing the AP2 domain (residues 36 to 165 of the wild-type protein) but not the B3 domain. This construct carries a kanamycin selection. P21276 is an overexpression construct encoding a truncated version of the G867 protein (residues 139 to 309 from the wild-type protein) containing the B3 domain but not the AP2 domain. This construct carries a kanamycin selection.

Lines 1041-1060 were transformed with P21275, a construct in which a truncated version of G867 comprising the AP2 domain was overexpressed. Plants harboring this construct exhibited no consistent differences in morphology to wild-type controls.

Lines 881-889, lines 1001-1016, and lines 1361-1380 contained P21276, a construct in which a truncated version of G867 containing the B3 domain, but not the AP2 domain, was overexpressed. Plants from each of these three sets of lines showed a number pleiotropic but distinct alterations in morphology. The plants generally formed narrow strap like leaves, were slightly reduced in overall size, had reductions in trichome density, showed increased activity of secondary shoot meristems (in the primary rosette leaf axils), and had abnormalities in shoot phyllotaxy. Some of the lines were also noted to flower early and develop rather more rapidly than wild type.

These phenotypes were observed to varying extents in 6/9 lines from the 881-889 set: (#884, 885, 886, 887, 888, 889), 16/16 lines from the 1001-1016 set, and 19/20 lines (all except #1371) from the 1361-1380 set.

P21201 (SEQ ID NO: 67) is an overexpression construct encoding a G867 clone that has a GAL4 transactivation domain fused at the N terminus (35S::GAL4-G867). The construct carries a kanamycin resistance marker. Overexpression of this super-active form of G867, comprising a GAL4 transactivation domain fused to the N terminus of the protein, produced no consistent effects on *Arabidopsis* morphology. Two batches of lines containing construct P21201 have so far been obtained: lines 981-991 and 1141-1160. The majority of these lines appeared wild-type at all developmental stages.

P21193 (SEQ ID NO: 68) is an overexpression construct encoding a G867 clone that has a GAL4 transactivation domain fused at the C terminus (35S::G867-GAL4). The construct carries a kanamycin resistance marker. Overexpression of this super-active form of G867, comprising a GAL4 transactivation domain fused to the C terminus of the protein, produced no consistent effects on *Arabidopsis* morphology, except as noted below.

Two batches of lines containing construct P21193 have so far been obtained: 521-531 and 641-645. The majority of these plants appeared wild type, however, a number of lines (522, 523, 525) from the first batch were noted to be small at early stages of development. Of the ten lines submitted for physiological assays, the following showed a segregation on kanamycin plates in the T2 generation that was compatible with the transgene being present at a single locus: 521, 523, 525, 528, 530, 531, 642, and 643. Lines 641 and 644 showed a segregation that was compatible with insertions at multiple loci.

TABLE 25

Abiotic stress results with *Arabidopsis* plants transformed with P21276 encoding a truncated G867 protein containing the B3 domain but not the AP2 domain

| Project Type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| Dom neg deletion in secondary domain | 1002 | wt | wt | wt | wt | + | wt | wt | wt | wt |
| Dom neg deletion in secondary domain | 1006 | wt | wt | wt | wt | wt | wt | wt | wt | wt |
| Dom neg deletion in secondary domain | 1009 | wt | wt | wt | + | wt | + | wt | wt | wt |
| Dom neg deletion in secondary domain | 1010 | wt | wt | wt | wt | wt | wt | wt | wt | wt |
| Dom neg deletion in secondary domain | 1011 | wt | wt | wt | wt | wt | wt | wt | wt | wt |
| Dom neg deletion in secondary domain | 1012 | wt | wt | wt | wt | wt | wt | wt | wt | wt |
| Dom neg deletion in secondary domain | 1014 | wt | wt | wt | wt | wt | wt | wt | wt | wt |
| Dom neg deletion in secondary domain | 886 | wt | wt | wt | wt | wt | + | wt | wt | wt |
| Dom neg deletion in secondary domain | 887 | wt | wt | wt | wt | wt | wt | wt | wt | wt |
| Dom neg deletion in secondary domain | 889 | wt | wt | wt | wt | wt | + | wt | wt | wt |

TABLE 26

Abiotic stress results with *Arabidopsis* plants transformed with P21275 encoding a truncated G867 protein containing only the AP2 domain

| Project Type | Line | Germ in High NaCl | Germ in High Mannitol | Germ in High Sucrose | ABA | Germ in Heat | Germ in Cold | Growth in Heat | Desiccation | Growth in Cold |
|---|---|---|---|---|---|---|---|---|---|---|
| Dom neg deletion | 1021 | wt | wt | wt | wt | wt | wt | wt | wt | wt |
| Dom neg deletion | 1022 | wt | wt | wt | wt | wt | wt | wt | wt | wt |
| Dom neg deletion | 1027 | wt | wt | wt | wt | wt | wt | wt | wt | wt |
| Dom neg deletion | 1028 | wt | wt | wt | wt | wt | wt | wt | wt | wt |
| Dom neg deletion | 1030 | wt | wt | wt | wt | wt | wt | wt | wt | wt |
| Dom neg deletion | 1033 | wt | wt | wt | wt | wt | wt | wt | wt | + |
| Dom neg deletion | 1034 | wt | wt | wt | wt | wt | wt | wt | wt | wt |
| Dom neg deletion | 1036 | wt | wt | wt | wt | + | wt | wt | wt | + |
| Dom neg deletion | 1037 | wt | wt | wt | wt | + | wt | wt | wt | + |
| Dom neg deletion | 1038 | wt | wt | wt | wt | wt | wt | wt | wt | + |
| Dom neg deletion | 1442 | wt | wt | wt | wt | wt | wt | wt | + | wt |
| Dom neg deletion | 1448 | wt | wt | wt | wt | wt | wt | wt | wt | wt |
| Dom neg deletion | 1449 | wt | wt | wt | wt | wt | wt | wt | wt | wt |
| Dom neg deletion | 1451 | wt | wt | wt | wt | wt | wt | wt | wt | wt |
| Dom neg deletion | 1452 | wt | wt | wt | wt | wt | wt | wt | + | + |
| Dom neg deletion | 1454 | wt | wt | wt | wt | wt | wt | wt | wt | wt |
| Dom neg deletion | 1456 | wt | wt | wt | wt | wt | wt | wt | + | wt |
| Dom neg deletion | 1457 | wt | wt | wt | wt | wt | wt | wt | wt | wt |
| Dom neg deletion | 1458 | wt | wt | wt | wt | wt | wt | wt | wt | wt |
| Dom neg deletion | 1460 | wt | + | wt | wt | wt | wt | wt | + | wt |

Utilities

Based on the data from the above overexpression studies, G867 is a good candidate for improving stress tolerance in plants, including commercial species. However, given the undesirable morphologies that may arise from G867 overexpression, it might be advantageous to optimize the gene by use of alternative promoters or sequence modifications.

We have now isolated lines that overexpress a truncated version of the G867 protein containing the B3 domain but not the AP2 domain of the protein using overexpression constructs P21275 and P21276. Although a number of these lines are significantly more abiotic stress tolerant than wild-type controls (Tables 25 and 26), some of these plants do not exhibit the adverse morphological effects seen in plants constitutively overexpressing G867. This is particularly true for plants transformed with P21276. These results indicate that such sequence modifications for reducing adverse morphological effects in plants overexpressing G867 clade members may be effectively targeted outside of the AP2 domain.

Example XI

Identification of Homologous Sequences

This example describes identification of genes that are orthologous to *Arabidopsis thaliana* transcription factors from a computer homology search.

Homologous sequences, including those of paralogs and orthologs from *Arabidopsis* and other plant species, were identified using database sequence search tools, such as the Basic Local Alignment Search Tool (BLAST) (Altschul et al. (1990) *J. Mol. Biol.* 215: 403-410; and Altschul et al. (1997) *Nucleic Acid Res.* 25: 3389-3402). The tblastx sequence analysis programs were employed using the BLOSUM-62 scoring matrix (Henikoff and Henikoff (1992) *Proc. Natl. Acad. Sci.* 89: 10915-10919). The entire NCBI GenBank database was filtered for sequences from all plants except *Arabidopsis thaliana* by selecting all entries in the NCBI GenBank database associated with NCBI taxonomic ID 33090 (Viridiplantae; all plants) and excluding entries associated with taxonomic ID 3701 (*Arabidopsis thaliana*).

These sequences are compared to sequences representing genes of SEQ ID NO: 1, 3, 5, 7, 9, 11, 13, 15, 17, 19, 21, 23, 25, 27, 29, 31, 33, 35, 37, 39, 41, 43, 45, 47, 49, 51, using the Washington University TBLASTX algorithm (version 2.0a19 MP) at the default settings using gapped alignments with the filter "off". For each gene of SEQ ID NO: 1, 3, 5, 7, 9, 11, 13, 15, 17, 19, 21, 23, 25, 27, 29, 31, 33, 35, 37, 39, 41, 43, 45, 47, 49, 51, individual comparisons were ordered by probability score (P-value), where the score reflects the probability that a particular alignment occurred by chance. For example, a score of 3.6E-40 is 3.6×10-40. In addition to P-values, comparisons were also scored by percentage identity. Percentage identity reflects the degree to which two segments of DNA or protein are identical over a particular length. Examples of sequences so identified are presented in Table 6. The percent sequence identity among these sequences can be as low as 47%, or even lower sequence identity.

Candidate paralogous sequences were identified among *Arabidopsis* transcription factors through alignment, identity, and phylogenic relationships. Paralogs of G867 determined in this manner include G9, G993 and G1930. Candidate orthologous sequences were identified from proprietary unigene sets of plant gene sequences in *Zea mays, Glycine max* and *Oryza sativa* based on significant homology to *Arabidopsis* transcription factors. These candidates were reciprocally compared to the set of *Arabidopsis* transcription factors. If the candidate showed maximal similarity in the protein domain to the eliciting transcription factor or to a paralog of the eliciting transcription factor, then it was considered to be an ortholog. Identified non-*Arabidopsis* sequences that were shown in this manner to be orthologous to the *Arabidopsis* sequences are provided in Table 6.

Example XII

Screen of Plant cDNA Library for Sequence Encoding a Transcription Factor DNA Binding Domain That Binds To a Transcription Factor Binding Promoter Element and Demonstration of Protein Transcription Regulation Activity The "one-hybrid" strategy (Li and Herskowitz (1993) *Science* 262: 1870-1874) is used to screen for plant cDNA clones encoding a polypeptide comprising a transcription factor DNA binding domain, a conserved domain. In brief, yeast strains are constructed that contain a lacZ reporter gene with either wild-type or mutant transcription factor binding promoter element sequences in place of the normal UAS (upstream activator sequence) of the GAL4 promoter. Yeast reporter strains are constructed that carry transcription factor binding promoter element sequences as UAS elements are operably linked upstream (5') of a lacZ reporter gene with a minimal GAL4 promoter. The strains are transformed with a plant expression library that contains random cDNA inserts fused to the GAL4 activation domain (GAL4-ACT) and screened for blue colony formation on X-gal-treated filters (X-gal: 5-bromo-4-chloro-3-indolyl-β-D-galactoside; Invitrogen Corporation, Carlsbad Calif.). Alternatively, the strains are transformed with a cDNA polynucleotide encoding a known transcription factor DNA binding domain polypeptide sequence.

Yeast strains carrying these reporter constructs produce low levels of beta-galactosidase and form white colonies on filters containing X-gal. The reporter strains carrying wild-type transcription factor binding promoter element sequences are transformed with a polynucleotide that encodes a polypeptide comprising a plant transcription factor DNA binding domain operably linked to the acidic activator domain of the yeast GAL4 transcription factor, "GAL4-ACT". The clones that contain a polynucleotide encoding a transcription factor DNA binding domain operably linked to GAL4-ACT can bind upstream of the lacZ reporter genes carrying the wild-type transcription factor binding promoter element sequence, activate transcription of the lacZ gene and result in yeast forming blue colonies on X-gal-treated filters.

Upon screening about $2\times10^6$ yeast transformants, positive cDNA clones are isolated; i.e., clones that cause yeast strains carrying lacZ reporters operably linked to wild-type transcription factor binding promoter elements to form blue colonies on X-gal-treated filters. The cDNA clones do not cause a yeast strain carrying a mutant type transcription factor binding promoter elements fused to LacZ to turn blue. Thus, a polynucleotide encoding transcription factor DNA binding domain, a conserved domain, is shown to activate transcription of a gene.

Example XIII

Gel Shift Assays

The presence of a transcription factor comprising a DNA binding domain which binds to a DNA transcription factor binding element is evaluated using the following gel shift assay. The transcription factor is recombinantly expressed and isolated from *E. coli* or isolated from plant material. Total soluble protein, including transcription factor, (40 ng) is incubated at room temperature in 10 μl of 1× binding buffer (15 mM HEPES (pH 7.9), 1 mM EDTA, 30 mM KCl, 5% glycerol, 5% bovine serum albumin, 1 mM DTT) plus 50 ng poly(dl-dC):poly(dl-dC) (Pharmacia, Piscataway N.J.) with or without 100 ng competitor DNA. After 10 minutes incubation, probe DNA comprising a DNA transcription factor binding element (1 ng) that has been $^{32}$P-labeled by end-filling (Sambrook et al. (1989) supra) is added and the mixture incubated for an additional 10 minutes. Samples are loaded onto polyacrylamide gels (4% w/v) and fractionated by electrophoresis at 150V for 2 h (Sambrook et al. supra). The degree of transcription factor-probe DNA binding is visualized using autoradiography. Probes and competitor DNAs are prepared from oligonucleotide inserts ligated into the BamHI site of pUC118 (Vieira et al. (1987) *Methods Enzymol*. 153: 3-11). Orientation and concatenation number of the inserts are determined by dideoxy DNA sequence analysis (Sambrook et al. supra). Inserts are recovered after restriction digestion with EcoRI and HindIII and fractionation on polyacrylamide gels (12% w/v) (Sambrook et al. supra).

Example XIV

Introduction of Polynucleotides into Dicotyledonous Plants

SEQ ID NO: 1, 3, 5, 7, 9, 11, 13, 15, 17, 19, 21, 23, 25, 27, 29, 31, 33, 35, 37, 39, 41, 43, 45, 47, 49, 51, or polynucleotide sequences encoding SEQ ID NO: 2, 4, 6, 8, 10, 12, 14, 16, 18, 20, 22, 24, 26, 28, 30, 32, 34, 36, 38, 40, 42, 44, 46, 48, 50, 52, 53, paralogous, and orthologous sequences, including truncated sequences and sequences combined with an artificial activation domain, are recombined into pMEN20 or pMEN65 expression vectors and transformed into a plant. The vector may be introduced into a variety of monocot plants by well known means, including direct DNA transfer or *Agrobacterium tumefaciens*-mediated transformation. It is routine to produce transgenic plants using most dicot plants (see Weissbach and Weissbach, (1989) supra; Gelvin et al. (1990) supra; Herrera-Estrella et al. (1983) supra; Bevan (1984) supra; and Klee (1985) supra).

Example XV

Transformation of Cereal Plants with an Expression Vector

Cereal plants such as, but not limited to, corn, wheat, rice, sorghum, or barley, may also be transformed with the present polynucleotide sequences in pMEN20 or pMEN65 expression vectors for the purpose of modifying plant traits. For example, pMEN020 may be modified to replace the NptII coding region with the BAR gene of *Streptomyces hygroscopicus* that confers resistance to phosphinothricin. The KpnI and BglII sites of the Bar gene are removed by site-directed mutagenesis with silent codon changes.

The cloning vector may be introduced into a variety of cereal plants by means well known in the art such as, for example, direct DNA transfer or *Agrobacterium tumefaciens*-mediated transformation. It is now routine to produce transgenic plants of most cereal crops (Vasil (1994) *Plant Mol. Biol*, 25: 925-937) such as corn, wheat, rice, sorghum (Cassas et al. (1993) *Proc. Natl, Acad. Sci.* 90: 11212-11216), and barley (Wan and Lemeaux (1994) *Plant Physiol.* 104:37-48). DNA transfer methods such as the microprojectile can be used for corn (Fromm et al. (1990) *Bio/Technol.* 8: 833-839); Gordon-Kamm et al. (1990) *Plant Cell* 2: 603-618; Ishida (1990) *Nature Biotechnol.* 14:745-750), wheat (Vasil et al. (1992) *Bio/Technol.* 10:667-674; Vasil et al. (1993) *Bio/Technol.* 11:1553-1558; Weeks et al. (1993) *Plant Physiol.* 102: 1077-1084), and rice (Christou (1991) *Bio/Technol.* 9:957-962; Hiei et al. (1994) *Plant J.* 6:271-282; Aldemita and Hodges (1996) *Planta* 199:612-617; and Hiei et al. (1997) *Plant Mol. Biol.* 35:205-218). For most cereal plants, embryogenic cells derived from immature scutellum tissues are the preferred cellular targets for transformation (Hiei et al. (1997) *Plant Mol. Biol.* 35:205-218; Vasil (1994) *Plant Mol. Biol.* 25: 925-937).

Vectors according to the present invention may be transformed into corn embryogenic cells derived from immature scutellar tissue by using microprojectile bombardment, with the A188XB73 genotype as the preferred genotype (Fromm et al. (1990) *Bio/Technol.* 8: 833-839; Gordon-Kamm et al. (1990) *Plant Cell* 2: 603-618). After microprojectile bombardment the tissues are selected on phosphinothricin to identify the transgenic embryogenic cells (Gordon-Kamm et al. (1990) *Plant Cell* 2: 603-618). Transgenic plants are regenerated by standard corn regeneration techniques (Fromm et al. (1990) *Bio/Technol.* 8: 833-839; Gordon-Kamm et al. (1990) *Plant Cell* 2: 603-618).

The plasmids prepared as described above can also be used to produce transgenic wheat and rice plants (Christou (1991) *Bio/Technol.* 9:957-962; Hiei et al. (1994) *Plant J* 6:271-282; Aldemita and Hodges (1996) *Planta* 199:612-617; and Hiei et al. (1997) *Plant Mol. Biol.* 35:205-218) that coordinately express genes of interest by following standard transformation protocols known to those skilled in the art for rice and wheat (Vasil et al. (1992) *Bio/Technol.* 10:667-674; Vasil et al. (1993) *Bio/Technol.* 11:1553-1558; and Weeks et al. (1993) *Plant Physiol.* 102:1077-1084), where the bar gene is used as the selectable marker.

Example XVI

Transformation of Tomato and Soy Plants

Numerous protocols for the transformation of tomato and soy plants have been previously described, and are well known in the art. Gruber et al. ((1993) in *Methods in Plant Molecular Biology and Biotechnology*, p. 89-119, Glick and Thompson, eds., CRC Press, Inc., Boca Raton) describe several expression vectors and culture methods that may be used for cell or tissue transformation and subsequent regeneration. For soybean transformation, methods are described by Miki et al. (1993) in *Methods in Plant Molecular Biology and Biotechnology*, p. 67-88, Glick and Thompson, eds., CRC Press, Inc., Boca Raton; and U.S. Pat. No. 5,563,055, (Townsend and Thomas), issued Oct. 8, 1996.

There are a substantial number of alternatives to *Agrobacterium*-mediated transformation protocols, other methods for the purpose of transferring exogenous genes into soybeans or tomatoes. One such method is microprojectile-mediated transformation, in which DNA on the surface of microprojectile particles is driven into plant tissues with a biolistic device (see, for example, Sanford et al., (1987) *Part. Sci. Technol.* 5:27-37; Christou et al. (1992) *Plant. J.* 2: 275-281; Sanford (1993) *Methods Enzymol.* 217: 483-509; Klein et al. (1987) *Nature* 327: 70-73; U.S. Pat. No. 5,015,580 (Christou et al), issued May 14, 1991; and U.S. Pat. No. 5,322,783 (Tomes et al.), issued Jun. 21, 1994.

Alternatively, sonication methods (see, for example, Zhang et al. (1991) *Bio/Technology* 9: 996-997); direct uptake of DNA into protoplasts using $CaCl_2$ precipitation, polyvinyl alcohol or poly-L-ornithine (see, for example, Hain et al. (1985) *Mol. Gen. Genet.* 199: 161-168; Draper et al., *Plant Cell Physiol.* 23: 451-458 (1982)); liposome or spheroplast fusion (see, for example, Deshayes et al. (1985) *EMBO J.*, 4: 2731-2737; Christou et al. (1987) *Proc. Natl. Acad. Sci. U.S.A.* 84: 3962-3966); and electroporation of protoplasts and whole cells and tissues (see, for example, Donn et al. (1990) in *Abstracts of VIIth International Congress on Plant Cell and Tissue Culture IAPTC*, A2-38: 53; D'Halluin et al. (1992) *Plant Cell* 4: 1495-1505; and Spencer et al. (1994) *Plant Mol. Biol.* 24: 51-61) have been used to introduce foreign DNA and expression vectors into plants.

After plants or plant cells are transformed (and the latter regenerated into plants) the transgenic plant thus generated may be crossed with itself ("selfing") or a plant from the same line, a non-transformed or wild-type plant, or another transformed plant from a different transgenic line of plants. Crossing provides the advantages of being able to produce new and perhaps stable transgenic varieties. Genes and the traits they confer that have been introduced into a tomato or soybean line may be moved into distinct line of plants using traditional backcrossing techniques well known in the art. Transformation of tomato plants may be conducted using the protocols of Koornneef et al (1986) In *Tomato Biotechnology: Alan R. Liss, Inc.*, 169-178, and in U.S. Pat. No. 6,613,962, the latter method described in brief here. Eight day old cotyledon explants are precultured for 24 hours in Petri dishes containing a feeder layer of *Petunia hybrida* suspension cells plated on MS medium with 2% (w/v) sucrose and 0.8% agar supplemented with 10 µM α-naphthalene acetic acid and 4.4 µM 6-benzylaminopurine. The explants are then infected with a diluted overnight culture of *Agrobacterium tumefaciens* containing an expression vector comprising a polynucleotide of the invention for 5-10 minutes, blotted dry on sterile filter paper and cocultured for 48 hours on the original feeder layer plates. Culture conditions are as described above. Overnight cultures of *Agrobacterium tumefaciens* are diluted in liquid MS medium with 2% (w/v/) sucrose, pH 5.7) to an $OD_{600}$ of 0.8.

Following the cocultivation, the cotyledon explants are transferred to Petri dishes with selective medium consisting of MS medium supplemented with 4.56 µM zeatin, 67.3 µM vancomycin, 418.9 µM cefotaxime and 171.6 µM kanamycin sulfate, and cultured under the culture conditions described above. The explants are subcultured every three weeks onto fresh medium. Emerging shoots are dissected from the underlying callus and transferred to glass jars with selective medium without zeatin to form roots. The formation of roots in a medium containing kanamycin sulfate is regarded as a positive indication of a successful transformation.

Transformation of soybean plants may be conducted using the methods found in, for example, U.S. Pat. No. 5,563,055 (Townsend et al., issued Oct. 8, 1996), described in brief here. In this method soybean seed is surface sterilized by exposure to chlorine gas evolved in a glass bell jar. Seeds are germinated by plating on 1/10 strength agar solidified medium without plant growth regulators and culturing at 28° C. with a 16 hour day length. After three or four days, seed may be prepared for cocultivation. The seedcoat is removed and the elongating radicle removed 3 4 mm below the cotyledons.

Overnight cultures of *Agrobacterium tumefaciens* harboring the expression vector comprising a polynucleotide of the invention are grown to log phase, pooled, and concentrated by centrifugation. Inoculations are conducted in batches such that each plate of seed was treated with a newly resuspended pellet of *Agrobacterium*. The pellets are resuspended in 20 ml inoculation medium. The inoculum is poured into a Petri dish containing prepared seed and the cotyledonary nodes are macerated with a surgical blade. After 30 minutes the explants are transferred to plates of the same medium which has been solidified. Explants are embedded with the adaxial side up and level with the surface of the medium and cultured at 22° C. for three days under white fluorescent light. These plants may then be regenerated according to methods well established in the art, such as by moving the explants after three days to a liquid counter-selection medium (see U.S. Pat. No. 5,563,055).

The explants may then be picked, embedded and cultured in solidified selection medium. After one month on selective media transformed tissue becomes visible as green sectors of regenerating tissue against a background of bleached, less healthy tissue. Explants with green sectors are transferred to an elongation medium. Culture is continued on this medium with transfers to fresh plates every two weeks. When shoots are 0.5 cm in length they may be excised at the base and placed in a rooting medium.

Example XVII

Genes that Confer Significant Improvements to non-*Arabidopsis* Species

The function of specific orthologs of G867 may be analyzed through their ectopic overexpression in plants, using the CaMV 35S aor other appropriate promoter, identified above. These genes, which include polynucleotide sequences found in the Sequence Listing, Table 6 and FIG. 3, encode members of the AP2 transcription factors, such as those found in *Oryza sativa* (SEQ ID NO: 20, 30, 32, 34, 36, 52, and 53), *Arabidopsis thaliana* (SEQ ID NO 2, 4, 6, 8), *Glycine max* (SEQ ID NO: 18, 22, 24, 26, 28), *Zea mays* (SEQ ID NO: 38, 40, 50), *Triticum aestivum* (SEQ ID NO: 48), *Brassica oleracea* (SEQ ID NO: 42), and *Helianthus annuus* (SEQ ID NO: 44 and 46). The polynucleotide and polypeptide sequences derived from monocots may be used to transform both monocot and dicot plants, and those derived from dicots may be used to transform either group, although some of these sequences will function best if the gene is transformed into a plant from the same group as that from which the sequence is derived.

Seeds of these transgenic plants are subjected to germination assays to measure sucrose sensing. Sterile monocot seeds, including, but not limited to, corn, rice, wheat, rye and sorghum, as well as dicots including, but not limited to soybean and alfalfa, are sown on 80% MS medium plus vitamins with 9.4% sucrose; control media lack sucrose. All assay plates are then incubated at 22° C. under 24-hour light, 120-130 µEin/m$^2$/s, in a growth chamber. Evaluation of germination and seedling vigor is then conducted three days after planting. Overexpressors of these genes may be found to be more tolerant to high sucrose by having better germination, longer radicles, and more cotyledon expansion. These results would indicate that overexpressors of members of the G867 clade of transcription factor polypeptides are involved in sucrose-specific sugar sensing. These results have thus been determined in plants overexpressing rice G3389, G3391, corn G3432, or soy G3451, G3452, or G3455.

Plants overexpressing these orthologs may also be subjected to soil-based drought assays to identify those lines that are more tolerant to water deprivation than wild-type control plants. Generally, plants that overexpress a member of the G867 clade of transcription factor orthologs will appear significantly larger and greener, with less wilting or desiccation, than wild-type controls plants, particularly after a period of water deprivation is followed by rewatering and a subsequent incubation period.

Example XVIII

Identification of Orthologous and Paralogous Sequences

Orthologs to *Arabidopsis* genes may identified by several methods, including hybridization, amplification, or bioinformatically. This example describes how one may identify homologs to the *Arabidopsis* AP2 family transcription factor CBF 1 (polynucleotide SEQ ID NO: 54, encoded polypeptide SEQ ID NO: 55), which confers tolerance to abiotic stresses (Thomashow et al. (2002) U.S. Pat. No. 6,417,428), and an example to confirm the function of homologous sequences. In this example, orthologs to CBF 1 were found in canola (*Brassica napus*) using polymerase chain reaction (PCR).

Degenerate primers were designed for regions of AP2 binding domain and outside of the AP2 (carboxyl terminal domain):

```
Mol 368 (reverse)
5'- CAY CCN ATH TAY MGN GGN GT -3'     (SEQ ID NO: 62)

Mol 378 (forward)
5'- GGN ARN ARC ATN CCY TCN GCC -3'    (SEQ ID NO: 63)

(Y: C/T, N: A/C/G/T, H: A/C/T, M: A/C, R: A/G)
```

Primer Mol 368 is in the AP2 binding domain of CBF1 (amino acid sequence: His-Pro-Ile-Tyr-Arg-Gly-Val; SEQ ID NO: 94) while primer Mol 378 is outside the AP2 domain (carboxyl terminal domain) (amino acid sequence: Met-Ala-Glu-Gly-Met-Leu-Leu-Pro; SEQ ID NO: 95).

The genomic DNA isolated from *B. napus* was PCR-amplified by using these primers following these conditions: an initial denaturation step of 2 min at 93° C.; 35 cycles of 93° C. for 1 min, 55° C. for 1 min, and 72° C. for 1 min; and a final incubation of 7 min at 72° C. at the end of cycling.

The PCR products were separated by electrophoresis on a 1.2% agarose gel and transferred to nylon membrane and hybridized with the AT CBF 1 probe prepared from *Arabidopsis* genomic DNA by PCR amplification. The hybridized products were visualized by colorimetric detection system (Boehringer Mannheim) and the corresponding bands from a similar agarose gel were isolated using the Qiagen Extraction Kit (Qiagen). The DNA fragments were ligated into the TA clone vector from TOPO TA Cloning Kit (Invitrogen) and transformed into *E. coli* strain TOP 10 (Invitrogen).

Seven colonies were picked and the inserts were sequenced on an ABI 377 machine from both strands of sense and antisense after plasmid DNA isolation. The DNA sequence was edited by sequencer and aligned with the AtCBF1 by GCG software and NCBI blast searching.

The nucleic acid sequence and amino acid sequence of one canola ortholog found in this manner (bnCBF1; polynucleotide SEQ ID NO: 60 and polypeptide SEQ ID NO: 61) identified by this process is shown in the Sequence Listing.

The aligned amino acid sequences show that the bnCBF1 gene has 88% identity with the *Arabidopsis* sequence in the AP2 domain region and 85% identity with the *Arabidopsis* sequence outside the AP2 domain when aligned for two insertion sequences that are outside the AP2 domain.

Similarly, paralogous sequences to *Arabidopsis* genes, such as CBF1, may also be identified.

Two paralogs of CBF1 from *Arabidopsis thaliana*: CBF2 and CBF3. CBF2 and CBF3 have been cloned and sequenced as described below. The sequences of the DNA SEQ ID NO: 54, 56 and 58 and encoded proteins SEQ ID NO: 55, 57 and 59 are set forth in the Sequence Listing.

A lambda cDNA library prepared from RNA isolated from *Arabidopsis thaliana* ecotype Columbia (Lin and Thomashow (1992) *Plant Physiol.* 99: 519-525) was screened for recombinant clones that carried inserts related to the CBF1 gene (Stockinger et al. (1997) *Proc. Natl. Acad. Sci.* 94:1035-1040). CBF1 was $^{32}$P-radiolabeled by random priming (Sambrook et al. supra) and used to screen the library by the plaque-lift technique using standard stringent hybridization and wash conditions (Hajela et al. (1990) *Plant Physiol.* 93:1246-1252; Sambrook et al. supra) 6×SSPE buffer, 60° C. for hybridization and 0.1×SSPE buffer and 60° C. for washes). Twelve positively hybridizing clones were obtained and the DNA sequences of the cDNA inserts were determined. The results indicated that the clones fell into three classes. One class carried inserts corresponding to CBF1. The two other classes carried sequences corresponding to two different homologs of CBF1, designated CBF2 and CBF3. The nucleic acid sequences and predicted protein coding sequences for *Arabidopsis* CBF1, CBF2 and CBF3 are listed in the Sequence Listing (SEQ ID NOs:54, 56, 58 and SEQ ID NOs: 55, 57, and 59, respectively). The nucleic acid sequences and predicted protein coding sequence for *Brassica napus* CBF ortholog is listed in the Sequence Listing (SEQ ID NOs: 60 and 61, respectively).

A comparison of the nucleic acid sequences of *Arabidopsis* CBF1, CBF2 and CBF3 indicate that they are 83 to 85% identical as shown in Table 27.

TABLE 27

| | Percent identity[a] | |
|---|---|---|
| | DNA[b] | Polypeptide |
| cbf1/cbf2 | 85 | 86 |
| cbf1/cbf3 | 83 | 84 |
| cbf2/cbf3 | 84 | 85 |

[a]Percent identity was determined using the Clustal algorithm from the Megalign program (DNASTAR, Inc.).
[b]Comparisons of the nucleic acid sequences of the open reading frames are shown.

Similarly, the amino acid sequences of the three CBF polypeptides range from 84 to 86% identity, An alignment of the three amino acid sequences reveals that most of the differences in amino acid sequence occur in the acidic C-terminal half of the polypeptide. This region of CBF1 serves as an activation domain in both yeast and *Arabidopsis* (not shown).

Residues 47 to 106 of CBF 1 correspond to the AP2 domain of the protein, a DNA binding motif that to date, has only been found in plant proteins. A comparison of the AP2 domains of CBF1, CBF2 and CBF3 indicates that there are a few differences in amino acid sequence. These differences in amino acid sequence might have an effect on DNA binding specificity.

Example XIX

Transformation of Canola with a Plasmid Containing CBF1, CBF2, or CBF3

After identifying homologous genes to CBF 1, canola was transformed with a plasmid containing the *Arabidopsis* CBF 1, CBF2, or CBF3 genes cloned into the vector pGA643 (An (1987) *Methods Enzymol.* 253: 292). In these constructs the CBF genes were expressed constitutively under the CaMV 35 S apromoter. In addition, the CBF1 gene was cloned under the control of the *Arabidopsis* COR15 promoter in the same vector pGA643. Each construct was transformed into *Agrobacterium* strain GV3101. Transformed *Agrobacteria* were grown for 2 days in minimal AB medium containing appropriate antibiotics.

Spring canola (*B. napus* cv. Westar) was transformed using the protocol of Moloney et al. ((1989) *Plant Cell Reports* 8: 238) with some modifications as described. Briefly, seeds were sterilized and plated on half strength MS medium, containing 1% sucrose. Plates were incubated at 24° C. under 60-80 uE/m$^2$s light using 16 hour light/8 hour dark photoperiod. Cotyledons from 4-5 day old seedlings were collected, the petioles cut and dipped into the *Agrobacterium* solution. The dipped cotyledons were placed on co-cultivation medium at a density of 20 cotyledons/plate and incubated as described above for 3 days. Explants were transferred to the same media, but containing 300 mg/l timentin (SmithKline Beecham, Pa.) and thinned to 10 cotyledons/plate. After 7 days explants were transferred to Selection/Regeneration medium. Transfers were continued every 2-3 weeks (2 or 3 times) until shoots had developed. Shoots were transferred to Shoot-Elongation medium every 2-3 weeks. Healthy looking shoots were transferred to rooting medium. Once good roots had developed, the plants Were placed into moist potting soil.

The transformed plants were then analyzed for the presence of the NPTII gene/kanamycin resistance by ELISA, using the ELISA NPTII kit from 5Prime-3Prime Inc. (Boulder, Colo.). Approximately 70% of the screened plants were NPTII positive. Only those plants were further analyzed.

From Northern blot analysis of the plants that were transformed with the constitutively expressing constructs, showed expression of the CBF genes and all CBF genes were capable of inducing the *Brassica napus* cold-regulated gene BN115 (homolog of the *Arabidopsis* COR15 gene). Most of the transgenic plants appear to exhibit a normal growth phenotype. As expected, the transgenic plants are more freezing tolerant than the wild-type plants. Using the electrolyte leakage of leaves test, the wild-type control showed a 50% leakage at −2 to −3° C. Spring canola transformed with either CBF1 or CBF2 showed a 50% leakage at −6 to −7° C. Spring canola transformed with CBF3 shows a 50% leakage at about −10 to −15° C. Winter canola transformed with CBF3 may show a 50% leakage at about −16 to −20° C. Furthermore, if the spring or winter canola are cold acclimated the transformed plants may exhibit a further increase in freezing tolerance of at least −2° C.

To test salinity tolerance of the transformed plants, plants were watered with 150 mM NaCl. Plants overexpressing CBF1, CBF2 or CBF3 grew better compared with plants that had not been transformed with CBF1, CBF2 or CBF3.

These results demonstrate that homologs of *Arabidopsis* transcription factors can be identified and shown to confer similar functions in non-*Arabidopsis* plant species.

Example XX

Cloning of Transcription Factor Promoters

Promoters are isolated from transcription factor genes that have gene expression patterns useful for a range of applications, as determined by methods well known in the art (including transcript profile analysis with cDNA or oligonucleotide microarrays, Northern blot analysis, semi-quantitative or quantitative RT-PCR). Interesting gene expression profiles are revealed by determining transcript abundance for a selected transcription factor gene after exposure of plants to a range of different experimental conditions, and in a range of different tissue or organ types, or developmental stages. Experimental conditions to which plants are exposed for this purpose includes cold, heat, drought, osmotic challenge, and varied hormone concentrations (ABA, GA, auxin, cytokinin, salicylic acid, brassinosteroid). The tissue types and developmental stages include stem, root, flower, rosette leaves, cauline leaves, siliques, germinating seed, and meristematic tissue. The set of expression levels provides a pattern that is determined by the regulatory elements of the gene promoter.

Transcription factor promoters for the genes disclosed herein are obtained by cloning 1.5 kb to 2.0 kb of genomic sequence immediately upstream of the translation start codon for the coding sequence of the encoded transcription factor protein. This region includes the 5'-UTR of the transcription factor gene, which can comprise regulatory elements. The 1.5 kb to 2.0 kb region is cloned through PCR methods, using primers that include one in the 3' direction located at the translation start codon (including appropriate adaptor sequence), and one in the 5' direction located from 1.5 kb to 2.0 kb upstream of the translation start codon (including appropriate adaptor sequence). The desired fragments are PCR-amplified from *Arabidopsis* Col-0 genomic DNA using high-fidelity Taq DNA polymerase to minimize the incorporation of point mutation(s). The cloning primers incorporate two rare restriction sites, such as Not1 and Sfi1, found at low frequency throughout the *Arabidopsis* genome. Additional restriction sites are used in the instances where a Not1 or Sfi1 restriction site is present within the promoter.

The 1.5-2.0 kb fragment upstream from the translation start codon, including the 5'-untranslated region of the transcription factor, is cloned in a binary transformation vector immediately upstream of a suitable reporter gene, or a transactivator gene that is capable of programming expression of a reporter gene in a second gene construct. Reporter genes used include green fluorescent protein (and related fluorescent protein color variants), beta-glucuronidase, and luciferase. Suitable transactivator genes include LexA-GAL4, along with a transactivatable reporter in a second binary plasmid (as disclosed in U.S. patent application Ser. No. 09/958,131, incorporated herein by reference). The binary plasmid(s) is transferred into *Agrobacterium* and the structure of the plasmid confirmed by PCR. These strains are introduced into *Arabidopsis* plants as described in other examples, and gene expression patterns determined according to standard methods know to one skilled in the art for monitoring GFP fluorescence, beta-glucuronidase activity, or luminescence.

All publications and patent applications mentioned in this specification are herein incorporated by reference to the same extent as if each individual publication or patent application was specifically and individually indicated to be incorporated by reference.

The present invention is not limited by the specific embodiments described herein. The invention now being fully described, it will be apparent to one of ordinary skill in the art that many changes and modifications can be made thereto without departing from the spirit or scope of the claims. Modifications that become apparent from the foregoing description and accompanying figures fall within the scope of the following claims.

What is claimed is:

1. A transgenic plant that comprises a recombinant polynucleotide comprising a nucleotide sequence that encodes a member of the G867 clade of transcription factor polypeptides;

wherein the member of the G867 clade of transcription factor polypeptides comprises an AP2 domain, a B3 domain and a DML motif, wherein the AP2 domain, the B3 domain and the DML motif are at least 81%, 78% and 76% identical to the AP2 domain and the B3 domain and the DML motif of SEQ ID NO: 2, respectively.

2. The transgenic plant of claim 1, wherein the member of the G867 clade of transcription factor polypeptides is at least 64% identical to SEQ ID NO: 2.

3. The transgenic plant of claim 1, wherein the transgenic plant has greater tolerance to osmotic stress or cold than a control plant.

4. The transgenic plant of claim 3, wherein the osmotic stress is 150 mM NaCl or 9.4% (w/v) sucrose.

5. The transgenic plant of claim 1, wherein:

(a) the AP2 domain binds to a transcription-regulating region comprising the motif CAACA; and (b) the B3 domain binds to a transcription regulating region comprising the motif CACCTG; and wherein said binding of the AP2 domain and the B3 domain cooperatively enhances DNA binding affinity of the member of the G867 clade of transcription factor polypeptides.

6. A transgenic plant, wherein said transgenic plant comprises a recombinant polynucleotide comprising a nucleotide sequence that encodes SEQ ID NO: 2.

7. The transgenic plant of claim 6, wherein said nucleotide sequence comprises SEQ ID NO: 1.

8. The transgenic plant of claim 1, wherein the recombinant polynucleotide is operably linked to at least one regulatory element capable of regulating expression of the recombinant polynucleotide when the recombinant polynucleotide is transformed into a plant.

9. The transgenic plant of claim 8, wherein the regulatory element comprises an inducible or tissue specific promoter.

10. The transgenic plant of claim 8, wherein the regulatory element is selected from the group consisting of a SUC2 promoter, an RBCS3 promoter, an ARSK1 promoter, and an RD29A promoter.

11. A transgenic seed produced from the transgenic plant according to claim 1.

12. A method for producing a transgenic plant having greater tolerance to an osmotic stress or cold than a control plant, the method steps comprising:
(a) introducing an expression vector into a plant to produce the transgenic plant;
wherein the expression vector comprises a polynucleotide sequence encoding a member of the G867 clade of transcription factor polypeptides;
wherein the member of the G867 clade of transcription factor polypeptides comprises an AP2 domain, a B3 domain and a DML motif; and
wherein the AP2 domain, the B3 domain and the DML motif are at least 81%, 78% and 76% identical to the AP2 domain, the B3 domain and the DML motif of SEQ ID NO: 2, respectively,
(b) growing the transgenic plant; and
(c) selecting the transgenic plant on the basis of its greater tolerance to osmotic stress or cold than the control plant.

13. The method of claim 12, the method steps further comprising:
(d) selfing or crossing the transgenic plant with itself or another plant, respectively, to produce a transgenic seed.

14. The method of claim 12, wherein said greater osmotic stress tolerance is greater tolerance to salt or sucrose.

15. The method of claim 12, wherein said greater tolerance to an increased osmotic stress is greater tolerance to 150 mM NaCl or 9.4% (w/v) sucrose.

16. The method of claim 12, wherein said member of the G867 clade of transcription factor polypeptides is at least 64% identical to SEQ ID NO: 2.

17. A method of claim 12,
wherein the polynucleotide sequence is operably linked to an inducible or tissue specific promoter that controls expression of the polynucleotide sequence.

18. The method of claim 17, wherein the AP2 domain, the DML motif, and the B3 domain are at least 86%, 90%, and 87% identical to the AP2 domain, the DML motif, and the B3 domain of SEQ ID NO: 2, respectively.

19. The method of claim 17, wherein the transformed plant has a morphology that is substantially similar to the control plant.

20. The method of claim 17, wherein said greater osmotic stress tolerance is greater tolerance to salt or sucrose.

21. The method of claim 17, wherein said greater osmotic stress tolerance is greater tolerance to 150 mM NaCl or 9.4% (w/v) sucrose.

22. The method of claim 17, wherein the inducible or tissue specific promoter is selected from the group consisting of a SUC2 promoter, an RBCS3 promoter, an ARSK1 promoter, and an RD29A promoter.

23. A transgenic seed produced from the transformed plant produced by the method according to claim 17.

24. The method of claim 17, the method steps further comprising:
(d) selfing or crossing the transformed plant with itself or another plant, respectively, to produce a transgenic seed; and
(e) growing a progeny plant from the transgenic seed;
wherein the progeny plant has greater tolerance to an osmotic stress or cold than the control plant.

25. A transgenic seed produced from the progeny plant produced by the method according to claim 24.

26. The method of claim 9, wherein the AP2 domain and the B3 domain are at least 86% and 87% identical to the AP2 domain and the B3 domain of SEQ ID NO: 2, respectively.

27. A transgenic plant of claim 3, wherein the greater osmotic stress tolerance is greater tolerance to salt or sucrose.

28. A method for producing a transgenic plant, the method comprising:
(a) providing an expression vector comprising a polynucleotide sequence encoding SEQ ID NO: 2; and wherein the polynucleotide sequence is operably linked to an inducible or tissue specific promoter that controls expression of the polynucleotide sequence;
(b) transforming a target plant with the expression vector to produce the transformed plant;
(c) growing the transgenic plant; and
(d) selecting the transformed plant on the basis of its greater tolerance to an osmotic stress or cold than a control plant.

\* \* \* \* \*

SEQUENCE LISTING

```
<160> NUMBER OF SEQ ID NOS: 120

<210> SEQ ID NO 1
<211> LENGTH: 1281
<212> TYPE: DNA
<213> ORGANISM: Arabidopsis thaliana
<220> FEATURE:
<223> OTHER INFORMATION: G867 Predicted polypeptide sequence is
      paralogous to G9, G993, G1930

<400> SEQUENCE: 1
cacaacacaa acacatttct gttttctcca ttgtttcaaa ccataaaaaa aaacacagat      60
taaatggaat cgagtagcgt tgatgagagt actacaagta caggttccat ctgtgaaacc     120
ccggcgataa ctccggcgaa aaagtcgtcg gtaggtaact tatacaggat gggaagcgga     180
tcaagcgttg tgttagattc agagaacggc gtagaagctg aatctaggaa gcttccgtcg     240
tcaaaataca aaggtgtggt gccacaacca aacgaagat ggggagctca gatttacgag      300
aaacaccagc gcgtgtggct cgggacattc aacgaagaag acgaagccgc tcgtgcctac     360
gacgtcgcgg ttcacaggtt ccgtcgccgt gacgccgtca caaatttcaa agacgtgaag     420
atggacgaag acgaggtcga tttcttgaat tctcattcga aatctgagat cgttgatatg     480
```

```
ttgaggaaac atacttataa cgaagagtta gagcagagta aacggcgtcg taatggtaac    540
ggaaacatga ctaggacgtt gttaacgtcg gggttgagta atgatggtgt ttctacgacg    600
gggtttagat cggcggaggc actgtttgag aaagcggtaa cgccaagcga cgttgggaag    660
ctaaaccgtt tggttatacc gaaacatcac gcagagaaac attttccgtt accgtcaagt    720
aacgtttccg tgaaaggagt gttgttaac tttgaggacg ttaacgggaa agtgtggagg     780
ttccgttact cgtattggaa cagtagtcag agttatgttt tgactaaagg ttggagcagg    840
ttcgttaagg agaagaatct acgtgctggt gacgtggtta gtttcagtag atctaacggt    900
caggatcaac agttgtacat tgggtggaag tcgagatccg ggtcagattt agatgcgggt    960
cgggttttga gattgttcgg agttaacatt tcaccggaga gttcaagaaa cgacgtcgta   1020
ggaaacaaaa gagtgaacga tactgagatg ttatcgttgg tgtgtagcaa gaagcaacgc   1080
atctttcacg cctcgtaaca actcttcttc ttttttttc ttttgttgtt ttaataattt    1140
ttaaaaactc cattttcgtt ttctttattt gcatcggttt cttttcttctt gtttaccaaa  1200 ggttcatgag ttgtttttgt tgtattgatg aactgtaaat tttatttata ggataaattt   1260
taaaaaaaaa aaaaaaaaaa a                                             1281
```

<210> SEQ ID NO 2
<211> LENGTH: 344
<212> TYPE: PRT
<213> ORGANISM: Arabidopsis thaliana
<220> FEATURE:
<223> OTHER INFORMATION: G867 polypeptide Paralogous to G9, G993, G1930

<400> SEQUENCE: 2

```
Met Glu Ser Ser Ser Val Asp Glu Ser Thr Thr Ser Thr Gly Ser Ile
 1               5                  10                  15

Cys Glu Thr Pro Ala Ile Thr Pro Ala Lys Lys Ser Ser Val Gly Asn
            20                  25                  30

Leu Tyr Arg Met Gly Ser Gly Ser Val Val Leu Asp Ser Glu Asn
        35                  40                  45

Gly Val Glu Ala Glu Ser Arg Lys Leu Pro Ser Ser Lys Tyr Lys Gly
    50                  55                  60

Val Val Pro Gln Pro Asn Gly Arg Trp Gly Ala Gln Ile Tyr Glu Lys
65                  70                  75                  80

His Gln Arg Val Trp Leu Gly Thr Phe Asn Glu Glu Asp Glu Ala Ala
                85                  90                  95

Arg Ala Tyr Asp Val Ala Val His Arg Phe Arg Arg Asp Ala Val
            100                 105                 110

Thr Asn Phe Lys Asp Val Lys Met Asp Glu Asp Glu Val Asp Phe Leu
        115                 120                 125

Asn Ser His Ser Lys Ser Glu Ile Val Asp Met Leu Arg Lys His Thr
    130                 135                 140

Tyr Asn Glu Glu Leu Glu Gln Ser Lys Arg Arg Arg Asn Gly Asn Gly
145                 150                 155                 160

Asn Met Thr Arg Thr Leu Leu Thr Ser Gly Leu Ser Asn Asp Gly Val
                165                 170                 175

Ser Thr Thr Gly Phe Arg Ser Ala Glu Ala Leu Phe Glu Lys Ala Val
            180                 185                 190

Thr Pro Ser Asp Val Gly Lys Leu Asn Arg Leu Val Ile Pro Lys His
        195                 200                 205

His Ala Glu Lys His Phe Pro Leu Pro Ser Ser Asn Val Ser Val Lys
    210                 215                 220
```

```
Gly Val Leu Leu Asn Phe Glu Asp Val Asn Gly Lys Val Trp Arg Phe
225                 230                 235                 240

Arg Tyr Ser Tyr Trp Asn Ser Ser Gln Ser Tyr Val Leu Thr Lys Gly
                245                 250                 255

Trp Ser Arg Phe Val Lys Glu Lys Asn Leu Arg Ala Gly Asp Val Val
            260                 265                 270

Ser Phe Ser Arg Ser Asn Gly Gln Asp Gln Gln Leu Tyr Ile Gly Trp
        275                 280                 285

Lys Ser Arg Ser Gly Ser Asp Leu Asp Ala Gly Arg Val Leu Arg Leu
    290                 295                 300

Phe Gly Val Asn Ile Ser Pro Glu Ser Ser Arg Asn Asp Val Val Gly
305                 310                 315                 320

Asn Lys Arg Val Asn Asp Thr Glu Met Leu Ser Leu Val Cys Ser Lys
                325                 330                 335

Lys Gln Arg Ile Phe His Ala Ser
                340
```

<210> SEQ ID NO 3
<211> LENGTH: 1246
<212> TYPE: DNA
<213> ORGANISM: Arabidopsis thaliana
<220> FEATURE:
<223> OTHER INFORMATION: G9 Predicted polypeptide sequence is paralogous to G867, G993, G1930

<400> SEQUENCE: 3

```
gtgtttcttc tttctgctaa aaggttataa ttttttgtttc ttggtttggt gagaatcttc        60
aagaaactga acaaagaaa atggattcta gttgcataga cgagataagt tcctccactt         120
cagaatcttt ctccgccacc accgccaaga agctctctcc tcctcccgcg gcggcgttac        180
gcctctaccg gatgggaagc ggcgggagca gcgtcgtgtt ggatcccgag aacggcctag        240
agacggagtc acgaaagcta ccatcttcaa aatacaaagg tgttgttcct cagcctaacg        300
gaagatgggg agctcagatc tacgagaagc accaacgagt atggctcggg actttcaacg        360
agcaagaaga agctgctcgt tcctacgaca tcgcagcttg tagattccgt ggccgcgacg        420
ccgtcgtcaa cttcaagaac gttctggaag acggcgattt agcttttctt gaagctcact        480
caaaggccga atcgtcgac atgttgagaa acacacatta cgccgacgag cttgaacaga        540
acaataaacg gcagttgttt ctctccgtcg acgctaacgg aaaacgtaac ggatcgagta        600
ctactcaaaa cgacaaagtt ttaaagacgt gtgaagttct tttcgagaag gctgttacac        660
ctagcgacgt tgggaagcta aaccgtctcg tgatacctaa acaacacgcc gagaaacact        720
ttccgttacc gtcaccgtca ccggcagtga ctaaaggagt tttgatcaac ttcgaagacg        780
ttaacggtaa agtgtggagg ttccgttact catactggaa cagtagtcaa agttacgtgt        840
tgaccaaggg atggagtcga ttcgtcaagg agaagaatct tcgagccggt gatgttgtta        900
ctttcgagag atcgaccgga ctagagcggc agttatatat tgattggaaa gttcggtctg        960
gtccgagaga aaacccggtt caggtggtgg ttcggctttt cggagttgat atctttaatg       1020
tgaccaccgt gaagccaaac gacgtcgtgg ccgtttgcgg tggaaagaga tctcgagatg       1080
ttgatgatat gtttgcgtta cggtgttcca agaagcaggc gataatcaat gctttgtgac       1140
atatttcctt ttccgatttt atgctttcgt ttttttaattt ttttttttgt caagttgtgt       1200
aggttgtgat tcatgctagg ttgtatttag gaaaagagat aagacc                      1246
```

<210> SEQ ID NO 4

```
<211> LENGTH: 352
<212> TYPE: PRT
<213> ORGANISM: Arabidopsis thaliana
<220> FEATURE:
<223> OTHER INFORMATION: G9 polypeptide Paralogous to G867, G993, G1930

<400> SEQUENCE: 4
```

Met Asp Ser Ser Cys Ile Asp Glu Ile Ser Ser Thr Ser Glu Ser
1               5                   10                  15

Phe Ser Ala Thr Thr Ala Lys Lys Leu Ser Pro Pro Ala Ala Ala
            20                  25                  30

Leu Arg Leu Tyr Arg Met Gly Ser Gly Gly Ser Ser Val Val Leu Asp
        35                  40                  45

Pro Glu Asn Gly Leu Glu Thr Glu Ser Arg Lys Leu Pro Ser Ser Lys
    50                  55                  60

Tyr Lys Gly Val Val Pro Gln Pro Asn Gly Arg Trp Gly Ala Gln Ile
65                  70                  75                  80

Tyr Glu Lys His Gln Arg Val Trp Leu Gly Thr Phe Asn Glu Gln Glu
                85                  90                  95

Glu Ala Ala Arg Ser Tyr Asp Ile Ala Ala Cys Arg Phe Arg Gly Arg
            100                 105                 110

Asp Ala Val Val Asn Phe Lys Asn Val Leu Glu Asp Gly Asp Leu Ala
        115                 120                 125

Phe Leu Glu Ala His Ser Lys Ala Glu Ile Val Asp Met Leu Arg Lys
130                 135                 140

His Thr Tyr Ala Asp Glu Leu Glu Gln Asn Asn Lys Arg Gln Leu Phe
145                 150                 155                 160

Leu Ser Val Asp Ala Asn Gly Lys Arg Asn Gly Ser Ser Thr Thr Gln
                165                 170                 175

Asn Asp Lys Val Leu Lys Thr Cys Glu Val Leu Phe Glu Lys Ala Val
            180                 185                 190

Thr Pro Ser Asp Val Gly Lys Leu Asn Arg Leu Val Ile Pro Lys Gln
        195                 200                 205

His Ala Glu Lys His Phe Pro Leu Pro Ser Pro Ser Pro Ala Val Thr
    210                 215                 220

Lys Gly Val Leu Ile Asn Phe Glu Asp Val Asn Gly Lys Val Trp Arg
225                 230                 235                 240

Phe Arg Tyr Ser Tyr Trp Asn Ser Ser Gln Ser Tyr Val Leu Thr Lys
                245                 250                 255

Gly Trp Ser Arg Phe Val Lys Glu Lys Asn Leu Arg Ala Gly Asp Val
            260                 265                 270

Val Thr Phe Glu Arg Ser Thr Gly Leu Glu Arg Gln Leu Tyr Ile Asp
        275                 280                 285

Trp Lys Val Arg Ser Gly Pro Arg Glu Asn Pro Val Gln Val Val Val
    290                 295                 300

Arg Leu Phe Gly Val Asp Ile Phe Asn Val Thr Thr Val Lys Pro Asn
305                 310                 315                 320

Asp Val Val Ala Val Cys Gly Gly Lys Arg Ser Arg Asp Val Asp Asp
                325                 330                 335

Met Phe Ala Leu Arg Cys Ser Lys Lys Gln Ala Ile Ile Asn Ala Leu
            340                 345                 350

```
<210> SEQ ID NO 5
<211> LENGTH: 1239
<212> TYPE: DNA
<213> ORGANISM: Arabidopsis thaliana
<220> FEATURE:
```

<223> OTHER INFORMATION: G993 Predicted polypeptide sequence is
     paralogous to G867, G9, G1930

<400> SEQUENCE: 5

```
caaatatgga atacagctgt gtagacgaca gtagtacaac gtcagaatct ctctccatct    60
ctactactcc aaagccgaca acgacgacgg agaagaaact ctcttctccg ccggcgacgt   120
cgatgcgtct ctacagaatg ggaagcggcg gaagcagcgt cgttttggat tcagagaacg   180
gcgtcgagac cgagtcacgt aagcttcctt cgtcgaaata taaaggcgtt gtgcctcagc   240
ctaacggaag atggggagct cagatttacg agaagcatca gcgagtttgg ctcggtactt   300
tcaacgagga agaagaagct gcgtcttctt acgacatcgc cgtgaggaga ttccgcggcc   360
gcgacgccgt cactaacttc aaatctcaag ttgatggaaa cgacgccgaa tcggcttttc   420
ttgacgctca ttctaaagct gagatcgtgg atatgttgag gaaacacact tacgccgatg   480
agtttgagca gagtagacgg aagtttgtta acggcgacgg aaaacgctct gggttggaga   540
cggcgacgta cggaaacgac gctgttttga gagcgcgtga ggttttgttc gagaagactg   600
ttacgccgag cgacgtcggg aagctgaacc gtttagtgat accgaaacaa cacgcggaga   660
agcattttcc gttaccggcg atgacgacgg cgatggggat gaatccgtct ccgacgaaag   720
gcgttttgat taacttggaa gatagaacag ggaaagtgtg gcggttccgt tacagttact   780
ggaacagcag tcaaagttac gtgttgacca agggctggag ccggttcgtt aaagagaaga   840
atcttcgagc cggtgatgtg gtttgtttcg agagatcaac cggaccagac cggcaattgt   900
atatccactg gaaagtccgg tctagtccgg ttcagactgt ggttaggcta ttcggagtca   960
acattttcaa tgtgagtaac gagaaaccaa cgacgtcgc agtagagtgt gttggcaaga  1020
agagatctcg ggaagatgat ttgttttcgt tagggtgttc caagaagcag gcgattatca  1080
acatcttgtg acaaattctt ttttttttggt tttttttcttc aatttgtttc tccttttttca  1140
atattttgta ttgaaatgac aagttgtaaa ttaggacaag acaagaaaaa atgacaacta  1200
gacaaaatag tttttgttta aaaaaaaaaa aaaaaaaa                          1239
```

<210> SEQ ID NO 6
<211> LENGTH: 361
<212> TYPE: PRT
<213> ORGANISM: Arabidopsis thaliana
<220> FEATURE:
<223> OTHER INFORMATION: G993 polypeptide  Paralogous to G867, G9, G1930

<400> SEQUENCE: 6

```
Met Glu Tyr Ser Cys Val Asp Asp Ser Ser Thr Thr Ser Glu Ser Leu
1               5                   10                  15

Ser Ile Ser Thr Thr Pro Lys Pro Thr Thr Thr Thr Glu Lys Lys Leu
            20                  25                  30

Ser Ser Pro Ala Thr Ser Met Arg Leu Tyr Arg Met Gly Ser Gly
        35                  40                  45

Gly Ser Ser Val Val Leu Asp Ser Glu Asn Gly Val Glu Thr Glu Ser
    50                  55                  60

Arg Lys Leu Pro Ser Ser Lys Tyr Lys Gly Val Pro Gln Pro Asn
65                  70                  75                  80

Gly Arg Trp Gly Ala Gln Ile Tyr Glu Lys His Gln Arg Val Trp Leu
                85                  90                  95

Gly Thr Phe Asn Glu Glu Glu Glu Ala Ala Ser Ser Tyr Asp Ile Ala
            100                 105                 110

Val Arg Arg Phe Arg Gly Arg Asp Ala Val Thr Asn Phe Lys Ser Gln
        115                 120                 125
```

```
Val Asp Gly Asn Asp Ala Glu Ser Ala Phe Leu Asp Ala His Ser Lys
    130                 135                 140

Ala Glu Ile Val Asp Met Leu Arg Lys His Thr Tyr Ala Asp Glu Phe
145                 150                 155                 160

Glu Gln Ser Arg Arg Lys Phe Val Asn Gly Asp Gly Lys Arg Ser Gly
                165                 170                 175

Leu Glu Thr Ala Thr Tyr Gly Asn Asp Ala Val Leu Arg Ala Arg Glu
            180                 185                 190

Val Leu Phe Glu Lys Thr Val Thr Pro Ser Asp Val Gly Lys Leu Asn
        195                 200                 205

Arg Leu Val Ile Pro Lys Gln His Ala Glu Lys His Phe Pro Leu Pro
    210                 215                 220

Ala Met Thr Thr Ala Met Gly Met Asn Pro Ser Pro Thr Lys Gly Val
225                 230                 235                 240

Leu Ile Asn Leu Glu Asp Arg Thr Gly Lys Val Trp Arg Phe Arg Tyr
                245                 250                 255

Ser Tyr Trp Asn Ser Ser Gln Ser Tyr Val Leu Thr Lys Gly Trp Ser
            260                 265                 270

Arg Phe Val Lys Glu Lys Asn Leu Arg Ala Gly Asp Val Val Cys Phe
        275                 280                 285

Glu Arg Ser Thr Gly Pro Asp Arg Gln Leu Tyr Ile His Trp Lys Val
290                 295                 300

Arg Ser Ser Pro Val Gln Thr Val Val Arg Leu Phe Gly Val Asn Ile
                305                 310                 315                 320

Phe Asn Val Ser Asn Glu Lys Pro Asn Asp Val Ala Val Glu Cys Val
            325                 330                 335

Gly Lys Lys Arg Ser Arg Glu Asp Asp Leu Phe Ser Leu Gly Cys Ser
        340                 345                 350

Lys Lys Gln Ala Ile Ile Asn Ile Leu
        355                 360

<210> SEQ ID NO 7
<211> LENGTH: 1155
<212> TYPE: DNA
<213> ORGANISM: Arabidopsis thaliana
<220> FEATURE:
<223> OTHER INFORMATION: G1930 Predicted polypeptide sequence is
      paralogous to G867, G9, G993

<400> SEQUENCE: 7
attcacatta ctaatctctc aagatttcac aattttcttg tgattttctc tcagtttctt      60
atttcgtttc ataacatgga tgccatgagt agcgtagacg agagctctac aactacagat     120
tccattccgg cgagaaagtc atcgtctccg gcgagtttac tatatagaat gggaagcgga     180
acaagcgtgg tacttgattc agagaacggt gtcgaagtcg aagtcgaagc cgaatcaaga     240
aagcttcctt cttcaagatt caaaggtgtt gttcctcaac caaatggaag atggggagct     300
cagatttacg agaaacatca acgcgtgtgg cttggtactt tcaacgagga agacgaagca     360
gctcgtgctt acgacgtcgc ggctcaccgt ttccgtggcc gcgatgccgt tactaatttc     420
aaagacacga cgttcgaaga agaggttgag ttcttaaacg cgcattcgaa atcagagatc     480
gtagatatgt tgagaaaaca cacttacaaa gaagagttag accaaggaa acgtaaccgt      540 gacggtaacg gaaaagagac gacggcgttt gctttggctt cgatggtggt tatgacgggg     600
tttaaaacgg cggagttact gtttgagaaa acgtaacgc caagtgacgt cgggaaacta      660
aaccgtttag ttataccaaa acaccaagcg gagaaacatt ttccgttacc gttaggtaat     720
```

-continued

```
aataacgtct ccgttaaagg tatgctgttg aatttcgaag acgttaacgg gaaagtgtgg    780
aggttccgtt actcttattg gaatagtagt caaagttatg tgttgaccaa aggttggagt    840
agattcgtta agagaagag actttgtgct ggtgatttga tcagttttaa agatccaac     900 gatcaagatc aaaaattctt tatcgggtgg aaatcgaaat ccgggttgga tctagagacg    960
ggtcgggtta tgagattgtt tggggttgat atttctttaa acgccgtcgt tgtagtgaag   1020
gaaacaacgg aggtgttaat gtcgtcgtta aggtgtaaga agcaacgagt tttgtaataa   1080
caatttaaca acttgggaaa gaaaaaaaag cttttttgatt ttaatttctc ttcaacgtta   1140
atcttgctga gatta                                                    1155
```

<210> SEQ ID NO 8
<211> LENGTH: 333
<212> TYPE: PRT
<213> ORGANISM: Arabidopsis thaliana
<220> FEATURE:
<223> OTHER INFORMATION: G1930 polypeptide  Paralogous to G867, G9, G993

<400> SEQUENCE: 8

```
Met Asp Ala Met Ser Ser Val Asp Glu Ser Ser Thr Thr Thr Asp Ser
1               5                   10                  15

Ile Pro Ala Arg Lys Ser Ser Pro Ala Ser Leu Leu Tyr Arg Met
            20                  25                  30

Gly Ser Gly Thr Ser Val Val Leu Asp Ser Glu Asn Gly Val Glu Val
        35                  40                  45

Glu Val Glu Ala Glu Ser Arg Lys Leu Pro Ser Ser Arg Phe Lys Gly
    50                  55                  60

Val Val Pro Gln Pro Asn Gly Arg Trp Gly Ala Gln Ile Tyr Glu Lys
65                  70                  75                  80

His Gln Arg Val Trp Leu Gly Thr Phe Asn Glu Glu Asp Glu Ala Ala
                85                  90                  95

Arg Ala Tyr Asp Val Ala Ala His Arg Phe Arg Gly Arg Asp Ala Val
            100                 105                 110

Thr Asn Phe Lys Asp Thr Thr Phe Glu Glu Val Glu Phe Leu Asn
            115                 120                 125

Ala His Ser Lys Ser Glu Ile Val Asp Met Leu Arg Lys His Thr Tyr
130                 135                 140

Lys Glu Glu Leu Asp Gln Arg Lys Arg Asn Arg Asp Gly Asn Gly Lys
145                 150                 155                 160

Glu Thr Thr Ala Phe Ala Leu Ala Ser Met Val Val Met Thr Gly Phe
                165                 170                 175

Lys Thr Ala Glu Leu Leu Phe Glu Lys Thr Val Thr Pro Ser Asp Val
            180                 185                 190

Gly Lys Leu Asn Arg Leu Val Ile Pro Lys His Gln Ala Glu Lys His
        195                 200                 205

Phe Pro Leu Pro Leu Gly Asn Asn Val Ser Val Lys Gly Met Leu
    210                 215                 220

Leu Asn Phe Glu Asp Val Asn Gly Lys Val Trp Arg Phe Arg Tyr Ser
225                 230                 235                 240

Tyr Trp Asn Ser Ser Gln Ser Tyr Val Leu Thr Lys Gly Trp Ser Arg
                245                 250                 255

Phe Val Lys Glu Lys Arg Leu Cys Ala Gly Asp Leu Ile Ser Phe Lys
            260                 265                 270

Arg Ser Asn Asp Gln Asp Gln Lys Phe Phe Ile Gly Trp Lys Ser Lys
        275                 280                 285
```

Ser Gly Leu Asp Leu Glu Thr Gly Arg Val Met Arg Leu Phe Gly Val
    290                 295                 300

Asp Ile Ser Leu Asn Ala Val Val Val Lys Glu Thr Thr Glu Val
305                 310                 315                 320

Leu Met Ser Ser Leu Arg Cys Lys Lys Gln Arg Val Leu
                325                 330

<210> SEQ ID NO 9
<211> LENGTH: 1194
<212> TYPE: DNA
<213> ORGANISM: Arabidopsis thaliana
<220> FEATURE:
<223> OTHER INFORMATION: G2687

<400> SEQUENCE: 9

```
ctctgtctct cgtatctttc tactactctg tttcttgaat tctaatgaac aacatcgacg      60
acgcaaagac ggagacttca gtgtcttcag gttcaagcga ctctttcttg cctctcaaga     120
aacgcatgag acttgatgac gaaccagaaa acgccctagt ggtttcgtct tcaccaaaga     180
cggttgtggc ttctggcaat gtcaagtaca aggagtcgt tcagcaacag aacggtcatt      240
ggggtgccca gatttacgca gaccacaaaa ggatttggct tggaactttc aaatccgctg     300
atgaagccgc cacggcttac gatagtgcat ctatcaaact ccgaagcttt gacgctaact     360
cgcaccggaa cttcccttgg tctacaatca ctctcaacga accagacttt caaaattgct     420
acacaacaga gactgtgttg aacatgatca gagacggttc gtaccaacac aaattcagag     480
attttctcag aatcagatct cagattgttg cgagtatcaa catcggggga ccaaaacaag     540
cccgaggaga agtgaatcaa gaatcagaca agtgttttc ttgcacacag cttttcaga      600
aggaattgac accgagcgat gtagggaaac taaataggct tgtgatacct aaaaagtatg     660
cagtgaagta tatgcctttc ataagcgctg atcaaagcga aagaagag ggtgaaatag       720
taggatctgt ggaagatgtg gaggttgtgt tttacgacag agcaatgaga caatggaagt     780
ttaggtattg ttactggaaa agtagccaga gctttgtctt caccagagga tggaatagtt     840
tcgtgaagga gaagaatctc aaggagaagg atgttattgc cttctacact tgcgatgtcc     900
cgaacaatgt gaagacatta gaaggtcaaa gaagaacttt cttgatgatc gatgttcatt     960
gcttttcaga caacggttcc gtggtagctg aggaagtaag tatgacggtt catgacagtt    1020
cagtgcaagt aaagaaaaca gaaaacttgg ttagctccat gttagaagat aaagaaacca    1080
aatcagagga gaacaaagga gggtttatgc tgtttggtgt aaggatcgaa tgtccttagg    1140
gaattttcct ttaaaagttt cttacttcaa ctagaacttg ttttacttgt acct          1194
```

<210> SEQ ID NO 10
<211> LENGTH: 363
<212> TYPE: PRT
<213> ORGANISM: Arabidopsis thaliana
<220> FEATURE:
<223> OTHER INFORMATION: G2687 polypeptide

<400> SEQUENCE: 10

Met Asn Asn Ile Asp Asp Ala Lys Thr Glu Thr Ser Val Ser Ser Gly
1               5                   10                  15

Ser Ser Asp Ser Phe Leu Pro Lys Lys Arg Met Arg Leu Asp Asp
            20                  25                  30

Glu Pro Glu Asn Ala Leu Val Val Ser Ser Pro Lys Thr Val Val
        35                  40                  45

Ala Ser Gly Asn Val Lys Tyr Lys Gly Val Val Gln Gln Gln Asn Gly

|   |   |   |   |   |   | 50 |   |   |   |   | 55 |   |   |   |   | 60 |   |
|---|---|---|---|---|---|----|---|---|---|---|----|---|---|---|---|----|---|
| His | Trp | Gly | Ala | Gln | Ile | Tyr | Ala | Asp | His | Lys | Arg | Ile | Trp | Leu | Gly |
| 65 |   |   |   | 70 |   |   |   |   | 75 |   |   |   |   | 80 |

Thr Phe Lys Ser Ala Asp Glu Ala Ala Thr Ala Tyr Asp Ser Ala Ser
                85                  90                  95

Ile Lys Leu Arg Ser Phe Asp Ala Asn Ser His Arg Asn Phe Pro Trp
            100                 105                 110

Ser Thr Ile Thr Leu Asn Glu Pro Asp Phe Gln Asn Cys Tyr Thr Thr
            115                 120                 125

Glu Thr Val Leu Asn Met Ile Arg Asp Gly Ser Tyr Gln His Lys Phe
130                 135                 140

Arg Asp Phe Leu Arg Ile Arg Ser Gln Ile Val Ala Ser Ile Asn Ile
145                 150                 155                 160

Gly Gly Pro Lys Gln Ala Arg Gly Glu Val Asn Gln Glu Ser Asp Lys
                165                 170                 175

Cys Phe Ser Cys Thr Gln Leu Phe Gln Lys Glu Leu Thr Pro Ser Asp
            180                 185                 190

Val Gly Lys Leu Asn Arg Leu Val Ile Pro Lys Lys Tyr Ala Val Lys
            195                 200                 205

Tyr Met Pro Phe Ile Ser Ala Asp Gln Ser Glu Lys Glu Glu Gly Glu
210                 215                 220

Ile Val Gly Ser Val Glu Asp Val Glu Val Val Phe Tyr Asp Arg Ala
225                 230                 235                 240

Met Arg Gln Trp Lys Phe Arg Tyr Cys Tyr Trp Lys Ser Ser Gln Ser
                245                 250                 255

Phe Val Phe Thr Arg Gly Trp Asn Ser Phe Val Lys Glu Lys Asn Leu
            260                 265                 270

Lys Glu Lys Asp Val Ile Ala Phe Tyr Thr Cys Asp Val Pro Asn Asn
            275                 280                 285

Val Lys Thr Leu Glu Gly Gln Arg Lys Asn Phe Leu Met Ile Asp Val
290                 295                 300

His Cys Phe Ser Asp Asn Gly Ser Val Val Ala Glu Glu Val Ser Met
305                 310                 315                 320

Thr Val His Asp Ser Ser Val Gln Val Lys Lys Thr Glu Asn Leu Val
                325                 330                 335

Ser Ser Met Leu Glu Asp Lys Glu Thr Lys Ser Glu Glu Asn Lys Gly
            340                 345                 350

Gly Phe Met Leu Phe Gly Val Arg Ile Glu Cys
            355                 360

<210> SEQ ID NO 11
<211> LENGTH: 1216
<212> TYPE: DNA
<213> ORGANISM: Arabidopsis thaliana
<220> FEATURE:
<223> OTHER INFORMATION: G1957

<400> SEQUENCE: 11

```
caagaaccat ctcgtaaatc aagatttctc caaggaaaat cagataagtc ataatggatc    60
tatccctggc tccgacaaca acaacaagtt ccgaccaaga acaagacaga gaccaagaat   120
taacctccaa catcggagca agcagcagct ccggtcccag cggaaacaac aacaaccttc   180
cgatgatgat gattccacct ccggagaaag aacacatgtt cgacaaagtg gtaacaccaa   240
gcgacgtcgg aaaactcaac agactcgtga tccctaaaca acacgctgag aggtatttcc   300
ctctagactc ctcaaacaac caaaacggca cgcttttgaa cttccaagac agaaacggca   360
```

```
agatgtggag attccgttac tcgtattgga actctagcca gagctacgtt atgaccaaag      420
gatggagccg tttcgtcaaa gagaaaaagc tcgatgcagg agacattgtc tctttccaac      480
gaggcatcgg agatgagtca gaaagatcca aactttacat agattggagg catagacccg      540
acatgagcct cgttcaagca catcagtttg gtaattttgg tttcaatttc aatttcccga      600
ccacttctca atattccaac agatttcatc cattgccaga atataactcc gtcccgattc      660
accgggcttt aaacatcgga atcaccaacg ttcctatta aacacccag cgtcaagagt        720 tcgtagggta tggttatggg aatttagctg gaaggtgtta ctacacggga tcaccgttgg     780
atcataggaa cattgttgga tcagagccgt tggttataga ctcagtccct gtggttcccg      840
ggagattaac tccggtgatg ttaccgccgc ttcctccgcc tccttctacg gcgggaaaga      900
gactaaggct ctttggggtg aatatggaat gtggcaatga ctataatcaa caagaagagt      960
catggttggt gccacgtggc gaaattggtg catcttcttc ttcttcttca gctctacgac     1020
taaatttatc gactgatcat gatgatgata atgatgatgg tgatgatggc gatgatgatc     1080
aatttgctaa gaaagggaag tcttcacttt ctctcaattt caatccatga gaagtttcat     1140
catcttcttg ttttgaatct ctctttatat tgtttccatt agtaattttt actaagggta     1200
ttagattcta gctagt                                                     1216

<210> SEQ ID NO 12
<211> LENGTH: 358
<212> TYPE: PRT
<213> ORGANISM: Arabidopsis thaliana
<220> FEATURE:
<223> OTHER INFORMATION: G1957 polypeptide

<400> SEQUENCE: 12

Met Asp Leu Ser Leu Ala Pro Thr Thr Thr Ser Ser Asp Gln Glu
1               5                   10                  15

Gln Asp Arg Asp Gln Glu Leu Thr Ser Asn Ile Gly Ala Ser Ser
            20                  25                  30

Ser Gly Pro Ser Gly Asn Asn Asn Leu Pro Met Met Met Ile Pro
        35                  40                  45

Pro Pro Glu Lys Glu His Met Phe Asp Lys Val Val Thr Pro Ser Asp
    50                  55                  60

Val Gly Lys Leu Asn Arg Leu Val Ile Pro Lys Gln His Ala Glu Arg
65                  70                  75                  80

Tyr Phe Pro Leu Asp Ser Ser Asn Asn Gln Asn Gly Thr Leu Leu Asn
                85                  90                  95

Phe Gln Asp Arg Asn Gly Lys Met Trp Arg Phe Arg Tyr Ser Tyr Trp
            100                 105                 110

Asn Ser Ser Gln Ser Tyr Val Met Thr Lys Gly Trp Ser Arg Phe Val
        115                 120                 125

Lys Glu Lys Lys Leu Asp Ala Gly Asp Ile Val Ser Phe Gln Arg Gly
    130                 135                 140

Ile Gly Asp Glu Ser Glu Arg Ser Lys Leu Tyr Ile Asp Trp Arg His
145                 150                 155                 160

Arg Pro Asp Met Ser Leu Val Gln Ala His Gln Phe Gly Asn Phe Gly
                165                 170                 175

Phe Asn Phe Asn Phe Pro Thr Thr Ser Gln Tyr Ser Asn Arg Phe His
            180                 185                 190

Pro Leu Pro Glu Tyr Asn Ser Val Pro Ile His Arg Gly Leu Asn Ile
        195                 200                 205
```

```
Gly Asn His Gln Arg Ser Tyr Tyr Asn Thr Gln Arg Gln Glu Phe Val
        210                 215                 220

Gly Tyr Gly Tyr Gly Asn Leu Ala Gly Arg Cys Tyr Tyr Thr Gly Ser
225                 230                 235                 240

Pro Leu Asp His Arg Asn Ile Val Gly Ser Glu Pro Leu Val Ile Asp
                245                 250                 255

Ser Val Pro Val Val Pro Gly Arg Leu Thr Pro Val Met Leu Pro Pro
            260                 265                 270

Leu Pro Pro Pro Pro Ser Thr Ala Gly Lys Arg Leu Arg Leu Phe Gly
        275                 280                 285

Val Asn Met Glu Cys Gly Asn Asp Tyr Asn Gln Gln Glu Glu Ser Trp
290                 295                 300

Leu Val Pro Arg Gly Glu Ile Gly Ala Ser Ser Ser Ser Ser Ser Ala
305                 310                 315                 320

Leu Arg Leu Asn Leu Ser Thr Asp His Asp Asp Asn Asp Asp Asp Gly
                325                 330                 335

Asp Asp Gly Asp Asp Gln Phe Ala Lys Lys Gly Lys Ser Ser Leu
            340                 345                 350

Ser Leu Asn Phe Asn Pro
        355

<210> SEQ ID NO 13
<211> LENGTH: 1368
<212> TYPE: DNA
<213> ORGANISM: Arabidopsis thaliana
<220> FEATURE:
<223> OTHER INFORMATION: G1010

<400> SEQUENCE: 13
attcttcttc taaaaaatct tgacaacttt ttgttttttgt tttctttctc tgaattttttt     60 aaaagagaga gagctatgta gctatgaaac agtaagagat atagatatag agagacagag    120
aaagatgatg atcagtgaag ttaggctaaa cccacttttct atttatgtat aattaggtca    180
atcacatcac caatctcctc ctccaattct cctcctctcc ttccaaattc tagggttttg    240
cttgtatctc acccccttttc tcaattccct agggaaactg tgaatttcat caaattccat    300 tatttttttgg tcacacccttt aaagagatct gagagttcta aagatgatga cagatttatc    360
tctcacgaga gatgaagatg aagaagaagc aaagccctta gcagaagaag aaggagcgcg    420
tgaagtagca gacagagagc acatgttcga caaagttgtg actccaagtg atgtcggaaa    480
actaaaccga cttgtgatcc caaagcaaca cgcagagaga ttcttccctt tagattcatc    540
ttcaaacgag aaaggtttgc ttttaaactt cgaagatctc actggcaaat cttggaggtt    600
ccgttactct tactggaaca gtagtcaaag ctatgtcatg actaaaggtt ggagcagatt    660
cgttaaagac aaaaagcttg acgccggaga tattgtctct ttccaaagat gtgtcggaga    720
ttcaggaaga gatagccgtt tgtttattga tggaggaga agacctaaag tccctgacca    780
tcctcatttc gccgccggag ctatgttccc taggttttac agctttcctt cgaccaatta    840
cagtctttat aatcatcagc agcaacgtca tcatcacagt ggtggtggtt ataattatca    900
tcaaattccg agagaatttg gttatggtta cttcgttagg tcagtggatc agaggaacaa    960
tcctgcggct gcggtggctg atccgttggt gattgaatct gtgccggtga tgatgcacgg   1020
gagagctaat caggaacttg ttggaacggc cgggaagaga ctgaggcttt ttggagttga   1080
tatggaatgc ggcgagagcg gaatgaccaa cagtacggag gaggaatcat catcttccgg   1140
tggaagtttg ccacgtggag gcggtggtgg tgcttcatct tcctctttct ttcagctgag   1200
```

```
acttggaagc agcagtgaag atgatcactt cactaagaaa ggaaagtctt cattgtcttt    1260
tgatttggat caataataat gatgatgatg aaattagttg gtattttaag aaaaaaaaca    1320
tacatatata attctatata tatgacaaca taatgcattg atttcctt                 1368
```

<210> SEQ ID NO 14
<211> LENGTH: 310
<212> TYPE: PRT
<213> ORGANISM: Arabidopsis thaliana
<220> FEATURE:
<223> OTHER INFORMATION: G1010 polypeptide

<400> SEQUENCE: 14

```
Met Met Thr Asp Leu Ser Leu Thr Arg Asp Glu Asp Glu Glu Ala
1               5                   10                  15

Lys Pro Leu Ala Glu Glu Gly Ala Arg Glu Val Ala Asp Arg Glu
            20                  25                  30

His Met Phe Asp Lys Val Val Thr Pro Ser Asp Val Gly Lys Leu Asn
                35                  40                  45

Arg Leu Val Ile Pro Lys Gln His Ala Glu Arg Phe Phe Pro Leu Asp
    50                  55                  60

Ser Ser Asn Glu Lys Gly Leu Leu Leu Asn Phe Glu Asp Leu Thr
65                  70                  75                  80

Gly Lys Ser Trp Arg Phe Arg Tyr Ser Tyr Trp Asn Ser Ser Gln Ser
                85                  90                  95

Tyr Val Met Thr Lys Gly Trp Ser Arg Phe Val Lys Asp Lys Lys Leu
            100                 105                 110

Asp Ala Gly Asp Ile Val Ser Phe Gln Arg Cys Val Gly Asp Ser Gly
        115                 120                 125

Arg Asp Ser Arg Leu Phe Ile Asp Trp Arg Arg Pro Lys Val Pro
    130                 135                 140

Asp His Pro His Phe Ala Ala Gly Ala Met Phe Pro Arg Phe Tyr Ser
145                 150                 155                 160

Phe Pro Ser Thr Asn Tyr Ser Leu Tyr Asn His Gln Gln Gln Arg His
                165                 170                 175

His His Ser Gly Gly Tyr Asn Tyr His Gln Ile Pro Arg Glu Phe
            180                 185                 190

Gly Tyr Gly Tyr Phe Val Arg Ser Val Asp Gln Arg Asn Asn Pro Ala
        195                 200                 205

Ala Ala Val Ala Asp Pro Leu Val Ile Glu Ser Val Pro Val Met Met
    210                 215                 220

His Gly Arg Ala Asn Gln Glu Leu Val Gly Thr Ala Gly Lys Arg Leu
225                 230                 235                 240

Arg Leu Phe Gly Val Asp Met Glu Cys Gly Glu Ser Gly Met Thr Asn
                245                 250                 255

Ser Thr Glu Glu Glu Ser Ser Ser Gly Gly Ser Leu Pro Arg Gly
            260                 265                 270

Gly Gly Gly Gly Ala Ser Ser Ser Phe Phe Gln Leu Arg Leu Gly
        275                 280                 285

Ser Ser Ser Glu Asp Asp His Phe Thr Lys Lys Gly Lys Ser Ser Leu
    290                 295                 300

Ser Phe Asp Leu Asp Gln
305                 310
```

<210> SEQ ID NO 15
<211> LENGTH: 1065
<212> TYPE: DNA

-continued

```
<213> ORGANISM: Arabidopsis thaliana
<220> FEATURE:
<223> OTHER INFORMATION: G2690

<400> SEQUENCE: 15
atggatatgg acgagatgag caatgtagcc aagacaacga cagagacttc aggcttaact      60
gactctgtct tgagcctcac gaaacgcatg aaacctactg aggttacgac caccacaaaa     120
cctgccttgt ccaacacgac gaaattcaaa ggagttgttc agcaacgaa  cggtcattgg     180
ggtgctcaga tttacgcaga ccatcgaagg atttggcttg aactttcaa  atccgctcat     240
gaagccgctg ctgcttacga tagcgcatcg attaagcttc gaagctttga tgctaactcg     300
caccggaact tcccttggtc tgattttacc ctccatgaac cggactttca agagtgctac     360
acgacagaag ctgtgttgaa catgatcaga gacggttctt atcaacacaa gttcagagat     420
tttctcagaa tccggtctca gattgttgcg aatatcaaca tcgtgggatc aaaacaagtc     480
ttaggaggag gagaaggtgg tcaagaatcg aacaagtgtt tctcgtgcac gcagcttttt     540
cagaaagaac tgacaccgag cgatgtaggg aaactgaata ggcttgtgat acctaagaag     600
tatgcagtga agtatatgcc tttcataagc gatgatcaaa gcgagaaaga gacgagtgaa     660
ggagtagaag atgtggaggt tgtctttac  gacagagcaa tgagacaatg aagtttagg      720
tattgttact ggagaagtag ccagagcttt gtcttcacca gaggatggaa tggtttcgtg     780
aaggagaaga atctcaagga gaaagatatt attgtctttt acacttgcga tgtccccaac     840
aatgtgaaga cattagaagg ccaaagcaag accttcttga tgattgatgt tcatcacttt     900
tcaggcaacg gtttcgtggt tcccgaggaa gtaaacaaga cggttcatga gatttctgat     960
gaagagatga aaacagaaac cctctttacc tcgaaggtag aagaagaaac caaatcagag    1020
gagaagaaag gagggtttat gctgtttggt gttaggatcc aatag                     1065

<210> SEQ ID NO 16
<211> LENGTH: 354
<212> TYPE: PRT
<213> ORGANISM: Arabidopsis thaliana
<220> FEATURE:
<223> OTHER INFORMATION: G2690 polypeptide

<400> SEQUENCE: 16

Met Asp Met Asp Glu Met Ser Asn Val Ala Lys Thr Thr Thr Glu Thr
1               5                   10                  15

Ser Gly Leu Thr Asp Ser Val Leu Ser Leu Thr Lys Arg Met Lys Pro
            20                  25                  30

Thr Glu Val Thr Thr Thr Thr Lys Pro Ala Leu Ser Asn Thr Thr Lys
        35                  40                  45

Phe Lys Gly Val Val Gln Gln Gln Asn Gly His Trp Gly Ala Gln Ile
    50                  55                  60

Tyr Ala Asp His Arg Arg Ile Trp Leu Gly Thr Phe Lys Ser Ala His
65                  70                  75                  80

Glu Ala Ala Ala Ala Tyr Asp Ser Ala Ser Ile Lys Leu Arg Ser Phe
                85                  90                  95

Asp Ala Asn Ser His Arg Asn Phe Pro Trp Ser Asp Phe Thr Leu His
            100                 105                 110

Glu Pro Asp Phe Gln Glu Cys Tyr Thr Thr Glu Ala Val Leu Asn Met
        115                 120                 125

Ile Arg Asp Gly Ser Tyr Gln His Lys Phe Arg Asp Phe Leu Arg Ile
    130                 135                 140

Arg Ser Gln Ile Val Ala Asn Ile Asn Ile Val Gly Ser Lys Gln Val
```

```
          145                 150                 155                 160
Leu Gly Gly Gly Glu Gly Gly Gln Glu Ser Asn Lys Cys Phe Ser Cys
                165                 170                 175

Thr Gln Leu Phe Gln Lys Glu Leu Thr Pro Ser Asp Val Gly Lys Leu
            180                 185                 190

Asn Arg Leu Val Ile Pro Lys Lys Tyr Ala Val Lys Tyr Met Pro Phe
        195                 200                 205

Ile Ser Asp Asp Gln Ser Glu Lys Glu Thr Ser Glu Gly Val Glu Asp
    210                 215                 220

Val Glu Val Val Phe Tyr Asp Arg Ala Met Arg Gln Trp Lys Phe Arg
225                 230                 235                 240

Tyr Cys Tyr Trp Arg Ser Ser Gln Ser Phe Val Phe Thr Arg Gly Trp
                245                 250                 255

Asn Gly Phe Val Lys Glu Lys Asn Leu Lys Glu Lys Asp Ile Ile Val
            260                 265                 270

Phe Tyr Thr Cys Asp Val Pro Asn Asn Val Lys Thr Leu Glu Gly Gln
        275                 280                 285

Ser Lys Thr Phe Leu Met Ile Asp Val His His Phe Ser Gly Asn Gly
    290                 295                 300

Phe Val Val Pro Glu Glu Val Asn Lys Thr Val His Glu Ile Ser Asp
305                 310                 315                 320

Glu Glu Met Lys Thr Glu Thr Leu Phe Thr Ser Lys Val Glu Glu Glu
                325                 330                 335

Thr Lys Ser Glu Glu Lys Lys Gly Gly Phe Met Leu Phe Gly Val Arg
            340                 345                 350

Ile Gln

<210> SEQ ID NO 17
<211> LENGTH: 1253
<212> TYPE: DNA
<213> ORGANISM: Glycine max
<220> FEATURE:
<223> OTHER INFORMATION: G3451  Predicted polypeptide sequence is
      orthologous to G867, G9, G993, G1930

<400> SEQUENCE: 17
ctagaatccg tacaatctaa tcaacataac aaaaatggat gcaattagtt gcatggatga       60
gagcaccacc actgagtcac tctctataag tctttctccg acgtcatcgt cggagaaagc      120
gaagccttct tcgatgatta catcgtcgga gaaggtttct ctgtcccgc cgccgtcaaa      180 cagactatgc cgtgttggaa gcggcgcgag cgcagtcgtg gatcctgatg gcggcggcag     240
cggcgctgag gtagagtcgc ggaaactccc ctcgtcgaag tacaagggcg tggtgccca      300 gcccaacggc cgctggggtg cgcagattta cgagaagcac cagcgcgtgt ggcttggaac     360
gttcaacgag gaagacgagg cggcgcgtgc gtacgacatc gccgcgcagc ggttccgcgg     420
caaggacgcc gtcacgaact tcaagccgct cgccggcgcc gacgacgacg acggagaatc     480
ggagtttctc aactcgcatt ccaaacccga gatcgtcgac atgctgcgaa agcacacgta     540
caatgacgag ctggagcaga gcaagcgcag ccgcggcgtc gtccggcggc gaggctccgc     600
cgccgccggc accgcaaact caatttccgg cgcgtgcttt actaaggcac gtgagcagct     660
attcgagaag gctgttacgc cgagcgacgt tgggaaattg aaccgtttgg tgataccgaa     720
gcagcacgcg gagaagcact tccgttaca gagctctaac ggcgttagcg cgacgacgat      780
agcggcggtg acggcgacgc cgacggcggc gaagggcgtt tgttgaact tcgaagacgt      840 tggagggaaa gtgtggcggt tcgttactc gtattggaac agtagccaga gttacgtctt     900
```

```
aaccaaaggt tggagccggt tcgttaagga gaagaatctg aaagctggtg acacggtttg      960
ttttcaccgg tccactggac cggacaagca gctttacatc gattggaaga cgaggaatgt     1020
tgttaacaac gaggtcgcgt tgttcggacc ggtcggaccg gttgtcgaac cgatccagat     1080
ggttcggctc tttggggtta acattttgaa actacccggt tcagatacta ttgttggcaa     1140
taacaataat gcaagtgggt gctgcaatgg caagagaaga gaaatggaac tgttctcgtt     1200
agagtgtagc aagaaaccta agattattgg tgctttgtaa cgttacgtta ggc            1253
```

<210> SEQ ID NO 18
<211> LENGTH: 401
<212> TYPE: PRT
<213> ORGANISM: Glycine max
<220> FEATURE:
<223> OTHER INFORMATION: G3451 Orthologous to G867, G9, G993, G1930

<400> SEQUENCE: 18

```
Met Asp Ala Ile Ser Cys Met Asp Glu Ser Thr Thr Thr Glu Ser Leu
1               5                   10                  15

Ser Ile Ser Leu Ser Pro Thr Ser Ser Glu Lys Ala Lys Pro Ser
            20                  25                  30

Ser Met Ile Thr Ser Ser Glu Lys Val Ser Leu Ser Pro Pro Pro Ser
        35                  40                  45

Asn Arg Leu Cys Arg Val Gly Ser Gly Ala Ser Ala Val Val Asp Pro
    50                  55                  60

Asp Gly Gly Gly Ser Gly Ala Glu Val Glu Ser Arg Lys Leu Pro Ser
65                  70                  75                  80

Ser Lys Tyr Lys Gly Val Val Pro Gln Pro Asn Gly Arg Trp Gly Ala
                85                  90                  95

Gln Ile Tyr Glu Lys His Gln Arg Val Trp Leu Gly Thr Phe Asn Glu
            100                 105                 110

Glu Asp Glu Ala Ala Arg Ala Tyr Asp Ile Ala Ala Gln Arg Phe Arg
        115                 120                 125

Gly Lys Asp Ala Val Thr Asn Phe Lys Pro Leu Ala Gly Ala Asp Asp
    130                 135                 140

Asp Asp Gly Glu Ser Glu Phe Leu Asn Ser His Ser Lys Pro Glu Ile
145                 150                 155                 160

Val Asp Met Leu Arg Lys His Thr Tyr Asn Asp Glu Leu Glu Gln Ser
                165                 170                 175

Lys Arg Ser Arg Gly Val Val Arg Arg Gly Ser Ala Ala Ala Gly
            180                 185                 190

Thr Ala Asn Ser Ile Ser Gly Ala Cys Phe Thr Lys Ala Arg Glu Gln
        195                 200                 205

Leu Phe Glu Lys Ala Val Thr Pro Ser Asp Val Gly Lys Leu Asn Arg
    210                 215                 220

Leu Val Ile Pro Lys Gln His Ala Glu Lys His Phe Pro Leu Gln Ser
225                 230                 235                 240

Ser Asn Gly Val Ser Ala Thr Thr Ile Ala Ala Val Thr Ala Thr Pro
                245                 250                 255

Thr Ala Ala Lys Gly Val Leu Leu Asn Phe Glu Asp Val Gly Gly Lys
            260                 265                 270

Val Trp Arg Phe Arg Tyr Ser Tyr Trp Asn Ser Ser Gln Ser Tyr Val
        275                 280                 285

Leu Thr Lys Gly Trp Ser Arg Phe Val Lys Glu Lys Asn Leu Lys Ala
    290                 295                 300
```

```
Gly Asp Thr Val Cys Phe His Arg Ser Thr Gly Pro Asp Lys Gln Leu
305                 310                 315                 320

Tyr Ile Asp Trp Lys Thr Arg Asn Val Val Asn Asn Glu Val Ala Leu
                325                 330                 335

Phe Gly Pro Val Gly Pro Val Val Glu Pro Ile Gln Met Val Arg Leu
            340                 345                 350

Phe Gly Val Asn Ile Leu Lys Leu Pro Gly Ser Asp Thr Ile Val Gly
        355                 360                 365

Asn Asn Asn Asn Ala Ser Gly Cys Cys Asn Gly Lys Arg Arg Glu Met
    370                 375                 380

Glu Leu Phe Ser Leu Glu Cys Ser Lys Lys Pro Lys Ile Ile Gly Ala
385                 390                 395                 400

Leu

<210> SEQ ID NO 19
<211> LENGTH: 1067
<212> TYPE: DNA
<213> ORGANISM: Oryza sativa
<220> FEATURE:
<223> OTHER INFORMATION: Predicted polypeptide sequence is orthologous
      to G9

<400> SEQUENCE: 19
gcacgagcac ctgctttggc ttctccctct tcactgccct aattccttgc ttctctctcc     60
tctcctctct ctctctctct ctctctcgct gcagccatag cttagctttc ttggtgccaa    120 gatggggtg gtcagcttct cctcgacttc ctccggcgcg tccactgcca ccaccgagtc     180
cggcggcgcc gtgcggatgt cgccggagcc ggtggtggcg gtggcggcgg cggctcaaca    240
gctgccggtg gtgaagggag ttgactcggc ggatgaggtg gtgacgtcga agcccgcagc    300
ggcggcggtg gcgcagcagt cgtcgaggta caagggggtg gtgccgcagc cgaacgggcg    360 gtgggggcg cagatctacg agcgccacgc gcgggtgtgg ctcgggacgt tccccgacga    420
ggaggcggcg gcgcgggcct acgacgtggc ggcgctccgg taccgggggc gcgacgcggc    480
caccaacttc cccggggccg cggcgtcggc ggccgagctc gcgttcctcg ccgcgcactc    540
caaggccgag atcgtcgaca tgctgcggaa gcacacctac gccgacgagc tccgccaggg    600
cctccgccgc ggccgcggca tgggcgcccg cgcccagccc acgccatcgt gggcgcgcga    660
gccgctgttc gagaaggccg tgacgcccag cgacgtcggc aagctcaacc gcctcgtggt    720
gcccaagcag cacgccgaga agcacttccc gctccgccgc gcggcgagct ccgactccgc    780
ctccgccgcc gccaccggca agggcgtgct cctcaacttc gaggacggcg agggcaaggt    840
gtggcgattc cggtactcgt actggaacag cagccagagc tacgtgctga ccaagggggtg    900 gagccgattc gtgagggaga agggcctccg cgccggcgac accattgtct tctccccgct    960
cggcgtacgg ccccgacaag ctgctcttca tcgactgcaa gaagaacaac gcggcggtgg   1020
cggcgaccac cacctgcgcc ggcgacgaga ggccaaccac aaccaca              1067

<210> SEQ ID NO 20
<211> LENGTH: 315
<212> TYPE: PRT
<213> ORGANISM: Oryza sativa
<220> FEATURE:
<223> OTHER INFORMATION: Orthologous to G9

<400> SEQUENCE: 20

Met Gly Val Val Ser Phe Ser Ser Thr Ser Ser Gly Ala Ser Thr Ala
1               5                   10                  15
```

```
Thr Thr Glu Ser Gly Gly Ala Val Arg Met Ser Pro Glu Pro Val Val
            20                  25                  30

Ala Val Ala Ala Ala Ala Gln Gln Leu Pro Val Val Lys Gly Val Asp
        35                  40                  45

Ser Ala Asp Glu Val Val Thr Ser Lys Pro Ala Ala Ala Val Ala
50                  55                  60

Gln Gln Ser Ser Arg Tyr Lys Gly Val Val Pro Gln Pro Asn Gly Arg
65                  70                  75                  80

Trp Gly Ala Gln Ile Tyr Glu Arg His Ala Arg Val Trp Leu Gly Thr
                85                  90                  95

Phe Pro Asp Glu Glu Ala Ala Arg Ala Tyr Asp Val Ala Ala Leu
            100                 105                 110

Arg Tyr Arg Gly Arg Asp Ala Ala Thr Asn Phe Pro Gly Ala Ala Ala
        115                 120                 125

Ser Ala Ala Glu Leu Ala Phe Leu Ala Ala His Ser Lys Ala Glu Ile
    130                 135                 140

Val Asp Met Leu Arg Lys His Thr Tyr Ala Asp Glu Leu Arg Gln Gly
145                 150                 155                 160

Leu Arg Arg Gly Arg Gly Met Gly Ala Arg Ala Gln Pro Thr Pro Ser
                165                 170                 175

Trp Ala Arg Glu Pro Leu Phe Glu Lys Ala Val Thr Pro Ser Asp Val
            180                 185                 190

Gly Lys Leu Asn Arg Leu Val Val Pro Lys Gln His Ala Glu Lys His
        195                 200                 205

Phe Pro Leu Arg Arg Ala Ala Ser Ser Asp Ser Ala Ser Ala Ala Ala
    210                 215                 220

Thr Gly Lys Gly Val Leu Leu Asn Phe Glu Asp Gly Glu Gly Lys Val
225                 230                 235                 240

Trp Arg Phe Arg Tyr Ser Tyr Trp Asn Ser Ser Gln Ser Tyr Val Leu
                245                 250                 255

Thr Lys Gly Trp Ser Arg Phe Val Arg Glu Lys Gly Leu Arg Ala Gly
            260                 265                 270

Asp Thr Ile Val Phe Ser Pro Leu Gly Val Arg Pro Arg Gln Ala Ala
        275                 280                 285

Leu His Arg Leu Gln Glu Glu Gln Arg Gly Gly Gly Asp His His
    290                 295                 300

Leu Arg Arg Arg Arg Glu Ala Asn His Asn His
305                 310                 315

<210> SEQ ID NO 21
<211> LENGTH: 1081
<212> TYPE: DNA
<213> ORGANISM: Glycine max
<220> FEATURE:
<223> OTHER INFORMATION: G3452

<400> SEQUENCE: 21
caccaacaca aaatggatgg aggctgtgtc acagacgaaa ccaccacatc cagcgactct      60
ctttccgttc cgccgcccag ccgcgtcggc agcgttgcaa gcgccgtcgt cgaccccgac     120
ggttgttgcg tttccggcga ggccgaatcc cggaaactcc cttcgtcgaa atacaaaggc     180
gtggtgccgc aaccgaacgg tcgctgggga gctcagattt acgagaagca ccagcgcgtg     240
tggctcggca cttttcaacga ggaagacgaa gccgccagag cctacgacat cgccgcgctg     300
cgcttccgcg gccccgacgc cgtcaccaac ttcaagcctc ccgccgcctc cgacgacgcc     360
gagtccgagt tcctcaactc gcattccaag ttcgagatcg tcgacatgct ccgcaagcac     420
```

```
acctacgacg acgagctcca gcagagcacg cgcggtggta ggcgccgcct cgacgctgac    480
accgcgtcga gcggtgtgtt cgacgcgaaa gcgcgtgagc agctgttcga gaaaacggtt    540
acgccgagcg acgtcgggaa gctgaatcga ttagtgatac cgaagcagca cgcggagaag    600
cactttccgt taagcggatc cggcgacgaa agctcgccgt gcgtggcggg ggcttcggcg    660
gcgaagggaa tgttgttgaa ctttgaggac gttggaggga aagtgtggcg gtttcgttac    720
tcttattgga acagtagcca gagctacgtg cttaccaaag gatggagccg gttcgttaag    780
gagaagaatc ttcgagccgg tgacgcggtt cagttcttca gtcgaccgg accggaccgg    840 cagctatata tagactgcaa ggcgaggagt ggtgaggtta caataatgc tggcggtttg    900 tttgttccga ttggaccggt cgttgagccg gttcagatgg ttcggctttt cggggtcaac    960
cttttgaaac tacccgtacc cggttcggat ggtgtaggga agagaaaaga gatggaactg   1020
tttgcatttg aatgttgcaa gaagttaaaa gtaattggag cttttgtaaca ttacatagtg   1080 c                                                                   1081
```

<210> SEQ ID NO 22
<211> LENGTH: 351
<212> TYPE: PRT
<213> ORGANISM: Glycine max
<220> FEATURE:
<223> OTHER INFORMATION: G3452 polypeptide Orthologous to G867

<400> SEQUENCE: 22

Met Asp Gly Gly Cys Val Thr Asp Glu Thr Thr Thr Ser Ser Asp Ser
1               5                   10                  15

Leu Ser Val Pro Pro Ser Arg Val Gly Ser Val Ala Ser Ala Val
            20                  25                  30

Val Asp Pro Asp Gly Cys Cys Val Ser Gly Glu Ala Glu Ser Arg Lys
        35                  40                  45

Leu Pro Ser Ser Lys Tyr Lys Gly Val Val Pro Gln Pro Asn Gly Arg
    50                  55                  60

Trp Gly Ala Gln Ile Tyr Glu Lys His Gln Arg Val Trp Leu Gly Thr
65                  70                  75                  80

Phe Asn Glu Glu Asp Glu Ala Ala Arg Ala Tyr Asp Ile Ala Ala Leu
                85                  90                  95

Arg Phe Arg Gly Pro Asp Ala Val Thr Asn Phe Lys Pro Pro Ala Ala
            100                 105                 110

Ser Asp Asp Ala Glu Ser Glu Phe Leu Asn Ser His Ser Lys Phe Glu
        115                 120                 125

Ile Val Asp Met Leu Arg Lys His Thr Tyr Asp Asp Glu Leu Gln Gln
    130                 135                 140

Ser Thr Arg Gly Gly Arg Arg Leu Asp Ala Asp Thr Ala Ser Ser
145                 150                 155                 160

Gly Val Phe Asp Ala Lys Ala Arg Glu Gln Leu Phe Glu Lys Thr Val
                165                 170                 175

Thr Pro Ser Asp Val Gly Lys Leu Asn Arg Leu Val Ile Pro Lys Gln
            180                 185                 190

His Ala Glu Lys His Phe Pro Leu Ser Gly Ser Gly Asp Glu Ser Ser
        195                 200                 205

Pro Cys Val Ala Gly Ala Ser Ala Ala Lys Gly Met Leu Leu Asn Phe
    210                 215                 220

Glu Asp Val Gly Gly Lys Val Trp Arg Phe Arg Tyr Ser Tyr Trp Asn
225                 230                 235                 240

```
Ser Ser Gln Ser Tyr Val Leu Thr Lys Gly Trp Ser Arg Phe Val Lys
            245                 250                 255

Glu Lys Asn Leu Arg Ala Gly Asp Ala Val Gln Phe Phe Lys Ser Thr
        260                 265                 270

Gly Pro Asp Arg Gln Leu Tyr Ile Asp Cys Lys Ala Arg Ser Gly Glu
    275                 280                 285

Val Asn Asn Asn Ala Gly Gly Leu Phe Val Pro Ile Gly Pro Val Val
290                 295                 300

Glu Pro Val Gln Met Val Arg Leu Phe Gly Val Asn Leu Leu Lys Leu
305                 310                 315                 320

Pro Val Pro Gly Ser Asp Gly Val Gly Lys Arg Lys Glu Met Glu Leu
                325                 330                 335

Phe Ala Phe Glu Cys Cys Lys Lys Leu Lys Val Ile Gly Ala Leu
            340                 345                 350
```

<210> SEQ ID NO 23
<211> LENGTH: 1089
<212> TYPE: DNA
<213> ORGANISM: Glycine max
<220> FEATURE:
<223> OTHER INFORMATION: G3453  Predicted polypeptide sequence is
      orthologous to G867

<400> SEQUENCE: 23

```
atggatggag gcagtgtcac agacgaaacc accacaacca gcaactctct ttcggttccg      60
gcgaatctat ctccgccgcc tctcagcctt gacggaagcg gcgcaaccgc cgtcgtctac     120
cccgacggtt gttgcgtctc cggcgaagcc gaatcccgga actcccgtc ctcgaaatac     180
aaaggcgtgg tgccgcaacc gaacggtcgt tggggagctc agatttacga gaagcaccag     240
cgcgtgtggc tcggcacctt caacgaggaa gacgaagcct cagagccta cgacatcgtc     300
gcgcatcgct tccgcggccg cgacgccgtc actaacttca gcctctcgc cggcgccgac     360
gacgccgaag ccgagttcct cagcacgcat tccagtccg agatcgtcga catgctccgc     420
aggcacacct acgacaacga gctccagcag agcaccccg cgcggcaggcg ccgccgggac     480
gccgaaaccg cgtcgagcgg cgcgttcgac gcgaaggcgc gtgagcagct ggtcgagaaa     540
accgttacgc cgagcgacgt cgggaagctg aaccgattag tgataccaaa gcagcacgcg     600
gagaagcact ttccgttaag cggatccggc ggcgagcct tgccgtgcat ggcggcggct     660
gcggggggcga aaggaatgtt gctgaacttt gaggacgttg agggaaagt gtggcggttc     720
cgttactcgt attggaacag tagccagagc tacgtgctta ccaaaggatg gagccggttc     780
gttaaggaga agaatcttcg agctggtgac gcggttcagt tcttcaagtc gaccggactg     840
gaccggcaac tatatataga ctgcaaggcg aggagtggta aggttaacaa taatgctgcc     900
ggtttgttta ttccggttgg accggttgtt gagccggttc agatggtacg gcttttcggg     960
gtcgaccttt tgaaactacc cgtacccggt tcgatggta ttggggttgg ctgtgacggg    1020
aagagaaaag agatggagct gttttgcattt gaatgtagca agaagttaaa agtaattgga    1080
gctttgtaa                                                            1089
```

<210> SEQ ID NO 24
<211> LENGTH: 362
<212> TYPE: PRT
<213> ORGANISM: Glycine max
<220> FEATURE:
<223> OTHER INFORMATION: G3453 polypeptide  Orthologous to G867

<400> SEQUENCE: 24

```
Met Asp Gly Gly Ser Val Thr Asp Glu Thr Thr Thr Ser Asn Ser
1               5                   10                  15

Leu Ser Val Pro Ala Asn Leu Ser Pro Pro Leu Ser Leu Asp Gly
            20                  25                  30

Ser Gly Ala Thr Ala Val Val Tyr Pro Asp Gly Cys Cys Val Ser Gly
            35                  40                  45

Glu Ala Glu Ser Arg Lys Leu Pro Ser Ser Lys Tyr Lys Gly Val Val
        50                  55                  60

Pro Gln Pro Asn Gly Arg Trp Gly Ala Gln Ile Tyr Glu Lys His Gln
65                  70                  75                  80

Arg Val Trp Leu Gly Thr Phe Asn Glu Glu Asp Glu Ala Val Arg Ala
                85                  90                  95

Tyr Asp Ile Val Ala His Arg Phe Arg Gly Arg Asp Ala Val Thr Asn
            100                 105                 110

Phe Lys Pro Leu Ala Gly Ala Asp Asp Ala Glu Ala Glu Phe Leu Ser
            115                 120                 125

Thr His Ser Lys Ser Glu Ile Val Asp Met Leu Arg Arg His Thr Tyr
    130                 135                 140

Asp Asn Glu Leu Gln Gln Ser Thr Arg Gly Gly Arg Arg Arg Arg Asp
145                 150                 155                 160

Ala Glu Thr Ala Ser Ser Gly Ala Phe Asp Ala Lys Ala Arg Glu Gln
                165                 170                 175

Leu Val Glu Lys Thr Val Thr Pro Ser Asp Val Gly Lys Leu Asn Arg
            180                 185                 190

Leu Val Ile Pro Lys Gln His Ala Glu Lys His Phe Pro Leu Ser Gly
            195                 200                 205

Ser Gly Gly Gly Ala Leu Pro Cys Met Ala Ala Ala Gly Ala Lys
210                 215                 220

Gly Met Leu Leu Asn Phe Glu Asp Val Gly Gly Lys Val Trp Arg Phe
225                 230                 235                 240

Arg Tyr Ser Tyr Trp Asn Ser Ser Gln Ser Tyr Val Leu Thr Lys Gly
                245                 250                 255

Trp Ser Arg Phe Val Lys Glu Lys Asn Leu Arg Ala Gly Asp Ala Val
            260                 265                 270

Gln Phe Phe Lys Ser Thr Gly Leu Asp Arg Gln Leu Tyr Ile Asp Cys
        275                 280                 285

Lys Ala Arg Ser Gly Lys Val Asn Asn Asn Ala Ala Gly Leu Phe Ile
290                 295                 300

Pro Val Gly Pro Val Val Glu Pro Val Gln Met Val Arg Leu Phe Gly
305                 310                 315                 320

Val Asp Leu Leu Lys Leu Pro Val Pro Gly Ser Asp Gly Ile Gly Val
                325                 330                 335

Gly Cys Asp Gly Lys Arg Lys Glu Met Glu Leu Phe Ala Phe Glu Cys
            340                 345                 350

Ser Lys Lys Leu Lys Val Ile Gly Ala Leu
        355                 360
```

<210> SEQ ID NO 25
<211> LENGTH: 1188
<212> TYPE: DNA
<213> ORGANISM: Glycine max
<220> FEATURE:
<223> OTHER INFORMATION: G3454 Predicted polypeptide sequence is orthologous to G867

<400> SEQUENCE: 25

-continued

| | |
|---|---|
| atggatgcaa ttagttgcat ggatgagagc accaccaccg agtcactctc cataagtcag | 60 |
| gcgaagcctt cttcgacgat tatgtcgtcc gagaaggctt ctccttcccc gccgccgccg | 120 |
| aacaggctgt gccgcgtcgg tagcggtgct agcgcagtcg tggattccga cggcggcggc | 180 |
| gggggtggca gcaccgaggt ggagtcgcgg aagctcccct cgtccaagta aagggcgtc | 240 |
| gtgccccagc ccaacggccg ctggggctcg cagatttacg agaagcacca gcgcgtgtgg | 300 |
| ctgggaacgt tcaacgagga agacgaggcg gcgcgtgcgt acgacgtcgc cgtgcagcga | 360 |
| ttccgcggca aggactccgt cacgaacttc aagccgctcg ccggcgccga cgacgacgac | 420 |
| ggagaatcgg agtttctcaa ctcgcattcc aaacccgaga tcgtcgacat gctgcgaaag | 480 |
| cacacgtaca atgacgagct ggagcatagc aagcgcaacc gcggcgtcgt ccggcggcga | 540 |
| ggctccgccg ccgtcggcac cgcagactca atttccggcg cgtgctttac taatgcacgt | 600 |
| gagcagctat tcgagaaagc tgttacgccg agcgacgttt ggaaattgaa ccgtttggtg | 660 |
| ataccgaagc agcacgcgga gaagcacttt ccgttacaga gctctaacgg cgttagcgcg | 720 |
| acgacgatag cggcggtgac ggcgacgccg acggcggcga agggcgtttt gttgaacttc | 780 |
| gaagacgttg gagggaaagt gtggcggttt cgttactcgt attggaacag tagccagagt | 840 |
| tacgtcttaa ccaaaggttg gagccggttc gttaaggaga agaatctgaa agctggtgac | 900 |
| acggtttgtt ttcaccggtc cactggaccg gacaagcagc tttacatcga ttggaagacg | 960 |
| aggaatgttg ttaacaacga ggtcgcgttg ttcggaccgg tcggaccggt tgtcgaaccg | 1020 |
| atccagatgg ttcggctctt tggggttaac attttgaaac tacccggttc agatactatt | 1080 |
| gttggcaata acaataatgc aagtgggtgc tgcaatggca agaagagaga aatggaactg | 1140 |
| ttctcgttag agtgtagcaa gaaacctaag attattggtg ctttgtaa | 1188 |

<210> SEQ ID NO 26
<211> LENGTH: 395
<212> TYPE: PRT
<213> ORGANISM: Glycine max
<220> FEATURE:
<223> OTHER INFORMATION: G3454 polypeptide Orthologous to G867

<400> SEQUENCE: 26

Met Asp Ala Ile Ser Cys Met Asp Glu Ser Thr Thr Glu Ser Leu
1               5                   10                  15

Ser Ile Ser Gln Ala Lys Pro Ser Ser Thr Ile Met Ser Ser Glu Lys
            20                  25                  30

Ala Ser Pro Ser Pro Pro Pro Asn Arg Leu Cys Arg Val Gly Ser
        35                  40                  45

Gly Ala Ser Ala Val Val Asp Ser Asp Gly Gly Gly Gly Gly Ser
    50                  55                  60

Thr Glu Val Glu Ser Arg Lys Leu Pro Ser Ser Lys Tyr Lys Gly Val
65                  70                  75                  80

Val Pro Gln Pro Asn Gly Arg Trp Gly Ser Gln Ile Tyr Glu Lys His
                85                  90                  95

Gln Arg Val Trp Leu Gly Thr Phe Asn Glu Glu Asp Glu Ala Ala Arg
            100                 105                 110

Ala Tyr Asp Val Ala Val Gln Arg Phe Arg Gly Lys Asp Ser Val Thr
        115                 120                 125

Asn Phe Lys Pro Leu Ala Gly Ala Asp Asp Asp Gly Glu Ser Glu
    130                 135                 140

Phe Leu Asn Ser His Ser Lys Pro Glu Ile Val Asp Met Leu Arg Lys
145                 150                 155                 160

```
His Thr Tyr Asn Asp Glu Leu Glu His Ser Lys Arg Asn Arg Gly Val
                165                 170                 175

Val Arg Arg Arg Gly Ser Ala Ala Val Gly Thr Ala Asp Ser Ile Ser
            180                 185                 190

Gly Ala Cys Phe Thr Asn Ala Arg Glu Gln Leu Phe Glu Lys Ala Val
        195                 200                 205

Thr Pro Ser Asp Val Trp Lys Leu Asn Arg Leu Val Ile Pro Lys Gln
    210                 215                 220

His Ala Glu Lys His Phe Pro Leu Gln Ser Ser Asn Gly Val Ser Ala
225                 230                 235                 240

Thr Thr Ile Ala Ala Val Thr Ala Thr Pro Thr Ala Ala Lys Gly Val
                245                 250                 255

Leu Leu Asn Phe Glu Asp Val Gly Gly Lys Val Trp Arg Phe Arg Tyr
            260                 265                 270

Ser Tyr Trp Asn Ser Ser Gln Ser Tyr Val Leu Thr Lys Gly Trp Ser
        275                 280                 285

Arg Phe Val Lys Glu Lys Asn Leu Lys Ala Gly Asp Thr Val Cys Phe
    290                 295                 300

His Arg Ser Thr Gly Pro Asp Lys Gln Leu Tyr Ile Asp Trp Lys Thr
305                 310                 315                 320

Arg Asn Val Val Asn Asn Glu Val Ala Leu Phe Gly Pro Val Gly Pro
                325                 330                 335

Val Val Glu Pro Ile Gln Met Val Arg Leu Phe Gly Val Asn Ile Leu
            340                 345                 350

Lys Leu Pro Gly Ser Asp Thr Ile Val Gly Asn Asn Asn Ala Ser
        355                 360                 365

Gly Cys Cys Asn Gly Lys Arg Arg Glu Met Glu Leu Phe Ser Leu Glu
    370                 375                 380

Cys Ser Lys Lys Pro Lys Ile Ile Gly Ala Leu
385                 390                 395

<210> SEQ ID NO 27
<211> LENGTH: 1304
<212> TYPE: DNA
<213> ORGANISM: Glycine max
<220> FEATURE:
<223> OTHER INFORMATION: G3455  Predicted polypeptide sequence is
      orthologous to G867

<400> SEQUENCE: 27
ctcttagaat ccgtacggtc taatcaacac aacaaaatgg atgcaattag ttgcctggat      60
gagagcacca ccaccgagtc actctccata agtcaggcga agccttcttc gacgattatg     120
tcgtccgaga aggcttctcc ttccccgccg ccgccgaaca ggctgtgccg cgtcggtagc     180
ggtgctagcg cagtcgtgga ttccgacggc ggcggcgggg gtggcagcac cgaggtggag     240
tcgcggaagc tcccctcgtc caagtataag ggcgtcgtgc cccagcccaa cggccgctgg     300
ggctcgcaga tttacgagaa gcaccagcgc gtgtggctgg aacgttcaa cgaggaagac     360 gaggcggcgc gtgcgtacga cgtcgccgtg cagcgattcc gcggcaagga cgccgtcaca     420
aacttcaagc cgctctccgg caccgacgac gacgacgggg aatcggagtt tctcaactcg     480
cattcgaaat ccgagatcgt cgacatgctg cgtaagcata cgtacaatga cgagctggaa     540
caaagcaagc gcagccgcgg cttcgtacgt cggcgcggct ccgccgccgg cgccggaaac     600
ggaaactcaa tctccggcgc gtgtgttatg aaggcgcgtg agcagctatt ccagaaggcc     660
gttacgccga gcgacgttgg gaaactgaac cgtttggtga taccgaagca gcacgcggag     720
```

-continued

```
aagcactttc ctttacagag cgctgctaac ggcgttagcg cgacggcgac ggcggcgaag      780
ggcgttttgt tgaacttcga agacgttgga gggaaagtgt ggcggtttcg ttactcgtat      840
tggaacagta gccagagtta cgtcttgacc aaaggttgga gccggttcgt taaggagaag      900
aatctgaaag ccggtgacac ggtttgtttt caacggtcca ctggaccgga caggcagctt      960
tacatcgatt ggaagacgag gaatgttgtt aacgaggtcg cgttgttcgg accggttgtc     1020
gaaccgatcc agatggttcg gctctttggt gttaacattt tgaaactacc cggttcagat     1080
tctatcgcca ataacaataa tgcaagtggg tgctgcaatg caagagaag agaaatggaa      1140 ctcttttcat tagagtgtag caagaaacct aagattattg gtgctttgta gcgttacgtt     1200 acttttttg agttttttt tttttttga gttttgtgac tgatgaaaga aagaaggtac        1260
aagaagaacg gcggtgtagt ggcatagtgg catcgcaagt tggc                      1304
```

<210> SEQ ID NO 28
<211> LENGTH: 384
<212> TYPE: PRT
<213> ORGANISM: Glycine max
<220> FEATURE:
<223> OTHER INFORMATION: G3455 polypeptide Orthologous to G867

<400> SEQUENCE: 28

```
Met Asp Ala Ile Ser Cys Leu Asp Glu Ser Thr Thr Thr Glu Ser Leu
1               5                   10                  15

Ser Ile Ser Gln Ala Lys Pro Ser Ser Thr Ile Met Ser Ser Glu Lys
            20                  25                  30

Ala Ser Pro Ser Pro Pro Pro Asn Arg Leu Cys Arg Val Gly Ser
        35                  40                  45

Gly Ala Ser Ala Val Val Asp Ser Asp Gly Gly Gly Gly Gly Ser
    50                  55                  60

Thr Glu Val Glu Ser Arg Lys Leu Pro Ser Ser Lys Tyr Lys Gly Val
65                  70                  75                  80

Val Pro Gln Pro Asn Gly Arg Trp Gly Ser Gln Ile Tyr Glu Lys His
                85                  90                  95

Gln Arg Val Trp Leu Gly Thr Phe Asn Glu Glu Asp Glu Ala Ala Arg
            100                 105                 110

Ala Tyr Asp Val Ala Val Gln Arg Phe Arg Gly Lys Asp Ala Val Thr
        115                 120                 125

Asn Phe Lys Pro Leu Ser Gly Thr Asp Asp Asp Gly Glu Ser Glu
    130                 135                 140

Phe Leu Asn Ser His Ser Lys Ser Glu Ile Val Asp Met Leu Arg Lys
145                 150                 155                 160

His Thr Tyr Asn Asp Glu Leu Glu Gln Ser Lys Arg Ser Arg Gly Phe
                165                 170                 175

Val Arg Arg Arg Gly Ser Ala Ala Gly Ala Gly Asn Gly Asn Ser Ile
            180                 185                 190

Ser Gly Ala Cys Val Met Lys Ala Arg Glu Gln Leu Phe Gln Lys Ala
        195                 200                 205

Val Thr Pro Ser Asp Val Gly Lys Leu Asn Arg Leu Val Ile Pro Lys
    210                 215                 220

Gln His Ala Glu Lys His Phe Pro Leu Gln Ser Ala Ala Asn Gly Val
225                 230                 235                 240

Ser Ala Thr Ala Thr Ala Ala Lys Gly Val Leu Leu Asn Phe Glu Asp
                245                 250                 255

Val Gly Gly Lys Val Trp Arg Phe Arg Tyr Ser Tyr Trp Asn Ser Ser
            260                 265                 270
```

-continued

```
            Gln Ser Tyr Val Leu Thr Lys Gly Trp Ser Arg Phe Val Lys Glu Lys
                275                 280                 285

Asn Leu Lys Ala Gly Asp Thr Val Cys Phe Gln Arg Ser Thr Gly Pro
                290                 295                 300

Asp Arg Gln Leu Tyr Ile Asp Trp Lys Thr Arg Asn Val Val Asn Glu
            305                 310                 315                 320

Val Ala Leu Phe Gly Pro Val Val Glu Pro Ile Gln Met Val Arg Leu
                            325                 330                 335

Phe Gly Val Asn Ile Leu Lys Leu Pro Gly Ser Asp Ser Ile Ala Asn
                            340                 345                 350

Asn Asn Asn Ala Ser Gly Cys Cys Asn Gly Lys Arg Arg Glu Met Glu
                        355                 360                 365

Leu Phe Ser Leu Glu Cys Ser Lys Lys Pro Lys Ile Ile Gly Ala Leu
                    370                 375                 380

<210> SEQ ID NO 29
<211> LENGTH: 1291
<212> TYPE: DNA
<213> ORGANISM: Oryza sativa
<220> FEATURE:
<223> OTHER INFORMATION: G3388 AP002913b GI:12328560 Predicted
      polypeptide sequence is orthologous to G867

<400> SEQUENCE: 29
ctagacactg ccctaattac aacccatttg cttatctctc tcctctctct ctctctctcg     60
ctgcagccat agcttagcta gagctagagc tttcttggtg ccgagatggg ggtggtcagc    120
ttctcctcga cttcctccgg cgcgtccacg gccaccaccg agtccggcgg cgccgtgcgg    180
atgtcgccgg agccggtggt ggcggtggcg gcggcggctc aacagctacc ggtggtgaag    240
ggagttgact cggcggatga ggtggtgacg tcgaggccgg cggcggcggc ggcgcagcag    300
tcgtcgcggt acaaggggt ggtgccgcag ccgaacggga ggtgggggc gcagatctac     360 gagcggcacg cgcgggtgtg gctcgggacg ttccccgacg aggaggcggc ggcgcgggcc    420
tacgacgtgg cggcgctccg gtaccggggg cgcgacgcgg ccaccaactt ccccggggcc    480
gcggcgtcgg ccgccgagct cgcgttcctc gccgcgcact ccaaggccga gatcgtcgac    540
atgctccgga agcacaccta cgccgacgag ctccgccagg ggctccgccg cggccgcggc    600
atgggcgccc gcgcccagcc cacgccgtcg tgggcgcgcg agccgctgtt cgagaaggcc    660
gtgacgccca cgacgtcgg caagctcaac cgcctcgtgg tgcccaagca gcacgccgag    720
aagcacttcc cgctccgccg cgcggcgagc tccgactccg cctccgccgc cgccaccggc    780
aagggcgtgc tcctcaactt cgaggacggc gagggaaagg tgtggcgatt ccggtactcg    840
tactggaaca gcagccagag ctacgtgctg accaagggt ggagccgatt cgtgagggag     900
aagggcctcc gcgccggcga caccatagtc ttctcccgct cggcgtacgg ccccgacaag    960
ctgctcttca tcgactgcaa gaagaacaac gcggcggcgg cgaccaccac ctgcgccggc   1020
gacgagaggc caaccacaag cggcgccgaa ccacgcgtcg tgaggctctt cggcgtcgac   1080
atcgccggcg gcgattgccg gaagcgggag agggcggtgg agatggggca agaggtcttc   1140
ctactgaaga ggcaatgcgt ggttcatcag cgtactcctg ccctaggtgc cctgctgtta   1200
tagcatcaaa tcaaattcat atatagatca aatcaaatct tcttctcttc catcttttt    1260 gttgttcatc gtctgttgtt tcatcttcga g                                  1291

<210> SEQ ID NO 30
<211> LENGTH: 365
```

```
<212> TYPE: PRT
<213> ORGANISM: Oryza sativa
<220> FEATURE:
<223> OTHER INFORMATION: G3388 polypeptide GI:12328560  Orthologous to
      G867

<400> SEQUENCE: 30
```

| | | | | | | | | | | | | | | |
|---|---|---|---|---|---|---|---|---|---|---|---|---|---|---|
| Met | Gly | Val | Val | Ser | Phe | Ser | Thr | Ser | Ser | Gly | Ala | Ser | Thr | Ala |
| 1 | | | | 5 | | | | | 10 | | | | | 15 |
| Thr | Thr | Glu | Ser | Gly | Gly | Ala | Val | Arg | Met | Ser | Pro | Glu | Pro | Val | Val |
| | | | 20 | | | | | 25 | | | | | 30 | | |
| Ala | Val | Ala | Ala | Ala | Gln | Gln | Leu | Pro | Val | Val | Lys | Gly | Val | Asp |
| | | | 35 | | | | 40 | | | | | 45 | | |
| Ser | Ala | Asp | Glu | Val | Val | Thr | Ser | Arg | Pro | Ala | Ala | Ala | Ala | Gln |
| | 50 | | | | | 55 | | | | | 60 | | | |
| Gln | Ser | Ser | Arg | Tyr | Lys | Gly | Val | Val | Pro | Gln | Pro | Asn | Gly | Arg | Trp |
| 65 | | | | | 70 | | | | | 75 | | | | | 80 |
| Gly | Ala | Gln | Ile | Tyr | Glu | Arg | His | Ala | Arg | Val | Trp | Leu | Gly | Thr | Phe |
| | | | | 85 | | | | | 90 | | | | | 95 | |
| Pro | Asp | Glu | Glu | Ala | Ala | Arg | Ala | Tyr | Asp | Val | Ala | Ala | Leu | Arg |
| | | | 100 | | | | | 105 | | | | | 110 | |
| Tyr | Arg | Gly | Arg | Asp | Ala | Ala | Thr | Asn | Phe | Pro | Gly | Ala | Ala | Ala | Ser |
| | | 115 | | | | | 120 | | | | | 125 | | | |
| Ala | Ala | Glu | Leu | Ala | Phe | Leu | Ala | Ala | His | Ser | Lys | Ala | Glu | Ile | Val |
| | 130 | | | | | 135 | | | | | 140 | | | | |
| Asp | Met | Leu | Arg | Lys | His | Thr | Tyr | Ala | Asp | Glu | Leu | Arg | Gln | Gly | Leu |
| 145 | | | | | 150 | | | | | 155 | | | | | 160 |
| Arg | Arg | Gly | Arg | Gly | Met | Gly | Ala | Arg | Ala | Gln | Pro | Thr | Pro | Ser | Trp |
| | | | | 165 | | | | | 170 | | | | | 175 | |
| Ala | Arg | Glu | Pro | Leu | Phe | Glu | Lys | Ala | Val | Thr | Pro | Ser | Asp | Val | Gly |
| | | | 180 | | | | | 185 | | | | | 190 | | |
| Lys | Leu | Asn | Arg | Leu | Val | Val | Pro | Lys | Gln | His | Ala | Glu | Lys | His | Phe |
| | | | | 195 | | | | | 200 | | | | | 205 | |
| Pro | Leu | Arg | Arg | Ala | Ala | Ser | Ser | Asp | Ser | Ala | Ser | Ala | Ala | Thr |
| | 210 | | | | | 215 | | | | | 220 | | | | |
| Gly | Lys | Gly | Val | Leu | Leu | Asn | Phe | Glu | Asp | Gly | Glu | Gly | Lys | Val | Trp |
| 225 | | | | | 230 | | | | | 235 | | | | | 240 |
| Arg | Phe | Arg | Tyr | Ser | Tyr | Trp | Asn | Ser | Ser | Gln | Ser | Tyr | Val | Leu | Thr |
| | | | | 245 | | | | | 250 | | | | | 255 | |
| Lys | Gly | Trp | Ser | Arg | Phe | Val | Arg | Glu | Lys | Gly | Leu | Arg | Ala | Gly | Asp |
| | | | 260 | | | | | 265 | | | | | 270 | | |
| Thr | Ile | Val | Phe | Ser | Arg | Ser | Ala | Tyr | Gly | Pro | Asp | Lys | Leu | Leu | Phe |
| | | | 275 | | | | | 280 | | | | | 285 | | |
| Ile | Asp | Cys | Lys | Lys | Asn | Asn | Ala | Ala | Ala | Thr | Thr | Cys | Ala |
| | 290 | | | | | 295 | | | | | 300 | | | |
| Gly | Asp | Glu | Arg | Pro | Thr | Thr | Ser | Gly | Ala | Glu | Pro | Arg | Val | Val | Arg |
| 305 | | | | | 310 | | | | | 315 | | | | | 320 |
| Leu | Phe | Gly | Val | Asp | Ile | Ala | Gly | Gly | Asp | Cys | Arg | Lys | Arg | Glu | Arg |
| | | | | 325 | | | | | 330 | | | | | 335 | |
| Ala | Val | Glu | Met | Gly | Gln | Glu | Val | Phe | Leu | Leu | Lys | Arg | Gln | Cys | Val |
| | | | 340 | | | | | 345 | | | | | 350 | | |
| Val | His | Gln | Arg | Thr | Pro | Ala | Leu | Gly | Ala | Leu | Leu | Leu |
| | | | 355 | | | | | 360 | | | | | 365 |

```
<210> SEQ ID NO 31
<211> LENGTH: 1068
```

<212> TYPE: DNA
<213> ORGANISM: Oryza sativa
<220> FEATURE:
<223> OTHER INFORMATION: G3389 AP002913 Predicted polypeptide
      sequence is orthologous to G867

<400> SEQUENCE: 31

```
gctaggctgt tctctctttc cattcgtcaa gaactaccac gacgtcgaca tcataatcgt      60
cagagagctc gagaaatttt ttagtatctt tgatccagat cgatcatgga gcaagaagct     120
gccatggtcg tcttctcctg caactccggc tccggtgggt cgtcgtcgac gaccgattca     180
aagcaagagg aggaggagga ggaggagttg gccgcaatgg aggaagacga gttgatccac     240
gtcgtccagg cggcggagct gcggctgccg tcgtcgacga cggcgacgcg gccgtcgtcg     300
cggtacaagg gggtggtgcc gcagccgaac gggcggtggg gggcgcagat ctacgagcgg     360
cacgcgcggg tgtggctcgg gacgttcccc gacgaggagg cggcggcgcg cgcctacgac     420
gtggcggcgc tccgcttccg ggggcgcgac gccgtcacca accgcgcccc ggcggcggag     480
ggcgcgtccg ccggcgagct cgcgttcctg gccgcgcact ccaaggcgga ggtcgtggac     540
atgctgcgga agcacaccta cgacgacgag ctccagcagg gcctccgccg cggctcgcgc     600
gcgcagccga cgccgcggtg ggcgcgcgag ccgctgttcg agaaggccgt gacgccgagc     660
gacgtcggca agctcaaccg cctcgtggtg cccaagcagc aggccgagag gcatttcccg     720
ttcccgctcc gccgccacag ctccgacgcc gccggcaagg gcgtgctcct caacttcgag     780
gacggcgacg gcaaggtgtg gcgattccgg tactcgtact ggaacagcag ccagagttac     840
gtgctcacca aggggtggag ccgattcgtg agggagaagg gcctccgacc aggcgacacc     900
gtggccttct cccggtcggc ggcggcgtgg gggacggaga agcacctcct catcgactgc     960
aagaagatgg agaggaacaa cctggcaacc gtcgacgacg atgcccgtgt cgtcgtcaag    1020
ctgttcggcg ttgacatcgc cggagacaag acgaggtaac acgcaagc                 1068
```

<210> SEQ ID NO 32
<211> LENGTH: 317
<212> TYPE: PRT
<213> ORGANISM: Oryza sativa
<220> FEATURE:
<223> OTHER INFORMATION: G3389 polypeptide BAB21211.1 Orthologous to
      G867

<400> SEQUENCE: 32

```
Met Glu Gln Glu Ala Ala Met Val Val Phe Ser Cys Asn Ser Gly Ser
1               5                   10                  15

Gly Gly Ser Ser Ser Thr Thr Asp Ser Lys Gln Glu Glu Glu Glu Glu
                20                  25                  30

Glu Glu Leu Ala Ala Met Glu Glu Asp Glu Leu Ile His Val Val Gln
            35                  40                  45

Ala Ala Glu Leu Arg Leu Pro Ser Ser Thr Thr Ala Thr Arg Pro Ser
        50                  55                  60

Ser Arg Tyr Lys Gly Val Val Pro Gln Pro Asn Gly Arg Trp Gly Ala
65                  70                  75                  80

Gln Ile Tyr Glu Arg His Ala Arg Val Trp Leu Gly Thr Phe Pro Asp
                85                  90                  95

Glu Glu Ala Ala Ala Arg Ala Tyr Asp Val Ala Ala Leu Arg Phe Arg
            100                 105                 110

Gly Arg Asp Ala Val Thr Asn Arg Ala Pro Ala Ala Glu Gly Ala Ser
        115                 120                 125

Ala Gly Glu Leu Ala Phe Leu Ala Ala His Ser Lys Ala Glu Val Val
```

```
                130                 135                 140
Asp Met Leu Arg Lys His Thr Tyr Asp Asp Glu Leu Gln Gln Gly Leu
145                 150                 155                 160

Arg Arg Gly Ser Arg Ala Gln Pro Thr Pro Arg Trp Ala Arg Glu Pro
                165                 170                 175

Leu Phe Glu Lys Ala Val Thr Pro Ser Asp Val Gly Lys Leu Asn Arg
                180                 185                 190

Leu Val Val Pro Lys Gln Gln Ala Glu Arg His Phe Pro Phe Pro Leu
                195                 200                 205

Arg Arg His Ser Ser Asp Ala Ala Gly Lys Gly Val Leu Leu Asn Phe
                210                 215                 220

Glu Asp Gly Asp Gly Lys Val Trp Arg Phe Arg Tyr Ser Tyr Trp Asn
225                 230                 235                 240

Ser Ser Gln Ser Tyr Val Leu Thr Lys Gly Trp Ser Arg Phe Val Arg
                245                 250                 255

Glu Lys Gly Leu Arg Pro Gly Asp Thr Val Ala Phe Ser Arg Ser Ala
                260                 265                 270

Ala Ala Trp Gly Thr Glu Lys His Leu Leu Ile Asp Cys Lys Lys Met
                275                 280                 285

Glu Arg Asn Asn Leu Ala Thr Val Asp Asp Ala Arg Val Val Val
                290                 295                 300

Lys Leu Phe Gly Val Asp Ile Ala Gly Asp Lys Thr Arg
305                 310                 315

<210> SEQ ID NO 33
<211> LENGTH: 1348
<212> TYPE: DNA
<213> ORGANISM: Oryza sativa
<220> FEATURE:
<223> OTHER INFORMATION: G3390 AC130725 Predicted polypeptide sequence
      is orthologous to G867

<400> SEQUENCE: 33
cttcagaggc ttcacctttc atcagcttag ctagctagct gctcgatccg gcggcgtgat    60
cgatcgatct ctctgattct atcaggtgtt cgaccagatt ccatcgatgg acagcacgag   120
ctgtctcttg gacgacgcga gcagcggcgc gtccacgggc aagaaggcgg cggcggcggc   180
ggcgtcgaag gcgctgcagc gcgtgggcag cggcgccagc gcggtgatgg acgcggccga   240
gcctggcgcc gaggcggact cgggcggcga gcggcgcggc ggcggcggcg ggaagctgcc   300
gtcgtccaag tacaagggcg tggtgccgca accgaacggg cggtggggcg cgcagatata   360
cgagcggcac cagcgggtgt ggctcggcac gttcaccggc gaggcggagg cggcgcgcgc   420
ctacgacgtg gcggcgcagc ggttccgcgg ccgcgacgcc gtcaccaact tccgcccgct   480
cgccgagtcc gacccggagg ccgccgtcga gctccgcttc ctcgcgtccc gctccaaggc   540
cgaggtcgtc gacatgctcc gcaagcacac ctacctcgag gagctcacgc agaacaagcg   600
cgccttcgcc gccatctccc gccgccccc caagcacccc gcctcctctc cgacgtcctc   660
ctccgccgcg cgcgagcacc tgttcgacaa gacggtgacg cccagcgacg tcgggaagct   720
gaaccggctg gtgatcccca gcagcacgc cgagaagcac ttcccgctcc agctccctcc   780
ccctaccaca acctcctccg tcgccgccg cgccgacgcc gccgccggcg cggcgattg    840
caagggcgtc ctcctcaact tcgaggacgc cgccgggaag gtgtggaaat tccggtactc   900
ctactggaac agcagccaga gctacgtgct caccaagggg tggagccgct tcgtcaagga   960
gaagggcctc cacgccggcg acgccgtcgg cttctaccgc gccgccggta agaacgcgca  1020
```

-continued

```
gctcttcatc gactgcaagg tccgggcaaa acccaccacc gccgccgccg ccgccgcctt    1080
cctcagcgcg gtggccgccg ccgccgcgcc gccacccgcc gtgaaggcta tcaggctgtt    1140
cggtgtcgac ctgctcacgg cggcggcgcc ggagctgcag gacgccggcg gcgccgccat    1200
gaccaagagc aagagagcca tggacgccat ggctgagtca caagcacacg tggtttttaa    1260
gaagcaatgc atagagcttg cgctaaccta gctagcacgc tgatgcagct agcgttttt     1320 ttgctcattc gcttgcttgc ttaattat                                        1348
```

<210> SEQ ID NO 34
<211> LENGTH: 394
<212> TYPE: PRT
<213> ORGANISM: Oryza sativa
<220> FEATURE:
<223> OTHER INFORMATION: G3390 polypeptide Orthologous to G867

<400> SEQUENCE: 34

```
Met Asp Ser Thr Ser Cys Leu Leu Asp Asp Ala Ser Ser Gly Ala Ser
1               5                   10                  15

Thr Gly Lys Lys Ala Ala Ala Ala Ala Ser Lys Ala Leu Gln Arg
            20                  25                  30

Val Gly Ser Gly Ala Ser Ala Val Met Asp Ala Ala Glu Pro Gly Ala
        35                  40                  45

Glu Ala Asp Ser Gly Gly Glu Arg Arg Gly Gly Gly Gly Lys Leu
    50                  55                  60

Pro Ser Ser Lys Tyr Lys Gly Val Val Pro Gln Pro Asn Gly Arg Trp
65                  70                  75                  80

Gly Ala Gln Ile Tyr Glu Arg His Gln Arg Val Trp Leu Gly Thr Phe
                85                  90                  95

Thr Gly Glu Ala Glu Ala Ala Arg Ala Tyr Asp Val Ala Ala Gln Arg
            100                 105                 110

Phe Arg Gly Arg Asp Ala Val Thr Asn Phe Arg Pro Leu Ala Glu Ser
        115                 120                 125

Asp Pro Glu Ala Ala Val Glu Leu Arg Phe Leu Ala Ser Arg Ser Lys
    130                 135                 140

Ala Glu Val Val Asp Met Leu Arg Lys His Thr Tyr Leu Glu Glu Leu
145                 150                 155                 160

Thr Gln Asn Lys Arg Ala Phe Ala Ala Ile Ser Pro Pro Pro Lys
                165                 170                 175

His Pro Ala Ser Ser Pro Thr Ser Ser Ser Ala Ala Arg Glu His Leu
            180                 185                 190

Phe Asp Lys Thr Val Thr Pro Ser Asp Val Gly Lys Leu Asn Arg Leu
        195                 200                 205

Val Ile Pro Lys Gln His Ala Glu Lys His Phe Pro Leu Gln Leu Pro
    210                 215                 220

Pro Pro Thr Thr Thr Ser Ser Val Ala Ala Ala Ala Asp Ala Ala Ala
225                 230                 235                 240

Gly Gly Gly Asp Cys Lys Gly Val Leu Leu Asn Phe Glu Asp Ala Ala
                245                 250                 255

Gly Lys Val Trp Lys Phe Arg Tyr Ser Tyr Trp Asn Ser Ser Gln Ser
            260                 265                 270

Tyr Val Leu Thr Lys Gly Trp Ser Arg Phe Val Lys Glu Lys Gly Leu
        275                 280                 285

His Ala Gly Asp Ala Val Gly Phe Tyr Arg Ala Ala Gly Lys Asn Ala
    290                 295                 300

Gln Leu Phe Ile Asp Cys Lys Val Arg Ala Lys Pro Thr Thr Ala Ala
```

```
                  305                 310                 315                 320
Ala Ala Ala Ala Phe Leu Ser Ala Val Ala Ala Ala Ala Pro Pro
                    325                 330                 335

Pro Ala Val Lys Ala Ile Arg Leu Phe Gly Val Asp Leu Leu Thr Ala
                340                 345                 350

Ala Ala Pro Glu Leu Gln Asp Ala Gly Gly Ala Ala Met Thr Lys Ser
            355                 360                 365

Lys Arg Ala Met Asp Ala Met Ala Glu Ser Gln Ala His Val Val Phe
        370                 375                 380

Lys Lys Gln Cys Ile Glu Leu Ala Leu Thr
385                 390

<210> SEQ ID NO 35
<211> LENGTH: 1338
<212> TYPE: DNA
<213> ORGANISM: Oryza sativa
<220> FEATURE:
<223> OTHER INFORMATION: G3391 AP003450  Predicted polypeptide sequence
      is orthologous to G867

<400> SEQUENCE: 35
ggagagtagg agtgtgctag tgtgtgaggt ctactgaaat ggacagctcc agctgcctgg      60
tggatgatac caacagcggc ggctcgtcca cggacaagct gagggcgttg ccgccgcgg     120 cggcggagac ggcgccgctg agcgcatgg ggagcggggc gagcgcggtg gtggacgcgc     180
ccgagcctgg cgcggaggcg gactccgggt ccggggacg tgtgtgcggc ggcggcggcg     240
gcggtgccgg cggtgcggga gggaagctgc cgtcgtccaa gttcaagggc gtcgtgccgc     300
agcccaacgg gaggtggggc gcgcagatct acgagcggca ccagcgggtg tggctcggca     360
cgttcgccgg ggaggacgac gccgcgcgcg cctacgacgt cgccgcgcag cgcttccgcg     420
gccgcgacgc cgtcaccaac ttccgcccgc tcgccgaggc cgaccggac gccgccgccg     480 agcttcgctt cctcgccacg cgctccaagg ccgaggtcgt cgacatgctc cgcaagcaca     540
cctacttcga cgagctcgcg cagagcaagc gcaccttcgc cgcctccacg ccgtcggccg     600
cgaccaccac cgcctcccctc tccaacggcc acctctcgtc gccccgctcc cccttcgcgc     660
ccgccgcggc gcgcgaccac ctgttcgaca agacggtcac cccgagcgac gtgggcaagc     720
tgaacaggct cgtcataccg aagcagcacg ccgagaagca cttcccgcta cagctcccgt     780
ccgccggcgg cgagagcaag ggtgtcctcc tcaacttcga ggacgccgcc ggcaaggtgt     840
ggcggttccg gtactcgtac tggaacagca gccagagcta cgtgctaacc aagggctgga     900
gccgcttcgt caaggagaag ggtctccacg ccgacggcaa gctcttcatc gactgcaagt     960
tagtacggtc gaccggcgcc gccctcgcgt cgcccgctga tcagccagcg ccgtcgccgg    1020
tgaaggccgt caggctcttc ggcgtggacc tgctcacggc gccggcgccg gtcgaacaga    1080
tggccgggtg caagagagcc agggacttgg cggcgacgac gcctccacaa gcggcggcgt    1140
tcaagaagca atgcatagag ctggcactag tatagagtta gcactattag ctcgatcttc    1200
tctagctagt gtcttttttg ctcccatgca tcataattca ggtggtagct agcttagtcc    1260
cttgttgatc ctatctacta atctcacttg gttttttttg ttaatttatt cgcccatgtt    1320
cttgcttgct ttgctgta                                                  1338

<210> SEQ ID NO 36
<211> LENGTH: 378
<212> TYPE: PRT
<213> ORGANISM: Oryza sativa
<220> FEATURE:
```

<223> OTHER INFORMATION: G3391 polypeptide AP003450 Orthologous to G867

<400> SEQUENCE: 36

```
Met Asp Ser Ser Cys Leu Val Asp Asp Thr Asn Ser Gly Gly Ser
1               5                   10                  15

Ser Thr Asp Lys Leu Arg Ala Leu Ala Ala Ala Ala Glu Thr Ala
            20                  25                  30

Pro Leu Glu Arg Met Gly Ser Gly Ala Ser Ala Val Asp Ala Ala
        35                  40                  45

Glu Pro Gly Ala Glu Ala Asp Ser Gly Ser Gly Gly Arg Val Cys Gly
50                  55                  60

Gly Gly Gly Gly Gly Ala Gly Gly Ala Gly Gly Lys Leu Pro Ser Ser
65                  70                  75                  80

Lys Phe Lys Gly Val Val Pro Gln Pro Asn Gly Arg Trp Gly Ala Gln
                85                  90                  95

Ile Tyr Glu Arg His Gln Arg Val Trp Leu Gly Thr Phe Ala Gly Glu
            100                 105                 110

Asp Asp Ala Ala Arg Ala Tyr Asp Val Ala Ala Gln Arg Phe Arg Gly
        115                 120                 125

Arg Asp Ala Val Thr Asn Phe Arg Pro Leu Ala Glu Ala Asp Pro Asp
130                 135                 140

Ala Ala Ala Glu Leu Arg Phe Leu Ala Thr Arg Ser Lys Ala Glu Val
145                 150                 155                 160

Val Asp Met Leu Arg Lys His Thr Tyr Phe Asp Glu Leu Ala Gln Ser
                165                 170                 175

Lys Arg Thr Phe Ala Ala Ser Thr Pro Ser Ala Ala Thr Thr Thr Ala
            180                 185                 190

Ser Leu Ser Asn Gly His Leu Ser Ser Pro Arg Ser Pro Phe Ala Pro
        195                 200                 205

Ala Ala Ala Arg Asp His Leu Phe Asp Lys Thr Val Thr Pro Ser Asp
210                 215                 220

Val Gly Lys Leu Asn Arg Leu Val Ile Pro Lys Gln His Ala Glu Lys
225                 230                 235                 240

His Phe Pro Leu Gln Leu Pro Ser Ala Gly Gly Glu Ser Lys Gly Val
                245                 250                 255

Leu Leu Asn Phe Glu Asp Ala Ala Gly Lys Val Trp Arg Phe Arg Tyr
            260                 265                 270

Ser Tyr Trp Asn Ser Ser Gln Ser Tyr Val Leu Thr Lys Gly Trp Ser
        275                 280                 285

Arg Phe Val Lys Glu Lys Gly Leu His Ala Asp Gly Lys Leu Phe Ile
290                 295                 300

Asp Cys Lys Leu Val Arg Ser Thr Gly Ala Ala Leu Ala Ser Pro Ala
305                 310                 315                 320

Asp Gln Pro Ala Pro Ser Pro Val Lys Ala Val Arg Leu Phe Gly Val
                325                 330                 335

Asp Leu Leu Thr Ala Pro Ala Pro Val Glu Gln Met Ala Gly Cys Lys
            340                 345                 350

Arg Ala Arg Asp Leu Ala Ala Thr Thr Pro Pro Gln Ala Ala Ala Phe
        355                 360                 365

Lys Lys Gln Cys Ile Glu Leu Ala Leu Val
370                 375
```

<210> SEQ ID NO 37
<211> LENGTH: 1290

```
<212> TYPE: DNA
<213> ORGANISM: Zea mays
<220> FEATURE:
<223> OTHER INFORMATION: G3432  Predicted polypeptide sequence is
      orthologous to G867

<400> SEQUENCE: 37
ctatagctag cactagcagt ggtgcacact gaaatggaca gcgccagcag cctcgtggac      60
gacaccagta gcggtggcgg cggcggcgcg tccacggaca agctaagggc tctggccgtc     120
ttcgccgccg cctcggggac gccgctggag cgcatgggca gcggcgccag cgcggtcgtg     180
gacgcggccg agccgggcgc cgaggcggac tccggttccg gtgccgccgc ggtgagcgtc     240
ggcgggaagc tgccgtcgtc aaggtacaag ggcgtggtgc cgcagcccaa cgggcggtgg     300
ggcgcgcaga tctacgagcg ccaccagcgc gtgtggctcg gcaccttcgc gggcgaggcc     360
gacgcggcgc gcgcctacga cgtcgcggcg cagcggttcc gcggccgcga cgcggtcacc     420
aacttccgcc cgctcgcgga cgccgacccg gacgccgccg ccgagctccg gttcctggcg     480
tcccgctcca aggccgaggt cgtcgacatg ctccgcaagc acacctactt cgacgagctc     540
gcgcagaaca gcgcgccctt cgccgccgcg tccgcgtccg cggccaccgc ctcgtcgctg     600
gccaacaacc cttcttccta cgcgtcgctc tccccgcga ccgcgacggc cgccgcgcgg      660
gagcacctct cgacaagac ggtcaccccc agcgacgtgg gcaagctgaa ccggctggtg      720
atcccgaagc agcacgccga gaagcacttc ccgctgcagc tcccatccgc cggcggcgag     780
agcaagggcg tgctcctcaa cctggaggac gccgcgggca aggtgtggcg gttccgctac     840
tcgtactgga acagcagcca gagctacgtg ctcaccaagg gctggagccg cttcgtcaag     900
gagaagggcc tccaagccgg cgacgtcgtc ggcttctacc gctccgctgc cggcgccgac     960
accaagctct tcatcgactg caagctgcgg cccaacagcg tcgtcgtcgc ctcgacggca    1020
ggcccgtcgc ctccggcgcc ggtggcgaag gccgtgcgtc tcttcggcgt cgacctgctg    1080
acggcaccgg ccaccgccgc ggcgccggcg gaggccgtgg ccgggtgcaa gagagccagg    1140
gacttgggtt cgccccgca ggcggcgttc aagaagcagc tcgtggagct ggcactagtg     1200
tagattaatg ctacgagcg atcgatcttt ccctggctag ctagtctttt ttttttttgc     1260
tcgatcgctc aactcagatg gtagcatcat                                     1290

<210> SEQ ID NO 38
<211> LENGTH: 389
<212> TYPE: PRT
<213> ORGANISM: Zea mays
<220> FEATURE:
<223> OTHER INFORMATION: G3432 polypeptide  Orthologous to G867

<400> SEQUENCE: 38

Met Asp Ser Ala Ser Ser Leu Val Asp Asp Thr Ser Ser Gly Gly Gly
1               5                   10                  15

Gly Gly Ala Ser Thr Asp Lys Leu Arg Ala Leu Ala Val Phe Ala Ala
            20                  25                  30

Ala Ser Gly Thr Pro Leu Glu Arg Met Gly Ser Gly Ala Ser Ala Val
        35                  40                  45

Val Asp Ala Ala Glu Pro Gly Ala Glu Ala Asp Ser Gly Ser Gly Ala
    50                  55                  60

Ala Ala Val Ser Val Gly Gly Lys Leu Pro Ser Ser Arg Tyr Lys Gly
65                  70                  75                  80

Val Val Pro Gln Pro Asn Gly Arg Trp Gly Ala Gln Ile Tyr Glu Arg
                85                  90                  95
```

```
His Gln Arg Val Trp Leu Gly Thr Phe Ala Gly Glu Ala Asp Ala Ala
            100                 105                 110

Arg Ala Tyr Asp Val Ala Ala Gln Arg Phe Arg Gly Arg Asp Ala Val
        115                 120                 125

Thr Asn Phe Arg Pro Leu Ala Asp Ala Asp Pro Asp Ala Ala Ala Glu
130                 135                 140

Leu Arg Phe Leu Ala Ser Arg Ser Lys Ala Glu Val Val Asp Met Leu
145                 150                 155                 160

Arg Lys His Thr Tyr Phe Asp Glu Leu Ala Gln Asn Lys Arg Ala Phe
                165                 170                 175

Ala Ala Ala Ser Ala Ser Ala Ala Thr Ala Ser Ser Leu Ala Asn Asn
            180                 185                 190

Pro Ser Ser Tyr Ala Ser Leu Ser Pro Ala Thr Ala Thr Ala Ala Ala
        195                 200                 205

Arg Glu His Leu Phe Asp Lys Thr Val Thr Pro Ser Asp Val Gly Lys
    210                 215                 220

Leu Asn Arg Leu Val Ile Pro Lys Gln His Ala Glu Lys His Phe Pro
225                 230                 235                 240

Leu Gln Leu Pro Ser Ala Gly Glu Ser Lys Gly Val Leu Leu Asn
                245                 250                 255

Leu Glu Asp Ala Ala Gly Lys Val Trp Arg Phe Arg Tyr Ser Tyr Trp
            260                 265                 270

Asn Ser Ser Gln Ser Tyr Val Leu Thr Lys Gly Trp Ser Arg Phe Val
        275                 280                 285

Lys Glu Lys Gly Leu Gln Ala Gly Asp Val Val Gly Phe Tyr Arg Ser
    290                 295                 300

Ala Ala Gly Ala Asp Thr Lys Leu Phe Ile Asp Cys Lys Leu Arg Pro
305                 310                 315                 320

Asn Ser Val Val Ala Ser Thr Ala Gly Pro Ser Pro Ala Pro
                325                 330                 335

Val Ala Lys Ala Val Arg Leu Phe Gly Val Asp Leu Leu Thr Ala Pro
            340                 345                 350

Ala Thr Ala Ala Pro Ala Glu Ala Val Ala Gly Cys Lys Arg Ala
        355                 360                 365

Arg Asp Leu Gly Ser Pro Pro Gln Ala Ala Phe Lys Lys Gln Leu Val
    370                 375                 380

Glu Leu Ala Leu Val
385

<210> SEQ ID NO 39
<211> LENGTH: 1200
<212> TYPE: DNA
<213> ORGANISM: Zea mays
<220> FEATURE:
<223> OTHER INFORMATION: G3433  Predicted polypeptide sequence is
      orthologous to G867

<400> SEQUENCE: 39
atggacagcg ccagcagcct cgtggacgac accagcggca gcggcggcgg cgcgtgcacg      60
gacaagctaa gggctttggc cgccgccgcc gcctccgcct cggggccacc gccggagcgc     120
atgggcagcg agccagcgc ggtcgtggac gggccgagc cgggcgccga ggcggactcc      180
ggctccgccc cggcctccgt cgccgccgtc gcggcgggcg tgggcgggaa gctgccgtcg     240
tccaggtaca agggcgtggt gccgcagccc aacggcggt ggggcgcgca gatctacgag      300
cgccacctgc gcgtgtggct cggcaccttc acgggcgagg ccgaggccgc gcgcgcctac     360
```

```
gacgtggccg cgcagcggtt ccgggggcgc gacgccgtca ccaacttccg cccgctcgcg      420
gagtcggact tggaccccga cgccgccgcc gagctccggt tcctcgcgtc ccggtccaag      480
gccgaggtcg tcgacatgct ccgcaagcac acctacggcg aggagctcgc gcagaacagg      540
cgcgccttcg ccgctgcggc ggcgtccctg gcctcgccgc agctgccgcc ggccaagaac      600
actagcccgg cggcggcgcg cgagcacatg ttcgacaagg tgctgacccc gagcgacgta      660
ggcaagctca accggctggt ggtgccaaag cagcacgcgg agcggttctt ccgcgcggcc      720
ggcgccgggt cgacgcagct gtgcttccag gaccgcggcg gggcgctgtg gcagttccgc      780
tactcctact gggggagcag ccagagctat gtcatgacca aggggtggag ccgcttcgtc      840
cgcgccgcac gacttgccgc gggggacacc gtcaccttct cccgcagcgg cggcggccga      900
tacttcatcg agtaccgcca ctgccagcgc cggcgccgcg acgtcgatat cagcttcggc      960
gacgctgcca ccgtgccggc gtggccgagg ccgatagtta tcggaaccgc ggccatgaat     1020
aatgggggtg caacggtggc gtccgccacc atcgccggcc atgacatcga ggtggcagtg     1080
gcaccctcgg gggcgaggag cttcaggctc ttcgggttca atgttgagtg cagcggcgac     1140
gatgcaccgg caccggcacc tgctcccgcc gaagtggagt atgtcgacgg cgacacctag     1200
```

<210> SEQ ID NO 40
<211> LENGTH: 399
<212> TYPE: PRT
<213> ORGANISM: Zea mays
<220> FEATURE:
<223> OTHER INFORMATION: G3433 polypeptide  Orthologous to G867

<400> SEQUENCE: 40

```
Met Asp Ser Ala Ser Ser Leu Val Asp Asp Thr Ser Gly Ser Gly
1               5                   10                  15

Gly Ala Cys Thr Asp Lys Leu Arg Ala Leu Ala Ala Ala Ala Ser
                20                  25                  30

Ala Ser Gly Pro Pro Glu Arg Met Gly Ser Gly Ala Ser Ala Val
                35                  40                  45

Val Asp Ala Ala Glu Pro Gly Ala Glu Ala Asp Ser Gly Ser Ala Pro
50                  55                      60

Ala Ser Val Ala Ala Val Ala Ala Gly Val Gly Gly Lys Leu Pro Ser
65                  70                  75                  80

Ser Arg Tyr Lys Gly Val Val Pro Gln Pro Asn Gly Arg Trp Gly Ala
                85                  90                  95

Gln Ile Tyr Glu Arg His Leu Arg Val Trp Leu Gly Thr Phe Thr Gly
                100                 105                 110

Glu Ala Glu Ala Ala Arg Ala Tyr Asp Val Ala Ala Gln Arg Phe Arg
            115                 120                 125

Gly Arg Asp Ala Val Thr Asn Phe Arg Pro Leu Ala Glu Ser Asp Leu
        130                 135                 140

Asp Pro Asp Ala Ala Ala Glu Leu Arg Phe Leu Ala Ser Arg Ser Lys
145                 150                 155                 160

Ala Glu Val Val Asp Met Leu Arg Lys His Thr Tyr Gly Glu Glu Leu
                165                 170                 175

Ala Gln Asn Arg Arg Ala Phe Ala Ala Ala Ala Ser Leu Ala Ser
            180                 185                 190

Pro Gln Leu Pro Pro Ala Lys Asn Thr Ser Pro Ala Ala Ala Arg Glu
        195                 200                 205

His Met Phe Asp Lys Val Leu Thr Pro Ser Asp Val Gly Lys Leu Asn
    210                 215                 220
```

```
Arg Leu Val Val Pro Lys Gln His Ala Glu Arg Phe Phe Pro Ala Ala
225                 230                 235                 240

Gly Ala Gly Ser Thr Gln Leu Cys Phe Gln Asp Arg Gly Gly Ala Leu
            245                 250                 255

Trp Gln Phe Arg Tyr Ser Tyr Trp Gly Ser Ser Gln Tyr Val Met
        260                 265                 270

Thr Lys Gly Trp Ser Arg Phe Val Arg Ala Ala Arg Leu Ala Ala Gly
            275                 280                 285

Asp Thr Val Thr Phe Ser Arg Ser Gly Gly Gly Arg Tyr Phe Ile Glu
290                 295                 300

Tyr Arg His Cys Gln Arg Arg Arg Asp Val Asp Ile Ser Phe Gly
305                 310                 315                 320

Asp Ala Ala Thr Val Pro Ala Trp Pro Arg Pro Ile Val Ile Gly Thr
                325                 330                 335

Ala Ala Met Asn Asn Gly Gly Ala Thr Val Ala Ser Ala Thr Ile Ala
            340                 345                 350

Gly His Asp Ile Glu Val Ala Val Ala Pro Ser Gly Ala Arg Ser Phe
            355                 360                 365

Arg Leu Phe Gly Phe Asn Val Glu Cys Ser Gly Asp Asp Ala Pro Ala
    370                 375                 380

Pro Ala Pro Ala Pro Ala Glu Val Glu Tyr Val Asp Gly Asp Thr
385                 390                 395

<210> SEQ ID NO 41
<211> LENGTH: 969
<212> TYPE: DNA
<213> ORGANISM: Brassica oleraceae
<220> FEATURE:
<223> OTHER INFORMATION: BZ458719  Predicted sequence is orthologous to
      G867, G9, G993, G1930

<400> SEQUENCE: 41
caacccggcc cgtatcctgt tccaacccag cctttgtact tccacacaat atacaactgt      60
tgatcctgac cgttagatct tttaaaactg atcaaatcac cggcacagag tctcttctct     120
ttaacgaacc tgctccaacc tttagtcaac acgtagcttt gactactgtt ccaatacgag     180
taacggaacc tccacacttt cccgttaacg tcttcgaaat tcaacagcgt ccctctcacg     240
gagacgtcgc cggttaacgg taacggaaaa tgtttctccg cttggtgttt cggtatcact     300
aaacggttta gcttcccgac gtcactcggc gttaccgttt tctcaaacag acactccgcc     360
gttttaaacc ccgtcacaac cgtaacgtta gcaaacgccg tctcttccgt gtctccgtta     420
ccaccgttac gtttgcgttt cctctgctct aactcttctt tgtaagtgtg tttcctcaac     480
atatcaacga tctcatattt cgaatgtgcg tttaagaact ttacttcgtc ccgtcacct     540 tcaccgttac ggaacgtcgt gtctggtttg aaattagtga cggcgtcaga gccgcggaaa     600
cggtgagcgg cgacgtcgta gacacgcgcc gcttcttctt cttcgttgaa tgtcccgagc     660
caaacgcgct tgtgcttctc gtatatctga gctccccatc ttccgtttgg ctgagggacg     720
acgcctttga attttgacga cgggagcttt cttgattctg cttcgacgcc gttctgggaa     780
tcgagaacca cgcttgaacc gcttcccatt ctgtataaac tcgccggaga tgacgacttc     840
gccgtcttcg gcggcggtgt atcttagccg gagtgtggat ggaaactgta cttgttgagc     900
tctccatcac actactcaca gctttcatat tagagaaatc acaagaaagt tgtgaaattt     960
gagaatgaa                                                              969

<210> SEQ ID NO 42
```

```
<211> LENGTH: 288
<212> TYPE: PRT
<213> ORGANISM: Brassica oleraceae
<220> FEATURE:
<221> NAME/KEY: misc_feature
<222> LOCATION: (288)..(288)
<223> OTHER INFORMATION: Xaa can be any naturally occurring amino acid
<220> FEATURE:
<223> OTHER INFORMATION: BZ458719 predicted polypeptide  Orthologous to
      G867, G9, G993, G1930

<400> SEQUENCE: 42

Asp Thr Pro Pro Lys Thr Ala Lys Ser Ser Pro Ala Ser Leu
1               5                   10                  15

Tyr Arg Met Gly Ser Gly Ser Ser Val Val Leu Asp Ser Gln Asn Gly
            20                  25                  30

Val Glu Ala Glu Ser Arg Lys Leu Pro Ser Ser Lys Phe Lys Gly Val
        35                  40                  45

Val Pro Gln Pro Asn Gly Arg Trp Gly Ala Gln Ile Tyr Glu Lys His
    50                  55                  60

Lys Arg Val Trp Leu Gly Thr Phe Asn Glu Glu Glu Ala Ala Arg
65              70                  75                  80

Val Tyr Asp Val Ala Ala His Arg Phe Arg Gly Ser Asp Ala Val Thr
                85                  90                  95

Asn Phe Lys Pro Asp Thr Thr Phe Arg Asn Gly Glu Gly Asp Gly Asp
            100                 105                 110

Glu Val Lys Phe Leu Asn Ala His Ser Lys Tyr Glu Ile Val Asp Met
        115                 120                 125

Leu Arg Lys His Thr Tyr Lys Glu Glu Leu Glu Gln Arg Lys Arg Lys
    130                 135                 140

Arg Asn Gly Gly Asn Gly Asp Thr Glu Glu Thr Ala Phe Ala Asn Val
145                 150                 155                 160

Thr Val Val Thr Gly Phe Lys Thr Ala Glu Cys Leu Phe Glu Lys Thr
                165                 170                 175

Val Thr Pro Ser Asp Val Gly Lys Leu Asn Arg Leu Val Ile Pro Lys
            180                 185                 190

His Gln Ala Glu Lys His Phe Pro Leu Pro Leu Thr Gly Asp Val Ser
        195                 200                 205

Val Arg Gly Thr Leu Leu Asn Phe Glu Asp Val Asn Gly Lys Val Trp
    210                 215                 220

Arg Phe Arg Tyr Ser Tyr Trp Asn Ser Ser Gln Ser Tyr Val Leu Thr
225                 230                 235                 240

Lys Gly Trp Ser Arg Phe Val Lys Glu Lys Arg Leu Cys Ala Gly Asp
                245                 250                 255

Leu Ile Ser Phe Lys Arg Ser Asn Gly Gln Asp Gln Gln Leu Tyr Ile
            260                 265                 270

Val Trp Lys Tyr Lys Gly Trp Val Gly Thr Gly Tyr Gly Pro Gly Xaa
        275                 280                 285

<210> SEQ ID NO 43
<211> LENGTH: 756
<212> TYPE: DNA
<213> ORGANISM: Helianthus annuus
<220> FEATURE:
<223> OTHER INFORMATION: BQ971511  Predicted sequence is orthologous to
      G867, G9, G993, G1930

<400> SEQUENCE: 43
ttggaagcgg agccagcgtg gtttctgacc cggaagtgga agccttgtcg aggaagctac      60
```

```
cgtcgtcgag atataaaggc gttgttccgc aagcgaatgg ccgttgggga gctcagattt      120
atgagaaaca tcaagggta tggcttggca cgtttaacga cgaagacgaa gccgcgaaag       180
cgtacgacgt cgcggtccaa cgctttcgcg gacgagacgc agtaacaaac ttcaagcaac      240
tcgtcaccga cgacaacgcc gctgcctttg aagcaacttt cttaaaccgt cactcaaaat     300
ccgaaatagt tgacatgcta agaaaacaca catacaatga cgagttagaa caaagcaaaa     360
gaaccatcaa cacacacaaa accctatttc aaaccgggtt caaccttccc ggaccggtt      420 gcaccatgcc acgcgaacac ctcttccaaa aaaccgtcac accaagcgac gttggcaaac     480
taaaccggct cgtgatacca aaacaacatg ctgaaaaaca ctttccggtt caaaaaggca    540
tcagttcaaa gggagttttg ttacacttcg aagataccga gtcaaaagtt tggcgatttc     600
ggtattcata ttggaatagt agccagagtt atgtgttaac caaagggtgg agccggtttg    660
ttaaagaaaa gaaccttaaa gccggtgata gcgttagctt tcacagctcg accggaacgg    720
ataagcagtt ttacattcac tgggagtcaa aaccg                                756
```

<210> SEQ ID NO 44
<211> LENGTH: 252
<212> TYPE: PRT
<213> ORGANISM: Helianthus annuus
<220> FEATURE:
<221> NAME/KEY: misc_feature
<222> LOCATION: (252)..(252)
<223> OTHER INFORMATION: Xaa can be any naturally occurring amino acid
<220> FEATURE:
<223> OTHER INFORMATION: BQ971511 predicted polypeptide Orthologous to
      G867, G9, G993, G1930

<400> SEQUENCE: 44

```
Gly Ser Gly Ala Ser Val Val Ser Asp Pro Glu Val Glu Ala Leu Ser
1               5                   10                  15

Arg Lys Leu Pro Ser Ser Arg Tyr Lys Gly Val Val Pro Gln Ala Asn
            20                  25                  30

Gly Arg Trp Gly Ala Gln Ile Tyr Glu Lys His Gln Arg Val Trp Leu
        35                  40                  45

Gly Thr Phe Asn Asp Glu Asp Glu Ala Ala Lys Ala Tyr Asp Val Ala
    50                  55                  60

Val Gln Arg Phe Arg Gly Arg Asp Ala Val Thr Asn Phe Lys Gln Leu
65                  70                  75                  80

Val Thr Asp Asp Asn Ala Ala Ala Phe Glu Ala Thr Phe Leu Asn Arg
                85                  90                  95

His Ser Lys Ser Glu Ile Val Asp Met Leu Arg Lys His Thr Tyr Asn
            100                 105                 110

Asp Glu Leu Glu Gln Ser Lys Arg Thr Ile Asn Thr His Lys Thr Leu
        115                 120                 125

Phe Gln Thr Gly Phe Asn Leu Pro Gly Pro Gly Cys Thr Met Pro Arg
    130                 135                 140

Glu His Leu Phe Gln Lys Thr Val Thr Pro Ser Asp Val Gly Lys Leu
145                 150                 155                 160

Asn Arg Leu Val Ile Pro Lys Gln His Ala Glu Lys His Phe Pro Val
                165                 170                 175

Gln Lys Gly Ile Ser Ser Lys Gly Val Leu Leu His Phe Glu Asp Thr
            180                 185                 190

Glu Ser Lys Val Trp Arg Phe Arg Tyr Ser Tyr Trp Asn Ser Ser Gln
        195                 200                 205

Ser Tyr Val Leu Thr Lys Gly Trp Ser Arg Phe Val Lys Glu Lys Asn
    210                 215                 220
```

```
Leu Lys Ala Gly Asp Ser Val Ser Phe His Ser Ser Thr Gly Thr Asp
225                 230                 235                 240

Lys Gln Phe Tyr Ile His Trp Glu Ser Lys Thr Xaa
            245                 250
```

<210> SEQ ID NO 45
<211> LENGTH: 743
<212> TYPE: DNA
<213> ORGANISM: Helianthus annuus
<220> FEATURE:
<223> OTHER INFORMATION: BU025988  Predicted sequence is orthologous to
      G867, G9, G993, G1930

<400> SEQUENCE: 45

```
ttggaagcgg atccagcgtg gttcttgacc cagaaggagg cgtggaagtt gaagctcagt      60
cgagaaagct accctcgtcg cgatacaaag gtgtcgttcc acaaccgaat ggccgttggg     120
gagctcagat ttacgagaaa caccaaaggg tatggttagg tacgttcaac gacgaagatg     180
aagctgcaaa ggcgtacgat gttgccgtac aacgcttccg cggccgagac gcggtcacaa     240
acattaagca ggttgatgcc gacgataaag aggccgcgat ggaagcaagt ttcttaagcc     300
gccattcgga gtcagaaatt gttgacatgc ttagaaaaca cacatacaat gacgagctag     360
aacaaagcaa aagaagctgc acctcacacc aaaccctttc tcaaaccggt ttaaccaaca     420
ccacccgttt agtctccatg aagccacgcg aacacctctt ccagaaaacc gtgaccccta     480
gcgacgtagg aaagctgaac cggctcgtta taccaaaaca cacgcggag aaacacttcc     540
cggttcaaaa agggagcaat tcaaaaggag ttcttttaca tttcgaagat aaagggtcaa     600
aagtatggag atttcgttac tcttactgga acagtagcca gagttatgtt ttaaccaaag     660
gctggagccg gttcgtgaaa gaaaaaaatc taaaagccgg agatagcgtc agcttttcaaa    720
gctcaaccgg accggataag cag                                              743
```

<210> SEQ ID NO 46
<211> LENGTH: 247
<212> TYPE: PRT
<213> ORGANISM: Helianthus annuus
<220> FEATURE:
<223> OTHER INFORMATION: BU025988 predicted polypeptide  Orthologous to
      G867, G9, G993, G1930

<400> SEQUENCE: 46

```
Gly Ser Gly Ser Ser Val Val Leu Asp Pro Glu Gly Val Glu Val
1               5                   10                  15

Glu Ala Gln Ser Arg Lys Leu Pro Ser Ser Arg Tyr Lys Gly Val Val
                20                  25                  30

Pro Gln Pro Asn Gly Arg Trp Gly Ala Gln Ile Tyr Glu Lys His Gln
            35                  40                  45

Arg Val Trp Leu Gly Thr Phe Asn Asp Glu Asp Glu Ala Ala Lys Ala
    50                  55                  60

Tyr Asp Val Ala Val Gln Arg Phe Arg Gly Arg Asp Ala Val Thr Asn
65                  70                  75                  80

Ile Lys Gln Val Asp Ala Asp Lys Glu Ala Ala Met Glu Ala Ser
                85                  90                  95

Phe Leu Ser Arg His Ser Glu Ser Glu Ile Val Asp Met Leu Arg Lys
            100                 105                 110

His Thr Tyr Asn Asp Glu Leu Glu Gln Ser Lys Arg Ser Cys Thr Ser
        115                 120                 125

His Gln Thr Leu Ser Gln Thr Gly Leu Thr Asn Thr Thr Arg Leu Val
```

```
                130                 135                 140
Ser Met Lys Pro Arg Glu His Leu Phe Gln Lys Thr Val Thr Pro Ser
145                 150                 155                 160

Asp Val Gly Lys Leu Asn Arg Leu Val Ile Pro Lys Gln His Ala Glu
                165                 170                 175

Lys His Phe Pro Val Gln Lys Gly Ser Asn Ser Lys Gly Val Leu Leu
                180                 185                 190

His Phe Glu Asp Lys Gly Ser Lys Val Trp Arg Phe Arg Tyr Ser Tyr
                195                 200                 205

Trp Asn Ser Ser Gln Ser Tyr Val Leu Thr Lys Gly Trp Ser Arg Phe
                210                 215                 220

Val Lys Glu Lys Asn Leu Lys Ala Gly Asp Ser Val Ser Phe Gln Ser
225                 230                 235                 240

Ser Thr Gly Pro Asp Lys Gln
                245

<210> SEQ ID NO 47
<211> LENGTH: 1470
<212> TYPE: DNA
<213> ORGANISM: Triticum aestivum
<220> FEATURE:
<223> OTHER INFORMATION: BT009310 Predicted sequence is orthologous to
      G867, G9, G993, G1930

<400> SEQUENCE: 47
gcacgaggct agcttcagct tttagctaag ctctacttcc ctcccgagct aagcatcttc      60
ttgatttctc ggtgatcgga ttcggatgga cagcgcaaga agctgcctcg tggacgacgt     120
gagcagcggc gcgtccacgg gcaagaaggc ctctccgtcc ccggccgcgc cggcgaccaa     180
gccgctgcag cgcgtgggca gcggggccag cgcggtcatg gacgcgccgg agcccggcgc     240
cgaggcggac tccggccgcg tcggcaggct gccgtcctcc aagtacaagg gcgtggtgcc     300
gcagcccaac gggcgctggg gcgcgcagat ctacgagcgc caccagcgcg tctggctcgg     360
caccttcacg ggggaggccg aggctgcgcg cgcctacgac gcggcggcgc agcgcttccg     420
cggccgcgac gcagtcacca acttccgccc gctcaccgag tccgacccgg aggacgccgc     480
cgagctccgc ttcctcgctg cccgctccaa ggccgaggtc gtcgacatgc tgcgcaagca     540
cacctatccc gacgagctcg tcagtacaag gcgcgcctac ttcgccgccg ctgcggcgtc     600
ctcccctaca tcgtcctcgg tgcctcccgc ctcgtcgccc tcttcggcgg cttcgccctc     660
gccggcggcg cggcgcgagc acctgttcga caagacggtc acgcccagcg acgtggggaa     720
gctgaaccgg cttgtgatac cgaagcagca cgccgagaag cactttcctc tccagcttcc     780
ttccgccggc gccgccgtgt ccggcgagtg caagggcatg cttctcaact cgacgactc     840 ggccggcaag gtgtggaggt tccggtactc gtactggaac agcagccaga gctacgtgct     900
caccaagggc tggagccgct tgtcaagga agggcctg cacgccggcg acgccgtcgg     960
gttctaccgc tctgcctcag gcagcaacca gctcttcatc gactgcaagc tccggtccaa    1020
gaccacgacg atgacgacga ctttcgtcaa cgcggcggcc gccccgtcgc cggcacccgt    1080
gatgaggacc gtgcgactct cggcgtcga ccttctcacg gcgccggcgc cgagtcacgc    1140
gcccgagcac gaggactgca gcatggtgcc caagacaagc aagagatcca tggacgccaa    1200
cgcagcggcc actccggcgc acgcggtctg gaagaagcgg tgcatagact tcgcgctgac    1260
ctagccagct agcgtttttc ctccatggtt gctttgcttg cctccaaatt tccatgttag    1320
tagcttagag ctcttgatcg gtccaagtgt ttgcctttt tttcctcttc ttctcataca    1380
```

```
caagttagct ctaaatccag tcttctttaa ttaatctact gtaaattaag cccgttctcg    1440
aaaaaaaaaa aaaaaaaaaa aaaaaaaaaa                                    1470
```

<210> SEQ ID NO 48
<211> LENGTH: 392
<212> TYPE: PRT
<213> ORGANISM: Triticum aestivum
<220> FEATURE:
<223> OTHER INFORMATION: BT009310 predicted polypeptide  Orthologous to
      G867, G9, G993, G1930

<400> SEQUENCE: 48

```
Met Asp Ser Ala Arg Ser Cys Leu Val Asp Val Ser Gly Ala
1               5                   10                  15

Ser Thr Gly Lys Lys Ala Ser Pro Ser Pro Ala Ala Pro Ala Thr Lys
            20                  25                  30

Pro Leu Gln Arg Val Gly Ser Gly Ala Ser Ala Val Met Asp Ala Pro
        35                  40                  45

Glu Pro Gly Ala Glu Ala Asp Ser Gly Arg Val Gly Arg Leu Pro Ser
    50                  55                  60

Ser Lys Tyr Lys Gly Val Val Pro Gln Pro Asn Gly Arg Trp Gly Ala
65                  70                  75                  80

Gln Ile Tyr Glu Arg His Gln Arg Val Trp Leu Gly Thr Phe Thr Gly
                85                  90                  95

Glu Ala Glu Ala Ala Arg Ala Tyr Asp Ala Ala Ala Gln Arg Phe Arg
            100                 105                 110

Gly Arg Asp Ala Val Thr Asn Phe Arg Pro Leu Thr Glu Ser Asp Pro
        115                 120                 125

Glu Asp Ala Ala Glu Leu Arg Phe Leu Ala Ala Arg Ser Lys Ala Glu
    130                 135                 140

Val Val Asp Met Leu Arg Lys His Thr Tyr Pro Asp Glu Leu Ala Gln
145                 150                 155                 160

Tyr Lys Arg Ala Tyr Phe Ala Ala Ala Ala Ser Ser Pro Thr Ser
                165                 170                 175

Ser Ser Val Pro Pro Ala Ser Ser Pro Ser Ser Ala Ala Ser Pro Ser
            180                 185                 190

Pro Ala Ala Arg Arg Glu His Leu Phe Asp Lys Thr Val Thr Pro Ser
        195                 200                 205

Asp Val Gly Lys Leu Asn Arg Leu Val Ile Pro Lys Gln His Ala Glu
    210                 215                 220

Lys His Phe Pro Leu Gln Leu Pro Ser Ala Gly Ala Ala Val Ser Gly
225                 230                 235                 240

Glu Cys Lys Gly Met Leu Leu Asn Phe Asp Asp Ser Ala Gly Lys Val
                245                 250                 255

Trp Arg Phe Arg Tyr Ser Tyr Trp Asn Ser Ser Gln Ser Tyr Val Leu
            260                 265                 270

Thr Lys Gly Trp Ser Arg Phe Val Lys Glu Lys Gly Leu His Ala Gly
        275                 280                 285

Asp Ala Val Gly Phe Tyr Arg Ser Ala Ser Gly Ser Asn Gln Leu Phe
    290                 295                 300

Ile Asp Cys Lys Leu Arg Ser Lys Thr Thr Met Thr Thr Thr Phe
305                 310                 315                 320

Val Asn Ala Ala Ala Ala Pro Ser Pro Ala Pro Val Met Arg Thr Val
                325                 330                 335

Arg Leu Phe Gly Val Asp Leu Leu Thr Ala Pro Ala Pro Ser His Ala
            340                 345                 350
```

```
Pro Glu His Glu Asp Cys Ser Met Val Pro Lys Thr Ser Lys Arg Ser
        355                 360                 365

Met Asp Ala Asn Ala Ala Ala Thr Pro Ala His Ala Val Trp Lys Lys
        370                 375                 380

Arg Cys Ile Asp Phe Ala Leu Thr
385                 390

<210> SEQ ID NO 49
<211> LENGTH: 914
<212> TYPE: DNA
<213> ORGANISM: Zea mays
<220> FEATURE:
<223> OTHER INFORMATION: CC616336   Predicted sequence is orthologous to
      G867, G9, G993, G1930

<400> SEQUENCE: 49
gaagagctgc tgcttgccgc cggcggaacg gtagaacccg acggcgtcgc cggcgtggag      60 cccttctcc ttgacgaagc ggctccaccc cttggtcagc acgtagctct ggctgctgtt     120
ccagtacgag taccggaacc tccacgcctt cccggcggcg tcctcgaagt tgaggagcac    180
gcccttgcac tcgccgccac taccgacgcc cgccgccgcc gccgccggga gctgcagcgg    240
gaagtgcttc tccgcgtgct gcttcggtat caccagccgg ttcagcttcc ccacgtcgct    300
cggcgtcacc gtcttgtcga agaggtgctc gcgcgccgcc gcgggcgacg acgacgacga    360
ggcggcgggc ggacggcggt tattctcggg cggcggcgag gcggccgggg acgccgcggc    420
gaaggcgcgc ctgttgtgcg cgagctcctc gccgtaggtg tgcttgcgga gcatgtcgac    480
gacctcggcc ttggaccggg acgcgaggaa ccggagctcg acggcggcct ccggctccga    540
ctccgccagc gggcggaagt tggtgacggc gtcgcggccc cggaaccgct gcgcggccac    600
gtcgtaggcg cgcgcggcct cggcctcgcc cgtgaacgtg ccgagccaca cgcgctggtg    660
ccgctcgtag atctgcgcgc cccaccgccc gttgggctgt ggcaccacgc ccttgtactt    720
ggacgacggc agcttcccgc tgaccccgcc ggggcccgc cccgcgccgc ccgagtctgc    780
ctcggcgccc ggctccgccg cgtccatcac cgcgctggtg ccgctgccca cgcgctgtag    840
cggcttgccg gtcgccgcag ccggagccgg cgccggtttc ttgcccgtgg acgcgccgct    900
gctcgcgtcg tcca                                                      914

<210> SEQ ID NO 50
<211> LENGTH: 304
<212> TYPE: PRT
<213> ORGANISM: Zea mays
<220> FEATURE:
<223> OTHER INFORMATION: CC616336 predicted polypeptide  Orthologous to
      G867, G9, G993, G1930

<400> SEQUENCE: 50

Asp Asp Ala Ser Ser Gly Ala Ser Thr Gly Lys Lys Pro Ala Pro Ala
1               5                   10                  15

Pro Ala Ala Ala Thr Gly Lys Pro Leu Gln Arg Val Gly Ser Gly Thr
            20                  25                  30

Ser Ala Val Met Asp Ala Ala Glu Pro Gly Ala Glu Ala Asp Ser Gly
        35                  40                  45

Gly Ala Gly Arg Ala Pro Gly Gly Val Ser Gly Lys Leu Pro Ser Ser
    50                  55                  60

Lys Tyr Lys Gly Val Val Pro Gln Pro Asn Gly Arg Trp Gly Ala Gln
65                  70                  75                  80

Ile Tyr Glu Arg His Gln Arg Val Trp Leu Gly Thr Phe Thr Gly Glu
```

```
                    85                  90                  95
Ala Glu Ala Ala Arg Ala Tyr Asp Val Ala Ala Gln Arg Phe Arg Gly
            100                 105                 110

Arg Asp Ala Val Thr Asn Phe Arg Pro Leu Ala Glu Ser Glu Pro Glu
            115                 120                 125

Ala Ala Val Glu Leu Arg Phe Leu Ala Ser Arg Ser Lys Ala Glu Val
            130                 135                 140

Val Asp Met Leu Arg Lys His Thr Tyr Gly Glu Leu Ala His Asn
145                 150                 155                 160

Arg Arg Ala Phe Ala Ala Ser Pro Ala Ser Pro Pro Glu
            165                 170                 175

Asn Asn Arg Arg Pro Pro Ala Ala Ser Ser Ser Ser Pro Ala Ala
            180                 185                 190

Ala Arg Glu His Leu Phe Asp Lys Thr Val Thr Pro Ser Asp Val Gly
            195                 200                 205

Lys Leu Asn Arg Leu Val Ile Pro Lys Gln His Ala Glu Lys His Phe
210                 215                 220

Pro Leu Gln Leu Pro Ala Ala Ala Ala Gly Val Gly Ser Gly Gly
225                 230                 235                 240

Glu Cys Lys Gly Val Leu Leu Asn Phe Glu Asp Ala Ala Gly Lys Ala
            245                 250                 255

Trp Arg Phe Arg Tyr Ser Tyr Trp Asn Ser Ser Gln Ser Tyr Val Leu
            260                 265                 270

Thr Lys Gly Trp Ser Arg Phe Val Lys Glu Lys Gly Leu His Ala Gly
            275                 280                 285

Asp Ala Val Gly Phe Tyr Arg Ser Ala Gly Gly Lys Gln Gln Leu Phe
            290                 295                 300

<210> SEQ ID NO 51
<211> LENGTH: 1182
<212> TYPE: DNA
<213> ORGANISM: Oryza sativa
<220> FEATURE:
<223> OTHER INFORMATION: AAAA01000997  Predicted sequence is orthologous
      to G867, G9, G993, G1930

<400> SEQUENCE: 51
atggacagca cgagctgtct cttggacgac gcgagcagcg gcgcgtccac gggcaagaag      60
gcggcggcgg cggcggcgtc gaaggcgctg cagcgcgtgg gcagcggcgc cagcgcggtg     120
atggacgcgg ccgagcctgg cgccgaggcg gactcgggcg gcgagcggcg cggcggcggc     180
ggcgggaagc tgccgtcgtc caagtacaag ggcgtggtgc cgcaaccgaa cgggcggtgg     240
ggcgcgcaga tatacgagcg gcaccagcgg gtgtggctcg gcacgttcac cggcgaggcg     300
gaggcggcgc gcgcctacga cgtggcggcg cagcggttcc gcggccgcga cgccgtcacc     360
aacttccgcc cgctcgccga gtccgacccg gaggccgctg tcgagctccg cttcctcgcg     420
tcccgctcca aggccgaggt cgtcgacatg ctccgcaagc acacctacct cgaggagctc     480
acgcagaaca gcgcgccctt cgccgccatc tcccgccgc ccccaagca cccgccctcc      540 tctccgccgt cctccgccgc cgcgcgcgag cacctgttcg acaagacggt gacgcccagc     600
gacgtcggga gctgaaccg gctggtgatc cccaagcagc acgccgagaa gcacttcccg     660
ctccagctcc ctcccctac acaacctcc tccgtcgccg ccgccgccga cgccgccgcc      720
ggcggcggcg agtgcaaggg agtcctcctc aacttcgagg acgccgccgg gaaggtgtgg     780
aaattccggt actcctactg gaacagcagc cagagctacg tgctcaccaa ggggtggagc     840
```

```
cgcttcgtca aggacaaggg gctccacgcc ggcgacgccg tcggcttcta ccgcgccgcc      900
ggtaagaacg cgcagctctt catcgactgc aaggtccggg caaaacccac caccgccgcc      960
gccgccgccg ccttcctcag cgcggtggcc gccgccgccg cgccgccacc cgccgtgaag     1020
gctatcaggc tgttcggtgt cgacctgctc acggcggcgg cgccggagct gcaggacgcc     1080
ggcggcgccg ccatgaccaa gagcaagaga gccatggacg ccatggctga gtcacaagcg     1140
cacgtggttt ttaagaagca atgcatagag ctcgcgctaa cc                        1182
```

<210> SEQ ID NO 52  
<211> LENGTH: 394  
<212> TYPE: PRT  
<213> ORGANISM: Oryza sativa  
<220> FEATURE:  
<223> OTHER INFORMATION: AAAA01000997 predicted polypeptide Orthologous to G867, G9, G993, G1930

<400> SEQUENCE: 52

```
Met Asp Ser Thr Ser Cys Leu Leu Asp Asp Ala Ser Ser Gly Ala Ser
1               5                   10                  15

Thr Gly Lys Lys Ala Ala Ala Ala Ala Ser Lys Ala Leu Gln Arg
            20                  25                  30

Val Gly Ser Gly Ala Ser Ala Val Met Asp Ala Ala Glu Pro Gly Ala
        35                  40                  45

Glu Ala Asp Ser Gly Gly Glu Arg Arg Gly Gly Gly Gly Lys Leu
    50                  55                  60

Pro Ser Ser Lys Tyr Lys Gly Val Val Pro Gln Pro Asn Gly Arg Trp
65                  70                  75                  80

Gly Ala Gln Ile Tyr Glu Arg His Gln Arg Val Trp Leu Gly Thr Phe
                85                  90                  95

Thr Gly Glu Ala Glu Ala Ala Arg Ala Tyr Asp Val Ala Ala Gln Arg
            100                 105                 110

Phe Arg Gly Arg Asp Ala Val Thr Asn Phe Arg Pro Leu Ala Glu Ser
        115                 120                 125

Asp Pro Glu Ala Ala Val Glu Leu Arg Phe Leu Ala Ser Arg Ser Lys
    130                 135                 140

Ala Glu Val Val Asp Met Leu Arg Lys His Thr Tyr Leu Glu Glu Leu
145                 150                 155                 160

Thr Gln Asn Lys Arg Ala Phe Ala Ala Ile Ser Pro Pro Pro Lys
                165                 170                 175

His Pro Ala Ser Ser Pro Pro Ser Ala Ala Ala Arg Glu His Leu
            180                 185                 190

Phe Asp Lys Thr Val Thr Pro Ser Asp Val Gly Lys Leu Asn Arg Leu
        195                 200                 205

Val Ile Pro Lys Gln His Ala Glu Lys His Phe Pro Leu Gln Leu Pro
    210                 215                 220

Pro Pro Thr Thr Thr Ser Ser Val Ala Ala Ala Asp Ala Ala
225                 230                 235                 240

Gly Gly Gly Glu Cys Lys Gly Val Leu Leu Asn Phe Glu Asp Ala Ala
                245                 250                 255

Gly Lys Val Trp Lys Phe Arg Tyr Ser Tyr Trp Asn Ser Ser Gln Ser
            260                 265                 270

Tyr Val Leu Thr Lys Gly Trp Ser Arg Phe Val Lys Asp Lys Gly Leu
        275                 280                 285

His Ala Gly Asp Ala Val Gly Phe Tyr Arg Ala Ala Gly Lys Asn Ala
    290                 295                 300
```

```
Gln Leu Phe Ile Asp Cys Lys Val Arg Ala Lys Pro Thr Thr Ala Ala
305                 310                 315                 320

Ala Ala Ala Ala Phe Leu Ser Ala Val Ala Ala Ala Ala Pro Pro
                325                 330                 335

Pro Ala Val Lys Ala Ile Arg Leu Phe Gly Val Asp Leu Leu Thr Ala
            340                 345                 350

Ala Ala Pro Glu Leu Gln Asp Ala Gly Gly Ala Ala Met Thr Lys Ser
        355                 360                 365

Lys Arg Ala Met Asp Ala Met Ala Glu Ser Gln Ala His Val Val Phe
    370                 375                 380

Lys Lys Gln Cys Ile Glu Leu Ala Leu Thr
385                 390
```

<210> SEQ ID NO 53
<211> LENGTH: 393
<212> TYPE: PRT
<213> ORGANISM: Oryza sativa
<220> FEATURE:
<223> OTHER INFORMATION: OSC26104.C1.p13.fg polypeptide Orthologous
      to G867, G9, G993, G1930

<400> SEQUENCE: 53

```
Met Asp Ser Ser Cys Leu Val Asp Asp Thr Asn Ser Gly Gly Ser
1               5                   10                  15

Ser Thr Asp Lys Leu Arg Ala Leu Ala Ala Ala Ala Glu Thr Ala
            20                  25                  30

Pro Leu Glu Arg Met Gly Ser Gly Ala Ser Ala Val Val Asp Ala Ala
        35                  40                  45

Glu Pro Gly Ala Glu Ala Asp Ser Gly Ser Gly Gly Arg Val Cys Gly
50                  55                  60

Gly Gly Gly Gly Gly Ala Gly Ala Gly Gly Lys Leu Pro Ser Ser
65                  70                  75                  80

Lys Phe Lys Gly Val Val Pro Gln Pro Asn Gly Arg Trp Gly Ala Gln
                85                  90                  95

Ile Tyr Glu Arg His Gln Arg Val Trp Leu Gly Thr Phe Ala Gly Glu
            100                 105                 110

Asp Asp Ala Ala Arg Ala Tyr Asp Val Ala Ala Gln Arg Phe Arg Gly
        115                 120                 125

Arg Asp Ala Val Thr Asn Phe Arg Pro Leu Ala Glu Ala Asp Pro Asp
130                 135                 140

Ala Ala Ala Glu Leu Arg Phe Leu Ala Thr Arg Ser Lys Ala Glu Val
145                 150                 155                 160

Val Asp Met Leu Arg Lys His Thr Tyr Phe Asp Glu Leu Ala Gln Ser
                165                 170                 175

Lys Arg Thr Phe Ala Ala Ser Thr Pro Ser Ala Ala Thr Thr Thr Ala
            180                 185                 190

Ser Leu Ser Asn Gly His Leu Ser Pro Arg Ser Pro Phe Ala Pro
        195                 200                 205

Ala Ala Ala Arg Asp His Leu Phe Asp Lys Thr Val Thr Pro Ser Asp
210                 215                 220

Val Gly Lys Leu Asn Arg Leu Val Ile Pro Lys Gln His Ala Glu Lys
225                 230                 235                 240

His Phe Pro Leu Gln Leu Pro Ser Ala Gly Gly Glu Ser Lys Gly Val
                245                 250                 255

Leu Leu Asn Phe Glu Asp Ala Ala Gly Lys Val Trp Arg Phe Arg Tyr
            260                 265                 270
```

```
Ser Tyr Trp Asn Ser Ser Gln Ser Tyr Val Leu Thr Lys Gly Trp Ser
        275                 280                 285

Arg Phe Val Lys Glu Lys Gly Leu His Ala Gly Asp Val Val Gly Phe
    290                 295                 300

Tyr Arg Ser Ala Ala Ser Ala Gly Asp Asp Gly Lys Leu Phe Ile Asp
305                 310                 315                 320

Cys Lys Leu Val Arg Ser Thr Gly Ala Ala Leu Ala Ser Pro Ala Asp
                325                 330                 335

Gln Pro Ala Pro Ser Pro Val Lys Ala Val Arg Leu Phe Gly Val Asp
                340                 345                 350

Leu Leu Thr Ala Pro Ala Pro Val Glu Gln Met Ala Gly Cys Lys Arg
                355                 360                 365

Ala Arg Asp Leu Ala Ala Thr Thr Pro Pro Gln Ala Ala Ala Phe Lys
    370                 375                 380

Lys Gln Cys Ile Glu Leu Ala Leu Val
385                 390

<210> SEQ ID NO 54
<211> LENGTH: 929
<212> TYPE: DNA
<213> ORGANISM: Arabidopsis thaliana
<220> FEATURE:
<223> OTHER INFORMATION: CBF1  G40

<400> SEQUENCE: 54
cttgaaaaag aatctacctg aaaagaaaaa aagagagag  agatataaat agctttacca    60
agacagatat actatctttt attaatccaa aaagactgag aactctagta actacgtact   120
acttaaacct tatccagttt cttgaaacag agtactctga tcaatgaact catttcagc    180
tttttctgaa atgtttggct ccgattacga gcctcaaggc ggagattatt gtccgacgtt   240
ggccacgagt tgtccgaaga aaccggcggg ccgtaagaag tttcgtgaga ctcgtcaccc   300
aatttacaga ggagttcgtc aaagaaactc cggtaagtgg gtttctgaag tgagagagcc   360
aaacaagaaa accaggattt ggctcgggac tttccaaacc gctgagatgg cagctcgtgc   420
tcacgacgtc gctgcattag ccctccgtgg ccgatcagca tgtctcaact cgctgactc   480
ggcttggcgg ctacgaatcc cggagtcaac atgcgccaag gatatccaaa agcggctgc   540
tgaagcggcg ttggcttttc aagatgagac gtgtgatacg acgaccacga atcatggcct   600
ggacatggag gagacgatgg tggaagctat ttatacaccg aacagagcg aaggtgcgtt    660
ttatatggat gaggagacaa tgtttgggat gccgactttg ttggataata tggctgaagg   720
catgcttta ccgccgccgt ctgttcaatg gaatcataat tatgacggcg aaggagatgg    780
tgacgtgtcg ctttggagtt actaatattc gatagtcgtt tccatttttg tactatagtt   840
tgaaaatatt ctagttcctt tttttagaat ggttccttca tttattttta ttttattgtt   900
gtagaaacga gtggaaaata attcaatac                                    929

<210> SEQ ID NO 55
<211> LENGTH: 213
<212> TYPE: PRT
<213> ORGANISM: Arabidopsis thaliana
<220> FEATURE:
<223> OTHER INFORMATION: CBF1  G40 polypeptide

<400> SEQUENCE: 55

Met Asn Ser Phe Ser Ala Phe Ser Glu Met Phe Gly Ser Asp Tyr Glu
1                   5                   10                  15

Pro Gln Gly Gly Asp Tyr Cys Pro Thr Leu Ala Thr Ser Cys Pro Lys
```

```
                20                  25                  30
Lys Pro Ala Gly Arg Lys Lys Phe Arg Glu Thr Arg His Pro Ile Tyr
             35                  40                  45
Arg Gly Val Arg Gln Arg Asn Ser Gly Lys Trp Val Ser Glu Val Arg
         50                  55                  60
Glu Pro Asn Lys Lys Thr Arg Ile Trp Leu Gly Thr Phe Gln Thr Ala
 65                  70                  75                  80
Glu Met Ala Ala Arg Ala His Asp Val Ala Ala Leu Ala Leu Arg Gly
                 85                  90                  95
Arg Ser Ala Cys Leu Asn Phe Ala Asp Ser Ala Trp Arg Leu Arg Ile
            100                 105                 110
Pro Glu Ser Thr Cys Ala Lys Asp Ile Gln Lys Ala Ala Glu Ala
         115                 120                 125
Ala Leu Ala Phe Gln Asp Glu Thr Cys Asp Thr Thr Thr Asn His
    130                 135                 140
Gly Leu Asp Met Glu Glu Thr Met Val Glu Ala Ile Tyr Thr Pro Glu
145                 150                 155                 160
Gln Ser Glu Gly Ala Phe Tyr Met Asp Glu Gly Thr Met Phe Gly Met
                165                 170                 175
Pro Thr Leu Leu Asp Asn Met Ala Glu Gly Met Leu Leu Pro Pro Pro
            180                 185                 190
Ser Val Gln Trp Asn His Asn Tyr Asp Gly Glu Gly Asp Gly Asp Val
            195                 200                 205
Ser Leu Trp Ser Tyr
    210

<210> SEQ ID NO 56
<211> LENGTH: 803
<212> TYPE: DNA
<213> ORGANISM: Arabidopsis thaliana
<220> FEATURE:
<223> OTHER INFORMATION: CBF2  G41

<400> SEQUENCE: 56
ctgatcaatg aactcatttt ctgcctttc tgaaatgttt ggctccgatt acgagtctcc      60
ggtttcctca ggcggtgatt acagtccgaa gcttgccacg agctgcccca agaaaccagc    120
gggaaggaag aagtttcgtg agactcgtca cccaatttac agaggagttc gtcaaagaaa    180
ctccggtaag tgggtgtgtg agttgagaga gccaaacaag aaaacgagga tttggctcgg    240
gactttccaa accgctgaga tggcagctcg tgctcacgac gtcgccgcca tagctctccg    300
tggcagatct gcctgtctca atttcgctga ctcggcttgg cggctacgaa tcccggaatc    360
aacctgtgcc aaggaaatcc aaaaggcggc ggctgaagcc gcgttgaatt ttcaagatga    420
gatgtgtcat atgacgacgg atgctcatgg tcttgacatg gaggagacct ggtggaggc     480
tatttatacg ccggaacaga gccaagatgc gttttatatg gatgaagagg cgatgttggg    540
gatgtctagt tgttggata acatggccga agggatgctt ttaccgtcgc cgtcggttca    600
atggaactat aattttgatg tcagggaga tgatgacgtg tccttatgga gctattaaaa    660
ttcgattttt atttccattt tggtattat agctttttat acatttgatc cttttttaga    720
atggatcttc ttctttttt ggttgtgaga acgaatgta aatggtaaaa gttgttgtca    780
aatgcaaatg ttttgagtg cag                                            803

<210> SEQ ID NO 57
<211> LENGTH: 207
<212> TYPE: PRT
```

```
<213> ORGANISM: Arabidopsis thaliana
<220> FEATURE:
<223> OTHER INFORMATION: CBF2 G41 polypeptide

<400> SEQUENCE: 57

Met Phe Gly Ser Asp Tyr Glu Ser Pro Val Ser Ser Gly Gly Asp Tyr
1               5                   10                  15

Ser Pro Lys Leu Ala Thr Ser Cys Pro Lys Lys Pro Ala Gly Arg Lys
            20                  25                  30

Lys Phe Arg Glu Thr Arg His Pro Ile Tyr Arg Gly Val Arg Gln Arg
        35                  40                  45

Asn Ser Gly Lys Trp Val Cys Glu Leu Arg Glu Pro Asn Lys Lys Thr
    50                  55                  60

Arg Ile Trp Leu Gly Thr Phe Gln Thr Ala Glu Met Ala Ala Arg Ala
65                  70                  75                  80

His Asp Val Ala Ala Ile Ala Leu Arg Gly Arg Ser Ala Cys Leu Asn
                85                  90                  95

Phe Ala Asp Ser Ala Trp Arg Leu Arg Ile Pro Glu Ser Thr Cys Ala
            100                 105                 110

Lys Glu Ile Gln Lys Ala Ala Ala Glu Ala Ala Leu Asn Phe Gln Asp
        115                 120                 125

Glu Met Cys His Met Thr Thr Asp Ala His Gly Leu Asp Met Glu Glu
    130                 135                 140

Thr Leu Val Glu Ala Ile Tyr Thr Pro Glu Gln Ser Gln Asp Ala Phe
145                 150                 155                 160

Tyr Met Asp Glu Glu Ala Met Leu Gly Met Ser Ser Leu Leu Asp Asn
                165                 170                 175

Met Ala Glu Gly Met Leu Leu Pro Ser Pro Ser Val Gln Trp Asn Tyr
            180                 185                 190

Asn Phe Asp Val Glu Gly Asp Asp Val Ser Leu Trp Ser Tyr
            195                 200                 205

<210> SEQ ID NO 58
<211> LENGTH: 908
<212> TYPE: DNA
<213> ORGANISM: Arabidopsis thaliana
<220> FEATURE:
<221> NAME/KEY: misc_feature
<222> LOCATION: (851)..(851)
<223> OTHER INFORMATION: n is a, c, g, or t
<220> FEATURE:
<223> OTHER INFORMATION: CBF3 G42

<400> SEQUENCE: 58
cctgaactag aacagaaaga gagagaaact attatttcag caaaccatac caacaaaaaa      60
gacagagatc ttttagttac cttatccagt ttcttgaaac agagtactct tctgatcaat     120
gaactcattt tctgcttttt ctgaaatgtt tggctccgat tacgagtctt cggtttcctc     180
aggcggtgat tatattccga cgcttgcgag cagctgcccc aagaaaccgg cgggtcgtaa     240
gaagtttcgt gagactcgtc acccaatata cagaggagtt cgtcggagaa actccggtaa     300
gtgggtttgt gaggttagag aaccaaacaa gaaaacaagg atttggctcg gaacatttca     360
aaccgctgag atggcagctc gagctcacga cgttgccgct ttagcccttc gtggccgatc     420
agcctgtctc aatttcgctg actcggcttg gagactccga atcccggaat caacttgcgc     480
taaggacatc caaaaggcgg cggctgaagc tgcgttggcg tttcaggatg agatgtgtga     540
tgcgacgacg gatcatggct tcgacatgga ggagacgttg gtggaggcta tttacacggc     600
ggaacagagc gaaaatgcgt tttatatgca cgatgaggcg atgtttgaga tgccgagttt     660
```

```
gttggctaat atggcagaag ggatgctttt gccgcttccg tccgtacagt ggaatcataa    720
tcatgaagtc gacggcgatg atgacgacgt atcgttatgg agttattaaa actcagatta    780
ttatttccat ttttagtacg atacttttta ttttattatt attttagat ccttttttag    840 aatggaatct ncattatgtt tgtaaaactg agaaacgagt gtaaattaaa ttgattcagt    900
ttcagtat                                                              908

<210> SEQ ID NO 59
<211> LENGTH: 216
<212> TYPE: PRT
<213> ORGANISM: Arabidopsis thaliana
<220> FEATURE:
<223> OTHER INFORMATION: CBF3  G42 polypeptide

<400> SEQUENCE: 59

Met Asn Ser Phe Ser Ala Phe Ser Glu Met Phe Gly Ser Asp Tyr Glu
1               5                   10                  15

Ser Ser Val Ser Ser Gly Gly Asp Tyr Ile Pro Thr Leu Ala Ser Ser
                20                  25                  30

Cys Pro Lys Lys Pro Ala Gly Arg Lys Lys Phe Arg Glu Thr Arg His
            35                  40                  45

Pro Ile Tyr Arg Gly Val Arg Arg Arg Asn Ser Gly Lys Trp Val Cys
        50                  55                  60

Glu Val Arg Glu Pro Asn Lys Lys Thr Arg Ile Trp Leu Gly Thr Phe
65                  70                  75                  80

Gln Thr Ala Glu Met Ala Ala Arg Ala His Asp Val Ala Ala Leu Ala
                85                  90                  95

Leu Arg Gly Arg Ser Ala Cys Leu Asn Phe Ala Asp Ser Ala Trp Arg
            100                 105                 110

Leu Arg Ile Pro Glu Ser Thr Cys Ala Lys Asp Ile Gln Lys Ala Ala
        115                 120                 125

Ala Glu Ala Ala Leu Ala Phe Gln Asp Glu Met Cys Asp Ala Thr Thr
    130                 135                 140

Asp His Gly Phe Asp Met Glu Glu Thr Leu Val Glu Ala Ile Tyr Thr
145                 150                 155                 160

Ala Glu Gln Ser Glu Asn Ala Phe Tyr Met His Asp Glu Ala Met Phe
                165                 170                 175

Glu Met Pro Ser Leu Leu Ala Asn Met Ala Glu Gly Met Leu Leu Pro
            180                 185                 190

Leu Pro Ser Val Gln Trp Asn His Asn His Glu Val Asp Gly Asp Asp
        195                 200                 205

Asp Asp Val Ser Leu Trp Ser Tyr
    210                 215

<210> SEQ ID NO 60
<211> LENGTH: 632
<212> TYPE: DNA
<213> ORGANISM: Brassica napus
<220> FEATURE:
<223> OTHER INFORMATION: bnCBF1

<400> SEQUENCE: 60
cacccgatat accggggagt tcgtctgaga aagtcaggta agtgggtgtg tgaagtgagg    60
gaaccaaaca agaaatctag aatttggctt ggaactttca aaacagctga gatggcagct    120
cgtgctcacg acgtcgctgc cctagccctc cgtggaagag gcgcctgcct caattatgcg    180
gactcggctt ggcggctccg catcccggag acaacctgcc acaaggatat ccagaaggct    240
```

```
gctgctgaag ccgcattggc ttttgaggct gagaaaagtg atgtgacgat gcaaaatggc    300
cagaacatgg aggagacgac ggcggtggct tctcaggctg aagtgaatga cacgacgaca    360
gaacatggca tgaacatgga ggaggcaacg gcagtggctt ctcaggctga ggtgaatgac    420
acgacgacgg atcatggcgt agacatggag gagacaatgg tggaggctgt tttactggg     480 gaacaaagtg aagggtttaa catggcgaag gagtcgacgg tggaggctgc tgttgttacg    540
gaggaaccga gcaaaggatc ttacatggac gaggagtgga tgctcgagat gccgaccttg    600
ttggctgata tggcagaagg gatgctcctg cc                                  632
```

```
<210> SEQ ID NO 61
<211> LENGTH: 208
<212> TYPE: PRT
<213> ORGANISM: Brassica napus
<220> FEATURE:
<223> OTHER INFORMATION: bnCBF1 polypeptide

<400> SEQUENCE: 61
```

```
His Pro Ile Tyr Arg Gly Val Arg Leu Arg Lys Ser Gly Lys Trp Val
1               5                   10                  15

Cys Glu Val Arg Glu Pro Asn Lys Lys Ser Arg Ile Trp Leu Gly Thr
            20                  25                  30

Phe Lys Thr Ala Glu Met Ala Ala Arg Ala His Asp Val Ala Ala Leu
        35                  40                  45

Ala Leu Arg Gly Arg Gly Ala Cys Leu Asn Tyr Ala Asp Ser Ala Trp
    50                  55                  60

Arg Leu Arg Ile Pro Glu Thr Thr Cys His Lys Asp Ile Gln Lys Ala
65                  70                  75                  80

Ala Ala Glu Ala Ala Leu Ala Phe Glu Ala Glu Lys Ser Asp Val Thr
                85                  90                  95

Met Gln Asn Gly Gln Asn Met Glu Glu Thr Thr Ala Val Ala Ser Gln
            100                 105                 110

Ala Glu Val Asn Asp Thr Thr Thr Glu His Gly Met Asn Met Glu Glu
        115                 120                 125

Ala Thr Ala Val Ala Ser Gln Ala Glu Val Asn Asp Thr Thr Thr Asp
    130                 135                 140

His Gly Val Asp Met Glu Glu Thr Met Val Glu Ala Val Phe Thr Gly
145                 150                 155                 160

Glu Gln Ser Glu Gly Phe Asn Met Ala Lys Glu Ser Thr Val Glu Ala
                165                 170                 175

Ala Val Val Thr Glu Glu Pro Ser Lys Gly Ser Tyr Met Asp Glu Glu
            180                 185                 190

Trp Met Leu Glu Met Pro Thr Leu Leu Ala Asp Met Ala Glu Gly Met
        195                 200                 205
```

```
<210> SEQ ID NO 62
<211> LENGTH: 20
<212> TYPE: DNA
<213> ORGANISM: artificial sequence
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
```

```
<223> OTHER INFORMATION: n is a, c, g, or t
<220> FEATURE:
<223> OTHER INFORMATION: Mol 368 reverse primer

<400> SEQUENCE: 62
caycchatht aymgnggngt                                                   20

<210> SEQ ID NO 63
<211> LENGTH: 21
<212> TYPE: DNA
<213> ORGANISM: artificial sequence
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<223> OTHER INFORMATION: Mol 378 forward primer

<400> SEQUENCE: 63
ggnarnarca tnccytcngc c                                                 21

<210> SEQ ID NO 64
<211> LENGTH: 22
<212> TYPE: PRT
<213> ORGANISM: Arabidopsis thaliana
<220> FEATURE:
<223> OTHER INFORMATION: DML motif of G867

<400> SEQUENCE: 64

His Ser Lys Ser Glu Ile Val Asp Met Leu Arg Lys His Thr Tyr Asn
1               5                   10                  15

Glu Glu Leu Glu Gln Ser
            20

<210> SEQ ID NO 65
<211> LENGTH: 419
<212> TYPE: DNA
<213> ORGANISM: artificial sequence
<220> FEATURE:
<223> OTHER INFORMATION: P21275

<400> SEQUENCE: 65
tcgaccttat acaggatggg aagcggatca agcgttgtgt tagattcaga gaacggcgta      60
gaagctgaat ctaggaagct tccgtcgtca aaatacaaag gtgtggtgcc acaaccaaac     120
ggaagatggg gagctcagat ttacgagaaa caccagcgcg tgtggctcgg acattcaac     180 gaagaagacg aagccgctcg tgcctacgac gtcgcggttc acaggttccg tcgccgtgac     240
gccgtcacaa atttcaaaga cgtgaagatg gacgaagacg aggtcgattt cttgaattct     300
cattcgaaat ctgagatcgt tgatatgttg aggaaacata cttataacga agagttagag     360
cagagtaaac ggcgtcgtaa tggtaacgga aacatgacta ggacgtagtt aacgtcggc      419

<210> SEQ ID NO 66
<211> LENGTH: 548
<212> TYPE: DNA
```

<213> ORGANISM: artificial sequence
<220> FEATURE:
<223> OTHER INFORMATION: P21276

<400> SEQUENCE: 66

| | | | | | |
|---|---|---|---|---|---|
| tcgacctgag | atcgttgata | tgttgaggaa | acatacttat | aacgaagagt | tagagcagag | 60 |
| taaacggcgt | cgtaatggta | acggaaacat | gactaggacg | ttgttaacgt | cggggttgag | 120 |
| taatgatggt | gtttctacga | cggggtttag | atcggcggag | gcactgtttg | agaaagcggt | 180 |
| aacgccaagc | gacgttggga | agctaaaccg | tttggttata | ccgaaacatc | acgcagagaa | 240 |
| acattttccg | ttaccgtcaa | gtaacgtttc | cgtgaaagga | gtgttgttga | actttgagga | 300 |
| cgttaacggg | aaagtgtgga | ggttccgtta | ctcgtattgg | aacagtagtc | agagttatgt | 360 |
| tttgactaaa | ggttggagca | ggtcgttaa | ggagaagaat | ctacgtgctg | gtgacgtggt | 420 |
| tagtttcagt | agatctaacg | gtcaggatca | acagttgtac | attgggtgga | agtcgagatc | 480 |
| cgggtcagat | ttagatgcgg | gtcgggtttt | gagattgttc | ggagttaaca | tttgaccgga | 540 |
| gagttcgc | | | | | | 548 |

<210> SEQ ID NO 67
<211> LENGTH: 1176
<212> TYPE: DNA
<213> ORGANISM: artificial sequence
<220> FEATURE:
<223> OTHER INFORMATION: P21201

<400> SEQUENCE: 67

| | | | | | |
|---|---|---|---|---|---|
| tcgacgaatc | gagtagcgtt | gatgagagta | ctacaagtac | aggttccatc | tgtgaaaccc | 60 |
| cggcgataac | tccggcgaaa | aagtcgtcgg | taggtaactt | atacaggatg | ggaagcggat | 120 |
| caagcgttgt | gttagattca | gagaacggcg | tagaagctga | atctaggaag | cttccgtcgt | 180 |
| caaaatacaa | aggtgtggtg | ccacaaccaa | acgaagatg | gggagctcag | atttacgaga | 240 |
| aacaccagcg | cgtgtggctc | gggacattca | acgaagaaga | cgaagccgct | cgtgcctacg | 300 |
| acgtcgcggt | tcacaggttc | cgtcgccgtg | acgccgtcac | aaatttcaaa | gacgtgaaga | 360 |
| tggacgaaga | cgaggtcgat | ttcttgaatt | ctcattcgaa | atctgagatc | gttgatatgt | 420 |
| tgaggaaaca | tacttataac | gaagagttag | agcagagtaa | acggcgtcgt | aatggtaacg | 480 |
| gaaacatgac | taggacgttg | ttaacgtcgg | ggttgagtaa | tgatggtgtt | tctacgacgg | 540 |
| ggtttagatc | ggcggaggca | ctgtttgaga | aagcggtaac | gccaagcgac | gttgggaagc | 600 |
| taaaccgttt | ggttataccg | aaacatcacg | cagagaaaca | ttttccgtta | ccgtcaagta | 660 |
| acgtttccgt | gaaaggagtg | ttgttgaact | ttgaggacgt | taacgggaaa | gtgtggaggt | 720 |
| tccgttactc | gtattggaac | agtagtcaga | gttatgtttt | gactaaaggt | tggagcaggt | 780 |
| cgttaagga | gaagaatcta | cgtgctggtg | acgtggttag | tttcagtaga | tctaacggtc | 840 |
| aggatcaaca | gttgtacatt | gggtggaagt | cgagatccgg | gtcagattta | gatgcgggtc | 900 |
| gggttttgag | attgttcgga | gttaacattt | gaccggagag | ttcaagaaac | gacgtcgtag | 960 |
| gaaacaaaag | agtgaacgat | actgagatgt | tatcgttggt | gtgtagcaag | aagcaacgca | 1020 |
| tctttcacgc | ctcgtaacaa | ctcttcttct | ttttttttct | tttgttgttt | taataatttt | 1080 |
| taaaaactcc | attttcgttt | tctttatttg | catcggtttc | tttcttcttg | tttaccaaag | 1140 |
| gttcatgagt | tgtttttgtt | gtattgatga | actggc | | | 1176 |

<210> SEQ ID NO 68
<211> LENGTH: 1041
<212> TYPE: DNA

```
<213> ORGANISM: artificial sequence
<220> FEATURE:
<223> OTHER INFORMATION: P21193

<400> SEQUENCE: 68
taaatggaat cgagtagcgt tgatgagagt actacaagta caggttccat ctgtgaaacc      60
ccggcgataa ctccggcgaa aaagtcgtcg gtaggtaact tatacaggat gggaagcgga     120
tcaagcgttg tgttagattc agagaacggc gtagaagctg aatctaggaa gcttccgtcg     180
tcaaaataca aaggtgtggt gccacaacca aacggaagat ggggagctca gatttacgag     240
aaacaccagc gcgtgtggct cgggacattc aacgaagaag acgaagccgc tcgtgcctac     300
gacgtcgcgg ttcacaggtt ccgtcgccgt gacgccgtca caatttcaa agacgtgaag      360
atggacgaag acgaggtcga tttcttgaat tctcattcga aatctgagat cgttgatatg     420
ttgaggaaac atacttataa cgaagagtta gagcagagta acggcgtcg taatggtaac      480
ggaaacatga ctaggacgtt gttaacgtcg gggttgagta atgatggtgt ttctacgacg     540
gggtttagat cggcggaggc actgtttgag aaagcggtaa cgccaagcga cgttgggaag     600
ctaaaccgtt tggttatacc gaaacatcac gcagagaaac attttccgtt accgtcaagt     660
aacgtttccg tgaaaggagt gttgttgaac tttgaggacg ttaacgggaa agtgtggagg     720
ttccgttact cgtattggaa cagtagtcag agttatgttt tgactaaagg ttggagcagg     780
ttcgttaagg agaagaatct acgtgctggt gacgtggtta gtttcagtag atctaacggt     840
caggatcaac agttgtacat tgggtggaag tcgagatccg ggtcagattt agatgcgggt     900
cgggttttga gattgttcgg agttaacatt tcaccggaga gttcaagaaa cgacgtcgta     960
ggaaacaaaa gagtgaacga tactgagatg ttatcgttgg tgtgtagcaa gaagcaacgc    1020
atctttcacg cctcgcaatt c                                              1041

<210> SEQ ID NO 69
<211> LENGTH: 16
<212> TYPE: PRT
<213> ORGANISM: artificial sequence
<220> FEATURE:
<221> NAME/KEY: misc_feature
<222> LOCATION: (3)..(3)
<223> OTHER INFORMATION: Xaa can be K or R
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<223> OTHER INFORMATION: CBF conserved consecutive amino acid residues

<400> SEQUENCE: 69

Pro Lys Xaa Pro Ala Gly Arg Xaa Lys Phe Xaa Glu Thr Arg His Pro
1               5                   10                  15

<210> SEQ ID NO 70
<211> LENGTH: 5
<212> TYPE: PRT
<213> ORGANISM: artificial sequence
<220> FEATURE:
<223> OTHER INFORMATION: CBF conserved consecutive amino acid residues

<400> SEQUENCE: 70

Asp Ser Ala Trp Arg
1               5
```

```
<210> SEQ ID NO 71
<211> LENGTH: 693
<212> TYPE: DNA
<213> ORGANISM: Helianthus annuus

<400> SEQUENCE: 71
ttggaagcgg atccagcgtg gttcttgacc cagaaggagg cgtggaagtt gaagctcagt      60
cgagaaagct accctcgtcg cgatacaaag gtgtcgttcc acaaccgaat ggccgttggg     120
gagctcagat ttacgagaaa caccaaaggg tatggttagg tacgttcaac gacgaagatg     180
aagctgcaaa ggcgtacgat gttgccgtac aacgcttccg cggccgagac gcggtcacaa     240
acattaagca ggttgatgcc gacgataaag aggccgcgat ggaagcaagt ttcttaagcc     300
gccattcgaa gtcagaaatt gttgacatgc ttagaaaaca cacatacaat gacgagctag     360
aacaaagcaa agaagctgc acctcacacc aaacccttc tcaaaccggt ttatccaaca      420
ccacccgttt agtctccatg aagccacgcg aacatctctt ccagaaaacc gtgacccta     480 gcgacgtagg aaagctgaac cggctcgtta taccaaaaca acacgcggag aaacacttcc     540
cggttcaaaa agggagcaat tcaaaaggag ttcttttaca tttcgaagat aaagggtcaa     600
aagtatggag atttcgttac tcttactgga acagtagcca gagttatgtt ttaaccaaag     660
gctggagccg gttcgtgaaa gaaaaaaatc taa                                 693

<210> SEQ ID NO 72
<211> LENGTH: 760
<212> TYPE: DNA
<213> ORGANISM: Medicago truncatula
<220> FEATURE:
<221> NAME/KEY: misc_feature
<222> LOCATION: (5)..(5)
<223> OTHER INFORMATION: n is a, c, g, or t

<400> SEQUENCE: 72
tgatnacgcc aagctcgaaa ttaaccctca ctaaagggaa caaaagctgg agctccaccg      60
cggtggcggc cgctctagaa ctagtggatc ccccgggctg caggaattcg cacgaggca     120 tatctctctt attttgactc atacaacaaa cacaaactat ttcatttct accaaaaatg      180 gatggaggta gttgcataga cgaaagcact acaactgaat cattttcaat aacaatatcg     240
ccaacaaaga aaccgtcaac gccgccacct cccaacagcc tatgccgcgt tggcagcggc     300
gcaagcgctg ttgtggactc tgatggcagc ggcgttggcg aagctgagtc acggaagctt     360
ccttcttcga agtacaaagg tgttgtacca caaccaaatg gtcgttgggg agcacagatt     420
tacgaaaagc accagcgtgt gtggcttgga acatttaacc aagaagacga agctgctaaa     480
gcttatgatg ttgccgcaca acgtttccgc ggcaaagatg ctgtaacaaa ctttaaacca     540
ctctctgacc acaacaacga tgacatggaa ctcgagtttc tcaactcgca ttccaagtca     600
gagattgtgg acatgttaag aaaacataca tacaatgacg aactggaaca gagcaagcgc     660
agtcatggct tcgtcagcag acgaagccat ggctgttctg actctgttaa ctttgccagc     720
tcggcataca ataccgataa aaaggcacgt gaagctctgt                           760

<210> SEQ ID NO 73
<211> LENGTH: 304
<212> TYPE: DNA
<213> ORGANISM: Lotus japonicus

<400> SEQUENCE: 73
tttcttaact cgcactcgaa atctgagatc gtcgacatgc tgagaaagca tacttacaat      60
```

| | |
|---|---|
| gacgagctgg agcagagcaa gcgcagccgc ggactcgtgg gccggaaacg cgccgccggg | 120 |
| gaaaatttat ccggttcggc gcagggcgcg tgtgtgagga aggcgcgtga gcctctgttt | 180 |
| gagaaggcag ttaccccgag cgatgtaggg aagctgaacc gtttggtgat accgaagcag | 240 |
| catgcggaga agcactttcc gttacagagc gtgggcgtgg ccgggggcgt ggcgggaaac | 300 |
| gtgt | 304 |

```
<210> SEQ ID NO 74
<211> LENGTH: 582
<212> TYPE: DNA
<213> ORGANISM: Populus balsamifera

<400> SEQUENCE: 74
```

| | |
|---|---|
| acttcaagca agttaatgag caccgaagat gatgaaatag aggctgcttt cctgaacgct | 60 |
| cattccaaag ctgaaatcgt cgacatgttg aggaaacaca cgtacaacga cgagctagag | 120 |
| caaagcaaaa ggaaccacag gagtaacagt ggggtaaatg ggaagcagta caagaataca | 180 |
| gcaagctatg agaataatag ttatgatcat ggttgtggtc gggtgttgaa agcgcgtgaa | 240 |
| cagcttttg agaaagctgt gactccgagt gatgtcggga aattgaatcg gcttgtgata | 300 |
| ccaaaacaac atgcggaaaa gcattttcct ttgcaaagta catcaagcaa tagtactaaa | 360 |
| ggtgtattgc ttaacttgga agatgtgagc ggcaaagtgt ggaggtttcg ttattcttat | 420 |
| tggaatagta gccaaagtta tgttttgaca aaggggtgga gcagatttgt taaagaaaag | 480 |
| aacttgaaag ctggtgacat tgtttgcttt caaagatcaa ctggacctga taagcagctt | 540 |
| tacattgatt ggaaagcaag aagcgggccc aaccaggttc aa | 582 |

```
<210> SEQ ID NO 75
<211> LENGTH: 857
<212> TYPE: DNA
<213> ORGANISM: Stevia rebaudiana
<220> FEATURE:
<221> NAME/KEY: misc_feature
<222> LOCATION: (525)..(525)
<223> OTHER INFORMATION: n is a, c, g, or t
<220> FEATURE:
<221> NAME/KEY: misc_feature
<222> LOCATION: (596)..(596)
<223> OTHER INFORMATION: n is a, c, g, or t
<220> FEATURE:
<221> NAME/KEY: misc_feature
<222> LOCATION: (598)..(598)
<223> OTHER INFORMATION: n is a, c, g, or t
<220> FEATURE:
<221> NAME/KEY: misc_feature
<222> LOCATION: (612)..(612)
<223> OTHER INFORMATION: n is a, c, g, or t
<220> FEATURE:
<221> NAME/KEY: misc_feature
<222> LOCATION: (646)..(646)
<223> OTHER INFORMATION: n is a, c, g, or t
<220> FEATURE:
<221> NAME/KEY: misc_feature
<222> LOCATION: (650)..(650)
<223> OTHER INFORMATION: n is a, c, g, or t
<220> FEATURE:
<221> NAME/KEY: misc_feature
<222> LOCATION: (666)..(666)
<223> OTHER INFORMATION: n is a, c, g, or t
<220> FEATURE:
<221> NAME/KEY: misc_feature
<222> LOCATION: (678)..(678)
<223> OTHER INFORMATION: n is a, c, g, or t
<220> FEATURE:
<221> NAME/KEY: misc_feature
<222> LOCATION: (683)..(683)
<223> OTHER INFORMATION: n is a, c, g, or t
<220> FEATURE:
```

```
<221> NAME/KEY: misc_feature
<222> LOCATION: (691)..(691)
<223> OTHER INFORMATION: n is a, c, g, or t
<220> FEATURE:
<221> NAME/KEY: misc_feature
<222> LOCATION: (710)..(710)
<223> OTHER INFORMATION: n is a, c, g, or t
<220> FEATURE:
<221> NAME/KEY: misc_feature
<222> LOCATION: (746)..(746)
<223> OTHER INFORMATION: n is a, c, g, or t
<220> FEATURE:
<221> NAME/KEY: misc_feature
<222> LOCATION: (756)..(756)
<223> OTHER INFORMATION: n is a, c, g, or t
<220> FEATURE:
<221> NAME/KEY: misc_feature
<222> LOCATION: (758)..(758)
<223> OTHER INFORMATION: n is a, c, g, or t
<220> FEATURE:
<221> NAME/KEY: misc_feature
<222> LOCATION: (760)..(760)
<223> OTHER INFORMATION: n is a, c, g, or t
<220> FEATURE:
<221> NAME/KEY: misc_feature
<222> LOCATION: (774)..(774)
<223> OTHER INFORMATION: n is a, c, g, or t
<220> FEATURE:
<221> NAME/KEY: misc_feature
<222> LOCATION: (807)..(807)
<223> OTHER INFORMATION: n is a, c, g, or t

<400> SEQUENCE: 75
ctctctctat tgtttctctc tctaaccaac tataatgaat ggaagctcgg cagatgatca     60
aagcacgacg actgaaacaa cttcaacggt tgccgctccg gtgaccacaa ctccggcaat    120
cggaagtgca ggcagcgtgg ttgttgacct tgaagtcggt ttggaagctg agtcaagaaa    180
gctgccatca tcaaggttca aggtgtagt cccacaacct aatggccgat ggggtgctca    240
gatttacgag aaacaccagc gcgtgtggct cggaacgttt aacgaagaac acgaagctgc    300
aaaagcatac gacaccgcgg tccaacggtt tcgcggtcgc gatgcggtca ctaacctcac    360
accggttcca gccgacaccg aagaagcgag ttttgaagca agttttttaa atgctcattc    420
taaagcagag attgttgata tgttgaggaa acatacatat aatgacgagc ttgaacaaag    480
taaacgaaac tttagcttac agaaaagccc ttttaacgac ccggntcgga tctggtcaca    540
agatggttaa cccacgtgag caattggttg aaaagattgt accectagcg atgttngnaa    600 acttaacccg gntagtgatc ccaaacaaca cgctgagaaa cacttnccgn tgcaaattgg    660 caaacnccctt ttaaaggngg tcnttttgca nttttggaag aatattgggn attgaaaagt    720
gttggcgaat ttcggttact tcgganttgg gaatantnan cccaaaggtt ttgntttgga    780
ccaaaaggat ggaaccccat ttcgttnaaa gaaaagaac cttgaaaacc cggggacaat    840
tgtaggtttt caaaaga                                                    857

<210> SEQ ID NO 76
<211> LENGTH: 673
<212> TYPE: DNA
<213> ORGANISM: Gossypium arboreum
<220> FEATURE:
<221> NAME/KEY: misc_feature
<222> LOCATION: (540)..(540)
<223> OTHER INFORMATION: n is a, c, g, or t
<220> FEATURE:
<221> NAME/KEY: misc_feature
<222> LOCATION: (556)..(556)
<223> OTHER INFORMATION: n is a, c, g, or t
<220> FEATURE:
<221> NAME/KEY: misc_feature
<222> LOCATION: (616)..(616)
```

```
<223> OTHER INFORMATION: n is a, c, g, or t
<220> FEATURE:
<221> NAME/KEY: misc_feature
<222> LOCATION: (673)..(673)
<223> OTHER INFORMATION: n is a, c, g, or t

<400> SEQUENCE: 76
agatatacga gaagcaccaa cgtgtttggc ttggcacttt caatgaagaa gatgaggcgg      60
ccaaagccta tgacatagca gctcaaaggt ttaggggtcg tgacgctgtc actaacttca     120
aacacctcca cgaaatggag gatgatgaca tccaaattgc cttcctcaat tcgcattcca     180
aggctgaaat cgtggacatg ttgcgtaagc atacctacaa tgatgagctt gagcagagtc     240
ggagaagcta tggtttcgat gggaatggga acgtattgt cagaaaggag gatggttttg      300
gcaccttagg ctttgagctc aaagcacgtg aacaactctt cgagaaagct gtgaccccaa     360
gcgatgtagg gaagttgaac cggcttgtga tacctaagca acatgcggag aagtactttc     420
ctttgcaaag cgggagtgct tcttccaaag gagttctttt gaacttcgaa gatgtgaccg     480
gcaaagtttg gaggtttagg tattcctatt ggaacagtag ccagagttat gtcctaacan     540
aagggtggag ccgctntgtt aaggagaaga acctgaaagc cgtgacattg ttagcttcca     600
gagatcaaca gggacngaga agcagctgta cattgactgg aaagcaagaa ccggttgggg     660
ttctggtttt gan                                                       673

<210> SEQ ID NO 77
<211> LENGTH: 604
<212> TYPE: DNA
<213> ORGANISM: Glycine max

<400> SEQUENCE: 77
ggacaagcac cagcgcgtgt ggcttggaac gttcaacgag aaagacgagg cggcgcgtgc      60
gtacgacatc gccgcgcagc ggttccgcgg caaggacgcc gtcacgaact tcaagccgct     120
cgccggcgcc gacgacgacg acggagaatc ggagtttctc aactcgcatt ccaaacccga     180
gatcgtcgac atgctgcgaa agcacacgta caatgacgag ctggagcaga gcaagcgcag     240
ccgcggcgtc gtccggcggc gaggctccgc cgccgccggc accgcaaact caatttccgg     300
cgcgtgcttt actaaggcac gtgagcagct attcgagaag gctgttacgc cgagcgacgt     360
tgggaaattg aaccgtttgg tgataccgaa gcagcacgcg gagaagcact ttccgttaca     420
gagctctaac ggcgttagcg cgacgacgat agcggcggtg acggcgacgc cgacggcggc     480
gaaaggcgtt ttgttgaact tcgaagacgt tggagggaaa gtggtggggt ttcgctactc     540
gtattggaac agtagccaga gttacgtctt aaccaaaggg tgggagccgt tggttaaaga     600
aaag                                                                 604

<210> SEQ ID NO 78
<211> LENGTH: 1048
<212> TYPE: DNA
<213> ORGANISM: Brassica napus

<400> SEQUENCE: 78
tacaaaggcg tctcccytca cccgaacggg cggtggggag ytcagattta cgagaagcac      60
cagcgcgtgt ggytcgggac tttcaacgag gaggacgagg cggcgcgttc ttacgacgtg     120
gcggttcacc gkttccgagg ccgagacgcc gtcacgaact tcaaargacg cgaggctcga     180
cgacggagag gtcgagtttt tgagttcgca ttcgaaatct gggatcgttg atatgctgag     240
gaagcatacg tatagcgagg agctagagca gagcaaacgc cgacgcaacg gtaatggaaa     300
```

```
cgcggttagg tcgacgacgc aaaacgacgg cgtttcgacg acggagttta gatcggcggt      360
gtctttgttt gagaaaactg tcacgcctag cgacgtggg aagctaaacc gtctagtgat       420
accgaaacac cacgcggaga aatattttcc gttgccgccg tcgagtaacg tttccgttaa      480
gggagtgttg ttgaacttcg aggacgtggc ggggaaagtg tggaggttcc gttactcgta     540
ttggaacagt agtcaaagct atgttctgac aaaaggttgg agccggtttg ttaaggagaa     600
gaatctgcgt gctggtgatg tggttagttt cagcagatcc gatggtcagg atcaacagct    660
atacattggg tggaagtcta gatccgggat cggatgtgga aacgggtcgg ggttttgaga    720
ctgttcggag tcaacgtttc accgcgggt tcaagaaacg acgtggtagg gaacaagaga     780
gtggtgaacg atactgagat gttatcgttg gtgtgtagta agaagcaacg catctttcac   840
gccttgtaac cactcctctt tcttgagttt taataacttt ttttaatccc actttccatt   900
tcttttttca gttgcatcag tttcttctta gtaccaaagg ttcatgagtt gatttattgt   960
aatgatgaac tgtatatctt atttatagga tcaaagatgt ctaaagaagt tttactagtg  1020
tgattatgtt tttaccagat cgcacttc                                      1048
```

```
<210> SEQ ID NO 79
<211> LENGTH: 718
<212> TYPE: DNA
<213> ORGANISM: Lactuca sativa

<400> SEQUENCE: 79
ttagaagcca gtttcttgaa ttcccattca aaagctgaga tcgtcgatat gttgaggaaa       60
cacacataca atgatgagct acaacaaagc aaaagaagct gcaacttaaa caaaacccct    120
tgtacaaacg ggtttagatc gggtcaacag ttggtcaacg cccggaaca actctctgag     180 aagacagtca ccccaagcga cgtcggaaaa cttaaccgat tagtgatacc aaagcagcac   240
gctgagaaac acttcccgtt gcaaagcgaa agcacttcca aaggtgttct tttacatttc    300
gaagacatcg ggatgaaagt atggagattt cgttactcat actggaatag tagtcagagc   360
tacgttttga ccaaagggtg gagccgattc gtgaaggaaa agaacttaaa agccggtgac    420
attgtgagct ttcaaagatc cacgggttca gacaagcaac tttacatcga ctggaagacc   480
aaaaacgggt cgggtagctc caatattcaa gaacaagtcc aaccggttca catgtttagg    540
ctgtttggag tcaatatatc tagtggtggc gttgaaagca gttgcaatgg gggttttgttt   600 gataatgttt cggactagct acctttttcc tagcgatgat gatgaggaac gaagctggaa    660
agtggtggga aacgaataga gcagggtgca agttgcaaaa gtttgtatat ttatatta      718
```

```
<210> SEQ ID NO 80
<211> LENGTH: 581
<212> TYPE: DNA
<213> ORGANISM: Ipomoea batatas

<400> SEQUENCE: 80
aattcggcac gaggctttct tttgctatct ctctagctat cttctttctc tctctaaaat       60
caagatcgaa ataatggatg caagcacctc cgagcaccat agatgagagc agttctagcg    120
actctatgtc cgttgcattg aatttgccgc cggccaccaa gtcgccggag agcctctgcc    180
gaatggggag cggcgcgagc gtgatcatcg acgcggagaa cggcgtggag gcggagtccg    240
gccggaaact gccgtcgtcg agattcaaag gcgtggttcc tcagccgaat gggcgttggg    300
gggctcaaat ctacgagaaa caccagcggg tgtggctggg gacgttcaac gaggaggagg    360
aagccgctag ggtgtacgac atcgccgccc agcgcttccg cggccgagac gccgttacca   420
```

```
atttcaagcc gttgtcggaa acaaccgcca acggagacga ctacgaggcc gtgttttttga    480 gctcccactc caaggcggag atcgtggata tgctccgaaa acacacttac gccgacgagc    540
tggagcagag ccgccgagcc ttcaacatta acaacaataa c                        581
```

<210> SEQ ID NO 81
<211> LENGTH: 740
<212> TYPE: DNA
<213> ORGANISM: Solanum tuberosum

<400> SEQUENCE: 81

```
cttcctaatt ttcctttttct catcaaacaa acaacacac acacaaaaca aaaaagttt      60 caaaaaatgg aaggaagtat tagtagcata gatcaagaga gtactactag tgactctctc    120
tccattgctc cggcggcatc gtcgtcaacg atgataaaat tgtcgacgac gataaaaccg    180
ccgccggaga gcggcctttg ccggatgggg agtggaacaa gtgtgataat tgatgctgaa    240
aatggtgttg aagctgaatc aagaaaactc ccatcttcaa ggtacaaagg tgtggtccca    300
caaccaaatg gccgttgggg cgcacaaatc tatgaaaagc atcaaagggt ttggttaggc    360
acattcaacg aggaaaatga agccgctagg gcttacgacg tcgcggccca gagattcagg    420
ggccgcgacg ctgtaacaaa tttcaaaccc ttgcttgaga atcaagaaag cgatgacatg    480
gaaatcgctt tcttgaattc gcattccaag gcggagattg ttgacatgct acgtaaacat    540
acgtacctcg atgagctaga acaaagtaag agattatttg gatttactaa agatggtatg    600 ataaaagaa aagaatggac aataattaag ttcgtttttt ggtagtacaa atgataaagt    660
caattgcaaa gcgcgtgaac agctatttga aaagctgtt acaccaagtg acgttggaaa    720
gctaataggc ttgtgatacc                                                740
```

<210> SEQ ID NO 82
<211> LENGTH: 681
<212> TYPE: DNA
<213> ORGANISM: Solanum lycopersicum

<400> SEQUENCE: 82

```
cttcctaatt ttcctttttct catcaaaaaa gacaaaacaa cacacacacc aaaaaaaaaa    60
tggaaggaag tattagtagc atagatcaag agagtactac tagtgactct ctctccattg    120
ctccggccgc gtcgtcatcg acgatgatta aatcgtcgac gacgataaaa ctgccgccgg    180
agagtggtct tgccggatg gggagtggaa caagtgtgat aattgatgct gaaaatggtg    240
ttgaagctga atcaagaaaa ctcccatctt caaggtacaa aggtgtggtc ccacaaccaa    300
atggtcgttg gggcgcacaa atctatgaaa agcatcagag ggtatggtta ggcacattca    360
acgaggaaaa tgaagccgct agggcttatg acatcgcggc ccagagattc agggggccgcg    420 acgctgtaac taatttcaaa cccttgcttg agaatcaaga aagcgatgac atggaaatcg    480
ctttcttgaa ttcacattcc aaggcggaga tcgttgacat gttacgtaaa catacgtata    540
tcgatgagtt ggaacaaagc aagagattgt ttggatttac taaagacggt atgataaaaa    600
ggaaagatgg actagtaatt agttcgttct ttggtagtaa aaatgataaa gtcaattgca    660
aagcgcgtga acagctatttt g                                              681
```

<210> SEQ ID NO 83
<211> LENGTH: 325
<212> TYPE: DNA
<213> ORGANISM: Hordeum vulgare

<400> SEQUENCE: 83

```
cagcctaacg ggcgctgggg cgcgcagatc tacgagaagc actcgcgggt gtggcttggc      60
acgttcgggg acgaggaagc cgccgcgtgc gcctacgacg tggccgcgct ccgcttccgc     120
ggccgcgacg ccgttaccaa ccaccagcgc ctgccggcgg cggaggggc cggctggtcg     180 tccacgagcg agctcgcctt cctcgccgac cactccaagg cagagatcgt cgacatgctc     240
cggaagcaca cctacgacga cgagctccgg cagggcctgc gccgcggcca cgggcgcgcg     300
cagcccacgc cggcgtgggc gcgag                                            325
```

```
<210> SEQ ID NO 84
<211> LENGTH: 930
<212> TYPE: DNA
<213> ORGANISM: Oryza sativa

<400> SEQUENCE: 84
```

```
atggagcaag aagctgccat ggtcgtcttc tcctgcaact ccggctccgg tgggtcgtcg      60
tcgacgaccg attcaaagca agaggaggag gaggaggagg agttggccgc aatggaggaa     120
gacgagttga tccacgtcgt ccaggcggcg gagctgcggc tgccgtcgtc gacgacggcg     180
acgcggccgt cgtcgcggta caaggggtg gtgccgcagc cgaacgggcg gtgggggcg      240 cagatctacg agcggcacgc gcgggtgtgg ctcgggacgt tccccgacga ggaggcggcg     300
gcgcgcgcct acgacgtggc ggcgctccgc ttccggggc gcgacgccgt caccaaccgc     360
gccccggcgg cggagggcgc gtccgccggc gagctcgcgt tcctggccgc gcactccaag     420
gcggaggtcg tggacatgct gcggaagcac acctacgacg acgagctcca gcagggcctc     480
cgccgcggct cgcgcgcgca gccgacgccg cggtgggcgc gcagccgct gttcgagaag     540 gccgtgacgc cgagcgacgt cggcaagctc aaccgcctcg tggtgcccaa gcagcaggcc     600
gagaggcatt tcccgttccc gctccgccgc cacagctccg acgccgccgg caagggcgtg     660
ctcctcaact tcgaggacgg cgacggcaag gtgtggcgat ccggtactc gtactggaac     720 agcagccaga gttacgtgct caccaagggg tggagccgat tcgtgaggga aagggcctc     780 cgaccaggcg acaccgtggc cttctcccgg tcggcggcgg cgtgggggac ggagaagcac     840
ctcctcatcg actgcaagaa gatggagagg aacaacctgg caaccgtcga cgacgatgcc     900
ccgtgtcgtc gtcaagctgt tcggcgttga                                      930
```

```
<210> SEQ ID NO 85
<211> LENGTH: 17
<212> TYPE: PRT
<213> ORGANISM: artificial sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (15)..(16)
<223> OTHER INFORMATION: Xaa can be any naturally occurring amino acid
<220> FEATURE:
<223> OTHER INFORMATION: DML motif consensus sequence

<400> SEQUENCE: 85
```

```
Ser Lys Xaa Glu Xaa Val Asp Met Leu Arg Lys His Thr Tyr Xaa Xaa
1               5                   10                  15

Glu
```

<210> SEQ ID NO 86
<211> LENGTH: 741
<212> TYPE: DNA
<213> ORGANISM: Helianthus annuus

<400> SEQUENCE: 86

```
ttggaagcgg agccagcgtg gtttctgacc cggaagtgga agccttgtcg aggaagctac      60
cgtcgtcgag atataaaggc gttgttccgc aagcgaatgg ccgttgggga gctcagattt     120
atgagaaaca tcaaagggta tggcttggca cgtttaacga cgaagacgaa gccgcgaaag     180
cgtacgacgt cgcggtccaa cgctttcgcg gacgagacgc agtaacaaac ttcaagcaac     240
tcgtcaccga cgacaacgcc gctgcctttg aagcaacttt cttaaaccgt cactcaaaat     300
ccgaaatagt tgacatgcta agaaaacaca catacaatga cgagttagaa caaagcaaaa     360
gaaccatcaa cacacacaaa accctatttc aaaccgggtt caaccttccc ggaccgggtt     420
gcaccatgcc acgcgaacac ctcttccaaa aaaccgtcac accaagcgac gttggcaaac     480
taaaccggct cgtgatacca aaacaacatg ctgaaaaaca ctttccggtt caaaaaggca     540
tcagttcaaa gggagttttg ttacacttcg aagatacaga gtcaaaagtt tggcgatttc     600
ggtattcata ttggaatagt agccagagtt atgtgttaac caaagggtgg agccggtttg     660
ttaaagaaaa gaacttaaaa gccggtgata gcgttagctt tcacagctcg accggaccgg     720
ataagcagtt ttacattcac t                                                741
```

<210> SEQ ID NO 87
<211> LENGTH: 393
<212> TYPE: PRT
<213> ORGANISM: Oryza sativa

<400> SEQUENCE: 87

```
Met Asp Ser Ser Ser Cys Leu Val Asp Asp Thr Asn Ser Gly Gly Ser
1               5                   10                  15
Ser Thr Asp Lys Leu Arg Ala Leu Ala Ala Ala Ala Glu Thr Ala
        20                  25                  30
Pro Leu Glu Arg Met Gly Ser Gly Ala Ser Ala Val Val Asp Ala Ala
    35                  40                  45
Glu Pro Gly Ala Glu Ala Asp Ser Gly Ser Gly Gly Arg Val Cys Gly
50                  55                  60
Gly Gly Gly Gly Gly Ala Gly Gly Ala Gly Lys Leu Pro Ser Ser
65                  70                  75                  80
Lys Phe Lys Gly Val Val Pro Gln Pro Asn Gly Arg Trp Gly Ala Gln
                85                  90                  95
Ile Tyr Glu Arg His Gln Arg Val Trp Leu Gly Thr Phe Ala Gly Glu
            100                 105                 110
Asp Asp Ala Ala Arg Ala Tyr Asp Val Ala Ala Gln Arg Phe Arg Gly
        115                 120                 125
Arg Asp Ala Val Thr Asn Phe Arg Pro Leu Ala Glu Ala Asp Pro Asp
    130                 135                 140
Ala Ala Ala Glu Leu Arg Phe Leu Ala Thr Arg Ser Lys Ala Glu Val
145                 150                 155                 160
Val Asp Met Leu Arg Lys His Thr Tyr Phe Asp Glu Leu Ala Gln Ser
                165                 170                 175
Lys Arg Thr Phe Ala Ala Ser Thr Pro Ser Ala Ala Thr Thr Thr Ala
            180                 185                 190
Ser Leu Ser Asn Gly His Leu Ser Ser Pro Arg Ser Pro Phe Ala Pro
        195                 200                 205
```

```
Ala Ala Ala Arg Asp His Leu Phe Asp Lys Thr Val Thr Pro Ser Asp
        210                 215                 220
Val Gly Lys Leu Asn Arg Leu Val Ile Pro Lys Gln His Ala Glu Lys
225                 230                 235                 240
His Phe Pro Leu Gln Leu Pro Ser Ala Gly Gly Glu Ser Lys Gly Val
                245                 250                 255
Leu Leu Asn Phe Glu Asp Ala Ala Gly Lys Val Trp Arg Phe Arg Tyr
            260                 265                 270
Ser Tyr Trp Asn Ser Ser Gln Ser Tyr Val Leu Thr Lys Gly Trp Ser
        275                 280                 285
Arg Phe Val Lys Glu Lys Gly Leu His Ala Gly Asp Val Val Gly Phe
            290                 295                 300
Tyr Arg Ser Ala Ala Ser Ala Gly Asp Asp Gly Lys Leu Phe Ile Asp
305                 310                 315                 320
Cys Lys Leu Val Arg Ser Thr Gly Ala Ala Leu Ala Ser Pro Ala Asp
                325                 330                 335
Gln Pro Ala Pro Ser Pro Val Lys Ala Val Arg Leu Phe Gly Val Asp
                340                 345                 350
Leu Leu Thr Ala Pro Ala Pro Val Glu Gln Met Ala Gly Cys Lys Arg
            355                 360                 365
Ala Arg Asp Leu Ala Ala Thr Thr Pro Pro Gln Ala Ala Ala Phe Lys
        370                 375                 380
Lys Gln Cys Ile Glu Leu Ala Leu Val
385                 390

<210> SEQ ID NO 88
<211> LENGTH: 1182
<212> TYPE: DNA
<213> ORGANISM: Oryza sativa

<400> SEQUENCE: 88
atggacagca cgagctgtct cttggacgac gcgagcagcg gcgcgtccac gggcaagaag        60
gcggcggcgg cggcggcgtc gaaggcgctg cagcgcgtgg gcagcggcgc cagcgcggtg       120
atggacgcgc cgagcctggc gccgaggcg gactcgggcg cgagcggcg cggcggcggc         180 ggcgggaagc tgccgtcgtc caagtacaag ggcgtggtgc cgcaaccgaa cgggcggtgg       240
ggcgcgcaga tatacgagcg gcaccagcgg gtgtggctcg gcacgttcac cggcgaggcg       300
gaggcggcgc gcgcctacga cgtggcggcg cagcggttcc gcggccgcga cgccgtcacc       360
aacttccgcc gctcgccga gtccgaccg gaggccgccg tcgagctccg cttcctcgcg         420
tcccgctcca aggccgaggt cgtcgacatg ctccgcaagc acacctacct cgaggagctc       480
acgcagaaca gcgcgccctt cgccgccatc tccccgccgc cccccaagca cccgcctcc        540 tctccgacgt cctcctccgc cgcgcgcgag cacctgttcg acaagacggt gacgcccagc       600
gacgtcggga gctgaaccg gctggtgatc cccaagcagc acgccgagaa gcacttcccg        660
ctccagctcc ctcccctac cacaacctcc tccgtcgccg ccgccgccga cgccgccgcc       720
ggcggcggcg attgcaaggg cgtcctcctc aacttcgagg acgccgccgg aaggtgtgg        780 aaattccggt actcctactg gaacagcagc cagagctacg tgctcaccaa ggggtggagc       840
cgcttcgtca aggagaaggg gctccacgcc ggcgacgccg tcggcttcta ccgcgccgcc       900
ggtaagaacg cgcagctctt catcgactgc aaggtccggg caaaacccac caccgccgcc       960
gccgccgccg ccttcctcag cgcggtggcc gccgccgccg cgccgccacc cgccgtgaag      1020
gctatcaggc tgttcggtgt cgacctgctc acggcggcgg cgccggagct gcaggacgcc      1080
```

```
ggcggcgccg ccatgaccaa gagcaagaga gccatggacg ccatggctga gtcacaagca    1140
cacgtggttt ttaagaagca atgcatagag cttgcgctaa cc                      1182
```

<210> SEQ ID NO 89
<211> LENGTH: 716
<212> TYPE: DNA
<213> ORGANISM: Brassica oleracea
<220> FEATURE:
<221> NAME/KEY: misc_feature
<222> LOCATION: (608)..(608)
<223> OTHER INFORMATION: n is a, c, g, or t

<400> SEQUENCE: 89

```
tctcagcgct gagctccatg tggtggaatt ctagatgaca gtactagcaa cacttcaggg     60
tctctctcca cctctactcc ctccgcgaag aagaaactct cccctcctcc acctcctccg    120
gcgacgatgc gtctctacag aatgggaagc ggcggaagca gcgtcgtgct ggattctgag    180
aacggcgtcg agactgagtc acgcaagctc ccgtcgtcga agttcaaagg cgttgtccct    240
cagcctaacg gaagatgggg agctcagatt tacgagaagc accagcgtgt ctggctcggc    300
actttcaacg aggaggaaga agccgcggct tcctacgaca tcgccgctag gagattccgc    360
ggccgcgacg ccgtcacgaa cttcaagtcg ccggcgatcg acgggaccga cgctgagtct    420
gctttcctcg aggctcattc taaggccgag atcgttgata tgctgaggaa acacacttac    480
gccgacgagc ttcaacagag caaacggaag ttccttgacg gtaacggaaa acggtgcggc    540
tcggggacgg cgacgatgag taacggaaac gacggcgttt cgagagcgcg tgaagttctt    600
ttcgaganag ccgttacgcc tagcgacgtc gggaagctta accggctggt gataccgaag    660
cagcacgcgg agaagcattt tccgttaccg gcgatgacga cggcgacggt ggtgga       716
```

<210> SEQ ID NO 90
<211> LENGTH: 612
<212> TYPE: DNA
<213> ORGANISM: Medicago truncatula

<400> SEQUENCE: 90

```
gcgtggtgcc acagcctaac ggacgttggg gagcacagat ttacgagaaa caccagcgtg     60
tgtggcttgg tacgttcaat gaagaagacg aagcagccag agcctatgac atagccgcct    120
tgagattccg tggaaaagat gctgttacaa attctaaaag tctcactggc gttggtaacg    180
acgccgacga aggtgaaact gagtttctga attcacattc taagtcggag attgttgata    240
tgcttcggaa acacacctac gatgacgagc ttaagcaaag catgcgtgac atgagcggtg    300
gaagacagcg gcgtaacgga gaattgaatg gtgcggtttc acgtggcgcg tgtgatgcta    360
aagcgcgtga gcagttgttt gagaaaacgg ttacgccgag tgacgtgggg aagttgaatc    420
ggttggtgat accgaaacag catgcggaga agcatttttcc gttgaatgca gttgctgttg    480
ccgtcgcatg cgacggagtc tcgacggctg ctgcggcggc gaagggtttg cttttgaatt    540
tcgaagacgt tggagggaaa gtgtggcgat ttcgttattc ttattggaat agtagccaga    600
gttatgtttt ga                                                       612
```

<210> SEQ ID NO 91
<211> LENGTH: 620
<212> TYPE: DNA
<213> ORGANISM: Hordeum vulgare

<400> SEQUENCE: 91

```
cggcacgagg cgtggtgccg cagcccaacg ggcggtgggg cgcgcagatc tacgagcggc     60
```

```
accagcgcgt gtggcttggc acgttccccg gggaggccga cgccgcgcgc gcctacgacg      120
tcgccgcgca gcgcttccgc ggccgcgacg ccgttaccaa cttccgcccg ctcgcggacg      180
ccgaccccga cgccgccgcc gagctccgct tcctcgccgc gcgctccaag gccgaggtcg      240
tcgacatgct ccgcaagcac acctacttcg acgagctcgc ccagagcaag cgcgccttcg      300
ccgcgtcggc cgcgctctcc gcgcccacca cctcgggcga cgccggcggc agcgcctcgc      360
cgccctcccc ggccgccgtg cgcgagcacc tcttcgacaa gaccgtcacg cccagcgacg      420
tcggcaagct gaacaggctg gtgataccga agcagaacgc cgagaagcac ttcccgctgc      480
agctcccggc cggcggcggc gagagcaagg gcctgctcct caacttcgag gacgatgcgg      540
gcaaggtgtg gcggttccgc tactcgtact ggaacagcag ccagagctac gtcctcacca      600
agggctggag ccgcttcgtg                                                  620

<210> SEQ ID NO 92
<211> LENGTH: 591
<212> TYPE: DNA
<213> ORGANISM: Brassica napus

<400> SEQUENCE: 92
gaggcgacga tgcgtctcta cagaatggga agcggcggaa gcagcgtggt tcttgattta       60
gagaacggcg tcgagacaga gtcgtcgcgt aagctcccgt cgtcgaagtt caaaggcgtc      120
gtccctcagc ctaacggaag gtggggagct cagatttacg agaagcacca gcgcgtgtgg      180
ttaggcacgt tcaacgagga ggaggaagcc gcggcttcct acgacatcgc cgctcggaga      240
ttccgcggtc gagacgccgt cacgaacttc aagtcgccgt cgagtgacgc ggagtctgct      300
ttcctcgagg ctcattccaa ggctgagatc gttgacatgc tgaggaagca cacttacgcc      360
gacgagcttc gacagagcga aaggaagttt cttgacggcg acggtaacgg aaaaaaacga      420
cgcgagtcga agacgacggt gactgacgaa aacgacggcg ttttgagaga agtgcttttc      480
gagaaagccg ttacgccgag cgacgtcggg aagcttaacc ggttggttat accgaaacag      540
cacgcggaga agcattttcc gttaccggtt tcggttactc cgtcaccgac g              591

<210> SEQ ID NO 93
<211> LENGTH: 805
<212> TYPE: DNA
<213> ORGANISM: Medicago truncatula

<400> SEQUENCE: 93
ttagttataa aaatatatat atatatttca cttcaaactt tgctagttat taacagaata       60
acagaaaaaa tggaattagg aggaagttcc acagatgaaa ctgtcacaag caatgactct      120
ctttcggcga acttatctac accgccgcca acgctgaact cactaagccg cgttggcagt      180
gctgctagct ccgtcgtgga tccagaaatc tacggcgtct ccggtgaggc ggagtctcgt      240
aaacttccat cgtcgaaata caaaggcgtg gtgccacagc ctaacggacg ttggggagca      300
cagatttacg agaaacacca gcgtgtgtgg cttggtacgt tcaatgaaga agacgaagca      360
gccagagcct atgacatagc cgccttgaga ttccgtggaa aagatgctgt tacaaattct      420
aaaagtctca ctggcgttgg taacgacgcc gacgaaggtg aaactgagtt tctgaattca      480
cattctaagt cggagattgt tgatatgctt cggaaacaca cctacgatga cgagcttaag      540
caaagcatgc gtgacatgag cggtggaaga cagcggcgta acggagaatt gaatggtgcg      600
gtttcacgtg gcgcgtgtga tgctaaagcg cgtgagcagt gtttgagaa aacggttacg       660 ccgagtgacg tggggaagtt gaatcggttg gtgataccga aacagcatgc ggagaagcat      720
```

```
tttccgttga atgcagttgc tgttgccgtc gcatgcgacg gagtctcgac ggctgctgcg    780
gcggcgaagg gtttgctttt gaatt                                          805
```

<210> SEQ ID NO 94
<211> LENGTH: 7
<212> TYPE: PRT
<213> ORGANISM: artificial sequence
<220> FEATURE:
<223> OTHER INFORMATION: Primer Mol 368

<400> SEQUENCE: 94

His Pro Ile Tyr Arg Gly Val
1               5

<210> SEQ ID NO 95
<211> LENGTH: 8
<212> TYPE: PRT
<213> ORGANISM: artificial sequence
<220> FEATURE:
<223> OTHER INFORMATION: Primer Mol 378

<400> SEQUENCE: 95

Met Ala Glu Gly Met Leu Leu Pro
1               5

<210> SEQ ID NO 96
<211> LENGTH: 22
<212> TYPE: PRT
<213> ORGANISM: Glycine max

<400> SEQUENCE: 96

His Ser Lys Ser Glu Ile Val Asp Met Leu Arg Lys His Thr Tyr Asn
1               5                   10                  15

Asp Glu Leu Glu Gln Ser
            20

<210> SEQ ID NO 97
<211> LENGTH: 22
<212> TYPE: PRT
<213> ORGANISM: Arabidopsis thaliana

<400> SEQUENCE: 97

His Ser Lys Ser Glu Ile Val Asp Met Leu Arg Lys His Thr Tyr Lys
1               5                   10                  15

Glu Glu Leu Asp Gln Arg
            20

<210> SEQ ID NO 98
<211> LENGTH: 22
<212> TYPE: PRT
<213> ORGANISM: Glycine max

<400> SEQUENCE: 98

His Ser Lys Pro Glu Ile Val Asp Met Leu Arg Lys His Thr Tyr Asn
1               5                   10                  15

Asp Glu Leu Glu Gln Ser
            20

<210> SEQ ID NO 99
<211> LENGTH: 22
<212> TYPE: PRT
<213> ORGANISM: Brassica oleracea

<400> SEQUENCE: 99

```
His Ser Lys Tyr Glu Ile Val Asp Met Leu Arg Lys His Thr Tyr Lys
1               5                   10                  15

Glu Glu Leu Glu Gln Arg
            20

<210> SEQ ID NO 100
<211> LENGTH: 22
<212> TYPE: PRT
<213> ORGANISM: Populus balsamifera

<400> SEQUENCE: 100

His Ser Lys Ala Glu Ile Val Asp Met Leu Arg Lys His Thr Tyr Asn
1               5                   10                  15

Asp Glu Leu Glu Gln Ser
            20

<210> SEQ ID NO 101
<211> LENGTH: 22
<212> TYPE: PRT
<213> ORGANISM: Brassica napus

<400> SEQUENCE: 101

His Ser Lys Ser Gly Ile Val Asp Met Leu Arg Lys His Thr Tyr Ser
1               5                   10                  15

Glu Glu Leu Glu Gln Ser
            20

<210> SEQ ID NO 102
<211> LENGTH: 22
<212> TYPE: PRT
<213> ORGANISM: Helianthus annuus

<400> SEQUENCE: 102

His Ser Glu Ser Glu Ile Val Asp Met Leu Arg Lys His Thr Tyr Asn
1               5                   10                  15

Asp Glu Leu Glu Gln Ser
            20

<210> SEQ ID NO 103
<211> LENGTH: 22
<212> TYPE: PRT
<213> ORGANISM: Lactuca sativa

<400> SEQUENCE: 103

His Ser Lys Ala Glu Ile Val Asp Met Leu Arg Lys His Thr Tyr Asn
1               5                   10                  15

Asp Glu Leu Gln Gln Ser
            20

<210> SEQ ID NO 104
<211> LENGTH: 22
<212> TYPE: PRT
<213> ORGANISM: Ipomoea batatas

<400> SEQUENCE: 104

His Ser Lys Ala Glu Ile Val Asp Met Leu Arg Lys His Thr Tyr Ala
1               5                   10                  15

Asp Glu Leu Glu Gln Ser
            20

<210> SEQ ID NO 105
<211> LENGTH: 22
<212> TYPE: PRT
```

<213> ORGANISM: Solanum tuberosum

<400> SEQUENCE: 105

His Ser Lys Ala Glu Ile Val Asp Met Leu Arg Lys His Thr Tyr Leu
1               5                   10                  15

Asp Glu Leu Glu Gln Ser
            20

<210> SEQ ID NO 106
<211> LENGTH: 22
<212> TYPE: PRT
<213> ORGANISM: Solanum lycopersicum

<400> SEQUENCE: 106

His Ser Lys Ala Glu Ile Val Asp Met Leu Arg Lys His Thr Tyr Ile
1               5                   10                  15

Asp Glu Leu Glu Gln Ser
            20

<210> SEQ ID NO 107
<211> LENGTH: 22
<212> TYPE: PRT
<213> ORGANISM: Glycine max

<400> SEQUENCE: 107

His Ser Lys Pro Glu Ile Val Asp Met Leu Arg Lys His Thr Tyr Asn
1               5                   10                  15

Asp Glu Leu Glu His Ser
            20

<210> SEQ ID NO 108
<211> LENGTH: 22
<212> TYPE: PRT
<213> ORGANISM: Zea mays

<400> SEQUENCE: 108

Arg Ser Lys Ala Glu Val Val Asp Met Leu Arg Lys His Thr Tyr Gly
1               5                   10                  15

Glu Glu Leu Ala His Asn
            20

<210> SEQ ID NO 109
<211> LENGTH: 22
<212> TYPE: PRT
<213> ORGANISM: Arabidopsis thaliana

<400> SEQUENCE: 109

His Ser Lys Ala Glu Ile Val Asp Met Leu Arg Lys His Thr Tyr Ala
1               5                   10                  15

Asp Glu Leu Glu Gln Asn
            20

<210> SEQ ID NO 110
<211> LENGTH: 22
<212> TYPE: PRT
<213> ORGANISM: Arabidopsis thaliana

<400> SEQUENCE: 110

His Ser Lys Ala Glu Ile Val Asp Met Leu Arg Lys His Thr Tyr Ala
1               5                   10                  15

Asp Glu Phe Glu Gln Ser
            20

<210> SEQ ID NO 111
<211> LENGTH: 22
<212> TYPE: PRT
<213> ORGANISM: Glycine max

<400> SEQUENCE: 111

His Ser Lys Phe Glu Ile Val Asp Met Leu Arg Lys His Thr Tyr Asp
1               5                   10                  15

Asp Glu Leu Gln Gln Ser
            20

<210> SEQ ID NO 112
<211> LENGTH: 22
<212> TYPE: PRT
<213> ORGANISM: Glycine max

<400> SEQUENCE: 112

His Ser Lys Ser Glu Ile Val Asp Met Leu Arg Arg His Thr Tyr Asp
1               5                   10                  15

Asn Glu Leu Gln Gln Ser
            20

<210> SEQ ID NO 113
<211> LENGTH: 22
<212> TYPE: PRT
<213> ORGANISM: Oryza sativa

<400> SEQUENCE: 113

His Ser Lys Ala Glu Ile Val Asp Met Leu Arg Lys His Thr Tyr Ala
1               5                   10                  15

Asp Glu Leu Arg Gln Gly
            20

<210> SEQ ID NO 114
<211> LENGTH: 22
<212> TYPE: PRT
<213> ORGANISM: Hordeum vulgare

<400> SEQUENCE: 114

His Ser Lys Ala Glu Ile Val Asp Met Leu Arg Lys His Thr Tyr Asp
1               5                   10                  15

Asp Glu Leu Arg Gln Gly
            20

<210> SEQ ID NO 115
<211> LENGTH: 22
<212> TYPE: PRT
<213> ORGANISM: Oryza sativa

<400> SEQUENCE: 115

His Ser Lys Ala Glu Val Val Asp Met Leu Arg Lys His Thr Tyr Asp
1               5                   10                  15

Asp Glu Leu Gln Gln Gly
            20

<210> SEQ ID NO 116
<211> LENGTH: 22
<212> TYPE: PRT
<213> ORGANISM: Oryza sativa

<400> SEQUENCE: 116

Arg Ser Lys Ala Glu Val Val Asp Met Leu Arg Lys His Thr Tyr Leu
1               5                   10                  15

```
Glu Glu Leu Thr Gln Asn
            20

<210> SEQ ID NO 117
<211> LENGTH: 22
<212> TYPE: PRT
<213> ORGANISM: Oryza sativa

<400> SEQUENCE: 117

Arg Ser Lys Ala Glu Val Val Asp Met Leu Arg Lys His Thr Tyr Phe
1               5                   10                  15

Asp Glu Leu Ala Gln Ser
            20

<210> SEQ ID NO 118
<211> LENGTH: 22
<212> TYPE: PRT
<213> ORGANISM: Zea mays

<400> SEQUENCE: 118

Arg Ser Lys Ala Glu Val Val Asp Met Leu Arg Lys His Thr Tyr Gly
1               5                   10                  15

Glu Glu Leu Ala Gln Asn
            20

<210> SEQ ID NO 119
<211> LENGTH: 22
<212> TYPE: PRT
<213> ORGANISM: Triticum aestivum

<400> SEQUENCE: 119

Arg Ser Lys Ala Glu Val Val Asp Met Leu Arg Lys His Thr Tyr Pro
1               5                   10                  15

Asp Glu Leu Ala Gln Tyr
            20

<210> SEQ ID NO 120
<211> LENGTH: 22
<212> TYPE: PRT
<213> ORGANISM: Zea mays

<400> SEQUENCE: 120

Arg Ser Lys Ala Glu Val Val Asp Met Leu Arg Lys His Thr Tyr Phe
1               5                   10                  15

Asp Glu Leu Ala Gln Asn
            20
```